(12) United States Patent
Izawa et al.

(10) Patent No.: US 10,358,434 B2
(45) Date of Patent: Jul. 23, 2019

(54) 2-(3-PYRIDINYL)-1H-BENZIMIDAZOLE DERIVATIVE COMPOUND AND MEDICAMENT CONTAINING SAME

(71) Applicants: NIHON MEDI-PHYSICS CO., LTD., Koto-ku, Tokyo (JP); Kyoto University, Sakyo-ku, Kyoto-shi, Kyoto (JP); National Hospital Organization, Meguro-ku, Tokyo (JP)

(72) Inventors: Akihiro Izawa, Tokyo (JP); Kei Akama, Tokyo (JP); Yuki Okumura, Tokyo (JP); Yurie Fukui, Tokyo (JP); Nobuya Kobashi, Tokyo (JP); Tsutomu Abe, Tokyo (JP); Yoshihiro Doi, Tokyo (JP); Miho Ikenaga, Tokyo (JP); Hideo Saji, Kyoto (JP); Hiroyuki Kimura, Kyoto (JP); Mitsuhide Naruse, Kyoto (JP)

(73) Assignees: NIHON MEDI-PHYSICS CO., LTD., Koto-Ku, Tokyo (JP); KYOTO UNIVERSITY, Kyoto-Shi, Kyoto (JP); NATIONAL HOSPITAL ORGANIZATION, Meguro-Ku, Tokyo (JP)

( * ) Notice: Subject to any disclaimer, the term of this patent is extended or adjusted under 35 U.S.C. 154(b) by 0 days.

(21) Appl. No.: 16/211,434

(22) Filed: Dec. 6, 2018

(65) Prior Publication Data
US 2019/0169169 A1 Jun. 6, 2019

Related U.S. Application Data

(62) Division of application No. 15/321,972, filed as application No. PCT/JP2015/068431 on Jun. 25, 2015, now Pat. No. 10,189,815.

(30) Foreign Application Priority Data

Jun. 26, 2014 (JP) .................................. 2014-131934

(51) Int. Cl.
*C07D 401/14* (2006.01)
*A61K 51/04* (2006.01)
*A61K 31/4439* (2006.01)
*A61K 51/00* (2006.01)

(52) U.S. Cl.
CPC ........ *C07D 401/14* (2013.01); *A61K 31/4439* (2013.01); *A61K 51/00* (2013.01); *A61K 51/0455* (2013.01); *C07B 2200/05* (2013.01)

(58) Field of Classification Search
None
See application file for complete search history.

(56) References Cited

U.S. PATENT DOCUMENTS

2009/0297447 A1  12/2009  Langstrom et al.
2013/0089502 A1   4/2013  Allolio et al.
2013/0317057 A1  11/2013  Hoyt et al.

FOREIGN PATENT DOCUMENTS

| JP | 2009-539822 A | 11/2009 |
| JP | 2013-534911 A | 9/2013 |
| JP | 2015-110563 A | 6/2015 |
| WO | WO 2007/144725 A1 | 12/2007 |
| WO | WO 2011/151411 A1 | 12/2011 |
| WO | WO 2012/012478 A1 | 1/2012 |

OTHER PUBLICATIONS

International Search Report (PCT/ISA/210) dated Aug. 18, 2015, by the Japanese Patent Office as the International Searching Authority for International Application No. PCT/JP2015/068431.
Written Opinion (PCT/ISA/237) dated Aug. 18, 2015, by the Japanese Patent Office as the International Searching Authority for International Application No. PCT/JP2015/068431.
PCT International Preliminary Report on Patentability (IPRP) and Written Opinion dated Jan. 5, 2017, in corresponding International Application No. PCT/JP2015/068431(7 pages).
Nanba et al.: "Histopathological Diagnosis of Primary Aldosteronism Using CYP11B2 Immunohistochemistry," Journal of Clinical Endocrinology & Metabolism, Apr. 2013, vol. 98, No. 4, pp. 1567-1574.

(Continued)

*Primary Examiner* — James W Rogers
(74) *Attorney, Agent, or Firm* — Buchanan, Ingersoll & Rooney PC

(57) ABSTRACT

Provided is a medicament comprising the compound represented by the following general formula (1) or a salt thereof:

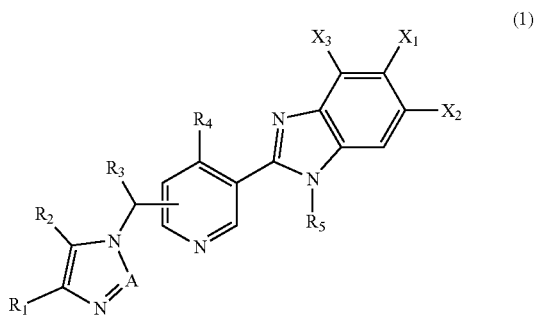

(1)

In the formula, $R_1$, $R_2$, $R_3$, $R_4$, $R_5$, $X_1$, $X_2$, and $X_3$ are defined. Methods for producing various radioactive compounds are also provided.

14 Claims, 29 Drawing Sheets

(56) References Cited

OTHER PUBLICATIONS

Amar et al.: "Aldosterone Synthase Inhibition With LCI699: A Proof-of-Concept Study in Patients With Primary Aldosteronism," Hypertension, Journal of the American Heart Association, Sep. 13, 2010, vol. 56, pp. 831-838.
De Jong et al.: "Etomidate Suppresses Adrenocortical Function by Inhibition of 11β-Hydroxylation," Journal of Clinical Endocrinology & Metabolism, 1984, vol. 59, No. 6, pp. 1143-1147.
Forman: "Clinical and Molecular Pharmacology of Etomidate," Anesthesiology, Mar. 2011, vol. 114, No. 3, pp. 695-707.
Zettinig et al.: "Positron emission tomography imaging of adrenal masses: $^{18}$F-fluorodeoxyglucose and the 11β-hydroxylase tracer $^{11}$C-metomidate," European Journal of Nuclear Medicine and Molecular Imaging, Sep. 2004, vol. 31, No. 9, pp. 1224-1230.
Wadsak et al.: "[$^{18}$F] FETO for adrenocortical PET imaging: a pilot study in healthy volunteers," European Journal of Nuclear Medicine and Molecular Imaging, Jun. 2006, vol. 33, No. 6, pp. 669-672.
Hahner et al.: "[$^{123}$I]Iodometomidate for Molecular Imaging of Adrenocortical Cytochrome P450 Family 11B Enzymes," Journal of Clinical Endocrinology & Metabolism, Jun. 2008, vol. 93, No. 6, pp. 2358-2365.
Burton et al.: "Evaluation of the Sensitivity and Specificity of $^{11}$C-Metomidate Positron Emission Tomography (PET)-CT for Lateralizing Aldosterone-Secretion by Conn's Adenomas," Journal of Clinical Endocrinology & Metabolism, Jan. 2012, vol. 97, No. 1, pp. 100-109.
Hahner et al.: "Functional Characterization of Adrenal Lesions Using [$^{123}$I]IMTO-SPECT/CT," Journal of Clinical Endocrinology & Metabolism, Apr. 2013, vol. 98, No. 4, pp. 1508-1518.
Extended Search Report issued by the European Patent Office in corresponding European Patent Application No. 15811977.6-1462 dated Dec. 20, 2017 (5 pages).
The First Office Action issued by The State Intellectual Property Office of People's Republic of China in corresponding Chinese Patent Application No. 201580032760.3 dated Jun. 5, 2018 (13 pages including partial English translation).
Examination report No. 1 for standard patent application issued by the Australian IP Government in corresponding Australian Patent Application No. 2015281060 dated Oct. 3, 2018.
The Second Office Action issued by the State Intellectual Property Office of People's Republic of China in corresponding Chinese Patent Application No. 201580032760.3 dated Mar. 5, 2019 (12 pages including partial English translation).

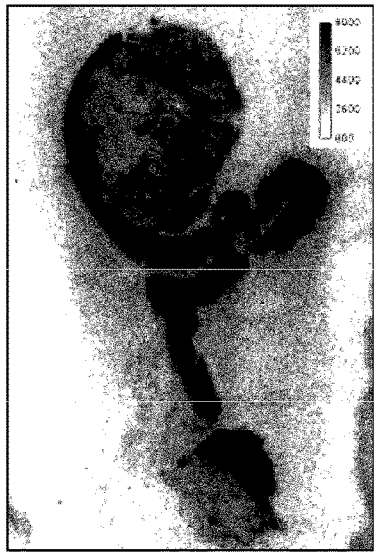 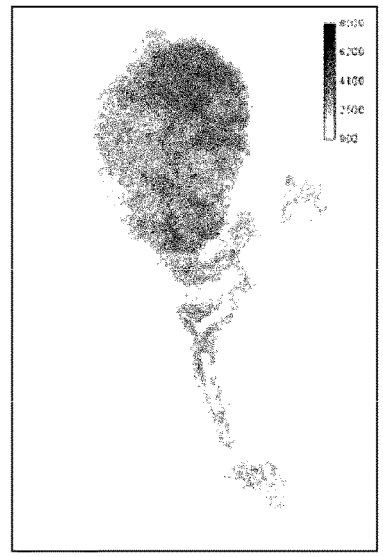
Fig. 25A　　　　　　　　　Fig. 25B
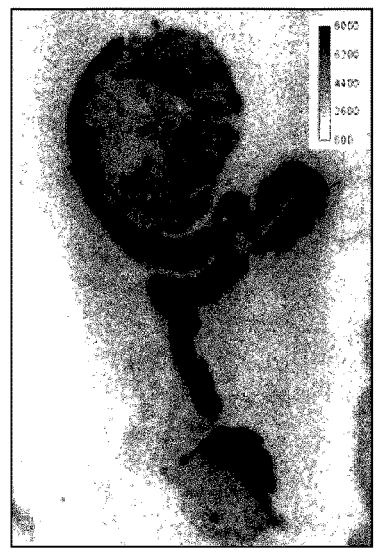 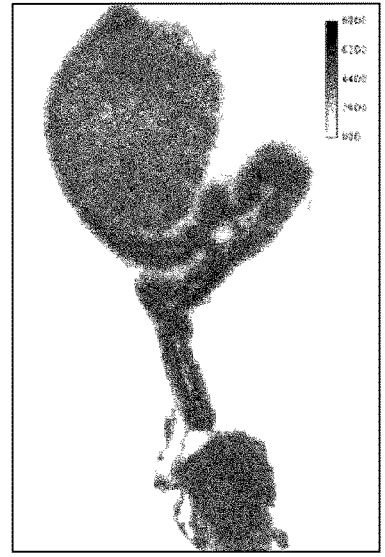
Fig. 26A　　　　　　　　　Fig. 26B

# 2-(3-PYRIDINYL)-1H-BENZIMIDAZOLE DERIVATIVE COMPOUND AND MEDICAMENT CONTAINING SAME

RELATED APPLICATIONS

This application is a Divisional of U.S. application Ser. No. 15/321,972, filed on Dec. 23, 2016, which is a U.S. National Stage of International Application No. PCT/JP2015/068431, filed on Jun. 25, 2015, which claims priority to Japanese Application No. 2014-131934, filed on Jun. 26, 2014, the entire contents of each of which is incorporated herein by reference.

TECHNICAL FIELD

The present invention relates to a 2-(3-pyridinyl)-1H-benzimidazole derivative compound and a medicament comprising the same.

BACKGROUND ART

As a disease developed as a result of abnormality in adrenal cortex, primary aldosteronism (PA) has been known. Primary aldosteronism is a disease in which CYP11B2 is overexpressed by adrenal adenoma or adrenal hyperplasia (Non Patent Literature 1), and autonomous production of aldosterone from adrenal gland is promoted, thereby causing hypertension or hypokalemia. In the case of unilateral adrenal lesion, it can be treated by surgical excision. However, in the case of bilateral adrenal lesion, a treatment with drug therapy is adopted.

As a drug therapy performed on primary aldosteronism, an aldosterone receptor antagonist is mainly used at present. As another target molecule in drug therapy, an aldosterone synthase, CYP11B2, has been considered (Non Patent Literature 2).

Etomidate has been used as an intravenous anesthetic in another country than Japan, and has been known to mainly bind to cortisol, corticosterone, and 11β hydroxylase (CYP11B1) necessary for biosynthesis of aldosterone and inhibits them, thereby suppressing steroid synthesis in adrenal cortex (Non Patent Literature 3). Thus, it has been reported that etomidate has such side effects that it causes reductions in concentrations of aldosterone and cortisol in plasma (Non Patent Literature 4).

In addition, in recent years, aiming for non-invasive local diagnosis of aldosterone-producing adenoma and other adrenal lesions, an attempt of imaging adrenal lesions by single-photon emission computed tomography (SPECT) or positron emission tomography (PET) has been made in humans. Patent Literatures 1 and 2 and Non Patent Literatures 5 to 8 have reported various types of radiolabeled compounds targeting adrenal steroid biosynthetic enzymes. For example, results of clinical studies are disclosed on $^{11}$C-labeled metomidate in Non Patent Literatures 5 and 8, on $^{18}$F-labeled etomidate in Non Patent Literature 6, and on $^{123}$I-labeled iodometomidate in Non Patent Literatures 7 and 9. It has been reported that adrenal lesions can be imaged using these radiolabeled compounds.

CITATION LIST

Patent Literature

Patent Literature 1: International Publication No. WO 2007/144725

Patent Literature 2: International Publication No. WO 2011/151411
Patent Literature 3: International Publication No. WO 2012/012478

Non Patent Literature

Non Patent Literature 1: Kazutaka Nanba et al., Journal of Clinical Endocrinology & Metabolism (2013) Vol. 98, No. 4, 1567-74
Non Patent Literature 2: Amar, et al., Hypertension, (2010) Vol. 56, 831 to 8
Non Patent Literature 3: de Jong et al., Journal of Clinical Endocrinology & Metabolism (1984) Vol. 59, No. 6, 1143 to 7
Non Patent Literature 4: Forman et al., Anesthesiology (2011) Vol. 114, No. 3, 695 to 707
Non Patent Literature 5: Georg Zettinig, et al., European Journal of Nuclear Medicine and Molecular Imaging (2004) Vol. 31, No. 9, pp. 1224 to 1230
Non Patent Literature 6: Wolfgang Wadsak, et al., European Journal of Nuclear Medicine and Molecular Imaging (2006) Vol. 33, No. 6, pp. 669 to 672
Non Patent Literature 7: Stefanie Hahner, et al., Journal of Clinical Endocrinology & Metabolism (2008) Vol. 93, No. 6, pp. 2358 to 2365
Non Patent Literature 8: Timothy J. Burton, et al., Journal of Clinical Endocrinology & Metabolism (2012) Vol. 97, No. 1, pp. 100 to 109
Non Patent Literature 9: Stefanie Hahner, et al., Journal of Clinical Endocrinology & Metabolism (2013) Vol. 98, No. 4, 1508 to 18

SUMMARY OF INVENTION

The present inventors have newly found that a compound having a certain selective inhibitory ability on CYP11B2 is specifically accumulated in an aldosterone-producing tumor.

Patent Literature 3 discloses a compound having high selectivity to CYP11B2. However, Patent Literature 3 does not disclose any relationship between the selective inhibitory ability of the compound on CYP11B2 and a specific accumulation of the compound in an aldosterone-producing tumor compared to the normal site of the adrenal gland.

The present invention has been made under the aforementioned circumstances, and aims at providing a compound capable of specifically accumulating in an aldosterone-producing tumor and having an ability to selectively inhibit CYP11B2, and a medicament comprising the same.

Specifically, in one aspect, the present invention provides a compound represented by the following general formula (1) or a salt thereof:

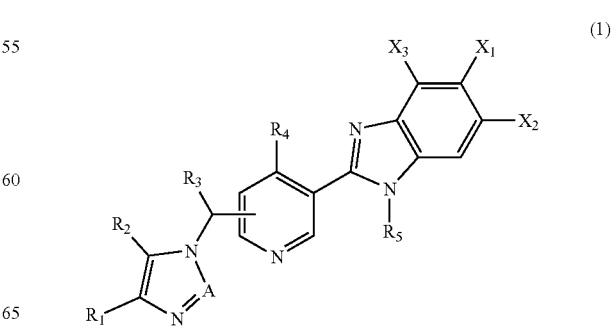

In the above general formula (1), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_5$ represents a linear alkyl group containing 1 to 5 carbon atoms in which a hydrogen atom is optionally replaced by a halogen atom, a cyclic alkyl group containing 3 to 5 carbon atoms in which a hydrogen atom is optionally replaced by a halogen atom, a hydroxyalkyl group containing 1 to 5 carbon atoms, or an o-, p- or m-halobenzyl group, A represents CH or a nitrogen atom, $X_1$ and $X_3$ each independently represent a hydrogen atom or a halogen atom, $X_2$ represents a hydrogen atom, a halogen atom or a nitrile group, provided that at least one of $X_1$, $X_2$ and $X_3$ represents a halogen atom, and each $R_a$ independently represents an alkyl group containing 1 to 10 carbon atoms.

In another aspect, the present invention provides a medicament comprising the above described compound or a salt thereof. The medicament according to the present invention can be preferably used as an image diagnostic agent for an adrenal disease, or a therapeutic agent for an aldosterone-producing tumor.

A radioactive medicament which comprises a radioactive compound of the above general formula (1) or a salt thereof can be used as an image diagnostic agent for nuclear medicine examination, where $R_5$ is a group represented by —$(CH_2)_nX_4$ (wherein n is an integer of 1 to 5 and $X_4$ is a halogen atom) and $X_4$ is a radioactive halogen atom, where $R_5$ is a p-halobenzyl group labeled with a radioactive halogen atom, or where $X_2$ or $R_2$ is a radioactive halogen atom. For example, when $^{18}F$, $^{34m}Cl$, $^{76}Br$, or $^{124}I$ is 1 selected as a radioactive halogen atom, the radioactive medicament can be used as an image diagnostic agent for use in positron emission tomography (PET). On the other hand, when $^{123}I$ is selected as a radioactive halogen atom, the radioactive medicament can be used as an image diagnostic agent for use in single-photon emission computed tomography (SPECT).

Moreover, a medicament comprising the compound according to the present invention or a salt thereof can be used as an image diagnostic agent for nuclear magnetic resonance imaging (MRI) by using an element suitable for the nuclear magnetic signal measurement, such as fluorine ($^{19}F$), as a halogen atom represented by $X_4$ in a case where $R_5$ is a group represented by —$(CH_2)_nX_4$ (wherein n is an integer of 1 to 5 and $X_4$ is a halogen atom), or as a halogen atom in a para-position in a case where $R_5$ is a p-halobenzyl group, or as a halogen atom represented by $X_2$ or $R_2$, in the above general formula (1).

Furthermore, a radioactive medicament which comprises a radioactive compound of the above general formula (1) or a salt thereof, can be used as an internal-use radiotherapeutic agent for an aldosterone-producing tumor, where $R_5$ is a group represented by —$(CH_2)_nX_4$ (wherein n is an integer of 1 to 5 and $X_4$ is a radioactive halogen atom), or where $R_5$ is a p-halobenzyl group labeled with a radioactive halogen atom, or where $X_2$ or $R_2$ is a radioactive halogen atom. At this time, $^{125}I$, $^{131}I$, or $^{211}At$ is preferably used as a radioactive halogen atom.

In another aspect, the present invention provides a compound represented by the following general formula (3) or a salt thereof:

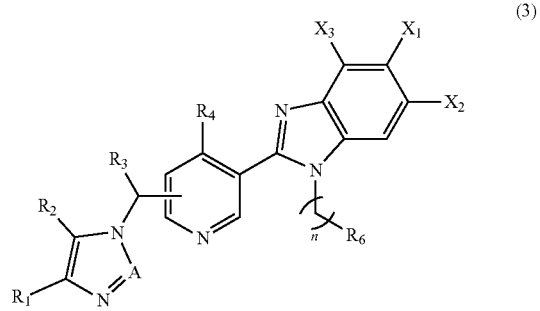

In the above general formula (3), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_6$ represents a halogen atom, a substituted or unsubstituted alkylsulfonyloxy group, or a substituted or unsubstituted arylsulfonyloxy group, n represents an integer of 1 to 5, A represents CH or a nitrogen atom, $X_1$ and $X_3$ each independently represent a hydrogen atom or a halogen atom, $X_2$ represents a hydrogen atom, a halogen atom or a nitrile group, provided that at least one of $X_1$, $X_2$ and $X_3$ is a halogen atom, and each $R_a$ independently represents an alkyl group containing 1 to 10 carbon atoms.

In addition, in another aspect, the present invention provides a compound represented by the following general formula (5) or a salt thereof:

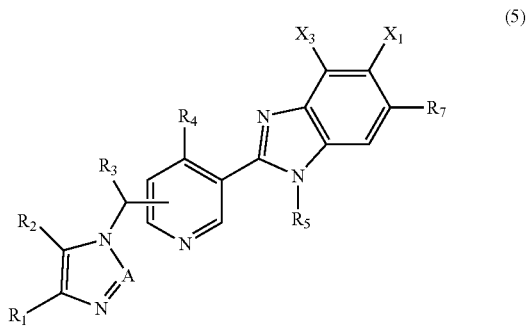

In the above general formula (5), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_5$ represents a linear alkyl group containing 1 to 5 carbon atoms in which a hydrogen atom is optionally replaced by a halogen atom, a cyclic alkyl group containing 3 to 5 carbon atoms in which a hydrogen atom is optionally replaced by a halogen atom, a hydroxyalkyl group containing 1 to 5 carbon atoms, or an o-, p- or m-halobenzyl group, $R_7$ represents a trialkyltin group or a trialkylsilyl group, A represents CH or a nitrogen atom, $X_1$ represents a hydrogen atom or a halogen atom, $X_3$ represents a hydrogen atom or a halogen atom, and each $R_a$ independently represents an alkyl group containing 1 to 10 carbon atoms.

Moreover, in another aspect, the present invention provides a compound represented by the following general formula (7) or a salt thereof:

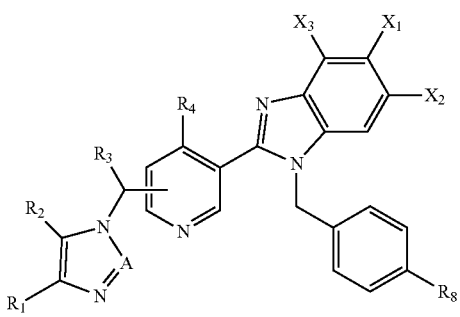

(7)

In the above general formula (7), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_8$ represents a trialkyltin group or a trialkylsilyl group, A represents CH or a nitrogen atom, $X_1$ represents a hydrogen atom or a halogen atom, $X_2$ represents a hydrogen atom, a halogen atom or a nitrile group, $X_3$ represents a hydrogen atom or a halogen atom, provided that at least one of $X_1$, $X_2$ and $X_3$ is a halogen atom, and each $R_a$ independently represents an alkyl group containing 1 to 10 carbon atoms.

Furthermore, in another aspect, the present invention provides a compound represented by the following general formula (8) or a salt thereof:

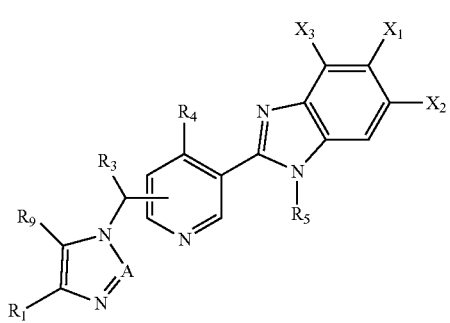

(8)

In the above general formula (8), $R_1$ represents a hydrogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_5$ represents a linear alkyl group containing 1 to 5 carbon atoms in which a hydrogen atom is optionally replaced by a halogen atom, a cyclic alkyl group containing 3 to 5 carbon atoms in which a hydrogen atom is optionally replaced by a halogen atom, a hydroxyalkyl group containing 1 to 5 carbon atoms, or an o-, p- or m-halobenzyl group, $R_9$ represents a trialkyltin group or a trialkylsilyl group, A represents CH or a nitrogen atom, $X_1$ represents a hydrogen atom or a halogen atom, $X_2$ represents a hydrogen atom, a halogen atom or a nitrile group, $X_3$ represents a hydrogen atom or halogen atom, provided that at least one of $X_1$, $X_2$ and $X_3$ is a halogen atom, and each $R_a$ independently represents an alkyl group containing 1 to 10 carbon atoms.

In another aspect, the present invention can provide a method for producing the compound represented by the above general formula (1) wherein $R_5$ is a group represented by $-(CH_2)_nX_4$ (wherein n is an integer of 1 to 5 and $X_4$ is a radioactive halogen atom) (namely, a radioactive compound represented by the following general formula (9)) or a salt thereof, from the compound represented by the above general formula (3) or a salt thereof according a radiohalogenation reaction:

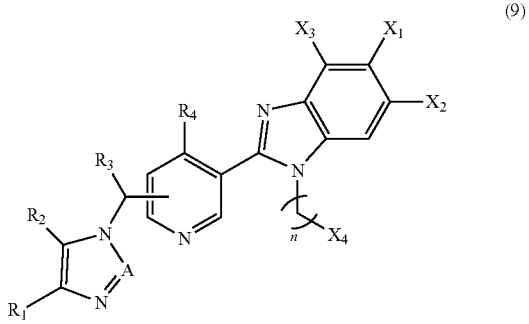

(9)

In the above general formula (9), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, A represents CH or a nitrogen atom, $X_1$ and $X_3$ each independently represent a hydrogen atom or a halogen atom, $X_2$ represents a hydrogen atom, a halogen atom or a nitrile group, provided that at least one of $X_1$, $X_2$ and $X_3$ is a halogen atom, $X_4$ represents a radioactive halogen atom, and each $R_a$ independently represents an alkyl group containing 1 to 10 carbon atoms.

In another aspect, the present invention can provide a method for producing a radioactive compound represented by the following general formula (10) or a salt thereof, from a compound represented by the following general formula (4) or a salt thereof, wherein, in the above general formula (3), $R_1$, $R_3$ and $R_4$ are hydrogen atoms, $R_2$ is a hydrogen atom or $CO_2R_a$, A is CH, $X_2$ is a halogen atom, $X_3$ is a hydrogen atom, and $R_a$ is an alkyl group containing 1 to 10 carbon atoms, by a radiohalogenation reaction:

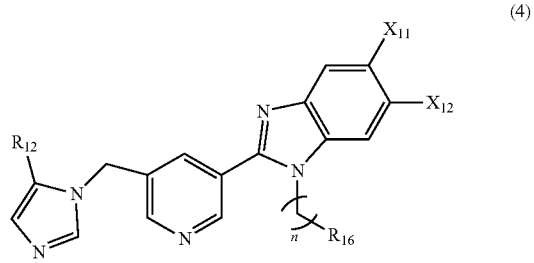

(4)

In the above general formula (4), $R_{12}$ represents a hydrogen atom or $CO_2R_a$, $X_{11}$ and $X_{12}$ each independently represent a different halogen atom, $R_{16}$ represents a halogen atom, a substituted or unsubstituted alkylsulfonyloxy group, or a substituted or unsubstituted arylsulfonyloxy group, n represents an integer of 1 to 5, and $R_a$ represents an alkyl group containing 1 to 10 carbon atoms.

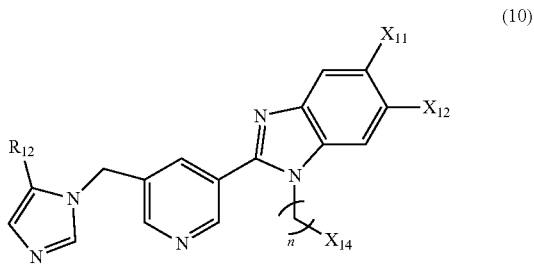

(10)

In the above general formula (10), $R_{12}$ represents a hydrogen atom or $CO_2R_a$, $X_{11}$ and $X_{12}$ each independently represent a different halogen atom, $X_{14}$ represents a radioactive halogen atom, n represents an integer of 1 to 5, and $R_a$ represents an alkyl group containing 1 to 10 carbon atoms.

Moreover, in another aspect of the present invention, the compound represented by the above general formula (1) wherein $X_2$ is a radioactive halogen atom (a radioactive compound represented by the following general formula (11)) or a salt thereof, can be produced from the compound represented by the above general formula (5) or a salt thereof by a radiohalogenation reaction:

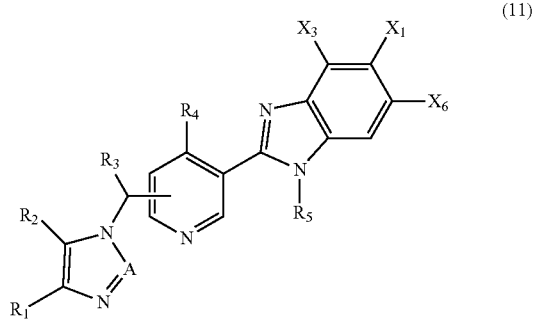

(11)

In the above general formula (11), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_5$ represents a linear alkyl group containing 1 to 5 carbon atoms in which a hydrogen atom is optionally replaced by a halogen atom, a cyclic alkyl group containing 3 to 5 carbon atoms in which a hydrogen atom is optionally replaced by a halogen atom, a hydroxyalkyl group containing 1 to 5 carbon atoms, or an o-, p- or m-halobenzyl group, A represents CH or a nitrogen atom, $X_1$ represents a hydrogen atom or a halogen atom, $X_3$ represents a hydrogen atom or a halogen atom, $X_6$ represents a radioactive halogen atom, and $R_a$ represents an alkyl group containing 1 to 10 carbon atoms.

In addition, in another aspect, the present invention can provide a method for producing a radioactive compound represented by the following general formula (12) or a salt thereof, from a compound represented by the following general formula (6) wherein, in the above general formula (5), $R_1$ is a hydrogen atom, $R_2$ is a hydrogen atom or $CO_2R_a$, $R_3$ and $R_4$ are hydrogen atoms, $R_5$ is $—(CH_2)_nX_{14}$ (wherein n is an integer of 1 to 5 and $X_{14}$ is a halogen atom), A is CH, and $X_3$ is a hydrogen atom or a salt thereof, by a radiohalogenation reaction:

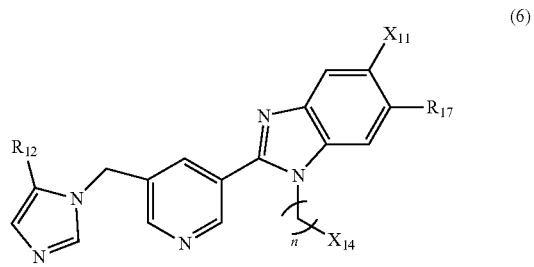

(6)

In the above general formula (6), $R_{12}$ represents a hydrogen atom or $CO_2R_a$, $R_{17}$ represents a trialkyltin group or a trialkylsilyl group, $X_{II}$ represents a hydrogen atom or a halogen atom, $X_{14}$ represents a halogen atom, n represents an integer of 1 to 5, and $R_a$ represents an alkyl group containing 1 to 10 carbon atoms.

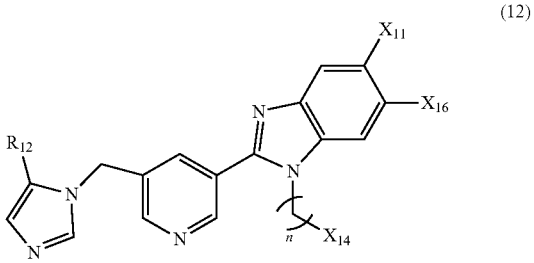

(12)

In the above general formula (12), $R_{12}$ represents a hydrogen atom or $CO_2R_a$, $X_{II}$ represents a hydrogen atom or a halogen atom, $X_{14}$ represents a halogen atom, $X_{16}$ represents a radioactive halogen atom, n represents an integer of 1 to 5, and $R_a$ represents an alkyl group containing 1 to 10 carbon atoms.

Moreover, in another aspect, the present invention can provide a method for producing a radioactive compound represented by the following general formula (13) or a salt thereof from the compound represented by the above general formula (7) or a salt thereof by a radiohalogenation reaction:

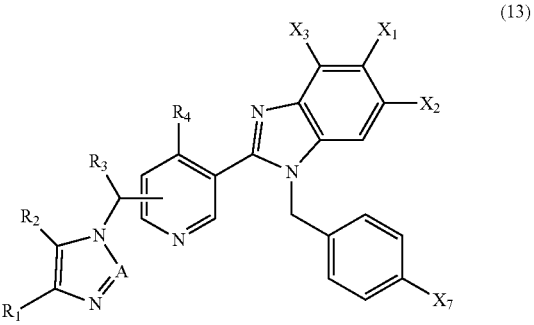

(13)

In the above general formula (13), $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, A represents CH or a nitrogen atom, $X_1$ represents a hydrogen atom or a halogen atom, $X_2$ represents a hydrogen atom, a halogen atom or a nitrile group, $X_3$ represents a hydrogen atom or a halogen atom, provided that at least one of $X_1$, $X_2$ and $X_3$ is a halogen atom, $X_7$ represents a radioactive halogen atom, and each $R_a$ independently represents an alkyl group containing 1 to 10 carbon atoms.

Furthermore, in another aspect, the present invention can provide a method for producing a radioactive compound represented by the following general formula (14) or a salt thereof from the compound represented by the above general formula (8) or a salt thereof by a radiohalogenation reaction:

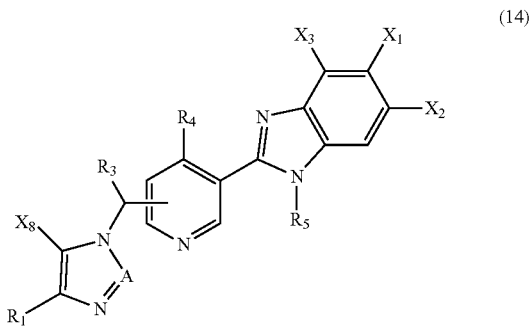

(14)

In the above general formula (14), $R_1$ represents a hydrogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_5$ represents a linear alkyl group containing 1 to 5 carbon atoms in which a hydrogen atom is optionally replaced by a halogen atom, a cyclic alkyl group containing 3 to 5 carbon atoms in which a hydrogen atom is optionally replaced by a halogen atom, a hydroxyalkyl group containing 1 to 5 carbon atoms, or an o-, p- or m-halobenzyl group, A represents CH or a nitrogen atom, $X_1$ represents a hydrogen atom or a halogen atom, $X_2$ represents a hydrogen atom, a halogen atom or a nitrile group, $X_3$ represents a hydrogen atom or a halogen atom, provided that at least one of $X_1$, $X_2$ and $X_3$ is a halogen atom, $X_8$ represents a radioactive halogen atom, and each $R_a$ independently represents an alkyl group containing 1 to 10 carbon atoms.

Further, the present invention can include the following [1] to [17] as specific aspects.

[1] A compound represented by the following general formula (2) or a salt thereof:

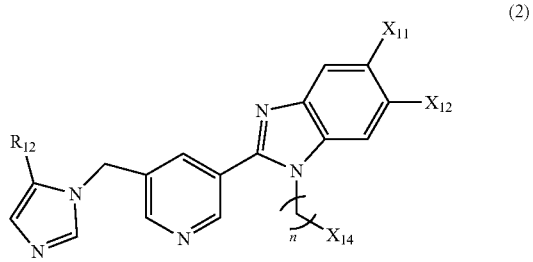

(2)

In the general formula (2), $R_{12}$ represents a hydrogen atom, a halogen atom or $CO_2R_a$, and it may optionally represent a hydrogen atom or $CO_2R_a$; $X_{11}$ represents a hydrogen atom or a halogen atom, and $X_{12}$ represents a halogen atom, wherein $X_{11}$ and $X_{12}$ each independently may optionally represent a different halogen atom; $X_{14}$ represents a halogen atom or a hydroxy group; n represents an integer of 1 to 5; and $R_a$ represents an alkyl group containing 1 to 10 carbon atoms.

[2] The compound according to the above [1] or a salt thereof, wherein, in the above general formula (2), $X_{14}$ represents a halogen atom.

[3] The compound according to the above [2] or a salt thereof, wherein, in the above general formula (2), $X_{14}$ represents a radioactive halogen atom.

[4] The compound according to the above [1] or [2] or a salt thereof, wherein, in the above general formula (2), $X_{12}$ represents a radioactive halogen atom.

[5] The compound according to any one of the above [1] to [4] or a salt thereof, wherein, in the above general formula (2), $R_{12}$ represents a hydrogen atom.

[6] The compound according to any one of the above [1] to [5] or a salt thereof, wherein, in the above general formula (2), $X_{11}$ represents a fluorine atom.

[7] The compound according to any one of the above [1] to [6] or a salt thereof, wherein, in the above general formula (2), n is an integer of 1 to 3.

[8] A medicament comprising the compound according to any one of the above [1] to [7] or a salt thereof.

[9] The medicament according to the above [8], which is an image diagnostic agent for an adrenal disease.

[10] The medicament according to the above [9], which is an image diagnostic agent for use in positron emission tomography.

[11] The medicament according to the above [9], which is an image diagnostic agent for use in single-photon emission computed tomography.

[12] The medicament according to the above [8], which is a therapeutic agent for an aldosterone-producing tumor.

[13] The medicament according to the above [12], which is an internal-use radiotherapeutic agent for an aldosterone-producing tumor.

[14] The compound represented by the above general formula (4) or a salt thereof.

[15] The compound represented by the above general formula (6) or a salt thereof, provided that, in the above general formula (6), $X_{11}$ represents a halogen atom.

[16] A method for producing the radioactive compound represented by the above general formula (10) or a salt thereof from the compound according to the above [14] or a salt thereof by a radiohalogenation reaction.

[17] A method for producing the radioactive compound represented by the above general formula (12) or a salt thereof from the compound according to the above [15] or a salt thereof by a radiohalogenation reaction, provided that, in the general formula (12), $X_{11}$ represents a halogen atom that is different from $X_{16}$.

According to the present invention, there are provided a compound capable of specifically accumulating in a human adrenal-producing tumor and having a CYP11B2 selective inhibitory ability, and a medicament comprising the same.

BRIEF DESCRIPTION OF DRAWINGS

FIG. 18A is an autoradiogram of 6-chloro-5-fluoro-1-(2-[$^{18}$F]fluoroethyl)-2-[5-(imidazol-1-ylmethyl)pyridin-3-yl]benzimidazole. FIG. 18B is an autoradiogram of (R)-[$^{123}$I]iodometomidate.

FIG. 19A is an autoradiogram of 6-bromo-5-fluoro-1-(2-[$^{18}$F]fluoroethyl)-2-[5-(imidazol-1-ylmethyl)pyridin-3-yl]benzimidazole. FIG. 19B is an autoradiogram of (R)-[$^{123}$I]iodometomidate.

FIG. 20A is an autoradiogram of 5-fluoro-1-(2-fluoroethyl)-2-[5-(imidazol-1-ylmethyl)pyridin-3-yl]-6-[$^{123}$I]iodobenzimidazole. FIG. 20B is an autoradiogram of (R)-[$^{123}$I]iodometomidate.

FIG. 21A is an autoradiogram of 6-chloro-5-fluoro-1-(3-[$^{18}$F]fluoropropyl)-2-[5-(imidazol-1-ylmethyl)pyridin-3-yl]benzimidazole. FIG. 21B is an autoradiogram of (R)-[$^{123}$I]iodometomidate.

FIG. 22A is an autoradiogram of (R)-[$^{123}$I]iodometomidate. FIG. 22B is an autoradiogram of methyl 1-[4-(1-cyclopropyl-6-[$^{123}$I]iodo-1H-imidazobenzo-2-yl)-3-pyridinylmethyl)]-1H-imidazolecarboxylate.

FIG. 23A is an autoradiogram of (R)-[$^{123}$I]iodometomidate. FIG. 23B is an autoradiogram of 1-cyclopropyl-2-[3-(1H-imidazol-1-ylmethyl)pyridin-5-yl]-6-[$^{123}$I]iodo-1H-benzimidazole.

FIG. 24A is an autoradiogram of (R)-[$^{123}$I]iodometomidate. FIG. 24B is an autoradiogram of 1-cyclopropyl-2-[3-(1H-1,2,3-triazol-1-ylmethyl)pyridin-5-yl]-6-[$^{123}$I]iodo-1H-benzimidazole.

FIGS. 25A and 25B are views showing the results of in vitro autoradiography, in which a human adrenal gland section expressing aldosterone-producing adenoma is used. FIG. 25A is an autoradiogram of (R)-[$^{123}$I]iodometomidate. FIG. 25B is an autoradiogram of 1-(2-fluoroethyl)-2-[5-{(imidazol-1-yl)methyl}pyridin-3-yl]-6-[$^{123}$I]iodobenzimidazole.

FIGS. 26A and 26B are views showing the results of in vitro autoradiography, in which a human adrenal gland section expressing aldosterone-producing adenoma is used. FIG. 26A is an autoradiogram of (R)-[$^{123}$I]iodometomidate. FIG. 26B is an autoradiogram of 6-chloro-5-fluoro-1-(4-[$^{123}$I]iodobenzyl)-2-[5-(1H-imidazol-1-ylmethyl)-3-pyridinyl]-1H-benzimidazole.

FIG. 27A is an autoradiogram of (R)-[$^{123}$I]iodometomidate. FIG. 27B is an autoradiogram of 2-[5-{(1H-imidazol-1-yl)methyl}pyridin-3-yl]-6-[$^{123}$I]iodo-1-isopropyl-1H-benzo[d]imidazole.

FIG. 28A is an autoradiogram of (R)-[$^{123}$I]iodometomidate. FIG. 28B is an autoradiogram of 2-[5-{(1H-imidazol-1-yl)methyl}pyridin-3-yl]-6-[$^{123}$I]iodo-1-methyl-1H-benzo[d]imidazole.

FIG. 29A is an autoradiogram of (R)-[$^{123}$I]iodometomidate. FIG. 29B is an autoradiogram of 2-[5-{(1H-imidazol-1-yl)methyl}pyridin-3-yl]-1-ethyl-6-[$^{123}$I]iodo-1H-benzo[d]imidazole.

FIG. 30A is an autoradiogram of (R)-[$^{123}$I]iodometomidate. FIG. 30B is an autoradiogram of 1-cyclopropyl-2-[5-(imidazol-1-ylmethyl)pyridin-3-yl]-6-[$^{123}$I]iodo-4-methoxybenzimidazole.

FIG. 31A is an autoradiogram of (R)-[$^{123}$I]iodometomidate. FIG. 31B is an autoradiogram of 6-chloro-5-fluoro-1-(2-fluoroethyl)-2-{5-(5-[$^{123}$I]iodo-1H-imidazol-1-ylmethyl)pyridin-3-yl}benzimidazole.

FIG. 32A shows a radio-TLC of a sample, and FIG. 32B shows a radio-TLC of the sample after incubation in plasma for 60 minutes.

FIG. 33A shows a radio-TLC of a sample, and FIG. 33B shows a radio-TLC of the sample after incubation in plasma for 60 minutes.

FIG. 34A shows a radio-TLC of a sample, and FIG. 34B shows a radio-TLC of the sample after incubation in plasma for 60 minutes.

FIG. 35A shows a radio-TLC of a sample, and FIG. 35B shows a radio-TLC of the sample after incubation in plasma for 60 minutes.

FIG. 36A shows a radio-TLC of a sample, and FIG. 36B shows a radio-TLC of the sample after incubation in plasma for 60 minutes.

FIG. 37A shows a radio-TLC of a sample, and FIG. 37B shows a radio-TLC of the sample after incubation in plasma for 60 minutes.

FIG. 38A shows a radio-TLC of a sample, and FIG. 38B shows a radio-TLC of the sample after incubation in plasma for 60 minutes.

FIG. 39A shows a radio-TLC of a sample, and FIG. 39B shows a radio-TLC of the sample after incubation in plasma for 60 minutes.

FIG. 40A shows at radio-TLC of a sample, and FIG. 40B shows a radio-TLC of the sample after incubation in plasma for 60 minutes.

FIG. 41A shows a radio-TLC of a sample, and FIG. 41B shows a radio-TLC of the sample after incubation in plasma for 60 minutes.

FIG. 42A shows a radio-TLC of a sample, and FIG. 42B shows a radio-TLC of the sample after incubation in plasma for 60 minutes.

FIG. 43A shows a radio-TLC of a sample, and FIG. 43B shows a radio-TLC of the sample after incubation in plasma for 60 minutes.

FIG. 44A shows a radio-TLC of a sample, and FIG. 44B shows a radio-TLC of the sample after incubation in plasma for 60 minutes.

FIG. 45A shows a radio-TLC of a sample, and FIG. 45B shows a radio-TLC of the sample after incubation in plasma for 60 minutes.

DESCRIPTION OF EMBODIMENTS

Figure 1:
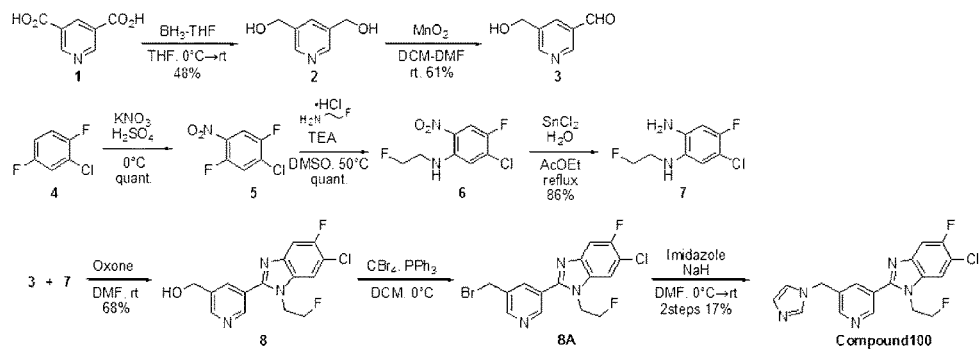
FIG. 1 is a drawing showing a synthesis example of 6-chloro-5-fluoro-1-(2-fluoroethyl)-2-[5-(imidazol-1-ylmethyl)pyridin-3-yl]benzimidazole.

In the present invention, the term "$CO_2R_a$" means a carboxylic acid ester group. $R_a$ is an alkyl group containing 1 to 10 carbon atoms, and the alkyl group may be either a straight-chain or branched-chain alkyl group. The alkyl group is preferably an alkyl group containing 1 to 5 carbon atoms (a methyl group, an ethyl group, an n-propyl group, an isopropyl group, an n-butyl group, an isobutyl group, a tert-butyl group, an n-pentyl group, an isopentyl group, or a neopentyl group), and it is more preferably an alkyl group containing 1 to 3 carbon atoms (a methyl group, an ethyl group, an n-propyl group, or an isopropyl group). As such "$CO_2R_a$", a "carboxylic acid methyl ester group," in which $R_a$ is a methyl group, is particularly preferable.

Moreover, in the present invention, the term "halogen atom" means at least one selected from a fluorine atom, a chlorine atom, a bromine atom, an iodine atom, and an astatine atom.

Furthermore, in the present invention, the term "hydroxyalkyl group" means a group represented by —$(CH_2)_m$OH. For example, in $R_3$ in the general formula (1), m is an integer of 1 to 10, and is preferably an integer of 1 to 3. In $R_5$ in the general formula (1), m is an integer of 1 to 5, and is preferably an integer of 1 to 3.

Further, in the present invention, the term "alkoxy group" means a group having a straight-chain or branched-chain alkyl group bound to an oxygen atom, and preferably includes a methoxy group, an ethoxy group, a propyl group, and an isopropyl group, and more preferably a methoxy group.

In the present invention, the term "linear alkyl group" means a noncyclic alkyl group, which may be either a straight-chain or branched-chain alkyl group, and preferably includes a methyl group, an ethyl group, a propyl group, an isopropyl group, an n-butyl group, an isobutyl group, a sec-butyl group, a tert-butyl group, an n-pentyl group, an isopentyl group, a neopentyl group, and a tert-pentyl group. In these linear alkyl groups, one or two or more hydrogen atoms may be substituted with halogen atoms, and preferably substituted with fluorine atoms. Specific examples include a fluoromethyl group, a 1-fluoroethyl group, a 1,1-difluoroethyl group, a 1,1,1-trifluoroethyl group, and a 1-fluoropropyl group.

Moreover, the "cyclic alkyl group" in the present invention includes a cyclopropyl group, a cyclobutyl group, and a cyclopentyl group. In these cyclic alkyl groups, one or two or more hydrogen atoms may be substituted with halogen atoms.

Furthermore, the term "halobenzyl group" is used in the present invention to mean a benzyl group in which the hydrogen atom in position 2, position 3, or position 4 of the benzene ring thereof is substituted with a halogen atom. A benzyl group in which the hydrogen atom in position 2 is substituted with a halogen atom is an o-halobenzyl group; a benzyl group in which the hydrogen atom in position 3 is substituted with a halogen atom is an m-halobenzyl group; and a benzyl group in which the hydrogen atom in position 4 is substituted with a halogen atom is a p-halobenzyl group. Among these, a p-halobenzyl group is preferable.

Further, in the present invention, the "salt" may be a pharmaceutically acceptable salt. Examples of the salt include salts derived from inorganic acids such as hydrochloric acid, hydrobromic acid, sulfuric acid, nitric acid and phosphoric acid, or from organic acids such as acetic acid, trifluoroacetic acid, maleic acid, succinic acid, mandelic acid, fumaric acid, malonic acid, pyruvic acid, oxalic acid, glycolic acid, salicylic acid, pyranosydilic acid (glucuronic acid, galacturonic acid, etc.), α-hydroxy acid (citric acid, tartaric acid, etc.), amino acid (aspartic acid, glutamic acid, etc.), aromatic acid (benzoic acid, cinnamic acid, etc.), or sulfonic acid (p-toluenesulfonic acid, ethanesulfonic acid, etc.).

In the present invention, the term "radioactive halogen atom" means at least one selected from the radioisotopes of fluorine, chlorine, bromine, iodine and astatine, and preferably, $^{18}F$, $^{34m}Cl$, $^{76}Br$, $^{123}I$, $^{124}I$, $^{125}I$, $^{131}I$ or $^{211}At$ can be used. Herein, the "radioactive iodine atom" is used in the present invention to mean any one of $^{123}I$, $^{124}I$, $^{125}I$ and $^{131}I$.

The compound represented by the above general formula (1) is preferably higher than iodometomidate in terms of selectivity to aldosterone production inhibition relative to cortisol production inhibition (i.e., $IC_{50}$ of cortisol production inhibition/$IC_{50}$ of aldosterone production inhibition), as measured in an inhibition experiment in which cells expressing each of human CYP11B1 and human CYP11B2 are used. Thereby, it becomes possible for the compound represented by the above general formula (1) to specifically accumulate in an aldosterone-producing tumor, in comparison to in the normal site of an adrenal gland.

This inhibition experiment can be carried out by the following operations. Human CYP11B1 and human CYP11B2 are allowed to individually express in Chinese hamster lung-derived fibroblasts. Subsequently, 11-deoxycortisol is added to the cells expressing human CYP11B1 to a final concentration of 100 nmol/L, and corticosterone is added to the cells expressing human CYP11B2 to a final concentration of 100 nmol/L. At the same time, a target compound used as an analytical sample is added to each of the cells to a final concentration of $10^{-4}$ to $10^4$ nmol/L. Thereafter, the concentration of cortisol as a metabolite of CYP11B1 is measured in the cells expressing human CYP11B1 according to ELISA (Enzyme-Linked ImmunoSorbent Assay), and the concentration of aldosterone as a metabolite of CYP11B2 is measured in the cells expressing human CYP11B2 according to ELISA. Provided that the aldosterone concentration and the cortisol concentration without addition of any target compound as a sample are each set at 100%, an inhibition curve is produced, and then inhibitory activity ($IC_{50}$) is calculated.

From the viewpoint of enhancing the selectivity to aldosterone production inhibition compared to cortisol production inhibition, it is preferable that, in the above general formula (1), $R_3$ is a hydrogen atom, $R_4$ is a hydrogen atom or an alkoxy group containing 1 to 10 carbon atoms, $R_5$ is a linear alkyl group containing 1 to 5 carbon atoms in which a hydrogen atom is optionally replaced by a halogen atom, a cyclic alkyl group containing 3 to 5 carbon atoms, or an o-, m-, p-halobenzyl group, $X_2$ is a halogen atom, and $X_3$ is a hydrogen atom. More preferably, $R_5$ is a methyl group, an ethyl group, a propyl group, an isopropyl group, a group represented by $—(CH_2)_nX_4$ (wherein n represents an integer of 1 to 5, and $X_4$ represents a halogen atom), a cyclopropyl group, or a p-halobenzyl group.

Adoption of any one of the following configurations (a) to (d) in the above general formula (1) enables the use of the compound as an image diagnostic agent for nuclear medicine examination or an internal-use radiotherapeutic agent.
(a) A radioactive halogen atom is used as a halogen atom represented by $R_2$.
(b) The group represented by $—(CH_2)_nX_4$ is used as $R_5$, and a radioactive halogen atom is used as a halogen atom represented by $X_4$.
(c) A p-halobenzyl group is used as $R_5$, and a radioactive halogen atom is used as a halogen atom introduced into the position 4 of the benzyl group.
(d) A radioactive halogen atom is used as a halogen atom represented by $X_2$.

Moreover, from the viewpoint of enhancing the selectivity to aldosterone production inhibition compared to cortisol production inhibition, $R_2$ is preferably a hydrogen atom or a halogen atom in the above general formula (1).

Furthermore, from the viewpoint of further enhancing the selectivity to aldosterone production inhibition compared to cortisol production inhibition, $R_5$ is preferably a methyl group, an ethyl group, a group represented by $—(CH_2)_nX_4$, or a cyclopropyl group in the above general formula (1). In the group represented by $—(CH_2)_nX_4$, n is an integer of, preferably 1 to 3, more preferably 2 or 3, and further preferably 2. $X_4$ is preferably a fluorine atom.

Further, from the viewpoint of still further enhancing the selectivity to aldosterone production inhibition compared to cortisol production inhibition, $X_1$ is preferably a hydrogen atom, a fluorine atom or a chlorine atom, and more preferably a hydrogen atom or a fluorine atom in the above general formula (1).

A specific aspect of the compound according to the present invention is the compound represented by the above general formula (2). The compound represented by the general formula (2) is the compound of the general formula (1) wherein $R_1$ is a hydrogen atom, $R_2$ is a hydrogen atom, a halogen atom or $CO_2R_a$ (wherein $R_a$ is an alkyl group containing 1 to 10 carbon atoms), $R_3$ and $R_4$ are hydrogen atoms, $R_5$ is a group represented by $—(CH_2)_nX_{14}$, A is CH, $X_1$ and $X_2$ are halogen atoms, and $X_3$ is a hydrogen atom. In the general formula (2), $R_{12}$ may be a hydrogen atom or $CO_2R_a$, or may be a hydrogen atom. In addition, in the general formula (2), $X_{11}$ and $X_{12}$ may each independently represent a different halogen atom where $X_{11}$ is preferably a fluorine atom. Preferably, $X_{14}$ is a fluorine atom, and n is an integer of 1 to 3.

A more preferred specific example of the present invention is a compound represented by the following general formula (1-1) which is the above general formula (1) wherein $R_1$, $R_2$, $R_3$, $X_1$ and $X_3$ each represent a hydrogen atom, or a salt thereof:

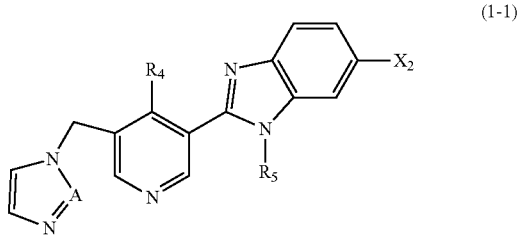

(1-1)

In the above general formula (1-1), $R_4$ is a hydrogen atom or an alkoxy group containing 1 to 10 carbon atoms (preferably, a methoxy group), $R_5$ is a linear alkyl group containing 1 to 5 carbon atoms or a cyclic alkyl group containing 3 to 5 carbon atoms, $X_2$ is a halogen atom, and A is CH or a nitrogen atom. Preferably, $X_2$ is a chlorine atom, a bromine atom, or an iodine atom. In the above general formula (1-1), $X_2$ may be a radioactive iodine atom.

Preferred aspects of the compound represented by the above general formula (1-1) are shown in Table 1.

TABLE 1

| Compound name | $R_4$ | $R_5$ | A | $X_2$ |
|---|---|---|---|---|
| 6-Chloro-1-methyl-2-[5-(imidazol-1-ylmethyl)pyridin-3-yl]benzimidazole | H | Methyl | CH | Cl |
| 6-Bromo-1-methyl-2-[5-(imidazol-1-ylmethyl)pyridin-3-yl]benzimidazole | H | Methyl | CH | Br |
| 6-Iodo-1-methyl-2-[5-(imidazol-1-ylmethyl)pyridin-3-yl]benzimidazole | H | Methyl | CH | I(*I) |
| 6-Chloro-1-ethyl-2-[5-(imidazol-1-ylmethyl)pyridin-3-yl]benzimidazole | H | Ethyl | CH | Cl |
| 6-Bromo-1-ethyl-2-[5-(imidazol-1-ylmethyl)pyridin-3-yl]benzimidazole | H | Ethyl | CH | Br |
| 1-Ethyl-6-iodo-2-[5-(imidazol-1-ylmethyl)pyridin-3-yl]benzimidazole | H | Ethyl | CH | I(*I) |
| 6-Chloro-1-isopropyl-2-[5-(imidazol-1-ylmethyl)pyridin-3-yl]benzimidazole | H | Iso-propyl | CH | Cl |
| 6-Bromo-1-isopropyl-2-[5-(imidazol-1-ylmethyl)pyridin-3-yl]benzimidazole | H | Iso-propyl | CH | Br |
| 6-Iodo-1-isopropyl-2-[5-(imidazol-1-ylmethyl)pyridin-3-yl]benzimidazole | H | Iso-propyl | CH | I(*I) |
| 6-Chloro-1-cyclopropyl-2-[5-(imidazol-1-ylmethyl)pyridin-3-yl]benzimidazole | H | Cyclo-propyl | CH | Cl |
| 6-Bromo-1-cyclopropyl-2-[5-(imidazol-1-ylmethyl)pyridin-3-yl]benzimidazole | H | Cyclo-propyl | CH | Br |
| 1-Cyclopropyl-6-iodo-2-[5-(imidazol-1-ylmethyl)pyridin-3-yl]benzimidazole | H | Cyclo-propyl | CH | I(*I) |
| 6-Chloro-1-methyl-2-[5-(1,2,3-triazol-1-ylmethyl)pyridin-3-yl]benzimidazole | H | Methyl | N | Cl |
| 6-Bromo-1-methyl-2-[5-(1,2,3-triazol-1-ylmethyl)pyridin-3-yl]benzimidazole | H | Methyl | N | Br |
| 6-Iodo-1-methyl-2-[5-(1,2,3-triazol-1-ylmethyl)pyridin-3-yl]benzimidazole | H | Methyl | N | I |
| 6-Chloro-1-ethyl-2-[5-(1,2,3-triazol-1-ylmethyl)pyridin-3-yl]benzimidazole | H | Ethyl | N | Cl |
| 6-Bromo-1-ethyl-2-[5-(1,2,3-triazol-1-ylmethyl)pyridin-3-yl]benzimidazole | H | Ethyl | N | Br |
| 1-Ethyl-6-iodo-2-[5-(1,2,3-triazol-1-ylmethyl)pyridin-3-yl]benzimidazole | H | Ethyl | N | I |
| 6-Chloro-1-isopropyl-2-[5-(1,2,3-triazol-1-ylmethyl)pyridin-3-yl]benzimidazole | H | Iso-propyl | N | Cl |
| 6-Bromo-1-isopropyl-2-[5-(1,2,3-triazol-1-ylmethyl)pyridin-3-yl]benzimidazole | H | Iso-propyl | N | Br |
| 6-Iodo-1-isopropyl-2-[5-(1,2,3-triazol-1-ylmethyl)pyridin-3-yl]benzimidazole | H | Iso-propyl | N | I |
| 6-Chloro-1-cyclopropyl-2-[5-(1,2,3-triazol-1-ylmethyl)pyridin-3-yl]benzimidazole | H | Cyclo-propyl | N | Cl |
| 6-Bromo-1-cyclopropyl-2-[5-(1,2,3-triazol-1-ylmethyl)pyridin-3-yl]benzimidazole | H | Cyclo-propyl | N | Br |
| 1-Cyclopropyl-6-iodo-2-[5-(1,2,3-triazol-1-ylmethyl)pyridin-3-yl]benzimidazole | H | Cyclo-propyl | N | I(*I) |
| 6-Chloro-1-methyl-2-[5-(5-methoxy-imidazol-1-ylmethyl)pyridin-3-yl]benzimidazole | Methoxy | Methyl | CH | Cl |
| 6-Bromo-1-methyl-2-[5-(5-methoxy-imidazol-1-ylmethyl)pyridin-3-yl]benzimidazole | Methoxy | Methyl | CH | Br |
| 6-Iodo-1-methyl-2-[5-(5-methoxy-imidazol-1-ylmethyl)pyridin-3-yl]benzimidazole | Methoxy | Methyl | CH | I |
| 6-Chloro-1-ethyl-2-[5-(5-methoxy-imidazol-1-ylmethyl)pyridin-3-yl]benzimidazole | Methoxy | Ethyl | CH | Cl |
| 6-Bromo-1-ethyl-2-[5-(5-methoxy-imidazol-1-ylmethyl)pyridin-3-yl]benzimidazole | Methoxy | Ethyl | CH | Br |
| 1-Ethyl-6-iodo-2-[5-(5-methoxyimidazol-1-ylmethyl)pyridin-3-yl]benzimidazole | Methoxy | Ethyl | CH | I |
| 6-Chloro-1-isopropyl-2-[5-(5-methoxy-imidazol-1-ylmethyl)pyridin-3-yl]benzimidazole | Methoxy | Iso-propyl | CH | Cl |
| 6-Bromo-1-isopropyl-2-[5-(5-methoxy-imidazol-1-ylmethyl)pyridin-3-yl]benzimidazole | Methoxy | Iso-propyl | CH | Br |
| 6-Iodo-1-isopropyl-2-[5-(5-methoxy-imidazol-1-ylmethyl)pyridin-3-yl]benzimidazole | Methoxy | Iso-propyl | CH | I |
| 6-Chloro-1-cyclopropyl-2-[5-(5-methoxyimidazol-1-ylmethyl)pyridin-3-yl]benzimidazole | Methoxy | Cyclo-propyl | CH | Cl |
| 6-Bromo-1-cyclopropyl-2-[5-(5-methoxyimidazol-1-ylmethyl)pyridin-3-yl]benzimidazole | Methoxy | Cyclo-propyl | CH | Br |
| 1-Cyclopropyl-6-iodo-2-[5-(5-methoxyimidazol-1-ylmethyl)pyridin-3-yl]benzimidazole | Methoxy | Cyclo-propyl | CH | I(*I) |

In addition, another more preferred specific example of the present invention is a compound represented by the following general formula (1-2) which is the above general formula (1) wherein $R_1$, $R_3$, $R_4$ and $X_3$ are hydrogen atoms, and A is CH, or a salt thereof:

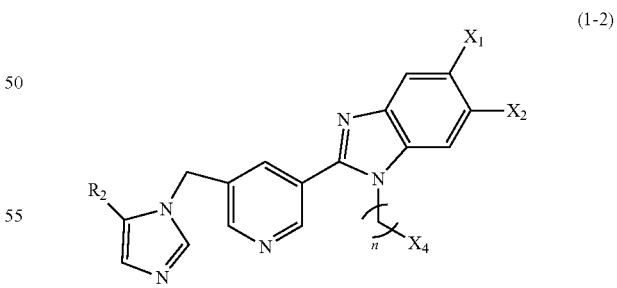

(1-2)

In the above general formula (1-2), $R_2$ is a hydrogen atom or a halogen atom, $X_1$ is a hydrogen atom or a fluorine atom, $X_2$ and $X_4$ are halogen atoms, and A is CH or a nitrogen atom. Preferably, $X_2$ is a chlorine atom, a bromine atom or an iodine atom, and $X_4$ is a fluorine atom. In the above general formula (1-2), $R_2$ may be a radioactive iodine atom, $X_2$ may be a radioactive iodine atom, and $X_4$ may be a radioactive fluorine atom.

Preferred aspects of the compound represented by the above general formula (1-2) are shown in Table 2.

TABLE 2

| Compound name | $R_2$ | $X_1$ | $X_2$ | $X_4$ | N |
|---|---|---|---|---|---|
| 6-Chloro-1-fluoromethyl-2-[5-(imidazol-1-ylmethyl)pyridin-3-yl]benzimidazole | H | H | Cl | F | 1 |
| 6-Chloro-1-(2-fluoroethyl)-2-[5-(imidazol-1-ylmethyl)pyridin-3-yl]benzimidazole | H | H | Cl | F | 2 |
| 6-Chloro-1-(3-fluoropropyl)-2-[5-(imidazol-1-ylmethyl)pyridin-3-yl]benzimidazole | H | H | Cl | F | 3 |
| 6-Bromo-1-fluoromethyl-2-[5-(imidazol-1-ylmethyl)pyridin-3-yl]benzimidazole | H | H | Br | F | 1 |
| 6-Bromo-1-(2-fluoroethyl)-2-[5-(imidazol-1-ylmethyl)pyridin-3-yl]benzimidazole | H | H | Br | F | 2 |
| 6-Bromo-1-(3-fluoropropyl)-2-[5-(imidazol-1-ylmethyl)pyridin-3-yl]benzimidazole | H | H | Br | F | 3 |
| 1-Fluoromethyl-6-iodo-2-[5-(imidazol-1-ylmethyl)pyridin-3-yl]benzimidazole | H | H | I | F | 1 |
| 1-(2-Fluoroethyl)-6-iodo-2-[5-(imidazol-1-ylmethyl)pyridin-3-yl]benzimidazole | H | H | I(*I) | F | 2 |
| 1-(3-Fluoropropyl)-6-iodo-2-[5-(imidazol-1-ylmethyl)pyridin-3-yl]benzimidazole | H | H | I | F | 3 |
| 6-Chloro-5-fluoro-1-fluoromethyl-2-[5-(imidazol-1-ylmethyl)pyridin-3-yl]benzimidazole | H | F | Cl | F | 1 |
| 6-Chloro-5-fluoro-1-(2-fluoroethyl)-2-[5-(imidazol-1-ylmethyl)pyridin-3-yl]benzimidazole | H | F | Cl | F($^{18}$F) | 2 |
| 6-Chloro-5-fluoro-1-(3-fluoropropyl)-2-(imidazol-1-ylmethyl)pyridin-3-yl]benzimidazole | H | F | Cl | F | 3 |
| 6-Bromo-5-fluoro-1-fluoromethyl-2-[5-(imidazol-1-ylmethyl)pyridin-3-yl]benzimidazole | H | F | Br | F | 1 |
| 6-Bromo-5-fluoro-1-(2-fluoroethyl)-2-[5-(imidazol-1-ylmethyl)pyridin-3-yl]benzimidazole | H | F | Br | F | 2 |
| 6-Bromo-5-fluoro-1-(3-fluoropropyl)-2-[5-(imidazol-1-ylmethyl)pyridin-3-yl]benzimidazole | H | F | Br | F | 3 |
| 5-Fluoro-6-iodo-1-fluoromethyl-2-[5-(imidazol-1-ylmethyl)pyridin-3-yl]benzimidazole | H | F | I | F | 1 |
| 5-Fluoro-1-(2-fluoroethyl)-2-[5-(imidazol-1-ylmethyl)pyridin-3-yl]6-iodobenzimidazole | H | F | I(*I) | F | 2 |
| 5-Fluoro-6-iodo-1-(3-fluoropropyl)-2-[5-(imidazol-1-ylmethyl)pyridin-3-yl]benzimidazole | H | F | I | F | 3 |
| 6-Chloro-1-fluoromethyl-2-[5-(5-fluoroimidazol-1-ylmethyl)pyridin-3-yl]benzimidazole | F | H | Cl | F | 1 |
| 6-Chloro-1-(2-fluoroethyl)-2-[5-(5-fluoroimidazol-1-ylmethyl)pyridin-3-yl]benzimidazole | F | H | Cl | F | 2 |
| 6-Chloro-1-(3-fluoropropyl)-2-[5-(5-fluoroimidazol-1-ylmethyl)pyridin-3-yl]benzimidazole | F | H | Cl | F | 3 |
| 6-Bromo-1-fluoromethyl-2-[5-(5-fluoroimidazol-1-ylmethyl)pyridin-3-yl]benzimidazole | F | H | Br | F | 1 |
| 6-Bromo-1-(2-fluoroethyl)-2-[5-(5-fluoroimidazol-1-ylmethyl)pyridin-3-yl]benzimidazole | F | H | Br | F | 2 |
| 6-Bromo-1-(3-fluoropropyl)-2-[5-(5-fluoroimidazol-1-ylmethyl)pyridin-3-yl]benzimidazole | F | H | Br | F | 3 |
| 1-Fluoromethyl-6-iodo-2-[5-(5-fluoroimidazol-1-ylmethyl)pyridin-3-yl]benzimidazole | F | H | I | F | 1 |
| 1-(2-Fluoroethyl)-6-iodo-2-[5-(5-fluoroimidazol-1-ylmethyl)pyridin-3-yl]benzimidazole | F | H | I | F | 2 |
| 1-(3-Fluoropropyl)-6-iodo-2-[5-(5-fluoroimidazol-1-ylmethyl)pyridin-3-yl]benzimidazole | F | H | I | F | 3 |
| 6-Chloro-5-fluoro-1-fluoromethyl-2-[5-(5-fluoroimidazol-1-ylmethyl)pyridin-3-yl]benzimidazole | F | F | Cl | F | 1 |
| 6-Chloro-5-fluoro-1-(2-fluoroethyl)-2-[5-(5-fluoroimidazol-1-ylmethyl)pyridin-3-yl]benzimidazole | F | F | Cl | F | 2 |
| 6-Chloro-5-fluoro-1-(3-fluoropropyl)-2-[5-(5-fluoroimidazol-1-ylmethyl)pyridin-3-yl]benzimidazole | F | F | Cl | F | 3 |
| 6-Bromo-5-fluoro-1-fluoromethyl-2-[5-(5-fluoroimidazol-1-ylmethyl)pyridin-3-yl]benzimidazole | F | F | Br | F | 1 |
| 6-Bromo-5-fluoro-1-(2-fluoroethyl)-2-[5-(5-fluoroimidazol-1-ylmethyl)pyridin-3-yl]benzimidazole | F | F | Br | F | 2 |
| 6-Bromo-5-fluoro-1-(3-fluoropropyl)-2-[5-(5-fluoroimidazol-1-ylmethyl)pyridin-3-yl]benzimidazole | F | F | Br | F | 3 |
| 5-Fluoro-6-iodo-1-fluoromethyl-2-[5-(5-fluoroimidazol-1-ylmethyl)pyridin-3-yl]benzimidazole | F | F | I | F | 1 |
| 5-Fluoro-6-iodo-1-(2-fluoroethyl)-2-[5-(5-fluoroimidazol-1-ylmethyl)pyridin-3-yl]benzimidazole | F | F | I | F | 2 |
| 5-Fluoro-6-iodo-1-(3-fluoropropyl)-2-[5-(5-fluoroimidazol-1-ylmethyl)pyridin-3-yl]benzimidazole | F | F | I | F | 3 |
| 6-Chloro-1-fluoromethyl)-5-(5-chloro-imidazol-1-ylmethyl)pyridin-3-yl]benzimidazole | Cl | H | Cl | F | 1 |
| 6-Chloro-1-(2-fluoroethyl)-2-[5-(5-chloroimidazol-1-ylmethyl)pyridin-3-yl]benzimidazole | Cl | H | Cl | F | 2 |
| 6-Chloro-1-(3-fluoropropyl)-2-[5-(5-chloroimidazol-1-ylmethyl)pyridin-3-yl]benzimidazole | Cl | H | Cl | F | 3 |
| 6-Bromo-1-fluoromethyl-2-[5-(5-chloroimidazol-1-ylmethyl)pyridin-3-yl]benzimidazole | Cl | H | Br | F | 1 |
| 6-Bromo-1-(2-fluoroethyl)-2-[5-(5-chloroimidazol-1-ylmethyl)pyridin-3-yl]benzimidazole | Cl | H | Br | F | 2 |
| 6-Bromo-1-(3-fluoropropyl)-2-[5-(5-chloroimidazol-1-ylmethyl)pyridin-3-yl]benzimidazole | Cl | H | Br | F | 3 |
| 1-Fluoromethyl-6-iodo-2-[5-(5-chloroimidazol-1-ylmethyl)pyridin-3-yl]benzimidazole | Cl | H | I | F | 1 |
| 1-(2-Fluoroethyl)-6-iodo-2-[5-(5-chloroimidazol-1-ylmethyl)pyridin-3-yl]benzimidazole | Cl | H | I | F | 2 |
| 1-(3-Fluoropropyl)-6-iodo-2-[5-(5-chloroimidazol-1-ylmethyl)pyridin-3-yl]benzimidazole | Cl | H | I | F | 3 |
| 6-Chloro-5-fluoro-1-fluoromethyl-2-[5-(5-chloroimidazol-1-ylmethyl)pyridin-3-yl]benzimidazole | Cl | F | Cl | F | 1 |
| 6-Chloro-5-fluoro-1-(2-fluoroethyl)-2-[5-(5-chloroimidazol-1-ylmethyl)pyridin-3-yl]benzimidazole | Cl | F | Cl | F | 2 |
| 6-Chloro-5-fluoro-1-(3-fluoropropyl)-2-[5-(5-chloroimidazol-1-ylmethyl)pyridin-3-yl]benzimidazole | Cl | F | Cl | F | 3 |
| 6-Bromo-5-fluoro-1-fluoromethyl-2-[5-(5-chloroimidazol-1-ylmethyl)pyridin-3-yl]benzimidazole | Cl | F | Br | F | 1 |
| 6-Bromo-5-fluoro-1-(2-fluoroethyl)-2-[5-(5-chloroimidazol-1-ylmethyl)pyridin-3-yl]benzimidazole | Cl | F | Br | F | 2 |

TABLE 2-continued

| Compound name | $R_2$ | $X_1$ | $X_2$ | $X_4$ | N |
|---|---|---|---|---|---|
| 6-Bromo-5-fluoro-1-(3-fluoropropyl)-2-[5-(5-chloroimidazol-1-ylmethyl)pyridin-3-yl]benzimidazole | Cl | F | Br | F | 3 |
| 5-Fluoro-1-fluoromethyl-6-iodo-2-[5-(5-chloroimidazol-1-ylmethyl)pyridin-3-yl]benzimidazole | Cl | F | I | F | 1 |
| 5-Fluoro-1-(2-fluoroethyl)-6-iodo-2-[5-(5-chloroimidazol-1-ylmethyl)pyridin-3-yl]benzimidazole | Cl | F | I | F | 2 |
| 5-Fluoro-1-(3-fluoropropyl)-6-iodo-2-[5-(5-chloroimidazol-1-ylmethyl)pyridin-3-yl]benzimidazole | Cl | F | I | F | 3 |
| 6-Chloro-1-fluoromethyl-2-[5-(5-bromoimidazol-1-ylmethyl)pyridin-3-yl]benzimidazole | Br | H | Cl | F | 1 |
| 6-Chloro-1-(2-fluoroethyl)-2-[5-(5-bromoimidazol-1-ylmethyl)pyridin-3-yl]benzimidazole | Br | H | Cl | F | 2 |
| 6-Chloro-1-(3-fluoropropyl)-2-[5-(5-bromoimidazol-1-ylmethyl)pyridin-3-yl]benzimidazole | Br | H | Cl | F | 3 |
| 6-Bromo-1-fluoromethyl-2-[5-(5-bromoimidazol-1-ylmethyl)pyridin-3-yl]benzimidazole | Br | H | Br | F | 1 |
| 6-Bromo-1-(2-fluoroethyl)-2-[5-(5-bromoimidazol-1-ylmethyl)pyridin-3-yl]benzimidazole | Br | H | Br | F | 2 |
| 6-Bromo-1-(3-fluoropropyl)-2-[5-(5-bromoimidazol-1-ylmethyl)pyridin-3-yl]benzimidazole | Br | H | Br | F | 3 |
| 1-Fluoromethyl-6-iodo-2-[5-(5-bromoimidazol-1-ylmethyl)pyridin-3-yl]benzimidazole | Br | H | I | F | 1 |
| 1-(2-Fluoroethyl)-6-iodo-2-[5-(5-bromoimidazol-1-ylmethyl)pyridin-3-yl]benzimidazole | Br | H | I | F | 2 |
| 1-(3-Fluoropropyl)-6-iodo-2-[5-(5-bromoimidazol-1-ylmethyl)pyridin-3-yl]benzimidazole | Br | H | I | F | 3 |
| 6-Chloro-5-fluoro-1-fluoromethyl-2-[5-(5-bromoimidazol-1-ylmethyl)pyridin-3-yl]benzimidazole | Br | F | Cl | F | 1 |
| 6-Chloro-5-fluoro-1-(2-fluoroethyl)-2-[5-(5-bromoimidazol-1-ylmethyl)pyridin-3-yl]benzimidazole | Br | F | Cl | F | 2 |
| 6-Chloro-5-fluoro-1-(3-fluoropropyl)-[5-(5-bromoimidazol-1-ylmethyl)pyridin-3-yl]benzimidazole | Br | F | Cl | F | 3 |
| 6-Bromo-5-fluoro-1-fluoromethyl-2-[5-(5-bromoimidazol-1-ylmethyl)pyridin-3-yl]benzimidazole | Br | F | Br | F | 1 |
| 6-Bromo-5-fluoro-1-(2-fluoroethyl)-2-[5-(5-bromoimidazol-1-ylmethyl)pyridin-3-yl]benzimidazole | Br | F | Br | F | 2 |
| 6-Bromo-5-fluoro-1-(3-fluoropropyl)-2-[5-(5-bromoimidazol-1-ylmethyl)pyridin-3-yl]benzimidazole | Br | F | Br | F | 3 |
| 5-Fluoro-1-fluoromethyl-6-iodo-2-[5-(5-bromoimidazol-1-ylmethyl)pyridin-3-yl]benzimidazole | Br | F | I | F | 1 |
| 5-Fluoro-1-(2-fluoroethyl)-6-iodo-2-[5-(5-bromoimidazol-1-ylmethyl)pyridin-3-yl]benzimidazole | Br | F | I | F | 2 |
| 5-Fluoro-1-(3-fluoropropyl)-6-iodo-2-[5-(5-bromoimidazol-1-ylmethyl)pyridin-3-yl]benzimidazole | Br | F | I | F | 3 |
| 6-Chloro-1-fluoromethyl-2-[5-(5-iodoimidazol-1-ylmethyl)pyridin-3-yl]benzimidazole | I | H | Cl | F | 1 |
| 6-Chloro-1-(2-fluoroethyl)-2-[5-(5-iodoimidazol-1-ylmethyl)pyridin-3-yl]benzimidazole | I | H | Cl | F | 2 |
| 6-Chloro-1-(3-fluoropropyl)-2-[5-(5-iodoimidazol-1-ylmethyl)pyridin-3-yl]benzimidazole | I | H | Cl | F | 3 |
| 6-Bromo-1-fluoromethyl-2-[5-(5-iodoimidazol-1-ylmethyl)pyridin-3-yl]benzimidazole | I | H | Br | F | 1 |
| 6-Bromo-1-(2-fluoroethyl)-2-[5-(5-iodoimidazol-1-ylmethyl)pyridin-3-yl]benzimidazole | I | H | Br | F | 2 |
| 6-Bromo-1-(3-fluoropropyl)-2-[5-(5-iodoimidazol-1-ylmethyl)pyridin-3-yl]benzimidazole | I | H | Br | F | 3 |
| 1-Fluoromethyl-6-iodo-2-[5-(5-iodoimidazol-1-ylmethyl)pyridin-3-yl]benzimidazole | I | H | I | F | 1 |
| 1-(2-Fluoroethyl)-6-iodo-2-[5-(5-iodoimidazol-1-ylmethyl)pyridin-3-yl]benzimidazole | I | H | I | F | 2 |
| 1-(3-Fluoropropyl)-6-iodo-2-[5-(5-iodoimidazol-1-ylmethyl)pyridin-3-yl]benzimidazole | I | H | I | F | 3 |
| 6-Chloro-5-fluoro-1-fluoromethyl-2-[5-(5-iodoimidazol-1-ylmethyl)pyridin-3-yl]benzimidazole | I | F | Cl | F | 1 |
| 6-Chloro-5-fluoro-1-(2-fluoroethyl)-2-[5-(5-iodoimidazol-1-ylmethyl)pyridin-3-yl]benzimidazole | I(*I) | F | Cl | F | 2 |
| 6-Chloro-5-fluoro-1-(3-fluoropropyl)-2-[5-(5-iodoimidazol-1-ylmethyl)pyridin-3-yl]benzimidazole | I | F | Cl | F | 3 |
| 6-Bromo-5-fluoro-1-fluoromethyl-2-[5-(5-iodoimidazol-1-ylmethyl)pyridin-3-yl]benzimidazole | I | F | Br | F | 1 |
| 6-Bromo-5-fluoro-1-(2-fluoroethyl)-2-[5-(5-iodoimidazol-1-ylmethyl)pyridin-3-yl]benzimidazole | I | F | Br | F | 2 |
| 6-Bromo-5-fluoro-1-(3-fluoropropyl)-2-[5-(5-iodoimidazol-1-ylmethyl)pyridin-3-yl]benzimidazole | I | F | Br | F | 3 |
| 5-Fluoro-1-fluoromethyl-6-iodo-2-[5-(5-iodoimidazol-1-ylmethyl)pyridin-3-yl]benzimidazole | I | F | I | F | 1 |
| 5-Fluoro-1-(2-fluoroethyl)-6-iodo-2-[5-(5-iodoimidazol-1-ylmethyl)pyridin-3-yl]benzimidazole | I | F | I | F | 2 |
| 5-Fluoro-1-(3-fluoropropyl)-6-iodo-2-[5-(5-iodoimidazol-1-ylmethyl)pyridin-3-yl]benzimidazole | I | F | I | F | 3 |

In addition, another more preferred specific example of the present invention is a compound represented by the following general formula (1-3) which is the above general formula (1) wherein $R_1$, $R_2$, $R_3$, $R_4$ and $X_3$ are hydrogen atoms, and A is CH, or a salt thereof:

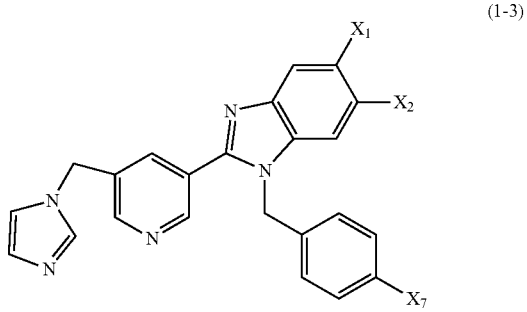

(1-3)

In the above general formula (1-3), $X_1$ and $X_2$ are hydrogen atoms or halogen atoms, provided that either $X_1$ or $X_2$ is a halogen atom, and $X_7$ is a halogen atom. In the above general formula (1-3), $X_7$ may be a radioactive iodine atom.

Preferred aspects of the compound represented by the above general formula (1-3) are shown in Table 3.

TABLE 3

| Compound name | $X_1$ | $X_2$ | $X_7$ |
|---|---|---|---|
| 6-Chloro-1-(4-fluorobenzyl)-2-[5-(imidazol-1-ylmethyl)pyridin-3-yl]benzimidazole | H | Cl | F |
| 6-Chloro-1-(4-chlorobenzyl)-2-[5-(imidazol-1-ylmethyl)pyridin-3-yl]benzimidazole | H | Cl | Cl |
| 1-(4-Bromobenzyl)-6-chloro-2-[5-(imidazol-1-ylmethyl)pyridin-3-yl]benzimidazole | H | Cl | Br |
| 6-Chloro-1-(4-iodobenzyl)-2-[5-(imidazol-1-ylmethyl)pyridin-3-yl]benzimidazole | H | Cl | I |
| 6-Bromo-1-(4-fluorobenzyl)-2-[5-(imidazol-1-ylmethyl)pyridin-3-yl]benzimidazole | H | Br | F |
| 6-Bromo-1-(4-chlorobenzyl)-2-[5-(imidazol-1-ylmethyl)pyridin-3-yl]benzimidazole | H | Br | Cl |
| 6-Bromo-1-(4-bromobenzyl)-2-[5-(imidazol-1-ylmethyl)pyridin-3-yl]benzimidazole | H | Br | Br |
| 6-Bromo-1-(4-iodobenzyl)-2-[5-(imidazol-1-ylmethyl)pyridin-3-yl]benzimidazole | H | Br | I |
| 1-(4-Fluorobenzyl)-6-iodo-2-[5-(imidazol-1-ylmethyl)pyridin-3-yl]benzimidazole | H | I | F |
| 1-(4-Chlorobenzyl)-6-iodo-2-[5-(imidazol-1-ylmethyl)pyridin-3-yl]benzimidazole | H | I | Cl |
| 1-(4-Bromobenzyl)-6-iodo-2-[5-(imidazol-1-ylmethyl)pyridin-3-yl]benzimidazole | H | I | Br |
| 1-(4-Iodobenzyl)-6-iodo-2-[5-(imidazol-1-ylmethyl)pyridin-3-yl]benzimidazole | H | I | I |
| 6-Chloro-5-fluoro-1-(4-fluorobenzyl)-2-[5-(imidazol-1-ylmethyl)pyridin-3-yl]benzimidazole | F | Cl | F |
| 6-Chloro-5-fluoro-1-(4-chlorobenzyl)-2-[5-(imidazol-1-ylmethyl)pyridin-3-yl]benzimidazole | F | Cl | Cl |
| 6-Chloro-5-fluoro-1-(4-bromobenzyl)-2-[5-(imidazol-1-ylmethyl)pyridin-3-yl]benzimidazole | F | Cl | Br |
| 6-Chloro-5-fluoro-1-(4-iodobenzyl)-2-[5-(imidazol-1-ylmethyl)pyridin-3-yl]benzimidazole | F | Cl | I(*I) |
| 6-Bromo-5-fluoro-1-(4-fluorobenzyl)-2-]5-(imidazol-1-ylmethyl)pyridin-3-yl]benzimidazole | F | Br | F |
| 6-Bromo-5-fluoro-1-(4-chlorobenzyl)-2-[5-(imidazol-1-ylmethyl)pyridin-3-yl]benzimidazole | F | Br | Cl |
| 6-Bromo-5-fluoro-1-(4-bromobenzyl)-2-[5-(imidazol-1-ylmethyl)pyridin-3-yl]benzimidazole | F | Br | Br |
| 6-Bromo-5-fluoro-1-(4-iodobenzyl)-2-[5-(imidazol-1-ylmethyl)pyridin-3-yl]benzimidazole | F | Br | I |
| 5-Fluoro-1-(4-fluorobenzyl)-6-iodo-2-[5-(imidazol-1-ylmethyl)pyridin-3-yl]benzimidazole | F | I | F |
| 5-Fluoro-1-(4-chlorobenzyl)-6-iodo-2-[5-(imidazol-1-ylmethyl)pyridin-3-yl]benzimidazole | F | I | Cl |
| 5-Fluoro-1-(4-bromobenzyl)-6-iodo-2-[5-(imidazol-1-ylmethyl)pyridin-3-yl]benzimidazole | F | I | Br |
| 5-Fluoro-6-iodo-1-(4-iodobenzyl)-2-[5-(imidazol-1-ylmethyl)pyridin-3-yl]benzimidazole | F | I | I |

In addition, another more preferred specific example of the present invention is a compound represented by the following general formula (1-4) which is the above general formula (1) wherein $R_1$ is $CO_2R_a$, $R_2$, $R_3$, $R_4$ and $X_3$ are hydrogen atoms, and A is CH, or a salt thereof:

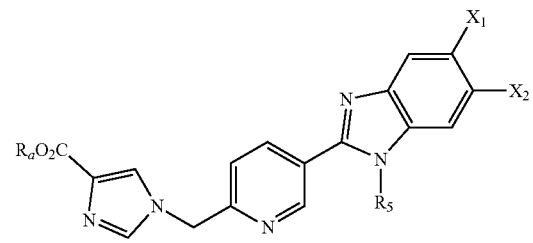

(1-4)

In the above general formula (1-4), $R_5$ is a linear alkyl group containing 1 to 5 carbon atoms in which a hydrogen atom is optionally replaced by a halogen atom, or a cyclic alkyl group containing 3 to 5 carbon atoms in which a hydrogen atom is optionally replaced by a halogen atom, $X_1$ and $X_2$ are hydrogen atoms or halogen atoms, and $R_a$ is an alkyl group containing 1 to 10 carbon atoms, and preferably, a linear alkyl group containing 1 to 5 carbon atoms or a cyclic alkyl group containing 3 to 5 carbon atoms. $R_5$ can be, for example, a methyl group, an ethyl group, a propyl group, an isopropyl group, or a cyclopropyl group. In the above general formula (1-4), $X_2$ may be a radioactive iodine atom.

Preferred aspects of the compound represented by the above general formula (1-4) are shown in Table 4.

TABLE 4

| Compound name | $R_a$ | $R_5$ | $X_1$ | $X_2$ |
|---|---|---|---|---|
| 6-Chloro-1-methyl-2-[6-(4-methylcarboxylateimidazol-1-ylmethyl)pyridin-3-yl]benzimidazole | Methyl | Methyl | H | Cl |
| 6-Chloro-1-ethyl-2-[6-(4-methylcarboxylateimidazol-1-ylmethyl)pyridin-3-yl]benzimidazole | Methyl | Ethyl | H | Cl |
| 6-Chloro-1-isopropyl-2-[6-(4-methylcarboxylateimidazol-1-ylmethyl)pyridin-3-yl]benzimidazole | Methyl | Isopropyl | H | Cl |
| 6-Chloro-1-cyclopropyl-2-[6-(4-methylcarboxylateimidazol-1-ylmethyl)pyridin-3-yl]benzimidazole | Methyl | Cyclopropyl | H | Cl |
| 6-Bromo-1-methyl-2-[6-(4-methylcarboxylateimidazol-1-ylmethyl)pyridin-3-yl]benzimidazole | Methyl | Methyl | H | Br |
| 6-Bromo-1-ethyl-2-[6-(4-methylcarboxylateimidazol-1-ylmethyl)pyridin-3-yl]benzimidazole | Methyl | Ethyl | H | Br |
| 6-Bromo-1-isopropyl-2-[6-(4-methylcarboxylateimidazol-1-ylmethyl)pyridin-3-yl]benzimidazole | Methyl | Isopropyl | H | Br |
| 6-Bromo-1-cyclopropyl-2-[6-(4-methylcarboxylateimidazol-1-ylmethyl)pyridin-3-yl]benzimidazole | Methyl | Cyclopropyl | H | Br |
| 1-Methyl-6-iodo-2-[6-(4-methylcarboxylateimidazol-1-ylmethyl)pyridin-3-yl]benzimidazole | Methyl | Methyl | H | I |
| 1-Ethyl-6-iodo-2-[6-(4-methylcarboxylateimidazol-1-ylmethyl)pyridin-3-yl]benzimidazole | Methyl | Ethyl | H | I |
| 1-Isopropyl-6-iodo-2-[6-(4-methylcarboxylateimidazol-1-ylmethyl)pyridin-3-yl]benzimidazole | Methyl | Isopropyl | H | I |
| 1-Cyclopropyl-2-[6-(4-methylcarboxylateimidazol-1-ylmethyl)pyridin-3-yl]6-iodobenzimidazole | Methyl | Cyclopropyl | H | I(*I) |
| 5-Chloro-6-fluoro-1-methyl-2-[6-(4-methylcarboxylateimidazol-1-ylmethyl)pyridin-3-yl]benzimidazole | Methyl | Methyl | F | Cl |
| 5-Chloro-6-fluoro-1-ethyl-2-[6-(4-methylcarboxylateimidazol-1-ylmethyl)pyridin-3-yl]benzimidazole | Methyl | Ethyl | F | Cl |

TABLE 4-continued

| Compound name | $R_a$ | $R_5$ | $X_1$ | $X_2$ |
|---|---|---|---|---|
| 5-Chloro-6-fluoro-1-isopropyl-2-[6-(4-methylcarboxylateimidazol-1-ylmethyl)pyridin-3-yl]benzimidazole | Methyl | Isopropyl | F | Cl |
| 5-Chloro-1-cyclopropyl-6-fluoro-2-[6-(4-methylcarboxylateimidazol-1-ylmethyl)pyridin-3-yl]benzimidazole | Methyl | Cyclopropyl | F | Cl |
| 5-Bromo-6-fluoro-1-methyl-2-[6-(4-methylcarboxylateimidazol-1-ylmethyl)pyridin-3-yl]benzimidazole | Methyl | Methyl | F | Br |
| 5-Bromo-1-ethyl-6-fluoro-2-[6-(4-methylcarboxylateimidazol-1-ylmethyl)pyridin-3-yl]benzimidazole | Methyl | Ethyl | F | Br |
| 5-Bromo-6-fluoro-1-isopropyl-2-[6-(4-methylcarboxylateimidazol-1-ylmethyl)pyridin-3-yl]benzimidazole | Methyl | Isopropyl | F | Br |
| 5-Bromo-1-cyclopropyl-6-fluoro-2-[6-(4-methylcarboxylateimidazol-1-ylmethyl)pyridin-3-yl]benzimidazole | Methyl | Cyclopropyl | F | Br |
| 5-Fluoro-6-iodo-1-methyl-2-[6-(4-methylcarboxylateimidazol-1-ylmethyl)pyridin-3-yl]benzimidazole | Methyl | Methyl | F | I |
| 1-Ethyl-5-fluoro-6-iodo-2-[6-(4-methylcarboxylateimidazol-1-ylmethyl)pyridin-3-yl]benzimidazole | Methyl | Ethyl | F | I |
| 5-Fluoro-1-isopropyl-6-iodo-2-[6-(4-methylcarboxylateimidazol-1-ylmethyl)pyridin-3-yl]benzimidazole | Methyl | Isopropyl | F | I |
| 1-Cyclopropyl-5-fluoro-6-iodo-2-[6-(4-methylcarboxylateimidazol-1-ylmethyl)pyridin-3-yl]benzimidazole | Methyl | Cyclopropyl | F | I |

It is to be noted that, in Tables 1 to 4, the symbol "*I" indicates a radioactive iodine atom. In addition, the item in parentheses indicates a more preferred aspect.

(Scheme 1, Step a-2). The 3,5-pyridinedicarboxylic acid compound or the 3,6-pyridinedicarboxylic acid compound, or an esterified form thereof, may be subjected to a selective reduction reaction to obtain a monool form (Scheme 1, Step b-1), so that a monoaldehyde form (Part [A]) may be obtained (Scheme 1, Step b-2).

Moreover, a pyridine compound is dibrominated (Scheme 1, Step c-1), a Turbo Grignard reagent is prepared so as to act dimethylformamide thereon to obtain a monoaldehyde form (Scheme 1, Step c-2). The aldehyde is reduced to obtain a monoalcohol (Scheme 1, Step c-3), and the other bromo group is subjected to the same reaction as that in Step c-2, so that a monoaldehyde form (Part [A]) may be obtained (Scheme 1, Step c-4).

Furthermore, a hydroxy group may be protected before or after Steps a-2, b-2, and c-4. As protective groups for the hydroxy group, the protective groups described in Greene's Protective Groups in Organic Synthesis (Wiley-Interscience; 4th edition) can be used, for example.

It is to be noted that, in Scheme 1, $R_p$ and $R_q$ each represent hydrogen or an alkyl group (e.g., a methyl group), $R_s$ represents hydrogen or a protective group for hydroxy group, and $R_4$ is the same as $R_4$ in the above general formula (1).

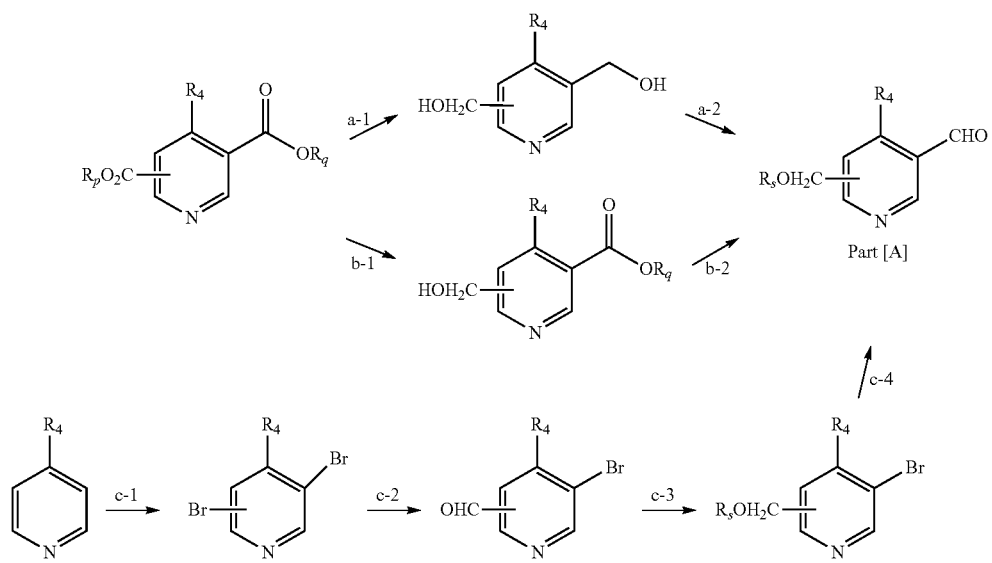

Scheme 1

Next, an example of the method for producing the compound according to the present invention will be explained using the following Schemes 1 to 4.

First, a 3,5-pyridinedicarboxylic acid compound or a 3,6-pyridinedicarboxylic acid compound, or an esterified form thereof, is used as a starting substance for a pyridine ring portion, and it is reduced to obtain a diol (Scheme 1, Step a-1). Subsequently, a selective oxidation reaction is performed thereon to obtain a monoaldehyde form (Part [A])

On the other hand, as starting substances for a benzimidazole portion, a linear or cyclic alkylamine compound, or a benzylamine compound, and a 2-fluoronitrobenzene compound are used, and they undergo coupling according to an aromatic substitution reaction, so as to obtain Part [B] (Scheme 2, Step d). In Scheme 2, $X_1$, $X_2$, $X_3$ and $R_5$ are the same as those in the compound represented by the above general formula (1). Q in Part [B] is a nitro group which may further be reduced to an amino group.

Scheme 2

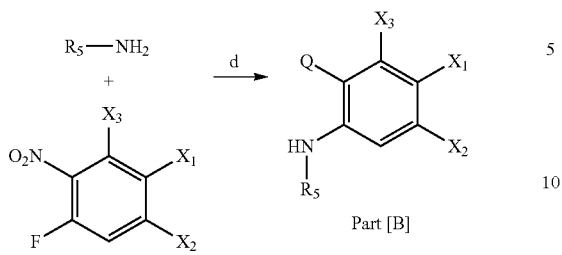

Subsequently, a cyclocondensation reaction is carried out using Part [A] obtained in Scheme 1 and Part [B] obtained in Scheme 2, so as to form a benzimidazole ring (Scheme 3, Step e). When $R_s$ is a protective group for hydroxy group, the protective group is removed. As a deprotection method, the method described in Greene's Protective Groups in Organic Synthesis (Wiley-Interscience; 4th edition) can be used, for example.

Thereafter, the hydroxy group in the hydroxymethyl group introduced into position 3 of the pyridine ring is converted to a leaving group (L) (Scheme 3, Step f). Examples of the leaving group (L) used herein include a halogen atom, a substituted or unsubstituted alkylsulfonyloxy group, and a substituted or unsubstituted arylsulfonyloxy group. In Scheme 3, L is preferably a chlorine atom, a bromine atom, an iodine atom, a methanesulfonyloxy group, a benzenesulfonyloxy group, a p-toluenesulfonyloxy group, a p-nitrobenzenesulfonyloxy group, or a trifluoromethanesulfonyloxy group. By these operations, Part [A+B] can be obtained.

Scheme 3

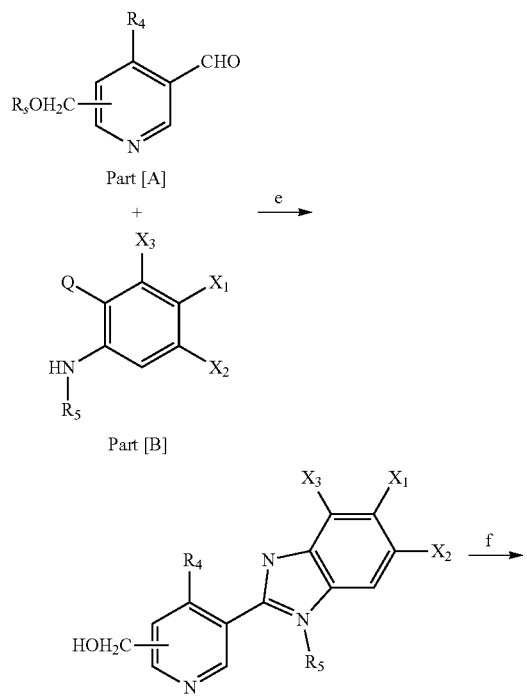

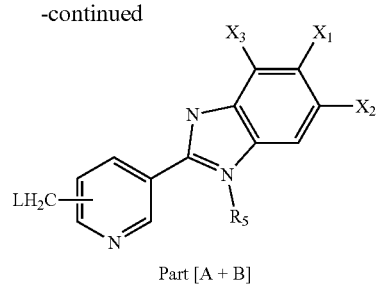

According to a nucleophilic substitution reaction using an imidazole compound or a triazole compound as Part C, Part C is introduced into Part [A+B] obtained in Scheme 3 (Scheme 4, Step g). In Part C, $R_1$, $R_2$ and A are the same as those in the compound represented by the above general formula (1).

Scheme 4

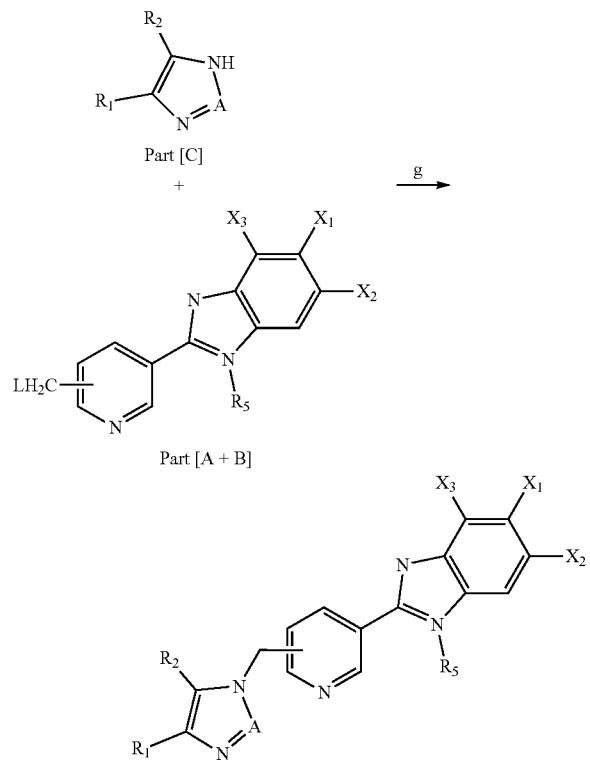

The compound of the above general formula (1) wherein $R_5$ is a group represented by $-(CH_2)_nX_4$ in which n is an integer of 1 to 5 and $X_4$ is a radioactive halogen atom, i.e., the radioactive compound represented by the above general formula (9) or a salt thereof, can be produced from the compound of the above general formula (3) or a salt thereof by a radiohalogenation reaction.

For example, the compound of the above general formula (2) wherein $X_{14}$ is a radioactive halogen atom, i.e., the compound of the above general formula (1-2) wherein $X_4$ is a radioactive halogen atom, or the radioactive compound of the above general formula (10) or a salt thereof, can be produced from the compound of the above general formula (4) or a salt thereof by a radiohalogenation reaction.

In the present invention, the substituted or unsubstituted alkylsulfonyloxy group is preferably an alkylsulfonyloxy group containing 1 to 12 carbon atoms. In the substituted alkylsulfonyloxy group, the hydrogen atom in the alkyl chain may be substituted with a halogen atom. In addition, in the present invention, the substituted or unsubstituted arylsulfonyloxy group is preferably a substituted or unsubstituted benzenesulfonyloxy group, and more preferably a substituted benzenesulfonyloxy group. In the substituted arylsulfonyloxy group, the hydrogen atom in the aryl ring is preferably substituted with an alkyl group containing 1 to 12 carbon atoms, or a nitro group. Preferred specific examples of the substituted or unsubstituted alkylsulfonyloxy group and the substituted or unsubstituted arylsulfonyloxy group include a methanesulfonyloxy group, a benzenesulfonyloxy group, a p-toluenesulfonyloxy group, a p-nitrobenzenesulfonyloxy group, and a trifluoromethanesulfonyloxy group.

Hereafter, an example of the method for producing the radioactive compound represented by the above general formula (10) will be explained using Scheme 5. A compound represented by the above general formula (10) wherein $X_{14}$ is a hydroxy group is used as a starting substance, and the group represented by $R_{16}$ in the above general formula (4) (a halogen atom, a substituted or unsubstituted alkylsulfonyloxy group, or a substituted or unsubstituted arylsulfonyloxy group) is introduced into the hydroxy group to obtain the compound represented by the above general formula (4) as a labeling precursor (Scheme 5, Step h). Subsequently, a nucleophilic substitution reaction is carried out on the group represented by $R_{16}$, using a radioactive halide ion, so as to obtain the radioactive compound represented by the above general formula (10) (Scheme 5, Step i).

Scheme 5

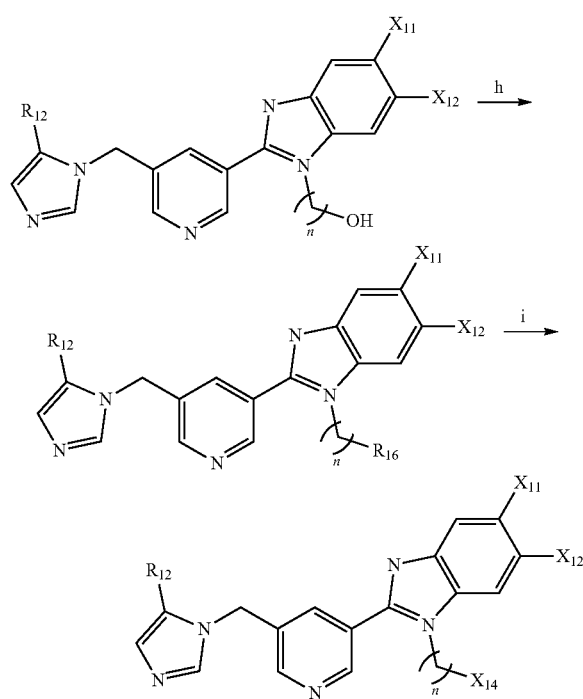

Herein, the "radioactive halide ion" includes a radioactive fluoride ion (e.g., [$^{18}$F] fluoride ion), a radioactive chloride ion (e.g., [$^{34m}$Cl] chloride ion), a radioactive bromide ion (e.g., [$^{76}$Br] bromide ion), and a radioactive iodide ion (e.g., [$^{123}$I] iodide ion, [$^{124}$I] iodide ion, [$^{125}$I] iodide ion, and [$^{131}$I] iodide ion). When a radioactive fluoride ion is used, preferred labeling precursors are the compounds represented by the general formula (4) wherein $R_{16}$ is a chlorine atom, a bromine atom, an iodine atom, a substituted or unsubstituted alkylsulfonyloxy group, or a substituted or unsubstituted arylsulfonyloxy group. In addition, when a radioactive chloride ion is used, preferred labeling precursors are the compounds represented by the general formula (4) wherein $R_{16}$ is a bromine atom, an iodine atom, a substituted or unsubstituted alkylsulfonyloxy group, or a substituted or unsubstituted arylsulfonyloxy group. Moreover, when a radioactive bromide ion is used, preferred labeling precursors are the compounds represented by the general formula (4) wherein $R_{16}$ is an iodine atom, a substituted or unsubstituted alkylsulfonyloxy group, or a substituted or unsubstituted arylsulfonyloxy group. Furthermore, when a radioactive iodide ion is used, preferred labeling precursors are the compounds represented by the general formula (4) wherein $R_{16}$ is a substituted or unsubstituted alkylsulfonyloxy group, or a substituted or unsubstituted arylsulfonyloxy group. The nucleophilic substitution reaction using these radioactive halide ions is preferably carried out in the presence of a base such as an alkaline metal carbonate (e.g., sodium carbonate or potassium carbonate).

For instance, by carrying out a radioactive fluorination reaction using a radioactive fluoride ion, a radioactive compound represented by the general formula (10) wherein $X_{14}$ is a radioactive fluorine atom can be obtained. The radioactive fluorination reaction is preferably carried out in the presence of a base, and may also be carried out in a presence of various types of phase transfer catalysts such as 4,7,13,16,21,24-hexaoxa-1,10-diazabicyclo[8.8.8]-hexacosane (trade name: KRYPTOFIX 222).

Moreover, a compound represented by the above general formula (1) wherein $X_2$ is a radioactive halogen atom, i.e., a radioactive compound represented by the above general formula (11) or a salt thereof, can be produced from a compound represented by the above general formula (5) or a salt thereof by a radiohalogenation reaction.

For example, the group represented by $R_7$ in the following general formula (5-1) can be substituted with a radioactive halogen atom (preferably, a radioactive iodine atom) by subjecting, to a radiohalogenation reaction, a compound represented by the following general formula (5-1) which is the above general formula (5) wherein $R_1$, $R_2$ and $R_3$ are hydrogen atoms, $R_4$ is a hydrogen atom or an alkoxy group containing 1 to 10 carbon atoms, $R_5$ is a linear alkyl group containing 1 to 5 carbon atoms or a cyclic alkyl group containing 3 to 5 carbon atoms, and $X_1$ and $X_3$ are hydrogen atoms, or a salt thereof. Thereby, the compound represented by the above general formula (1-1) (wherein $X_2$ is a radioactive halogen atom, and preferably, a radioactive iodine atom) or a salt thereof can be produced.

(5-1)

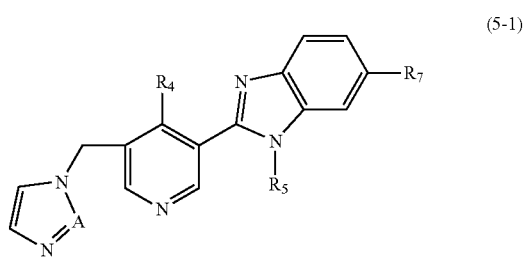

In the above general formula (5-1), $R_4$ represents a hydrogen atom or an alkoxy group containing 1 to 10 carbon atoms, $R_5$ represents a linear alkyl group containing 1 to 5 carbon atoms or a cyclic alkyl group containing 3 to 5 carbon atoms, $R_7$ represents a trialkyltin group or a trialkylsilyl group, and A represents CH or a nitrogen atom.

In addition, for example, the group represented by $R_7$ in the following general formula (5-2) can be substituted with a radioactive halogen atom (preferably, a radioactive iodine atom) by subjecting, to a radiohalogenation reaction, a compound represented by the following general formula (5-2) which is the general formula (5) wherein $R_1$ represents $CO_2R_a$, $R_2$, $R_3$ and $R_4$ represent hydrogen atoms, $R_5$ represents a linear alkyl group containing 1 to 5 carbon atoms in which a hydrogen atom is optionally replaced by a halogen atom, or a cyclic alkyl group containing 3 to 5 carbon atoms in which a hydrogen atom is optionally replaced by a halogen atom, A represents CH, and $X_3$ represents a hydrogen atom, or a salt thereof. Thereby, the compound represented by the above general formula (1-4) (wherein $X_2$ represents a radioactive halogen atom, and preferably a radioactive iodine atom) or a salt thereof can be produced.

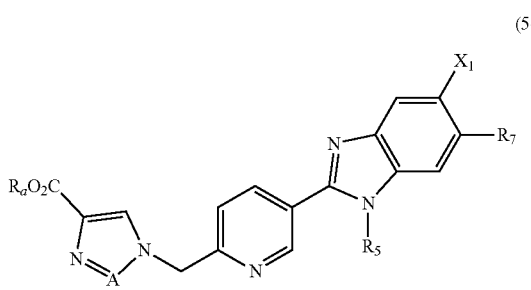

(5-2)

In the above general formula (5-2), $R_5$ represents a linear alkyl group containing 1 to 5 carbon atoms in which a hydrogen atom is optionally replaced by a halogen atom, or a cyclic alkyl group containing 3 to 5 carbon atoms in which a hydrogen atom is optionally replaced by a halogen atom, $R_7$ represents a trialkyltin group or a trialkylsilyl group, A represents CH or a nitrogen atom, $X_1$ represents a hydrogen atom or a halogen atom, and $R_a$ represents an alkyl group containing 1 to 10 carbon atoms.

For example, a compound represented by the above general formula (2) wherein $X_{12}$ represents a radioactive halogen atom, i.e., a compound represented by the above general formula (1-2) wherein $X_2$ is a radioactive halogen atom, or the radioactive compound represented by the above general formula (12) or a salt thereof can be produced from a compound represented by the above general formula (6) or a salt thereof by a radiohalogenation reaction.

Moreover, a compound represented by the above general formula (1) wherein $R_5$ is a p-halobenzyl group labeled with a radioactive halogen atom, i.e., radioactive compound represented by the above general formula (13) or a salt thereof can be produced from a compound represented by the above general formula (7) or a salt thereof by a radiohalogenation reaction.

For example, the group represented by $R_8$ in the following general formula (7-1) can be substituted with a radioactive halogen atom (preferably, a radioactive iodine atom) by subjecting, to a radiohalogenation reaction, a compound represented by the following general formula (7-1) which is the above general formula (7) wherein $R_1$, $R_2$, $R_3$ and $R_4$ are hydrogen atoms, A is CH, $X_2$ is a hydrogen atom or a halogen atom, provided that either $X_1$ or $X_2$ is a halogen atom, and $X_3$ is a hydrogen atom, or a salt thereof. Thereby, the compound represented by the above general formula (1-3) (wherein $X_2$ is a radioactive halogen atom, and preferably a radioactive iodine atom) or a salt thereof can be produced.

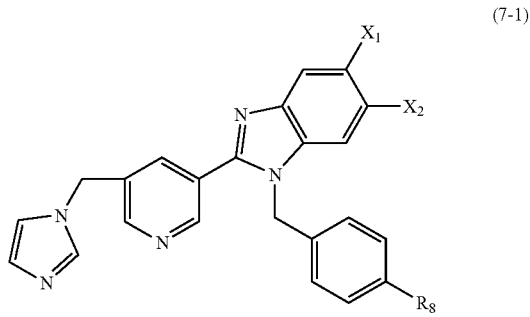

(7-1)

In the above general formula (7-1), $R_8$ represents a trialkyltin group or a trialkylsilyl group, and $X_1$ and $X_2$ each independently represent a hydrogen atom or a halogen atom, provided that either $X_1$ or $X_2$ is a halogen atom.

Moreover, a compound represented by the above general formula (1) wherein $R_2$ is a radioactive halogen atom, i.e., a radioactive compound represented by the above general formula (14) or a salt thereof can be produced from a compound represented by the above general formula (8) or a salt thereof by a radiohalogenation reaction.

For example, the group represented by $R_9$ in the following general formula (8-1) can be substituted with a radioactive halogen atom (preferably, a radioactive iodine atom) by subjecting, to a radiohalogenation reaction, a compound represented by the following general formula (8-1) which is the above general formula (8) wherein $R_1$, $R_3$ and $R_4$ are hydrogen atoms, $R_5$ is $-(CH_2)_nX_{14}$ (wherein n is an integer of 1 to 5, and $X_{14}$ is a halogen atom), A is CH, $X_2$ is a hydrogen atom or a halogen atom, and $X_3$ is a hydrogen atom, provided that either $X_1$ or $X_2$ is a halogen atom, or a salt thereof. Thereby, the compound represented by the above general formula (1-2) (wherein $R_2$ is a radioactive halogen atom, and preferably a radioactive iodine atom) or a salt thereof can be produced.

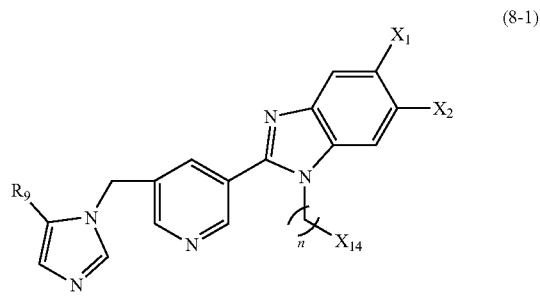

(8-1)

In the above general formula (8-1), $R_9$ represents a trialkyltin group or a trialkylsilyl group, $X_1$ represents a hydrogen atom or a halogen atom, $X_2$ represents a hydrogen atom or a halogen atom, provided that either $X_1$ or $X_2$ is a halogen atom, and $X_{14}$ represents a halogen atom.

In the present invention, the "trialkyltin group" includes tri(C1-C6 alkyl)tin groups, and among others, a tributyl tin group is more preferable. The trialkylsilyl group includes tri(C1-C6 alkyl)silyl groups, and among others, a trimethylsilyl group is more preferable. It is to be noted that the "C1-C6 alkyl" means an alkyl group containing 1 to 6 carbon atoms.

Hereinafter, an example of the method for producing the radioactive compound represented by the above general formula (12) will be explained using Scheme 6. The compound represented by the above general formula (12) is used as a starting substance, and the halogen group represented by $X_{16}$ in the compound is substituted with the group represented by $R_{17}$ (a trialkyltin group or a trialkylsilyl group) to obtain the compound represented by the above general formula (6) as a labeling precursor (Scheme 6, Step j). Subsequently, a radiohalogenation reaction is performed to obtain the radioactive compound represented by the above general formula (12) (Scheme 6, Step k).

Scheme 6

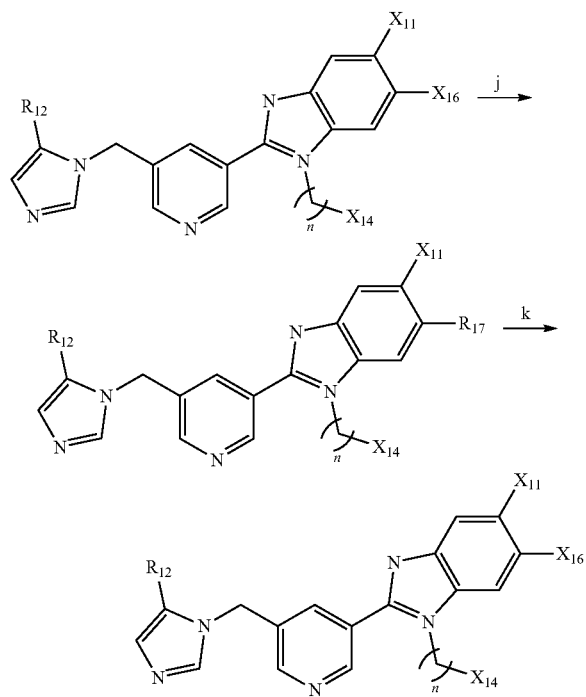

The radiohalogenation reaction in Step k may be carried out using a radioactive halogen prepared as an electrophile, and this reaction can be carried out, for example, using a radioactive halogen molecule or a radioactive acetyl hypohalite. However, a radioactive halogen comprising a halogen atom that is different from the halogen atom represented by $X_1$ in the above general formula (3) is used. The radioactive halogen molecule includes a radioactive fluorine molecule, a radioactive chlorine molecule, a radioactive bromine molecule, a radioactive iodine molecule, and a radioactive astatine molecule. The radioactive acetyl hypohalite includes a radioactive acetyl hypofluorite, a radioactive acetyl hypochlorite, a radioactive acetyl hypobromite, and a radioactive acetyl hypoiodite. Alternatively, the compound may be reacted with radioactive sodium halide or radioactive potassium halide under acidic conditions in the presence of an oxidant. The oxidant includes, for example, chloramine-T, hydrogen peroxide water, peracetic acid, and succinimide halide.

For example, the radioactive compound represented by the general formula (11) wherein $X_6$ is a radioactive iodine atom can be obtained by performing a radioactive iodination reaction using an alkaline metal radioactive iodide. The radioactive iodination reaction is preferably carried out by allowing the compound to react with an alkaline metal radioactive iodide and an oxidant under acidic conditions. Examples of the alkaline metal radioactive iodide that can be used herein include a sodium compound of radioactive iodine and a potassium compound of radioactive iodine. Examples of the oxidant that can be used herein include chloramine-T, hydrogen peroxide water, peracetic acid, N-chlorosuccinimide, and N-bromosuccinimide.

As an example, the compound is allowed to react with radioactive sodium iodide (e.g., [$^{123}$I] sodium iodide, [$^{124}$I] sodium iodide, [$^{125}$I] sodium iodide, or [$^{131}$I] sodium iodide) under acidic conditions, such as hydrochloric acid, in the presence of an oxidant such as hydrogen peroxide water, to perform a radioactive iodination reaction, so as to obtain the radioactive compound of the general formula (11) wherein $X_6$ is a radioactive iodine atom.

When the radioactive compound represented by the above general formula (9), the above general formula (10), the above general formula (11), the above general formula (12), the above general formula (13) or the above general formula (14) or a salt thereof is used as a medicament, unreacted radioactive halogen and insoluble impurities are desirably purified therefrom with a membrane filter, a column filled with various types of fillers, HPLC, etc. after completion of the radiohalogenation reaction.

In the present invention, a medicament can also be prepared from the thus produced compound or a salt thereof. In the present description, the term "medicament" can be defined to be a preparation comprising the compound represented by the above general formula (1) or a salt thereof in a form suitable for administration into a living body. This medicament can be administered orally or parenterally (e.g., intravenous, subcutaneous, intramuscular, intrathecal, local, transrectal, transdermal, transnasal or transpulmonary administration). Examples of the administration form for oral administration include dosage forms such as tablets, capsules, pills, granules, fine granules, powders, liquids and solutions, syrups, or suspensions. On the other hand, examples of the administration form for parenteral administration include forms such as aqueous formulations for injection, oily formulations for injection, suppositories, transnasal formulations, and transdermal formulations (lotions, emulsions, ointments, creams, jellies, gels, or patches (tapes, transdermal patches, poultices, etc.), powders for external use, etc.).

The medicament according to the present invention is prepared by a conventionally known technique, and it can comprise a nontoxic and inactive carrier that has been generally used in the field of pharmaceutical production. The type of a carrier that can be contained in the medicament of the present invention is not limited, as long as it is ordinarily used in the field of pharmaceutical production and it does not react with the compound represented by the above general formula (1) or a salt thereof. Examples of such a carrier include an excipient, a binder, a lubricant, a stabilizer, a disintegrator, a buffer, a solubilizer, a tonicity agent, a solubilizer, a pH adjuster, a surfactant, an emulsifier, a suspending agent, a disperser, an anti-settling agent, a thickener, a viscosity adjuster, a gelatinizer, a soothing agent, a preservative, a plasticizer, a transdermal absorption promoter, an antioxidant, a moisturizer, an antiseptic, and a perfume. These carriers can also be used in an appropriate combination with two or more.

Since the compound represented by the above general formula (1) has a certain selective inhibitory ability on human aldosterone synthase (CYP11B2), the medicament according to the present invention can specifically accumulate in an aldosterone-producing tumor. Accordingly, the medicament according to the present invention can be used as a therapeutic agent for an aldosterone-producing tumor.

Moreover, when the medicament according to the present invention is introduced into a living body, it can accumulate specifically in an aldosterone-producing tumor since the compound represented by the general formula (1) has a certain selective inhibitory ability on CYP11B2. Thus, by using a radioactive halogen atom as a halogen atom represented by $X_4$ when $R_5$ is —$(CH_2)_nX_4$ (wherein n is an integer of 1 to 5 and $X_4$ is a halogen atom), a halogen atom represented by $X_2$, a halogen atom represented by $R_2$ or a halogen atom of a p-halobenzyl group represented by $R_5$ in the above general formula (1), for example, by using a radioactive halogen atom as a halogen atom represented by $X_{12}$ or $X_{14}$ in the above general formula (2), an aldosterone-producing tumor can be imaged by noninvasively detecting radiation from the outside of the living body with a radiation detector, a single-photon emission computed tomography scanner, a positron emission tomography scanner, scintigraphy or the like. Accordingly, the medicament of the present invention can be used as an image diagnostic agent for nuclear medicine examination, and specifically can be used as an image diagnostic agent for positron emission tomography or as an image diagnostic agent for single-photon emission computed tomography. For example, when a positron emission radionuclide such as $^{18}F$, $^{76}Br$ or $^{124}I$ is used as a radioactive halogen atom, the present medicament can be used as an image diagnostic agent for positron emission tomography, and when $^{123}I$ is used as a radioactive halogen atom, the present medicament can be used as an image diagnostic agent for single-photon emission computed tomography. In addition, by using an element suitable for nuclear magnetic signal measurement, such as $^{19}F$, as a halogen atom represented by $X_4$ when $R_5$ is —$(CH_2)_nX_4$ (wherein n is an integer of 1 to 5 and $X_4$ is a halogen atom), a halogen atom represented by $X_2$, a halogen atom represented by $R_2$ or a halogen atom of a p-halobenzyl group represented by $R_5$ in the above general formula (1), for example, as a halogen atom represented by $X_{12}$ or $X_{14}$ in the above general formula (2), an aldosterone-producing tumor can be imaged by employing a nuclear magnetic resonance imaging apparatus.

Moreover, by using a nuclide, such as $^{123}I$ having a relatively long half-life, $^{131}I$ emitting β-ray, or $^{211}At$ emitting a-ray, as a radioactive halogen atom represented by $X_4$ when $R_5$ is —$(CH_2)_nX_4$ (wherein n is an integer of 1 to 5 and $X_4$ is a halogen atom), a radioactive halogen atom represented by $X_2$, a radioactive halogen atom represented by $R_2$ or a radioactive halogen atom of a radioactive halogen-labeled p-halobenzyl group represented by $R_5$ in the above general formula (1), for example, as a radioactive halogen atom represented by $X_{12}$ or $X_{14}$ in the above general formula (2), the medicament according to the present invention can also be used as an internal-use radiotherapeutic agent for an aldosterone-producing tumor.

EXAMPLES

Hereinafter, the present invention will be described in more detail by way of the following Examples. However, the present invention is not limited to the contents of the Examples.

Hereinafter, the present invention will be described in more detail by way of the following Examples. However, the present invention is not limited to the contents of the Examples. It is to be noted that, in the below-mentioned Examples, the names of individual compounds subjected to experiments are defined as follows.

Compound 100: 6-Chloro-5-fluoro-1-(2-fluoroethyl)-2-[5-(imidazol-1-ylmethyl)pyridin-3-yl]benzimidazole Compound [$^{18}F$] 100: 6-Chloro-5-fluoro-1-(2-[$^{18}F$]fluoroethyl)-2-[5-(imidazol-1-ylmethyl)pyridin-3-yl]benzimidazole Compound 200: 6-Bromo-5-fluoro-1-(2-fluoroethyl)-2-[5-(imidazol-1-ylmethyl)pyridin-3-yl]benzimidazole Compound [$^{18}F$] 200: 6-Bromo-5-fluoro-1-(2-[$^{18}F$]fluoroethyl)-2-[5-(imidazol-1-ylmethyl)pyridin-3-yl]benzimidazole Compound 300: 2-{6-Bromo-5-fluoro-2-[5-(5-methylcarboxylateimidazol-1-ylmethyl)pyridin-3-yl]benzimidazol-1-yl}ethanol Compound 400: 5-Fluoro-1-(2-fluoroethyl)-2-[5-(imidazol-1-ylmethyl)pyridin-3-yl]-6-iodobenzimidazole Compound [$^{123}I$] 400: 5-Fluoro-1-(2-fluoroethyl)-2-[5-(imidazol-1-ylmethyl)pyridin-3-yl]-6-[$^{123}I$]iodobenzimidazole Compound 500: 6-Chloro-5-fluoro-1-(3-fluoropropyl)-2-[5-(imidazol-1-ylmethyl)pyridin-3-yl]benzimidazole Compound [$^{18}F$] 500: 6-Chloro-5-fluoro-1-(3-[$^{18}F$]fluoropropyl)-2-[5-(imidazol-1-ylmethyl)pyridin-3-yl]benzimidazole Compound 601: Methyl 1-[4-(1-cyclopropyl-6-iodo-1H-imidazobenzo-2-yl)-3-pyridinylmethyl)]-1H-imidazolecarboxylate Compound [$^{123}I$] 601: Methyl 1-[4-(1-cyclopropyl-6-[$^{123}I$]iodo-1H-imidazobenzo-2-yl)-3-pyridinylmethyl)]-1H-imidazolecarboxylate Compound 602: 1-Cyclopropyl-2-[3-(1H-imidazol-1-ylmethyl)pyridin-5-yl]-6-iodo-1H-benzimidazole Compound [$^{123}I$] 602: 1-Cyclopropyl-2-[3-(1H-imidazol-1-ylmethyl)pyridin-5-yl]-6-[$^{123}I$]iodo-1H-benzimidazole Compound 603: 1-Cyclopropyl-2-[3-(1H-1,2,3-triazol-1-ylmethyl)pyridin-5-yl]-6-iodo-1H-benzimidazole Compound [$^{123}I$] 603: 1-Cyclopropyl-2-[3-(1H-1,2,3-triazol-1-ylmethyl)pyridin-5-yl]-6-[$^{123}I$]iodo-1H-benzimidazole Compound 604: 1-(2-Fluoroethyl)-2-[5-{(imidazol-1-yl)methyl}pyridin-3-yl]-6-iodobenzimidazole Compound [$^{123}I$] 604: 1-(2-Fluoroethyl)-2-[5-{(imidazol-1-yl)methyl}pyridin-3-yl]-6-[$^{123}I$]iodobenzimidazole Compound 605: 6-Chloro-5-fluoro-1-(4-iodobenzyl)-2-[5-(1H-imidazol-1-ylmethyl)-3-pyridinyl]-1H-benzimidazole Compound [$^{123}I$] 605: 6-Chloro-5-fluoro-1-(4-[$^{123}I$]iodobenzyl)-2-[5-(1H-imidazol-1-ylmethyl)-3-pyridinyl]-1H-benzimidazole Compound 606: 2-[5-{(1H-imidazol-1-yl)methyl}pyridin-3-yl]-6-iodo-1-isopropyl-1H-benzo[d]imidazole Compound [$^{123}I$] 606: 2-[5-{(1H-imidazol-1-yl)methyl}pyridin-3-yl]-6-[$^{123}I$]iodo-1-isopropyl-1H-benzo[d]imidazole Compound 607: 2-[5-{(1H-imidazol-1-yl)methyl}pyridin-3-yl]-6-iodo-1-methyl-1H-benzo[d]imidazole Compound [$^{123}I$] 607: 2-[5-{(1H-imidazol-1-yl)methyl}pyridin-3-yl]-6-[$^{123}I$]iodo-1-methyl-1H-benzo[d]imidazole Compound 608: 2-[5-{(1H-imidazol-1-yl)methyl}pyridin-3-yl]-1-ethyl-6-iodo-1H-benzo[d]imidazole Compound [$^{123}$I] 608: 2-[5-{(1H-imidazol-1-yl) methyl}pyridin-3-yl]-1-ethyl-6-[$^{123}$I]iodo-1H-benzo[d] imidazole Compound 609: 1-Cyclopropyl-2-[5-(imidazol-1-ylmethyl) pyridin-3-yl]-6-iodo-4-methoxybenzimidazole Compound [$^{123}$I] 609: 1-Cyclopropyl-2-[5-(imidazol-1-ylmethyl)pyridin-3-yl]-6-[$^{123}$I]iodo-4-methoxybenzimidazole Compound 610: 6-Chloro-5-fluoro-1-(2-fluoroethyl)-2-{5-(5-iodo-1H-imidazol-1-ylmethyl)pyridin-3-yl}benzimidazole Compound [$^{123}$I] 610: 6-Chloro-5-fluoro-1-(2-fluoroethyl)-2-{5-(5-[$^{123}$I]iodo-1H-imidazol-1-ylmethyl)pyridin-3-yl}benzimidazole In the following Examples, the molecular structures of individual compounds were identified by $^1$H-NMR spectrum. As an NMR device, AVANCE III (manufactured by BURKER) was used, while referring to the signal 67.24 of deuterated chloroform or the signal 62.49 of deuterated dimethyl sulfoxide. All of chemical shifts are given as ppm on delta scale (δ), and the fine splittings of signals are indicated using abbreviations (s: singlet, d: doublet, t: triplet, dd: double doublet, dt: double triplet, dq: double quartet, m: multiplet, bs: broad singlet, quin: quintet, and sext: sextet).

Hereafter, the "room temperature" in the following Examples indicates 25° C.

In the examples of synthesizing individual compounds, each step in the synthesis of the compound was repeated multiple times, as necessary, so that the compound could be obtained in an amount necessary for use as an intermediate or the like in other syntheses.

(Example 1) Synthesis of Compound 100

In accordance with the scheme shown in FIG. 1, Compound 100 was synthesized.

Synthesis of 3,5-pyridinedimethanol (Compound 2)

3,5-Pyridinedicarboxylic acid (Compound 1) (836 mg, 5.00 mmol) was dissolved in tetrahydrofuran (15 mL), and a tetrahydrofuran solution of borane-tetrahydrofuran (1 mol/L, 25 mL, 25 mmol) was added dropwise to the above-obtained solution at 0° C. over 1 hour. Thereafter, the obtained mixture was stirred in an argon atmosphere at a room temperature for 3 days. After completion of the reaction, 6 mol/L hydrochloric acid (5 mL) was added to the reaction solution, and the obtained mixture was then stirred for 10 minutes. Thereafter, a 4 mol/L sodium hydroxide aqueous solution (10 mL) was added to the reaction mixture, so as to adjust the pH to pH 9. The reaction solution was concentrated under a reduced pressure, and the obtained crude product was then purified by silica gel chromatography (chloroform/methanol=5/1 (volume ratio)) to obtain Compound 2 (335 mg, 2.41 mmol, and yield: 48%).

$^1$H-NMR of Compound 2 (solvent: deuterated dimethyl sulfoxide, resonance frequency: 500 MHz) δ: 8.38 (d, J=2.0 Hz, 2H), 7.67 (s, 1H), 5.31 (t, J=5.7 Hz, 2H), 4.53 (d, J=5.7 Hz, 4H).

Synthesis of 5-hydroxymethyl-3-pyridinecarboxaldehyde (Compound 3)

Compound 2 (141 mg, 1.01 mmol) was dissolved in N,N'-dimethylformamide (2 mL) and dichloromethane (8 mL), and manganese dioxide (878 mg, 10.1 mmol) was then added to the above-obtained solution at a room temperature. The obtained mixture was stirred overnight in an argon atmosphere at the same temperature as described above. After completion of the reaction, a solution obtained by filtration of the reaction solution through Celite was concentrated under a reduced pressure, and the obtained crude product was then purified by silica gel chromatography (chloroform/methanol=10/1 (volume ratio)) to obtain Compound 3 (85.0 mg, 0.620 mmol, and yield: 61%).

$^1$H-NMR of Compound 3 (solvent: deuterated chloroform, resonance frequency: 500 MHz) δ: 10.15 (s, 1H), 9.01 (d, J=2.1 Hz, 1H), 8.85 (d, J=2.1 Hz, 1H), 8.21 (t, J=2.1 Hz, 1H), 4.86 (d, J=5.7 Hz, 1H), 1.97 (t, J=5.7 Hz, 1H).

Synthesis of 1-chloro-2,5-difluoro-4-nitrobenzene (Compound 5)

2,5-Difluoro-1-chlorobenzene (Compound 4) (1.10 mL, 10.0 mmol) was dissolved in concentrated sulfuric acid (12 mL), and potassium nitrate (1.12 g, 11.0 mmol) was then added to the solution under cooling on ice. The obtained mixture was stirred overnight in an argon atmosphere at a room temperature. After completion of the reaction, water was added to the reaction solution, and the obtained mixture was then extracted with dichloromethane three times. The combined dichloromethane layer was dried over anhydrous sodium sulfate, and was then concentrated under a reduced pressure, so as to obtain Compound 5 (1.98 g, 10.3 mmol, quantitative).

$^1$H-NMR of Compound 5 (solvent: deuterated chloroform, resonance frequency: 500 MHz) δ: 7.94 (dd, J=6.7, 1.1 Hz, 1H), 7.43 (dd, J=5.9, 3.9 Hz, 1H).

Synthesis of 5-chloro-4-fluoro-N-(2-fluoroethyl)-2-nitrobenzenamine (6)

Compound 5 (404 mg, 2.09 mmol) was dissolved in N,N'-dimethyl sulfoxide (10 mL), and triethylamine (1.19 mL, 6.27 mmol) and 2-fluoroethylamine hydrochloride (311 mg, 3.13 mmol) were then added to the above-obtained solution at a room temperature. The obtained mixture was stirred in an argon atmosphere at 50° C. for 2 hours. After completion of the reaction, water was added to the reaction solution, and the obtained mixture was then extracted with ethyl acetate three times. The combined ethyl acetate layer was dried over anhydrous sodium sulfate, and was then concentrated under a reduced pressure, so as to obtain Compound 6 (503 mg, 2.12 mmol, quantitative).

$^1$H-NMR of Compound 6 (solvent: deuterated chloroform, resonance frequency: 500 MHz) δ: 8.11 (s, 1H), 8.02 (d, J=9.2 Hz, 1H), 6.94 (d, J=6.2 Hz, 1H), 4.70 (dt, J=47, 4.9 Hz, 2H), 3.63 (dq, J=25, 4.9 Hz, 2H).

Synthesis of 5-chloro-4-fluoro-N-(2-fluoroethyl)-1,6-phenylenediamine (Compound 7)

Compound 6 (30 mg, 0.127 mmol) was dissolved in ethyl acetate (1.3 mL), and tin(II) chloride (120 mg, 0.634 mmol) and water (0.0229 mL, 0.127 mmol) were then added to the above-obtained solution. The obtained mixture was heated to reflux in an argon atmosphere for 2 hours. After completion of the reaction, a saturated sodium hydrogen carbonate aqueous solution was added to the reaction solution, and the precipitated solid was then filtrated. The obtained filtrate was extracted with ethyl acetate three times. The combined ethyl acetate layer was dried over anhydrous sodium sulfate, and was then concentrated under a reduced pressure. The obtained crude product was purified by silica gel chromatography (hexane/dichloromethane=1/2 (volume ratio), so as to obtain Compound 7 (22.8 mg, 0.110 mmol, and yield: 86%).

$^1$H-NMR of Compound 7 (solvent: deuterated chloroform, resonance frequency: 500 MHz) δ: 6.62 (d, J=7.0 Hz, 1H), 6.53 (d, J=10 Hz, 1H), 4.66 (dt, J=47.3, 4.8 Hz, 2H), 3.51 (s, 2H), 3.34 (dq, J=27, 4.8 Hz, 2H).

Synthesis of 5-[6-chloro-5-fluoro-1-(2-fluoroethyl)benzimidazol-2-yl]pyridine-3-methanol (Compound 8)

5-Hydroxymethyl-3-pyridinecarboxaldehyde (Compound 3) (125 mg, 0.909 mmol) was dissolved in N,N'-dimethylformamide (7 mL), and thereafter, Compound 7 (207 mg, 1.00 mmol) and potassium peroxymonosulfate (Oxone (registered trademark) Monopersulfate Compound, manufactured by Wako Pure Chemical Industries, Ltd.) (671 mg, 1.09 mmol) were added to the above-obtained solution at a room temperature. The obtained mixture was stirred in an argon atmosphere at the same temperature as described above for 30 minutes. After completion of the reaction, a saturated sodium thiosulfate aqueous solution and a saturated sodium hydrogen carbonate aqueous solution were added to the reaction solution at 0° C., and the obtained mixture was then extracted with ethyl acetate three times. The combined ethyl acetate layer was dried over anhydrous sodium sulfate, and was then concentrated under a reduced pressure. The obtained crude product was purified by silica gel chromatography (ethyl acetate→ethyl acetate/methanol=9/1 (volume ratio)) to obtain Compound 8 (199 mg, 0.616 mmol, and yield: 68%).

$^1$H-NMR of Compound 8 (solvent: deuterated chloroform, resonance frequency: 500 MHz) δ: 8.87 (d, J=2.1 Hz, 1H), 8.78 (d, J=1.9 Hz, 1H), 8.13 (s, 1H), 7.60 (d, J=9.1 Hz, 1H), 7.50 (d, J=6.3 Hz, 1H), 4.87 (d, J=5.6 Hz, 1H), 4.80 (dt, J=47, 4.8 Hz, 2H), 4.51 (dt, J=25, 4.9 Hz, 2H).

Synthesis of Compound 100

Compound 8 (60.0 mg, 0.185 mmol) was dissolved in dichloromethane (2.5 mL), and carbon tetrabromide (92.2 mg, 0.278 mmol) and triphenylphosphine (97.0 mg, 0.370 mmol) were then added to the above-obtained solution at 0° C. The obtained mixture was stirred in an argon atmosphere at the same temperature as described above for 2 hours. After completion of the reaction, the reaction solution was concentrated under a reduced pressure, and the obtained crude product was then purified by silica gel chromatography (ethyl acetate), so as to obtain a mixture (54.0 mg) containing 2-(5-bromomethylpyridin-3-yl)-6-chloro-5-fluoro-1-(2-fluoroethyl)benzimidazole (Compound 8A) was obtained.

Subsequently, imidazole (11.4 mg, 0.168 mmol) was dissolved in N,N'-dimethylformamide (0.7 mL), and sodium hydride (11.2 mg, 0.280 mmol) was then added to the solution at 0° C. The obtained mixture was stirred in an argon atmosphere at the same temperature as described above for 10 minutes. An N,N'-dimethylformamide solution (0.7 mL), in which the mixture (54.0 mg) containing Compound 8A had been dissolved, was added to the reaction solution at the same temperature as described above, and the thus obtained mixture was then stirred in an argon atmosphere at a room temperature for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (dichloromethane/methanol=10/1→5/1 (volume ratio)) to obtain Compound 100 (12.1 mg, 0.0324 mmol, two-step yield from Compound 8: 17%).

$^1$H-NMR of Compound 100 (solvent: deuterated chloroform, resonance frequency: 500 MHz) δ: 8.94 (d, J=2.0 Hz, 1H), 8.66 (d, J=2.0 Hz, 1H), 7.85 (t, J=2.0 Hz, 1H), 7.62 (s, 1H), 7.59 (d, J=9.1 Hz, 1H), 7.47 (d, J=6.2 Hz, 1H), 7.15 (s, 1H), 6.96 (s, 1H), 5.27 (s, 2H), 4.81 (t, J=4.7 Hz, 1H), 4.72 (t, J=4.7 Hz, 1H), 4.44 (t, J=4.7 Hz, 1H), 4.39 (t, J=4.7 Hz, 1H).

(Example 2) Synthesis of Compound [$^{18}$F] 100

Figure 2:
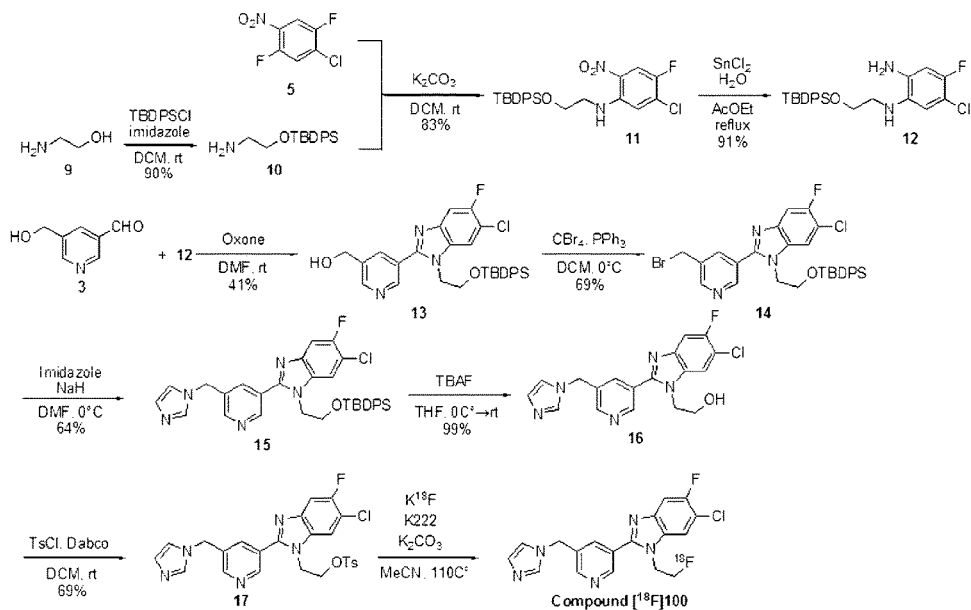
FIG. 2 is a drawing showing a synthesis example of 6-chloro-5-fluoro-1-(2-[$^{18}$F]fluoroethyl)-2-[5-(imidazol-1-ylmethyl)pyridin-3-yl]benzimidazole.

Compound [$^{18}$F] 100 was synthesized in accordance with the scheme shown in FIG. 2.

Synthesis of 2-(tert-butyldiphenylsilyloxy)ethylamine (Compound 10)

2-Aminoethanol (Compound 9) (0.729 mL, 12.0 mmol) was dissolved in dichloromethane (10 mL), and thereafter, 2.60 mL (10 mmol) of tert-butyldiphenylchlorosilane and imidazole (1.20 g, 15.0 mmol) were added to the solution at a room temperature. The obtained mixture was stirred overnight in an argon atmosphere at the same temperature as described above. After completion of the reaction, water was added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (ethyl acetate→ethyl acetate/methanol=10/1 (volume ratio)) to obtain Compound 10 (2.70 g, 9.00 mmol, and yield: 90%).

$^1$H-NMR of Compound 10 (solvent: deuterated chloroform, resonance frequency: 500 MHz) δ: 7.68-7.66 (m, 4H), 7.44-7.36 (m, 6H), 3.68 (t, J=5.3 Hz, 2H), 2.81 (t, J=5.3 Hz, 2H), 1.07 (s, 9H).

Synthesis of N-(5-chloro-4-fluoro-2-nitrophenyl)-2-(tert-butyldiphenylsilyloxy)ethylamine (Compound 11)

Compound 5 (1.94 g, 10.0 mmol) obtained by the method described in Example 1 was dissolved in dichloromethane (10 mL), and Compound 10 (3.29 g, 11.0 mmol) and potassium carbonate (2.07 g, 15.0 mmol) were then added to the solution at a room temperature. The obtained mixture was stirred overnight in an argon atmosphere at the same temperature as described above. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (hexane→hexane/ethyl acetate=20/1 (volume ratio)) to obtain Compound 11 (3.92 g, 8.28 mmol, and yield: 83%).

$^1$H-NMR of Compound 11 (solvent: deuterated chloroform, resonance frequency: 500 MHz) δ: 8.28 (bs, 1H), 7.99 (d, J=9.3 Hz, 1H), 7.66-7.64 (m, 4H), 7.45-7.36 (m, 6H), 6.88 (d, J=6.3 Hz, 1H), 3.90 (t, J=5.3 Hz, 2H), 3.40 (t, J=5.3 Hz, 2H), 1.06 (s, 9H).

Synthesis of 3-chloro-4-fluoro-N-[2-(tert-butyldiphenylsilyloxy)ethyl]-1,6-phenylenediamine (Compound 12)

Compound 11 (1.42 g, 3.00 mmol) was dissolved in ethyl acetate (10 mL), and tin(II) chloride (2.28 g, 12.0 mmol) and water (0.216 mL, 12.0 mmol) were then added to the solution. The obtained mixture was heated to reflux in an argon atmosphere for 4 hours. After completion of the reaction, a 4 mol/L sodium hydroxide aqueous solution was added to the reaction solution, and the precipitated deposit was then filtrated. The obtained filtrate was extracted with ethyl acetate twice. The combined ethyl acetate layer was dried over anhydrous sodium sulfate, and was then concentrated under a reduced pressure. The obtained crude product was purified by silica gel chromatography (hexane/ethyl acetate=5/1 (volume ratio)) to obtain Compound 12 (1.21 g, 2.74 mmol, and yield: 91%).

$^1$H-NMR of Compound 12 (solvent: deuterated chloroform, resonance frequency: 500 MHz) δ: 7.67-7.65 (m, 4H), 7.45-7.37 (m, 6H), 6.56 (d, J=7.1 Hz, 1H), 6.51 (d, J=10.1 Hz, 1H), 3.90 (t, J=5.2 Hz, 2H), 3.61 (s, 1H), 3.46 (s, 2H), 3.15 (s, 2H), 1.07 (s, 9H).

Synthesis of 5-{6-chloro-5-fluoro-1-[2-(tert-butyldiphenylsilyloxy)ethyl]benzimidazol-2-yl}pyridine-3-methanol (Compound 13)

Compound 3 (205 mg, 1.50 mmol) obtained by the method described in Example 1 was dissolved in N,N'-dimethylformamide (5 mL), and thereafter, an N,N'-dimethylformamide solution (5 mL), in which Compound 12 (665 mg, 1.50 mmol) had been dissolved, and potassium peroxymonosulfate (Oxone (registered trademark) Monopersulfate Compound, manufactured by Wako Pure Chemical Industries, Ltd.) (1.11 g, 1.80 mmol) were added to the above-obtained solution at a room temperature. The obtained mixture was stirred in an argon atmosphere at the same temperature as described above for 3 days. After completion of the reaction, a saturated sodium thiosulfate aqueous solution and a saturated sodium hydrogen carbonate aqueous solution were added to the reaction solution, the obtained mixture was then stirred for 1 hour, and the reaction mixture was then extracted with ethyl acetate twice. The combined ethyl acetate layer was dried over anhydrous sodium sulfate, and was then concentrated under a reduced pressure. The obtained crude product was purified by silica gel chromatography (ethyl acetate→ethyl acetate/methanol=20/1 (volume ratio)) to obtain Compound 13 (341 mg, 0.609 mmol, and yield: 41%).

$^1$H-NMR of Compound 13 (solvent: deuterated chloroform, resonance frequency: 500 MHz) δ: 8.94 (d, J=2.1 Hz, 1H), 8.73 (d, J=2.1 Hz, 1H), 8.11 (t, J=2.1 Hz, 1H), 7.59 (d, J=9.2 Hz, 1H), 7.42-7.36 (m, 6H), 7.30-7.27 (m, 5H), 4.77 (d, J=5.9 Hz, 2H), 4.39 (t, J=5.4 Hz, 2H), 3.94 (t, J=5.4 Hz, 2H), 1.99 (t, J=5.9 Hz, 1H), 0.89 (s, 9H).

Synthesis of 2-(5-bromomethylpyridin-3-yl)-6-chloro-5-fluoro-1-[2-(tert-butyldiphenylsilyloxy)ethyl]benzimidazole (Compound 14)

Compound 13 (272 mg, 0.486 mmol) was dissolved in dichloromethane (6 mL), and carbon tetrabromide (242 mg, 0.728 mmol) and triphenylphosphine (255 mg, 0.972 mmol) were then added to the solution at 0° C. The obtained mixture was stirred in an argon atmosphere at the same temperature as described above for 1 hour. After completion of the reaction, the reaction solution was concentrated under a reduced pressure, and the obtained crude product was then purified by silica gel chromatography (ethyl acetate/hexane=2/1 (volume ratio)) to obtain Compound 14 (212 mg, 0.340 mmol, and yield: 69%).

$^1$H-NMR of Compound 14 (solvent: deuterated chloroform, resonance frequency: 500 MHz) δ: 8.97 (d, J=2.2 Hz, 1H), 8.75 (d, J=2.2 Hz, 1H), 8.18 (t, J=2.2 Hz, 1H), 7.60 (d, J=9.2 Hz, 1H), 7.42-7.37 (m, 6H), 7.30-7.26 (m, 5H), 4.47 (s, 2H), 4.38 (t, J=5.4 Hz, 2H), 3.97 (t, J=5.4 Hz, 2H), 0.90 (s, 9H).

Synthesis of 6-chloro-5-fluoro-2-[5-(imidazol-1-ylmethyl)pyridin-3-yl]-1-[2-(tert-butyldiphenylsilyloxy)ethyl]benzimidazole (Compound 15)

Imidazole (27.5 mg, 0.404 mmol) was dissolved in N,N'-dimethylformamide (1 mL), and sodium hydride (20.2 mg, 0.506 mmol) was then added to the solution at 0° C. The obtained mixture was stirred in an argon atmosphere at the same temperature as described above for 10 minutes. An N,N'-dimethylformamide solution (1.5 mL), in which Compound 14 (210 mg, 0.337 mmol) had been dissolved, was added to the reaction solution at the same temperature as described above, and the thus obtained mixture was then stirred in an argon atmosphere at the same temperature as described above for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (dichloromethane/methanol=10/1 (volume ratio)) to obtain Compound 15 (132 mg, 0.216 mmol, and yield: 64%).

$^1$H-NMR of Compound 15 (solvent: deuterated chloroform, resonance frequency: 500 MHz) δ: 9.04 (d, J=2.1 Hz, 1H), 8.57 (d, J=2.1 Hz, 1H), 7.91 (t, J=2.1 Hz, 1H), 7.58 (d, J=9.2 Hz, 1H), 7.55 (s, 1H), 7.42-7.39 (m, 2H), 7.37-7.35 (m, 4H), 7.30-7.26 (m, 5H), 7.10 (s, 1H), 6.87 (s, 1H), 5.15 (s, 2H), 4.33 (t, J=5.4 Hz, 2H), 3.94 (t, J=5.4 Hz, 2H), 0.89 (s, 9H).

Synthesis of 2-{6-chloro-5-fluoro-2-[5-(imidazol-1-ylmethyl)pyridin-3-yl]benzimidazol-1-yl}ethanol (Compound 16)

Compound 15 (130 mg, 0.213 mmol) was dissolved in tetrahydrofuran (0.2 mL), and a tetrahydrofuran solution (1 mol/L) of tetrabutylammonium fluoride (0.320 mL, 0.320 mmol) was then added to the solution at 0° C. The obtained mixture was stirred in an argon atmosphere at a room temperature for 1 hour. After completion of the reaction, the reaction solution was concentrated under a reduced pressure, and the obtained crude product was then purified by silica gel chromatography (dichloromethane/methanol=10/1→8/1→5/1 (volume ratio)) to obtain Compound 16 (79.0 mg, 0.212 mmol, and yield: 99%).

$^1$H-NMR of Compound 16 (solvent: deuterated chloroform, resonance frequency: 500 MHz) δ: 9.06 (d, J=2.1 Hz, 1H), 8.64 (d, J=2.1 Hz, 1H), 7.88 (t, J=2.1 Hz, 1H), 7.59 (s, 1H), 7.54-7.49 (m, 2H), 7.10 (s, 1H), 6.97 (s, 1H), 5.27 (s, 2H), 4.20 (t, J=5.5 Hz, 2H), 4.00 (t, J=5.5 Hz, 2H), 2.92 (s, 1H).

Synthesis of 6-chloro-5-fluoro-2-[5-(imidazol-1-ylmethyl)pyridin-3-yl]-1-[2-(p-toluenesulfonyloxy)ethyl]benzimidazole (Compound 17)

Compound 16 (60.0 mg, 0.161 mmol) was dissolved in dichloromethane (2.0 mL), and p-toluenesulfonyl chloride (61.4 mg, 0.322 mmol) and 1,4-diazabicyclo[2,2,2]octane (45.2 mg, 0.403 mmol) were then added to the solution. The obtained mixture was stirred overnight in an argon atmosphere at a room temperature. After completion of the reaction, the reaction mixture was purified by silica gel chromatography (chloroform/methanol=10/1 (volume ratio)) to obtain Compound 17 (58.5 mg, 0.111 mmol, and yield: 69%).

$^1$H-NMR of Compound 17 (solvent: deuterated chloroform, resonance frequency: 500 MHz) δ: 8.86 (d, J=2.2 Hz, 1H), 8.66 (d, J=2.2 Hz, 1H), 7.91 (t, J=2.2 Hz, 1H), 7.66 (s, 1H), 7.52 (d, J=9.1 Hz, 1H), 7.41 (d, J=8.2 Hz, 2H), 7.17-7.15 (m, 2H), 7.11 (d, J=8.2 Hz, 2H), 7.03 (t, J=1.2 Hz, 1H), 5.30 (s, 2H), 4.36 (t, J=5.2 Hz, 2H), 4.26 (t, J=5.2 Hz, 2H), 2.37 (s, 3H).

Synthesis of Compound [$^{18}$F] 100

[$^{18}$F] Fluoride ion-containing [$^{18}$O] water (radioactivity: 4540 MBq, correction value at initiation of the synthesis) was supplied to a Sep-Pak column (trade name: Sep-Pak (registered trademark) Light Cartridge Accell™ Plus QMA Carbonate, manufactured by Waters, the amount of filler: 130 mg), so that the [$^{18}$F] fluoride ion was adsorbed and captured in the column. To this column, a potassium carbonate aqueous solution (42.4 µmol/L, 0.3 mL) and an acetonitrile solution (0.7 mL) of KRYPTOFIX 222 (trade name, manufactured by Merck) (14 mg, 37.2 µmol) were supplied, so that the [$^{18}$F] fluoride ion was eluted. The resultant was heated to 110° C. under a stream of argon gas, so that water was evaporated. Thereafter, acetonitrile (0.5 mL×2) was added to the residue, and the obtained mixture was then azeotropically distilled to dryness. To this reaction mixture, an acetonitrile solution (0.3 mL), in which Compound 17 (5 mg, 0.00951 mmol) had been dissolved, was added, and the thus obtained mixture was then heated at 110° C. for 10 minutes. After completion of the reaction, 1 mol/L hydrochloric acid (0.5 mL) was added to the reaction solution, and the obtained mixture was then subjected to HPLC under the below-mentioned conditions, so that a fraction with the same retention time as Compound 100 obtained in Example 1 was obtained as a fraction of Compound [$^{18}$F] 100.

<HPLC Conditions>
Column: Capcell Pak C18 MG (trade name, manufactured by Shiseido Japan, Co., Ltd., size: 10×250 mm)
Mobile phase: 0.1% by volume of trifluoroacetic acid-containing water/0.1% by volume of trifluoroacetic acid-containing acetonitrile (volume ratio)=gradient from 80/20 to 20/80 over 40 minutes
Flow rate: 3.0 mL/min
Detector: ultraviolet visible spectrophotometer (detection wavelength: 260 nm)

A liquid prepared by adding 10 mL of water to the aforementioned fraction was supplied to a Sep-Pak C18 column (trade name: Sep-Pak (registered trademark) Light C18 Cartridges, manufactured by Waters, the amount of filler: 130 mg), so that Compound [$^{18}$F] 100 was adsorbed and captured in the column. This column was washed with water (1 mL), and diethyl ether (6 mL) was then supplied to the resulting column to elute Compound [$^{18}$F] 100. Thereafter, diethyl ether was distilled away to obtain Compound [$^{18}$F] 100. The obtained radioactivity was 720 MBq immediately after completion of the synthesis (107 minutes after initiation of the synthesis). Moreover, a TLC analysis was carried out under the below-mentioned conditions. As a result, the radiochemical purity was 99.3%.

<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 3) Synthesis of Compound 200

Figure 3:
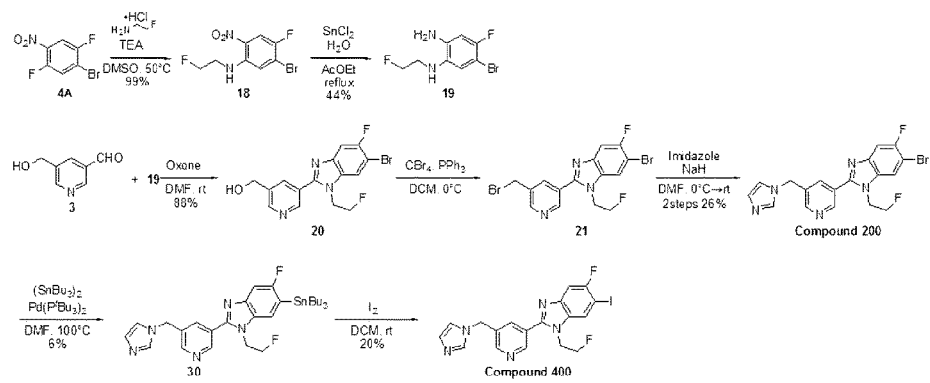
FIG. 3 is a drawing showing synthesis examples of 6-bromo-5-fluoro-1-(2-fluoroethyl)-2-[5-(imidazol-1-ylmethyl)pyridin-3-yl]benzimidazole and 5-fluoro-1-(2-fluoro-ethyl)-2-[5-(imidazol-1-ylmethyl)pyridin-3-yl]-6-iodobenzimidazole.

Compound 200 was synthesized in accordance with the scheme shown in FIG. 3.

Synthesis of 5-bromo-4-fluoro-N-(2-fluoroethyl)-2-nitrobenzenamine (Compound 18)

4-Bromo-2,5-difluoronitrobenzene (Compound 4A) (500 mg, 2.10 mmol) was dissolved in N,N'-dimethyl sulfoxide (10 mL), and triethylamine (1.20 mL, 6.30 mmol) and 2-fluoroethylamine hydrochloride (314 mg, 3.15 mmol) were then added to the solution at a room temperature. The obtained mixture was stirred in an argon atmosphere at 50° C. for 1.5 hours. After completion of the reaction, water was added to the reaction solution, and the obtained mixture was then extracted with ethyl acetate three times. The combined ethyl acetate layer was dried over anhydrous sodium sulfate, and was then concentrated under a reduced pressure, so as to obtain Compound 18 (585 mg, 2.08 mmol, and yield: 99%).

$^1$H-NMR of Compound 18 (solvent: deuterated chloroform, resonance frequency: 500 MHz) δ: 8.08 (s, 1H), 7.98 (d, J=8.6 Hz, 1H), 7.12 (d, J=5.7 Hz, 1H), 4.70 (dt, J=47, 4.9 Hz, 2H), 3.63 (dq, J=25, 4.9 Hz, 2H).

Synthesis of 5-bromo-4-fluoro-N-(2-fluoroethyl)-1,6-phenylenediamine (Compound 19)

Compound 18 (290 mg, 1.03 mmol) was dissolved in ethyl acetate (5.0 mL), and thereafter, tin(II) chloride (586 mg, 3.09 mmol) and water (0.0371 mL, 2.06 mmol) were added to the solution. The obtained mixture was heated to reflux in an argon atmosphere for 2 hours. Thereafter, tin(II) chloride (195 mg, 1.03 mmol) and water (0.0371 mL, 2.06 mmol) were further added to the reaction solution. The obtained mixture was heated to reflux in an argon atmosphere for 1 hour. After completion of the reaction, the reaction solution was concentrated under a reduced pressure, and the obtained crude product was then purified by silica gel chromatography (hexane/ethyl acetate=2/1 (volume ratio)) to obtain Compound 19 (113.0 mg, 0.450 mmol, and yield: 44%).

$^1$H-NMR of Compound 19 (solvent: deuterated chloroform, resonance frequency: 500 MHz) δ: 6.76 (d, J=6.6 Hz, 1H), 6.53 (d, J=9.5 Hz, 1H), 4.72-4.70 (m, 1H), 4.61 (t, J=4.7 Hz, 1H), 3.59 (bs, 2H), 3.40-3.37 (m, 2H), 3.33-3.30 (m, 1H).

Synthesis of 5-[6-bromo-5-fluoro-1-(2-fluoroethyl) benzimidazol-2-yl]pyridine-3-methanol (Compound 20)

Compound 3 (66.1 mg, 0.482 mmol) obtained by the method described in Example 1 was dissolved in N,N'-dimethylformamide (2.0 mL), and thereafter, Compound 19 (110 mg, 0.438 mmol) and potassium peroxymonosulfate (Oxone (registered trademark) Monopersulfate Compound, manufactured by Wako Pure Chemical Industries, Ltd.) (405 mg, 0.657 mmol) were added to the above-obtained solution at a room temperature. The obtained mixture was stirred in an argon atmosphere at the same temperature as described above for 2 hours. After completion of the reaction, a saturated sodium thiosulfate aqueous solution and a saturated sodium hydrogen carbonate aqueous solution were added to the reaction solution at 0° C., and the obtained mixture was then extracted with ethyl acetate three times. The combined ethyl acetate layer was dried over anhydrous sodium sulfate, and was then concentrated under a reduced pressure. The obtained crude product was purified by silica gel chromatography (chloroform/methanol=10/1 (volume ratio)) to obtain Compound 20 (142 mg, 0.386 mmol, and yield: 88%).

$^1$H-NMR of Compound 20 (solvent: deuterated chloroform, resonance frequency: 500 MHz) δ: 8.87 (d, J=2.1 Hz, 1H), 8.77 (d, J=2.1 Hz, 1H), 8.13 (s, 1H), 7.65 (d, J=5.8 Hz, 1H), 7.59 (d, J=8.7 Hz, 1H), 4.87-4.83 (m, 3H), 4.75 (t, J=4.8 Hz, 1H), 4.53 (t, J=4.8 Hz, 1H), 4.48 (t, J=4.8 Hz, 1H), 1.99 (d, J=5.6 Hz, 1H).

Synthesis of Compound 200

Compound 20 (140 mg, 0.380 mmol) was dissolved in dichloromethane (5.0 mL), and thereafter, carbon tetrabromide (189 mg, 0.570 mmol) and triphenylphosphine (199 mg, 0.760 mmol) were added to the solution at 0° C. The obtained mixture was stirred in an argon atmosphere at the same temperature as described above for 30 minutes. After completion of the reaction, the reaction solution was concentrated under a reduced pressure, and the obtained crude product was then purified by silica gel chromatography (chloroform/methanol=100/3 (volume ratio)), so as to obtain a mixture (300 mg) containing 2-(5-bromomethylpyridin-3-yl)-6-bromo-5-fluoro-1-(2-fluoroethyl)benzimidazole (Compound 21).

Imidazole (28.5 mg, 0.418 mmol) was dissolved in N,N'-dimethylformamide (0.5 mL), and thereafter, sodium hydride (18.2 mg, 0.456 mmol) and an N,N'-dimethylformamide solution (1.5 mL), in which the mixture (300 mg) containing Compound 21 had been dissolved, were added at 0° C. to the above-obtained solution. The obtained mixture was stirred in an argon atmosphere at 0° C. for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (chloroform/methanol=100/3→20/1→10/1 (volume ratio)) to obtain Compound 200 (41.5 mg, 0.0992 mmol, two-step yield from Compound 20: 26%).

$^1$H-NMR of Compound 200 (solvent: deuterated chloroform, resonance frequency: 500 MHz) δ: 8.94 (d, J=2.1 Hz, 1H), 8.66 (d, J=2.1 Hz, 1H), 7.85 (s, 1H), 7.63-7.57 (m, 3H), 7.15 (s, 1H), 6.96 (s, 1H), 5.27 (s, 2H), 4.81 (t, J=4.7 Hz, 1H), 4.72 (t, J=4.7 Hz, 1H), 4.44 (t, J=4.7 Hz, 1H), 4.39 (t, J=4.7 Hz, 1H).

(Example 4) Synthesis of Compound [$^{18}$F] 200

Figure 4:
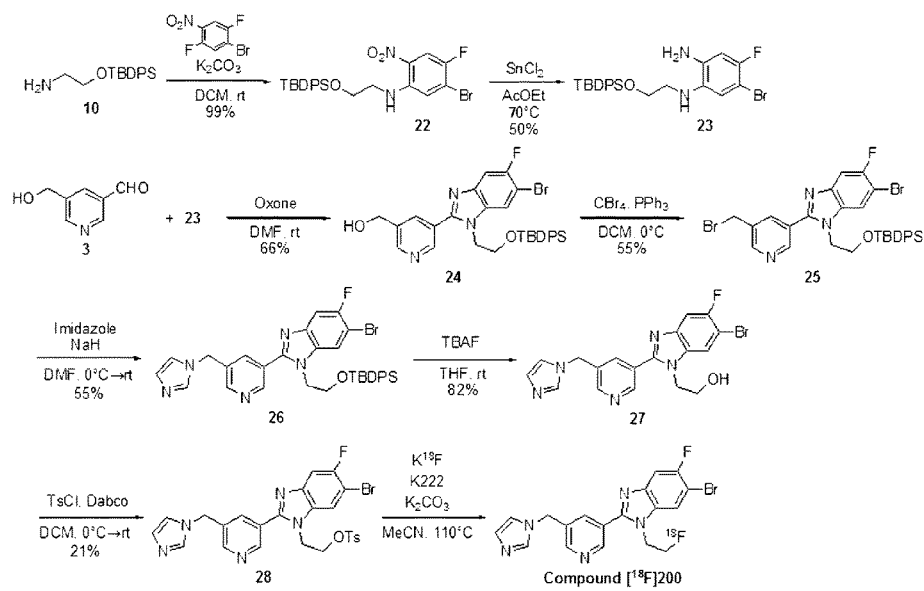
FIG. 4 is a drawing showing a synthesis example of 6-bromo-5-fluoro-1-(2-[$^{18}$F]fluoroethyl)-2-[5-(imidazol-1-ylmethyl)pyridin-3-yl]benzimidazole.

Compound [$^{18}$F] 200 was synthesized in accordance with the scheme shown in FIG. 4.

Synthesis of N-(5-bromo-4-fluoro-2-nitrophenyl)-2-(tert-butyldiphenylsilyloxy)ethylamine (Compound 22)

4-Bromo-2,5-difluoronitrobenzene (476 mg, 2.00 mmol) was dissolved in dichloromethane (5.0 mL), and thereafter, Compound 10 (749 mg, 2.50 mmol) obtained by the method described in Example 2 and potassium carbonate (553 mg, 4.00 mmol) were added to the above-obtained solution at a room temperature. The obtained mixture was stirred in an argon atmosphere at the same temperature as described above for three nights. After completion of the reaction, water was added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (hexane/ethyl acetate=5/1), so as to obtain Compound 22 (1.03 g, 1.99 mmol, and yield: 99%).

$^1$H-NMR of Compound 22 (solvent: deuterated chloroform, resonance frequency: 500 MHz) δ: 8.25 (bs, 1H), 7.95 (d, J=8.8 Hz, 1H), 7.66-7.64 (m, 4H), 7.45-7.36 (m, 6H), 7.06 (d, J=5.8 Hz, 1H), 3.90 (t, J=5.3 Hz, 2H), 3.41 (t, J=5.3 Hz, 2H), 1.06 (s, 9H).

Synthesis of 3-bromo-4-fluoro-N-[2-(tert-butyldiphenylsilyloxy)ethyl]-1,6-phenylenediamine (Compound 23)

Compound 22 (555 mg, 1.07 mmol) was dissolved in ethyl acetate (6.0 mL), and tin(II) chloride (1.02 g, 5.36 mmol) was then added to the solution at a room temperature. The obtained mixture was stirred overnight in an argon atmosphere at the same temperature as described above. Thereafter, the reaction solution was stirred in an argon atmosphere at 70° C. for 2 hours. Thereafter, tin(II) chloride (468 mg, 2.15 mmol) was added to the reaction solution, and the obtained mixture was then stirred in an argon atmosphere at 70° C. for 2 hours. After completion of the reaction, the reaction solution was concentrated under a reduced pressure, and the obtained crude product was then purified by silica gel chromatography (hexane/ethyl acetate=6/1→3/1 (volume ratio)) to obtain Compound 23 (257 mg, 0.527 mmol, and yield: 50%).

$^1$H-NMR of Compound 23 (solvent: deuterated chloroform, resonance frequency: 500 MHz) δ: 7.67-7.66 (m, 4H), 7.45-7.37 (m, 6H), 6.69 (d, J=6.6 Hz, 1H), 6.51 (d, J=9.6 Hz, 1H), 3.90 (t, J=5.1 Hz, 2H), 3.59 (bs, 1H), 3.49 (s, 2H), 3.15 (t, J=5.1 Hz, 2H), 1.07 (s, 9H).

Synthesis of 5-{6-bromo-5-fluoro-1-[2-(tert-butyldiphenylsilyloxy)ethyl]benzimidazol-2-yl}pyridine-3-methanol (Compound 24)

Compound 3 (150 mg, 1.09 mmol) obtained by the method described in Example 1 was dissolved in N,N'-dimethylformamide (2.0 mL), and thereafter, an N,N'-dimethylformamide solution (2.0 mL), in which Compound 23 (290 mg, 0.600 mmol) had been dissolved, and potassium peroxymonosulfate (Oxone (registered trademark) Monopersulfate Compound, manufactured by Wako Pure Chemical Industries, Ltd.) (553 mg, 0.900 mmol) were added to the above-obtained solution at a room temperature. The obtained mixture was stirred overnight in an argon atmosphere at the same temperature as described above. After completion of the reaction, a saturated sodium thiosulfate aqueous solution and a 10% potassium carbonate aqueous solution were added to the reaction solution, and the obtained mixture was then extracted with ethyl acetate twice. The combined ethyl acetate layer was washed with water, and it was dried over anhydrous sodium sulfate, and was then concentrated under a reduced pressure. The obtained crude product was purified by silica gel chromatography (dichloromethane/methanol=20/1 (volume ratio)) to obtain Compound 24 (240 mg, 0.397 mmol, and yield: 66%).

$^1$H-NMR of Compound 24 (solvent: deuterated chloroform, resonance frequency: 500 MHz) δ: 8.94 (d, J=2.1 Hz, 1H), 8.73 (d, J=2.1 Hz, 1H), 8.12 (s, 1H), 7.58 (d, J=8.8 Hz, 1H), 7.47 (d, J=5.9 Hz, 1H), 7.40-7.36 (m, 6H), 7.30-7.27 (m, 4H), 4.78 (d, J=5.9 Hz, 2H), 4.39 (t, J=5.4 Hz, 2H), 3.94 (t, J=5.4 Hz, 2H), 1.84 (t, J=5.9 Hz, 1H), 0.89 (s, 9H).

Synthesis of 6-bromo-2-(5-bromomethylpyridin-3-yl)-5-fluoro-1-[2-(tert-butyldiphenylsilyloxy)ethyl]benzimidazole (Compound 25)

Compound 24 (203 mg, 0.335 mmol) was dissolved in dichloromethane (5.0 mL), and thereafter, carbon tetrabromide (167 mg, 0.502 mmol) and triphenylphosphine (176 mg, 0.670 mmol) were added at 0° C. to the solution. The obtained mixture was stirred in an argon atmosphere at the same temperature as described above for 4 hours. After completion of the reaction, the reaction solution was concentrated under a reduced pressure, and the obtained crude product was then purified by silica gel chromatography (ethyl acetate/hexane=2/1 (volume ratio)) to obtain Compound 25 (123 mg, 0.184 mmol, and yield: 55%).

$^1$H-NMR of Compound 25 (solvent: deuterated chloroform, resonance frequency: 500 MHz) δ: 8.97 (d, J=2.1 Hz, 1H), 8.75 (d, J=2.1 Hz, 1H), 8.18 (t, J=2.1 Hz, 1H), 7.59 (d, J=8.8 Hz, 1H), 7.45 (d, J=5.9 Hz, 1H), 7.42-7.37 (m, 6H), 7.31-7.27 (m, 4H), 4.47 (s, 2H), 4.38 (t, J=5.3 Hz, 2H), 3.97 (t, J=5.3 Hz, 2H), 0.90 (s, 9H).

Synthesis of 6-bromo-5-fluoro-2-[5-(imidazol-1-ylmethyl)pyridin-3-yl]-1-[2-(tert-butyldiphenylsilyloxy)ethyl]benzimidazole (Compound 26)

Imidazole (6.4 mg, 0.0942 mmol) was dissolved in N,N'-dimethylformamide (0.5 mL), and sodium hydride (3.1 mg, 0.129 mmol) was then added at 0° C. to the solution. The obtained mixture was stirred in an argon atmosphere at the same temperature as described above for 10 minutes. Thereafter, an N,N'-dimethylformamide solution (0.5 mL), in which Compound 25 (57.2 mg, 0.860 mmol) had been dissolved, was added to the reaction solution at the same temperature as described above. The obtained mixture was stirred overnight in an argon atmosphere at a room temperature. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (dichloromethane/methanol=20/1 (volume ratio)) to obtain Compound 26 (31.1 mg, 0.0475 mmol, and yield: 55%).

$^1$H-NMR of Compound 26 (solvent: deuterated chloroform, resonance frequency: 500 MHz) δ: 9.05 (d, J=2.1 Hz, 1H), 8.57 (d, J=2.1 Hz, 1H), 7.91 (t, J=2.1 Hz, 1H), 7.58-7.55 (m, 2H), 7.44 (d, J=5.9 Hz, 1H), 7.42-7.36 (m, 6H), 7.30-7.27 (m, 4H), 7.09 (s, 1H), 6.87 (s, 1H), 5.15 (s, 2H), 4.33 (t, J=5.3 Hz, 2H), 3.94 (t, J=5.3 Hz, 2H), 0.89 (s, 9H).

Synthesis of 2-{6-bromo-5-fluoro-2-[5-(imidazol-1-ylmethyl)pyridin-3-yl]benzimidazol-1-yl}ethanol (Compound 27)

Compound 26 (29.8 mg, 0.0455 mmol) was dissolved in tetrahydrofuran (0.50 mL), and thereafter, tetrabutylammonium fluoride (0.0682 mL, 1 mol/L tetrahydrofuran solution, 0.0682 mmol) was added to the solution at a room temperature. The obtained mixture was stirred in an argon atmosphere at a room temperature for 1 hour. After completion of the reaction, the reaction solution was concentrated under a reduced pressure, and the obtained crude product was then purified by silica gel chromatography (dichloromethane/methanol=10/1→5/1 (volume ratio)) to obtain Compound 27 (15.6 mg, 0.0375 mmol, and yield: 82%).

$^1$H-NMR of Compound 27 (solvent: deuterated chloroform, resonance frequency: 500 MHz) δ: 9.02 (d, J=2.1 Hz, 1H), 8.58 (d, J=2.1 Hz, 1H), 7.97 (t, J=2.1 Hz, 1H), 7.62 (d, J=5.9 Hz, 1H), 7.51 (s, 1H), 7.42 (s, 1H), 7.00 (s, 1H), 6.94 (s, 1H), 5.21 (s, 2H), 4.36 (bs, 1H), 4.19 (t, J=5.2 Hz, 2H), 4.00 (t, J=5.2 Hz, 2H).

Synthesis of 6-bromo-5-fluoro-2-[5-(imidazol-1-ylmethyl)pyridin-3-yl]-1-[2-(tosyloxy)ethyl]benzimidazole (Compound 28)

Compound 27 (15.0 mg, 0.0360 mmol) was dissolved in dichloromethane (0.50 mL), and thereafter, p-toluenesulfonyl chloride (10.3 mg, 0.0540 mmol) and 1,4-diazabicyclo[2,2,2]octane (8.1 mg, 0.0720 mmol) were added at 0° C. to the above-obtained solution. The obtained mixture was stirred in an argon atmosphere at the same temperature as described above for 2 hours. Thereafter, the reaction mixture was stirred at a room temperature for 2 hours, and after that, p-toluenesulfonyl chloride (6.9 mg, 0.0360 mmol) and 1,4-diazabicyclo[2,2,2]octane (4.9 mg, 0.0480 mmol) were added to the reaction solution. The thus obtained mixture was stirred overnight at the same temperature as described above. After completion of the reaction, the reaction mixture was purified by silica gel chromatography (dichloromethane/methanol=10/1 (volume ratio)) to obtain Compound 28 (4.3 mg, 0.00754 mmol, and yield: 21%).

$^1$H-NMR of Compound 28 (solvent: deuterated chloroform, resonance frequency: 500 MHz) δ: 8.87 (d, J=2.1 Hz, 1H), 8.66 (d, J=2.1 Hz, 1H), 7.92 (t, J=2.1 Hz, 1H), 7.67 (s, 1H), 7.50 (d, J=8.6 Hz, 1H), 7.40 (d, J=8.2 Hz, 2H), 7.31 (d, J=5.8 Hz, 1H), 7.16 (s, 1H), 7.10 (d, J=8.2 Hz, 2H), 7.03 (s, 1H), 5.30 (s, 2H), 4.36 (t, J=5.1 Hz, 2H), 4.26 (t, J=5.1 Hz, 2H), 2.36 (s, 3H).

Synthesis of Compound [$^{18}$F] 200

[$^{18}$F] Fluoride ion-containing [$^{18}$O] water (radioactivity: 5150 MBq, correction value at initiation of the synthesis) was supplied to a Sep-Pak column (trade name: Sep-Pak (registered trademark) Light Cartridge Accell™ Plus QMA Carbonate, manufactured by Waters, the amount of filler: 130 mg), so that the [$^{18}$F] fluoride ion was adsorbed and captured in the column. To this column, a potassium carbonate aqueous solution (42.4 μmol/L, 0.3 mL) and an acetonitrile solution (0.7 mL) of KRYPTOFIX 222 (trade name, manufactured by Merck) (14 mg, 37.2 μmol) were supplied, so that the [$^{18}$F] fluoride ion was eluted. The resultant was heated to 110° C. under a stream of argon gas, so that water was evaporated. Thereafter, acetonitrile (0.5 mL×2) was added to the residue, and the obtained mixture was then azeotropically distilled to dryness. To this reaction mixture, an acetonitrile solution (0.3 mL), in which Compound 28 (4.3 mg, 0.00754 mmol) had been dissolved, was added, and the thus obtained mixture was then heated at 110° C. for 10 minutes. After completion of the reaction, water for injection (1.0 mL) was added to the reaction solution, and the obtained mixture was then subjected to HPLC under the below-mentioned conditions, so that a fraction with the same retention time as Compound 200 obtained in Example 3 was obtained as a fraction of Compound [$^{18}$F] 200.
<HPLC Conditions>
Column: Capcell Pak C18 MG (trade name, manufactured by Shiseido Japan, Co., Ltd., size: 10×250 mm)
Mobile phase: 0.1% by volume of trifluoroacetic acid-containing water/0.1% by volume of trifluoroacetic acid-containing acetonitrile (volume ratio)=gradient from 80/20 to 20/80 over 40 minutes
Flow rate: 3.0 mL/min
Detector: ultraviolet visible spectrophotometer (detection wavelength: 260 nm)

A liquid prepared by adding water (10 mL) to the aforementioned fraction was supplied to a Sep-Pak C18 column (trade name: Sep-Pak (registered trademark) Light C18 Cartridges, manufactured by Waters, the amount of filler: 130 mg), so that Compound [$^{18}$F] 200 was adsorbed and captured in the column. This column was washed with water (1 mL), and diethyl ether (6 mL) was then supplied to the resulting column to elute Compound [$^{18}$F] 200. Thereafter, diethyl ether was distilled away to obtain Compound [$^{18}$F] 200. The obtained radioactivity was 23.3 MBq immediately after completion of the synthesis (121 minutes after initiation of the synthesis). Moreover, a TLC analysis was carried out under the below-mentioned conditions. As a result, the radiochemical purity was 100%.
<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 5) Synthesis of Compound 300

Figure 5:
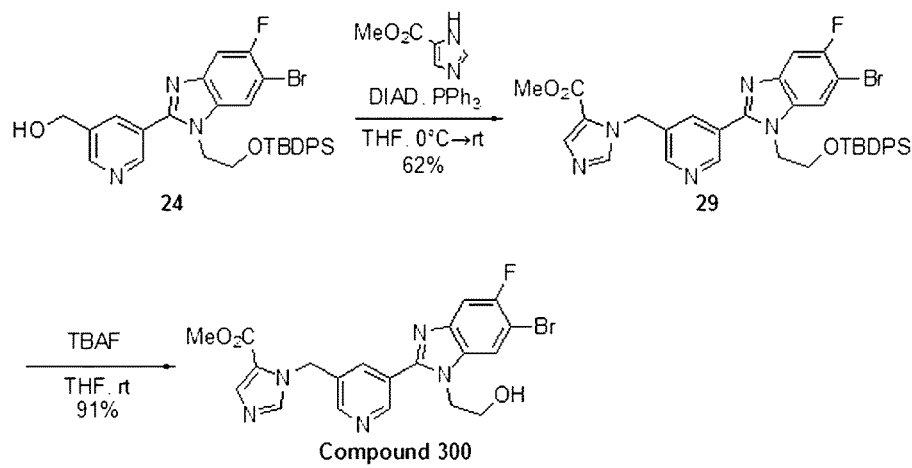
FIG. 5 is a drawing showing a synthesis example of 2-{6-bromo-5-fluoro-2-[5-(5-methylcarboxylateimidazol-1-ylmethyl)pyridin-3-yl]benzimidazol-1-yl}ethanol.

Compound 300 was synthesized in accordance with the scheme shown in FIG. 5.

Synthesis of 6-bromo-5-fluoro-2-[5-(5-methylcarboxylateimidazol-1-ylmethyl)pyridin-3-yl]-1-[2-(tert-butyldiphenylsilyloxy)ethyl]benzimidazole (Compound 29)

Compound 24 (80.0 mg, 0.132 mmol) synthesized by the method described in Example 4 was dissolved in tetrahydrofuran (1.0 mL), and thereafter, diisopropyl azodicarboxylate (56.9 µL, 0.265 mmol), triphenylphosphine (69.5 mg, 0.265 mmol) and methyl 4-imidazolecarboxylate (33.4 mg, 0.265 mmol) were added at 0° C. to the above-obtained solution. The obtained mixture was stirred overnight in an argon atmosphere at a room temperature. After completion of the reaction, the reaction solution was concentrated under a reduced pressure, and the obtained crude product was then purified by silica gel chromatography (dichloromethane/methanol=100/3→20/1→10/1 (volume ratio)) to obtain Compound 29 (58.0 mg, 0.0814 mmol, and yield: 62%).
$^1$H-NMR of Compound 29 (solvent: deuterated chloroform, resonance frequency: 500 MHz) δ: 9.01 (d, J=2.1 Hz, 1H), 8.60 (d, J=2.1 Hz, 1H), 7.98 (t, J=2.1 Hz, 1H), 7.76 (s, 1H), 7.70 (s, 1H), 7.57 (d, J=8.8 Hz, 1H), 7.45 (d, J=5.9 Hz, 1H), 7.42-7.37 (m, 6H), 7.30-7.27 (m, 4H), 5.55 (s, 2H), 4.34 (t, J=5.3 Hz, 2H), 3.94 (t, J=5.3 Hz, 2H), 3.76 (s, 3H), 0.89 (s, 9H).
Synthesis of Compound 300
Compound 29 (38.0 mg, 0.0533 mmol) was dissolved in tetrahydrofuran (0.2 mL), and thereafter, tetrabutylammonium fluoride (80.0 µL, tetrahydrofuran solution, 1 mol/L, 0.0800 mmol) was added to the solution at a room temperature. The obtained mixture was stirred in an argon atmosphere at the same temperature as described above for 4 hours. After completion of the reaction, the reaction solution was concentrated under a reduced pressure, and the obtained crude product was then purified by silica gel chromatography (dichloromethane/methanol=10: 1 (volume ratio)) to obtain Compound 300 (23.1 mg, 0.0487 mmol, and yield: 91%).
$^1$H-NMR of Compound 300 (solvent: deuterated chloroform, resonance frequency: 500 MHz) δ: 9.02 (d, J=2.1 Hz, 1H), 8.66 (d, J=2.1 Hz, 1H), 8.07 (t, J=2.1 Hz, 1H), 7.81 (s, 1H), 7.78 (d, J=0.9 Hz, 1H), 7.64 (d, J=5.9 Hz, 1H), 7.52 (d, J=8.7 Hz, 1H), 5.61 (s, 2H), 4.24 (t, J=5.2 Hz, 2H), 4.07 (q, J=5.2 Hz, 2H), 2.58 (t, J=5.2 Hz, 1H).

(Example 6) Synthesis of Compound 400

Compound 400 was synthesized in accordance with the scheme shown in FIG. 3.

Synthesis of 5-fluoro-1-(2-fluoroethyl)-2-[5-(imidazol-1-ylmethyl)pyridin-3-yl]-6-tributylstannylbenzimidazole (Compound 30)

Compound 200 (34.5 mg, 0.0830 mmol) synthesized by the method described in Example 3 was dissolved in N,N'-dimethylformamide (1.0 mL), and thereafter, bis(tributyltin) (125 µL, 0.249 mmol) and bis(tri-tert-butylphosphine)palladium (8.5 mg, 0.0166 mmol) were added to the above-obtained solution at a room temperature. The obtained mixture was stirred overnight in an argon atmosphere at 100° C. After completion of the reaction, the reaction solution was cooled, and ethyl acetate and water were then added thereto, followed by filtration. The filtrate was extracted with ethyl acetate twice. The combined ethyl acetate layer was dried over anhydrous sodium sulfate, and was then concentrated under a reduced pressure. The obtained crude product was purified by silica gel column chromatography (eluent: chloroform/methanol=20/1→10/1 (volume ratio)) to obtain Compound 30 (3.1 mg, 0.00493 mmol, yield: 6%).
$^1$H-NMR of Compound 30 (solvent: deuterated chloroform, resonance frequency: 500 MHz) δ: 8.94 (d, J=2.0 Hz, 1H), 8.63 (d, J=2.0 Hz, 1H), 7.88 (t, J=2.0 Hz, 1H), 7.62 (s, 1H), 7.44 (d, J=6.6 Hz, 1H), 7.33 (d, J=2.6 Hz, 1H), 7.15 (s, 1H), 6.97 (s, 1H), 5.26 (s, 2H), 4.82 (t, J=4.8 Hz, 1H), 4.73 (t, J=4.8 Hz, 1H), 4.48 (t, J=4.8 Hz, 1H), 4.43 (t, J=4.8 Hz, 1H), 1.67-1.50 (m, 6H), 1.40-1.28 (m, 6H), 1.24-1.08 (m, 6H), 0.89 (t, J=7.3 Hz, 9H).
Synthesis of Compound 400
Compound 30 (9.0 mg, 0.014 mmol) was dissolved in dichloromethane (0.50 mL), and iodine (9.1 mg, 0.070 mmol) was then added to the solution at a room temperature. The obtained mixture was stirred in an argon atmosphere at the same temperature as described above for 2 hours. After completion of the reaction, a saturated sodium thiosulfate aqueous solution and a saturated sodium hydrogen carbonate aqueous solution were added to the reaction solution, the obtained mixture was then stirred for 10 minutes, and the reaction solution was then extracted with chloroform twice. The combined chloroform layer was dried over anhydrous sodium sulfate, and was then concentrated under a reduced pressure. The obtained crude product was purified by silica gel column chromatography (eluent: chloroform/methanol=10/1 (volume ratio)) to obtain Compound 400 (1.3 mg, 0.00279 mmol, yield: 20%).

¹H-NMR of Compound 400 (solvent: deuterated chloroform, resonance frequency: 500 MHz) δ: 8.94 (d, J=2.1 Hz, 1H), 8.66 (d, J=2.1 Hz, 1H), 7.86-7.85 (m, 1H), 7.79 (d, J=5.2 Hz, 1H), 7.62 (s, 1H), 7.54 (d, J=8.1 Hz, 1H), 7.15 (s, 1H), 6.96 (s, 1H), 5.27 (s, 2H), 4.81 (t, J=4.7 Hz, 1H), 4.72 (t, J=4.7 Hz, 1H), 4.44 (t, J=4.7 Hz, 1H), 4.39 (t, J=4.7 Hz, 1H).

(Example 7) Synthesis of Compound [¹²³I] 400

To an acetonitrile solution (concentration: 1 mg/mL) (90 µL) of Compound 30 synthesized by the method described in Example 6, 1 mol/L hydrochloric acid (170 µL), a 1178 MBq [¹²³I] sodium iodide aqueous solution (60 µL), and a 30% (w/v) hydrogen peroxide aqueous solution (10 µL) were added. The mixed solution was left at rest at 40° C. for 10 minutes, and was then subjected to HPLC under the below-mentioned conditions, so that a fraction with the same retention time as Compound 400 obtained in Example 6 was obtained as a fraction of Compound [¹²³I] 400.
<HPLC Conditions>
Column: YMC PackPro C8 (trade name, manufactured by YMC, size: 4.5×150 mm)
Mobile phase: 0.1% by volume of trifluoroacetic acid-containing water/0.1% by volume of trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)
A liquid prepared by adding water (10 mL) to the aforementioned fraction was supplied to a Sep-Pak C18 column (trade name: Sep-Pak (registered trademark) Light C18 Cartridges, manufactured by Waters, the amount of filler: 130 mg), so that Compound [¹²³I] 400 was adsorbed and captured in the column. This column was washed with water (1 mL), and diethyl ether (6 mL) was then supplied to the resulting column to elute Compound [¹²³I] 400. Thereafter, diethyl ether was distilled away to obtain Compound [¹²³I] 400. The obtained radioactivity was 281 MBq immediately after completion of the synthesis (65 minutes after initiation of the synthesis). Moreover, a TLC analysis was carried out under the below-mentioned conditions. As a result, the radiochemical purity was 100%.
<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 8) Synthesis of Compound 500

Figure 6:
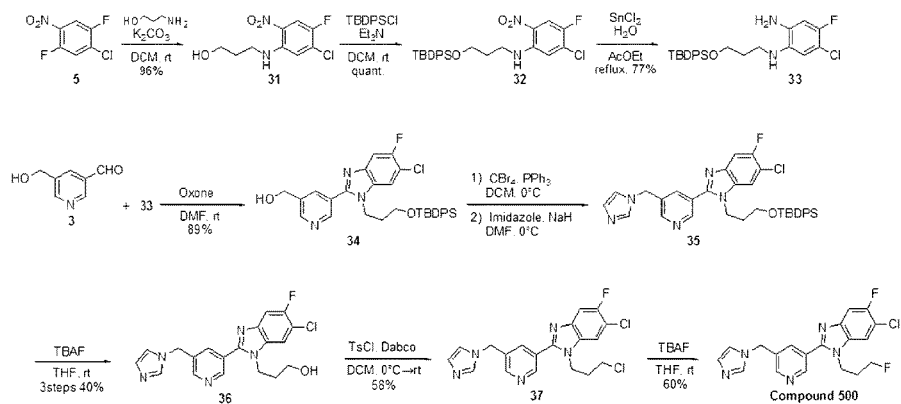
FIG. 6 is a drawing showing a synthesis example of 6-chloro-5-fluoro-1-(3-fluoropropyl)-2-[5-(imidazol-1-ylmethyl)pyridin-3-yl]benzimidazole.

Compound 500 was synthesized in accordance with the scheme shown in FIG. 6.

Synthesis of 3-[N-(5-chloro-4-fluoro-2-nitrophenyl)] amino-1-propanol (Compound 31)

Compound 5 (581 mg, 3.00 mmol) synthesized by the method described in Example 1 was dissolved in dichloromethane (5 mL), and 3-amino-1-propanol (0.69 mL, 9.00 mmol) and potassium carbonate (2.07 g, 15.0 mmol) were then added to the solution at a room temperature. The obtained mixture was stirred overnight in an argon atmosphere at the same temperature as described above. After completion of the reaction, water was added to the reaction solution, and the obtained mixture was then extracted with dichloromethane three times. The combined dichloromethane layer was dried over anhydrous sodium sulfate, and was then concentrated under a reduced pressure, so as to obtain Compound 31 (718 mg, 2.88 mmol, and yield: 96%).
¹H-NMR of Compound 31 (solvent: deuterated chloroform, resonance frequency: 500 MHz) δ: 8.13 (bs, 1H), 7.99 (d, J=9.3 Hz, 1H), 6.96 (d, J=6.3 Hz, 1H), 3.86 (t, J=4.9 Hz, 2H), 3.44 (dd, J=6.7, 5.2 Hz, 2H), 2.02-1.97 (m, 2H), 1.47 (s, 1H).

Synthesis of N-(5-chloro-4-fluoro-2-nitrophenyl)-3-(tert-butyldiphenylsilyloxy)-1-propylamine (Compound 32)

Compound 31 (718 mg, 2.88 mmol) was dissolved in dichloromethane (10 mL), and thereafter, tert-butyldiphenylchlorosilane (1.12 mL, 4.32 mmol) and triethylamine (0.803 mL, 5.76 mmol) were added to the solution at a room temperature. The obtained mixture was stirred overnight in an argon atmosphere at the same temperature as described above. After completion of the reaction, water was added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (hexane/ethyl acetate=20/1 (volume ratio)) to obtain Compound 32 (1.42 g, 2.91 mmol, quantitative).
¹H-NMR of Compound 32 (solvent: deuterated chloroform, resonance frequency: 500 MHz) δ: 7.98 (d, J=9.3 Hz, 1H), 7.90 (bs, 1H), 7.65-7.63 (m, 4H), 7.44-7.35 (m, 6H), 6.91 (d, J=6.2 Hz, 1H), 3.80 (t, J=5.7 Hz, 2H), 3.40 (dd, J=6.8, 5.6 Hz, 2H), 1.94-1.89 (m, 2H), 1.07 (s, 9H).

Synthesis of 3-chloro-4-fluoro-N-[3-(tert-butyldiphenylsilyloxy)-1-propyl]-1,6-phenylenediamine (Compound 33)

Compound 32 (1.42 g, 2.91 mmol) was dissolved in ethyl acetate (15 mL), and thereafter, tin(II) chloride (1.64 g, 8.64 mmol) and water (0.156 mL, 8.64 mmol) were added to the solution. The obtained mixture was heated to reflux in an argon atmosphere for 7 hours. After completion of the reaction, a 2 mol/L sodium hydroxide aqueous solution (15 mL) was added to the reaction solution, and the precipitated deposit was then filtrated. The obtained filtrate was extracted with ethyl acetate twice. The combined ethyl acetate layer was dried over anhydrous sodium sulfate, and was then concentrated under a reduced pressure. The obtained crude product was purified by silica gel chromatography (hexane/ethyl acetate=20/1→5/1 (volume ratio)) to obtain Compound 33 (1.01 g, 2.21 mmol, and yield: 77%).
¹H-NMR of Compound 33 (solvent: deuterated chloroform, resonance frequency: 500 MHz) δ: 7.67-7.66 (m, 4H), 7.44-7.36 (m, 6H), 6.56 (d, J=7.1 Hz, 1H), 6.49 (d, J=10.0 Hz, 1H), 3.82 (t, J=5.8 Hz, 2H), 3.35 (t, J=5.8 Hz, 2H), 3.35 (s, 2H), 3.23 (s, 1H), 1.91-1.86 (m, 2H), 1.07 (s, 9H).

Synthesis of 5-{6-chloro-5-fluoro-1-[3-(tert-butyldiphenylsilyloxy)-1-propyl]benzimidazol-2-yl}pyridine-3-methanol (Compound 34)

Compound 3 (140 mg, 1.02 mmol) synthesized by the method described in Example 1 was dissolved in N,N'-dimethylformamide (1 mL), and thereafter, an N,N'-dimethylformamide solution (2 mL), in which Compound 33 (512 mg, 1.12 mmol) had been dissolved, and potassium peroxymonosulfate (Oxone (registered trademark) Monopersulfate Compound, manufactured by Wako Pure Chemical Industries, Ltd.) (753 mg, 1.22 mmol) were added to the above-obtained solution at a room temperature. The obtained mixture was stirred in an argon atmosphere at the same temperature as described above for 30 minutes. After completion of the reaction, a saturated sodium thiosulfate aqueous solution and a saturated sodium hydrogen carbonate aqueous solution were added to the reaction solution, the obtained mixture was then stirred for 30 minutes, and the reaction mixture was then extracted with ethyl acetate twice. The combined ethyl acetate layer was dried over anhydrous sodium sulfate, and was then concentrated under a reduced pressure. The obtained crude product was purified by silica gel chromatography (ethyl acetate/methanol=50/1 (volume ratio)) to obtain Compound 34 (524 mg, 0.913 mmol, and yield: 89%).

$^1$H-NMR of Compound 34 (solvent: deuterated chloroform, resonance frequency: 500 MHz) δ: 8.86 (d, J=2.1 Hz, 1H), 8.72 (d, J=2.1 Hz, 1H), 8.08 (t, J=2.1 Hz, 1H), 7.60-7.56 (m, 6H), 7.47-7.42 (m, 2H), 7.39-7.36 (m, 4H), 4.79 (d, J=5.8 Hz, 2H), 4.40 (t, J=7.5 Hz, 2H), 3.66 (t, J=5.6 Hz, 2H), 1.99-1.94 (m, 2H), 1.90 (t, J=5.8 Hz, 1H), 1.05 (s, 9H).

Synthesis of 3-{6-chloro-5-fluoro-2-[5-(imidazol-1-ylmethyl)pyridin-3-yl]benzimidazol-1-yl]-1-propanol (Compound 36)

Compound 34 (524 mg, 0.913 mmol) was dissolved in dichloromethane (13 mL), and thereafter, carbon tetrabromide (363 mg, 1.10 mmol) and triphenylphosphine (359 mg, 1.37 mmol) were added at 0° C. to the solution. The obtained mixture was stirred in an argon atmosphere at the same temperature as described above for 1 hour. After completion of the reaction, the reaction solution was concentrated under a reduced pressure to obtain a crude product.

Imidazole (62.2 mg, 0.913 mmol) was dissolved in N,N'-dimethylformamide (0.3 mL), and sodium hydride (44.0 mg, 1.10 mmol) was then added at 0° C. to the solution. The obtained mixture was stirred in an argon atmosphere at the same temperature as described above for 10 minutes. An N,N'-dimethylformamide solution (0.7 mL), in which the above described crude product had been dissolved, was added to the reaction solution at the same temperature as described above. The obtained mixture was stirred in an argon atmosphere at the same temperature as described above for 3 hours. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (dichloromethane/methanol=20/1→10/1 (volume ratio)), so as to obtain a mixture (239 mg) containing 6-chloro-5-fluoro-2-[5-(imidazol-1-ylmethyl)pyridin-3-yl]-1-[3-(tert-butyldiphenylsilyloxy)-1-propyl]benzimidazole (Compound 35).

The mixture (239 mg) containing Compound 35 was dissolved in tetrahydrofuran (2 mL), and tetrabutylammonium fluoride (0.575 mL, 1 mol/L tetrahydrofuran solution, 0.575 mmol) was then added to the solution at a room temperature. The obtained mixture was stirred in an argon atmosphere at the same temperature as described above for 1 hour. After completion of the reaction, the reaction solution was concentrated under a reduced pressure, and the obtained crude product was then purified by silica gel chromatography (chloroform/methanol=5/1 (volume ratio)) to obtain Compound 36 (141 mg, 0.365 mmol, three-step yield from Compound 34: 40%).

$^1$H-NMR of Compound 36 (solvent: deuterated chloroform, resonance frequency: 500 MHz) δ: 9.02 (d, J=2.1 Hz, 1H), 8.67 (d, J=2.1 Hz, 1H), 7.73 (t, J=2.1 Hz, 1H), 7.65 (s, 1H), 7.56 (d, J=9.2 Hz, 1H), 7.51 (d, J=6.3 Hz, 1H), 7.15 (s, 1H), 7.00 (s, 1H), 5.31 (s, 2H), 4.26 (t, J=7.7 Hz, 2H), 3.64 (t, J=5.8 Hz, 2H), 2.02-1.99 (m, 2H).

Synthesis of 6-chloro-1-(3-chloropropyl)-5-fluoro-2-[5-(imidazol-1-ylmethyl)pyridin-3-yl]benzimidazole (Compound 37)

Compound 36 (78.5 mg, 0.203 mmol) was dissolved in dichloromethane (3 mL), and thereafter, p-toluenesulfonyl chloride (116 mg, 0.609 mmol) and 1,4-diazabicyclo[2,2,2]octane (137 mg, 1.22 mmol) were added at 0° C. to the solution. The obtained mixture was stirred overnight in an argon atmosphere at a room temperature. After completion of the reaction, the reaction mixture was purified by silica gel chromatography (dichloromethane/methanol=10/1 (volume ratio)) to obtain Compound 37 (47.7 mg, 0.118 mmol, and yield: 58%).

$^1$H-NMR of Compound 37 (solvent: deuterated chloroform, resonance frequency: 500 MHz) δ: 8.94 (d, J=2.1 Hz, 1H), 8.66 (d, J=2.1 Hz, 1H), 7.79 (t, J=2.1 Hz, 1H), 7.63 (s, 1H), 7.57 (d, J=9.1 Hz, 1H), 7.50 (d, J=6.2 Hz, 1H), 7.15 (s, 1H), 6.96 (s, 1H), 5.28 (s, 2H), 4.38 (t, J=7.4 Hz, 2H), 3.45 (t, J=5.8 Hz, 2H), 2.25-2.20 (m, 2H).

Synthesis of Compound 500

Compound 37 (14.0 mg, 0.0346 mmol) was dissolved in tetrahydrofuran (0.5 mL), and tetrabutylammonium fluoride (0.104 mL, 1 mol/L tetrahydrofuran solution, 0.104 mmol) was then added to the solution at a room temperature. The obtained mixture was stirred overnight in an argon atmosphere at the same temperature as described above. After completion of the reaction, the reaction solution was concentrated under a reduced pressure, and the obtained crude product was then purified by silica gel chromatography (dichloromethane/methanol=20/1→10/1 (volume ratio)) to obtain Compound 500 (8.1 mg, 0.0209 mmol, and yield: 60%).

$^1$H-NMR of Compound 500 (solvent: deuterated chloroform, resonance frequency: 500 MHz) δ: 8.94 (d, J=2.2 Hz, 1H), 8.66 (d, J=2.2 Hz, 1H), 7.79 (t, J=2.2 Hz, 1H), 7.62 (s, 1H), 7.58 (d, J=9.1 Hz, 1H), 7.48 (d, J=6.3 Hz, 1H), 7.15 (s, 1H), 6.96 (s, 1H), 5.28 (s, 2H), 4.45 (t, J=5.3 Hz, 1H), 4.36-4.32 (m, 3H), 2.21-2.10 (m, 2H).

(Example 9) Synthesis of Compound [$^{18}$F] 500

[$^{18}$F] Fluoride ion-containing $H_2^{18}O$ (radioactivity: 4110 MBq, correction value at initiation of the synthesis) was supplied to a Sep-Pak column (trade name: Sep-Pak (registered trademark) Light Cartridge Accell™ Plus QMA Carbonate, manufactured by Waters, the amount of filler: 130 mg), so that the [$^{18}$F] fluoride ion was adsorbed and captured in the column. To this column, a potassium carbonate aqueous solution (42.4 µmol/L, 0.3 mL) and an acetonitrile solution (0.7 mL) of KRYPTOFIX 222 (trade name, manufactured by Merck) (14 mg, 37.2 µmol) were supplied, so that the [$^{18}$F] fluoride ion was eluted. The resultant was heated to 110° C. under a stream of argon gas, so that water was evaporated. Thereafter, acetonitrile (0.5 mL×2) was added to the residue, and the obtained mixture was then azeotropically distilled to dryness. To this reaction mixture, an acetonitrile solution (0.3 mL), in which Compound 37 (5 mg, 0.00951 mmol) synthesized by the method described in Example 8 had been dissolved, was added, and the thus obtained mixture was then heated at 110° C. for 15 minutes. After completion of the reaction, 1 mol/L hydrochloric acid (0.5 mL) was added to the reaction solution, and the obtained mixture was then subjected to HPLC under the below-mentioned conditions, so that a fraction with the same retention time as Compound 500 obtained in Example 8 was obtained as a fraction of Compound [$^{18}$F] 500.

<HPLC Conditions>
Column: Capcell Pak C18 MG (trade name, manufactured by Shiseido Japan, Co., Ltd., size: 10×250 mm)
Mobile phase: 0.1% by volume of trifluoroacetic acid-containing water/0.1% by volume of trifluoroacetic acid-containing acetonitrile (volume ratio)=gradient from 80/20 to 20/80 over 40 minutes
Flow rate: 3.0 mL/min
Detector: ultraviolet visible spectrophotometer (detection wavelength: 260 nm)

A liquid prepared by adding water (10 mL) to the aforementioned fraction was supplied to a Sep-Pak C18 column (trade name: Sep-Pak (registered trademark) Light C18 Cartridges, manufactured by Waters, the amount of filler: 130 mg), so that Compound [$^{18}$F] 500 was adsorbed and captured in the column. This column was washed with water (1 mL), [$^{18}$F] 500 was then eluted, and diethyl ether was then distilled away to obtain [$^{18}$F] 500. The obtained radioactivity was 793 MBq immediately after completion of the synthesis (133 minutes after initiation of the synthesis). Moreover, a TLC analysis was carried out under the below-mentioned conditions. As a result, the radiochemical purity was 98.6%.

<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 10) Synthesis of Compound 601

Figure 7:
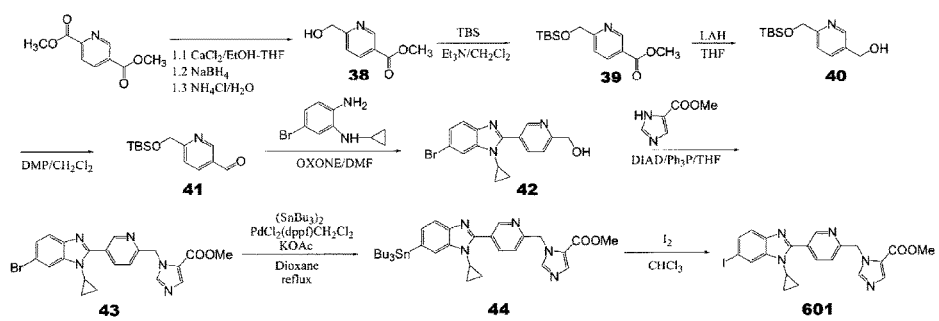
FIG. 7 is a drawing showing a synthesis example of methyl 1-[4-(1-cyclopropyl-6-iodo-1H-imidazobenzo-2-yl)-3-pyridinylmethyl)]-1H-imidazolecarboxylate.

Compound 601 was synthesized in accordance with the scheme shown in FIG. 7.

Synthesis of methyl-2-hydroxymethyl-5-pyridinecarboxylate (Compound 38)

Dimethyl-2,5-pyridinedicarboxylate (5.00 g, 25.6 mmol) was dissolved in tetrahydrofuran (60 mL) and ethanol (60 mL), and thereafter, calcium chloride (11.3 g, 102.4 mmol) and sodium borohydride (1.45 g, 38.4 mmol) were added to the above-obtained solution under cooling on ice. The obtained mixture was stirred for 17 hours. After completion of the reaction, a saturated ammonium chloride aqueous solution and water were added to the reaction solution, and the obtained mixture was then extracted with dichloromethane three times. The combined dichloromethane layer was dried over anhydrous magnesium sulfate, and was then concentrated under a reduced pressure. The obtained crude product was purified by silica gel column chromatography (eluent: chloroform) to obtain Compound 38 (3.69 g, 22.1 mmol).

$^1$H-NMR of Compound 38 (solvent: deuterated chloroform, resonance frequency: 500 MHz) δ: 9.16 (s, 1H), 8.29 (d, J=8.1 Hz, 1H), 7.37 (d, J=8.1 Hz, 1H), 4.83 (s, 2H), 3.96 (s, 3H).

Synthesis of methyl-2-(t-butyldimethylsiloxymethyl)-5-pyridinecarboxylate (Compound 39)

Compound 38 (1.00 g, 5.98 mmol) was dissolved in dichloromethane (20 mL), and thereafter, triethylamine (1.67 mL, 11.9 mmol) and t-butyldimethylchlorosilane (1.35 g, 8.97 mmol) were added to the solution. The obtained mixture was stirred for 21 hours. After completion of the reaction, water was added to the reaction solution, and the obtained mixture was then extracted with dichloromethane three times. The combined dichloromethane layer was dried over anhydrous magnesium sulfate, and was then concentrated under a reduced pressure. The obtained crude product was purified by silica gel column chromatography (eluent: chloroform) to obtain Compound 39 (607 mg, 2.16 mmol).

$^1$H-NMR of Compound 39 (solvent: deuterated chloroform, resonance frequency: 500 MHz) δ: 9.11 (s, 1H), 8.31 (d, J=8.2 Hz, 1H), 7.48 (d, J=8.2 Hz, 1H), 4.89 (s, 2H), 3.95 (s, 3H), 0.97 (s, 9H), 0.13 (s, 6H).

Synthesis of 2-(t-butyldimethylsiloxymethyl)-5-pyridinemethanol (Compound 40)

Lithium aluminum hydride (146 mg, 3.85 mmol) was suspended in tetrahydrofuran (10 mL), and thereafter, a solution prepared by dissolving Compound 39 (725 mg, 2.57 mmol) in tetrahydrofuran (5 mL) was added dropwise to the suspension under cooling on ice. The obtained mixture was stirred for 24 hours. After completion of the reaction, sodium sulfate decahydrate was added to the reaction solution, and the obtained mixture was then filtrated through Celite. The residue was washed with chloroform, and the resultant was combined with the filtrate, followed by vacuum concentration. The obtained crude product was purified by silica gel column chromatography (eluent: chloroform) to obtain Compound 40 (393 mg, 1.55 mmol).

$^1$H-NMR of Compound 40 (solvent: deuterated chloroform, resonance frequency: 500 MHz) δ: 8.47 (d, J=1.8 Hz, 1H), 7.73 (dd, J=8.0, 1.8 Hz, 1H), 7.51 (d, J=8.0 Hz, 1H), 4.83 (s, 2H), 4.72 (s, 2H), 0.96 (s, 9H), 0.12 (s, 6H).

Synthesis of 2-(t-butyldimethylsiloxymethyl)-5-pyridinecarbaldehyde (Compound 41)

Compound 40 (393 mg, 1.55 mmol) was dissolved in dichloromethane (15 mL), and thereafter, triethylamine (840 μL, 6.16 mmol) and a Dess-Martin reagent (1.30 g, 3.08 mmol) were added to the solution. The obtained mixture was stirred for 21 hours. After completion of the reaction, a saturated sodium hydrogen carbonate aqueous solution and a sodium thiosulfate aqueous solution were added to the reaction solution, and the obtained mixture was then extracted with dichloromethane three times. The combined dichloromethane layer was dried over anhydrous magnesium sulfate, and was then concentrated under a reduced pressure. The obtained crude product was purified by silica gel column chromatography (eluent: chloroform) to obtain Compound 41 (220 mg, 0.875 mmol).

$^1$H-NMR of Compound 41 (solvent: deuterated chloroform, resonance frequency: 500 MHz) δ: 10.09 (s, 1H), 8.97

(d, J=1.8 Hz, 1H), 8.19 (dd, J=8.1, 1.8 Hz, 1H), 7.71 (d, J=8.1 Hz, 1H), 4.91 (s, 2H), 0.97 (s, 9H), 0.14 (s, 6H).

Synthesis of 6-bromo-1-cyclopropyl-2-[2-(hydroxymethyl)pyridin-5-yl]-1H-benzimidazole (Compound 42)

4-Bromo-4-cyclopropylamino-aniline (204 mg, 0.900 mmol) and Compound 41 (189 mg, 0.750 mmol) were dissolved in dimethylformamide (4.0 mL), and thereafter, potassium peroxymonosulfate (Oxone (registered trademark) Monopersulfate Compound, manufactured by Wako Pure Chemical Industries, Ltd.) (553 mg, 0.900 mmol) was added to the solution. The obtained mixture was stirred at a room temperature for 1.5 hours. After completion of the reaction, a saturated sodium hydrogen carbonate aqueous solution and a saturated sodium thiosulfate aqueous solution were added to the reaction solution, and the obtained mixture was then extracted with chloroform three times. The combined chloroform layer was dried over anhydrous magnesium sulfate, and was then concentrated under a reduced pressure. The obtained crude product was purified by silica gel column chromatography (eluent: chloroform/methanol=10/1) to obtain Compound 42 (165 mg, 0.480 mmol).

$^1$H-NMR of Compound 42 (solvent: deuterated methanol, resonance frequency: 500 MHz) δ: 9.12 (s, 1H), 8.27 (d, J=8.6, 1H), 7.78 (s, 1H), 7.65 (d, J=8.6 Hz, 1H), 7.51 (d, J=8.6 Hz, 1H), 7.43 (d, J=8.6 Hz, 1H), 4.86 (s, 2H), 3.58-3.54 (m, 1H), 1.21-1.19 (m, 2H), 0.79-0.78 (m, 2H).

Synthesis of methyl 1-[4-(6-bromo-1-cyclopropyl-1H-imidazobenzo-2-yl)-3-pyridinylmethyl)]-1H-imidazolecarboxylate (Compound 43)

Compound 42 (165 mg, 0.480 mmol) was dissolved in tetrahydrofuran (15.0 mL), and thereafter, methyl 4-imidazolecarboxylate (90.7 mg, 0.72 mmol), diisopropyl azodicarboxylate (146 mg, 0.72 mmol) and triphenylphosphine (189 mg, 0.72 mmol) were added to the solution. The obtained mixture was stirred at a room temperature for 2 hours, and the solvent was then distilled away. The obtained crude product was purified by silica gel column chromatography (eluent: chloroform→chloroform/methanol=96/4) to obtain Compound 43 (129 mg, 0.327 mmol).

$^1$H-NMR of Compound 43 (solvent: deuterated chloroform, resonance frequency: 500 MHz) δ: 9.15 (s, 1H), 8.25 (d, J=8.1 Hz, 1H), 7.85 (s, 1H), 7.82 (s, 1H), 7.76 (s, 1H), 7.64 (d, J=8.6 Hz, 1H), 7.41 (d, J=8.6 Hz, 1H), 7.25 (d, J=8.1 Hz, 1H), 5.72 (s, 2H), 3.81 (s, 3H), 3.55-3.51 (m, 1H), 1.20-1.18 (m, 2H), 0.79-0.77 (m, 2H).

Synthesis of methyl 1-[4-(1-cyclopropyl-6-tributylstannyl-1H-imidazobenzo-2-yl)-3-pyridinylmethyl)]-1H-imidazolecarboxylate (Compound 44)

Compound 43 (19 mg, 0.04 mmol) was dissolved in 1,4-dioxane (1.0 mL), and thereafter, bis(tributyltin) (40 μL, 0.08 mmol), a PdCl$_2$ (dppf) dichloromethane complex (3.2 mg, 0.004 mmol) and potassium acetate (11 mg, 0.12 mmol) were added to the solution. The obtained mixture was heated in an argon atmosphere at 100° C. for 16 hours. After completion of the reaction, the reaction solution was cooled to a room temperature, and the solvent was then distilled away. The obtained crude product was purified by silica gel column chromatography (eluent: chloroform/methanol=96/4) to obtain Compound 44 (12.6 mg, 0.019 mmol).

$^1$H-NMR of Compound 44 (solvent: deuterated chloroform, resonance frequency: 500 MHz) δ: 9.16 (s, 1H), 8.26 (d, J=8.2, 1H), 7.85 (s, 1H), 7.82 (s, 1H), 7.78-7.75 (m, 1H), 7.69 (s, 1H), 7.61 (s, 1H), 7.24 (d, J=8.2 Hz, 1H), 5.72 (s, 2H), 3.81 (s, 3H), 3.59-3.55 (m, 1H), 1.67-1.51 (m, 6H), 1.40-1.32 (m, 6H), 1.19-1.05 (m, 8H), 0.90 (t, J=7.3 Hz, 9H), 0.80-0.76 (m, 2H).

Synthesis of Compound 601

Compound 44 (12.6 mg, 0.019 mmol) was dissolved in chloroform (1.0 mL), and iodine (2.5 mg, 0.02 mmol) was then added to the solution. The obtained mixture was stirred in an argon atmosphere at a room temperature for 2 hours. After completion of the reaction, the solvent was distilled away, and the obtained crude product was purified by silica gel column chromatography (eluent: chloroform→chloroform/methanol=96/4) to obtain Compound 601 (2.4 mg, 0.0048 mmol).

$^1$H-NMR of Compound 601 (solvent: deuterated chloroform, resonance frequency: 500 MHz) δ: 9.17 (s, 1H), 8.27 (d, J=8.1 Hz, 1H), 7.85 (s, 1H), 7.82 (s, 1H), 7.80-7.78 (m, 1H), 7.62-7.61 (m, 1H), 7.36-7.30 (m, 1H), 7.25 (d, J=8.1 Hz, 1H), 5.73 (s, 2H), 3.82 (s, 3H), 3.59-3.54 (m, 1H), 1.20-1.16 (m, 2H), 0.80-0.77 (m, 2H).

(Example 11) Synthesis of Compound [$^{123}$I] 601

An aqueous solution of [$^{123}$I] sodium iodide (519 MBq/30 μL) in 1 mol/L hydrochloric acid (85 μL) and a 30% (w/v) hydrogen peroxide aqueous solution (5 μL) were added to an acetonitrile solution (concentration: 1 mg/mL, 45 μL) of Compound 44 synthesized by the method described in Example 10. The mixed solution was left at rest at 40° C. for 10 minutes, and was then subjected to HPLC under the below-mentioned conditions, so that a fraction with the same retention time as Compound 601 obtained in Example 10 was obtained as a fraction of Compound [$^{123}$I] 601.

<HPLC Conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding 10 mL of water to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 601 was adsorbed and captured in the column. This column was washed with water (10 mL), and ethanol (1 mL) was then supplied to the column, so that Compound [$^{123}$I] 601 was eluted, and it was then diluted with a physiological saline to obtain a physiological saline aqueous solution of Compound [$^{123}$I] 601. The obtained radioactivity was 426 MBq immediately after completion of the synthesis (64 minutes after initiation of the synthesis). Moreover, a TLC analysis was carried out under the below-mentioned conditions. As a result, the radiochemical purity was 100%.

<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 12) Synthesis of Compound 602

Figure 8:
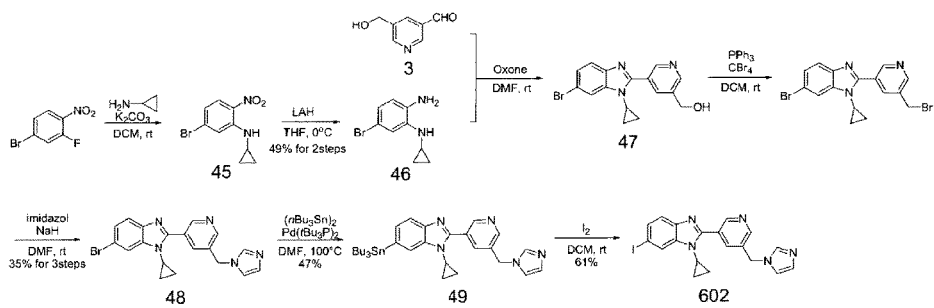
FIG. 8 is a drawing showing a synthesis example of 1-cyclopropyl-2-[3-(1H-imidazol-1-ylmethyl)pyridin-5-yl]-6-iodo-1H-benzimidazole.

Compound 602 was synthesized in accordance with the scheme shown in FIG. 8.

Synthesis of 4-bromo-4-cyclopropylamino-1-nitrobenzene (Compound 45)

4-Bromo-4-fluoro-1-nitrobenzene (2.00 g, 9.09 mmol) was dissolved in dichloromethane (50 mL), and thereafter, cyclopropylamine (1.90 mL, 27.3 mmol) and potassium carbonate (3.77 g, 27.3 mmol) were then added to the solution. The obtained mixture was stirred in an argon atmosphere for 24 hours. After completion of the reaction, a saturated ammonium chloride aqueous solution and water were added to the reaction solution, and the obtained mixture was then extracted with ethyl acetate three times. The combined ethyl acetate layer was washed with water and a saturated saline, and it was dried over anhydrous magnesium sulfate, and was then concentrated under a reduced pressure. The obtained crude product was purified by silica gel column chromatography (eluent: hexane/ethyl acetate=10/1) to obtain Compound 45 (2.25 g, 8.74 mmol).

$^1$H-NMR of Compound 45 (solvent: deuterated chloroform, resonance frequency: 500 MHz) δ: 8.08 (bs, 1H), 8.01 (d, J=2.1 Hz, 1H), 7.48 (d, J=9.1 Hz, 1H), 6.81 (dd, J=2.1, 9.1 Hz, 1H), 2.59-2.55 (m, 1H), 1.00-0.90 (m, 2H), 0.72-0.63 (m, 2H).

Synthesis of 4-bromo-4-cyclopropylamino-aniline (Compound 46)

Lithium aluminum hydride (663 mg, 17.5 mmol) was suspended in tetrahydrofuran (50 mL), and Compound 45 (2.25 g, 8.74 mmol) was then added to the suspension under cooling on ice. The obtained mixture was stirred in an argon atmosphere for 2 hours. Thereafter, sodium sulfate decahydrate was added to the reaction solution to terminate the reaction, and the reaction solution was then filtrated through Celite. The residue was washed with ethyl acetate, and was then combined with the filtrate, followed by vacuum concentration. The obtained crude product was purified by silica gel column chromatography (eluent: hexane/ethyl acetate=4/1) to obtain Compound 46 (1.02 g, 4.487 mmol, two-step yield from 4-bromo-4-fluoro-1-nitrobenzene: 49%).

$^1$H-NMR of Compound 46 (solvent: deuterated chloroform, resonance frequency: 500 MHz) δ: 7.12 (d, J=2.2 Hz, 1H), 6.68 (dd, J=2.2, 8.1 Hz, 1H), 6.55 (d, J=8.1 Hz, 1H), 3.97 (bs, 1H), 3.17 (bs, 2H), 2.46-2.40 (m, 1H), 0.78-0.72 (m, 2H), 0.54-0.51 (m, 2H).

Synthesis of 6-bromo-1-cyclopropyl-2-[3-(hydroxymethyl)pyridin-5-yl]-1H-benzimidazole (Compound 47)

Compound 46 (215 mg, 0.947 mmol), and Compound 3 (130 mg, 0.947 mmol) synthesized by the method described in Example 1, were dissolved in dimethylformamide (5.0 mL), and thereafter, potassium peroxymonosulfate (Oxone (registered trademark) Monopersulfate Compound, manufactured by Wako Pure Chemical Industries, Ltd.) (699 mg, 1.14 mmol) was added to the above-obtained solution. The obtained mixture was stirred at a room temperature for 2 hours. After completion of the reaction, a saturated sodium hydrogen carbonate aqueous solution and a saturated sodium thiosulfate aqueous solution were added to the reaction solution, and the obtained mixture was then extracted with ethyl acetate three times. The combined ethyl acetate layer was washed with water and a saturated saline, and it was dried over anhydrous magnesium sulfate, and was then concentrated under a reduced pressure. The obtained crude product was purified by silica gel column chromatography (eluent: chloroform/methanol=10/1) to obtain Compound 47 (292 mg, 0.848 mmol).

$^1$H-NMR of Compound 47 (solvent: deuterated methanol, resonance frequency: 500 MHz) δ: 9.03 (d, J=2.0 Hz, 1H), 8.71 (d, J=2.0 Hz, 1H), 8.40 (d, J=2.0 Hz, 1H), 7.92 (d, J=2.0 Hz, 1H), 7.61 (d, J=8.6 Hz, 1H), 7.46 (d, J=2.0, 8.6 Hz, 1H), 4.79 (s, 2H), 3.80-3.75 (m, 1H), 1.21-1.17 (m, 2H), 0.75-0.72 (m, 2H).

Synthesis of 6-bromo-1-cyclopropyl-2-[3-(1H-imidazol-1-ylmethyl)pyridin-5-yl]-1H-benzimidazole (Compound 48)

Compound 47 (292 mg, 0.848 mmol) was dissolved in dichloromethane (3.0 mL), and thereafter, triphenylphosphine (334 mg, 1.27 mmol) and carbon tetrabromide (422 mg, 1.27 mmol) were added to the solution. The obtained mixture was stirred at a room temperature for 1 hour, and the solvent was then distilled away under a reduced pressure. The residue was purified by flash silica gel column chromatography (chloroform), so as to obtain 265 mg (corresponding to 0.848 mmol) of a crude product.

Subsequently, sodium hydride (approximately 60%, dispersed in liquid paraffin) (33.9 mg, 0.846 mmol) was dissolved in dimethylformamide (5.0 mL), and imidazole (66.5 mg, 0.977 mmol) was then added to the solution. The obtained mixture was stirred at a room temperature for 15 minutes, and the above described crude product (265 mg, 0.848 mmol) was then added to the reaction mixture. The thus obtained mixture was stirred at a room temperature for 1 hour, and thereafter, a saturated ammonium chloride aqueous solution and water were added to the reaction mixture. The obtained mixture was extracted with ethyl acetate three times. The combined ethyl acetate layer was washed with water and a saturated saline, and it was dried over anhydrous magnesium sulfate, and was then concentrated under a reduced pressure. The obtained crude product was purified by silica gel column chromatography (eluent: chloroform/methanol=10/1) to obtain Compound 48 (129 mg, 0.327 mmol, three-step yield from Compound 46: 35%).

$^1$H-NMR of Compound 48 (solvent: deuterated chloroform, resonance frequency: 500 MHz) δ: 9.22 (d, J=2.1 Hz, 1H), 8.62 (d, J=2.1 Hz, 1H), 8.04 (t, J=2.1 Hz, 1H), 7.76 (d, J=1.7 Hz, 1H), 7.64 (d, J=8.6 Hz, 1H), 7.63 (s, 1H), 7.42 (dd, J=1.7, 8.6 Hz, 1H), 7.15 (s, 1H), 6.98 (bs, 1H), 5.27 (s, 2H), 3.48-3.44 (m, 1H), 1.15-1.11 (m, 2H), 0.75-0.72 (m, 2H).

Synthesis of 1-cyclopropyl-2-[3-(1H-imidazol-1-ylmethyl)pyridin-5-yl]-6-tributylstannyl-1H-benzimidazole (Compound 49)

Compound 48 (70.5 mg, 0.179 mmol) was dissolved in dimethylformamide (1.0 mL), and thereafter, bis(tributyltin) (179 μL, 0.358 mmol) and bis(tri-t-butylphosphine)palladium (9.2 mg, 0.018 mmol) were added to the solution. The obtained mixture was heated in an argon atmosphere at 100° C. for 4 hours. After completion of the reaction, the reaction solution was cooled to a room temperature, water was then added thereto, and the obtained mixture was then extracted with ethyl acetate three times. The combined ethyl acetate layer was washed with water and a saturated saline, and it was dried over anhydrous magnesium sulfate, and was then concentrated under a reduced pressure. The obtained crude product was purified by silica gel column chromatography (eluent: chloroform/methanol=10/1) to obtain Compound 49 (23.9 mg, 0.045 mmol, yield: 47%).

$^1$H-NMR of Compound 49 (solvent: deuterated chloroform, resonance frequency: 500 MHz) δ: 9.23 (d, J=2.0 Hz, 1H), 8.59 (d, J=2.0 Hz, 1H), 8.07 (t, J=2.0 Hz, 1H), 7.76 (d, J=8.3 Hz, 1H), 7.69 (s, 1H), 7.63 (s, 1H), 7.39 (d, J=8.3 Hz, 1H), 7.14 (s, 1H), 6.98 (s, 1H), 5.23 (s, 2H), 3.53-3.49 (m, 1H), 1.61-1.51 (m, 6H), 1.40-1.34 (m, 8H), 1.19-1.05 (m, 6H), 0.90 (t, J=7.3 Hz, 9H), 0.76-0.72 (m, 2H).

Synthesis of Compound 602

Compound 49 (19.2 mg, 0.0318 mmol) was dissolved in dichloromethane (1.0 mL), and iodine (4.04 mg, 0.0318 mmol) was then added to the solution. The obtained mixture was stirred in an argon atmosphere at a room temperature for 30 minutes. After completion of the reaction, a saturated sodium hydrogen carbonate aqueous solution and a saturated sodium thiosulfate aqueous solution were added to the reaction solution, and the obtained mixture was then extracted with chloroform three times. The combined chloroform layer was washed with water and a saturated saline, and it was dried over anhydrous magnesium sulfate, and was then concentrated under a reduced pressure. The obtained crude product was purified by silica gel column chromatography (eluent: chloroform/methanol=10/1) to obtain Compound 602 (8.2 mg, 0.019 mmol).

$^1$H-NMR of Compound 602 (solvent: deuterated chloroform, resonance frequency: 500 MHz) δ: 9.21 (d, J=2.1 Hz, 1H), 8.62 (d, J=2.1 Hz, 1H), 8.04 (t, J=2.1 Hz, 1H), 7.95 (s, 1H), 7.64 (bs, 1H), 7.60 (d, J=8.5 Hz, 1H), 7.53 (d, J=8.5 Hz, 1H), 7.16 (bs, 1H), 6.99 (bs, 1H), 5.27 (s, 2H), 3.47-3.43 (m, 1H), 1.15-1.11 (m, 2H), 0.75-0.71 (m, 2H).

(Example 13) Synthesis of Compound [$^{123}$I] 602

An aqueous solution of [$^{123}$I] sodium iodide (756 MBq/60 μL) in 1 mol/L hydrochloric acid (170 μL) and a 30% (w/v) hydrogen peroxide aqueous solution (10 μL) were added to an acetonitrile solution (concentration: 1 mg/mL, 90 μL) of Compound 49 synthesized by the method described in Example 12. The mixed solution was left at rest at 40° C. for 10 minutes, and was then subjected to HPLC under the below-mentioned conditions, so that a fraction with the same retention time as Compound 602 obtained in Example 12 was obtained as a fraction of Compound [$^{123}$I] 602.

<HPLC Conditions>
Column: YMC PackPro C8 (trade name, manufactured by YMC, size: 4.5×150 mm)
Mobile phase: 0.1% trifluoroacetic acid-containing water/ 0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding water (10 mL) to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 602 was adsorbed and captured in the column. This column was washed with water (10 mL), and ethanol (1 mL) was then supplied to the column, so that Compound [$^{123}$I] 602 was eluted, and it was then diluted with a physiological saline to obtain a physiological saline aqueous solution of Compound [$^{123}$I] 602. The obtained radioactivity was 153 MBq immediately after completion of the synthesis (42 minutes after initiation of the synthesis). Moreover, a TLC analysis was carried out under the below-mentioned conditions. As a result, the radiochemical purity was 100%.

<TLC Analysis Conditions>
TLC plate: Silica Gel 60 $F_{254}$ (product name, manufactured by Merck)
Development phase: ethyl acetate/methanol/diethylamine=10/2/1 (volume ratio)
RI detector: RitaStar, manufactured by Raytest (Example 14) Synthesis of Compound 603

Figure 9:
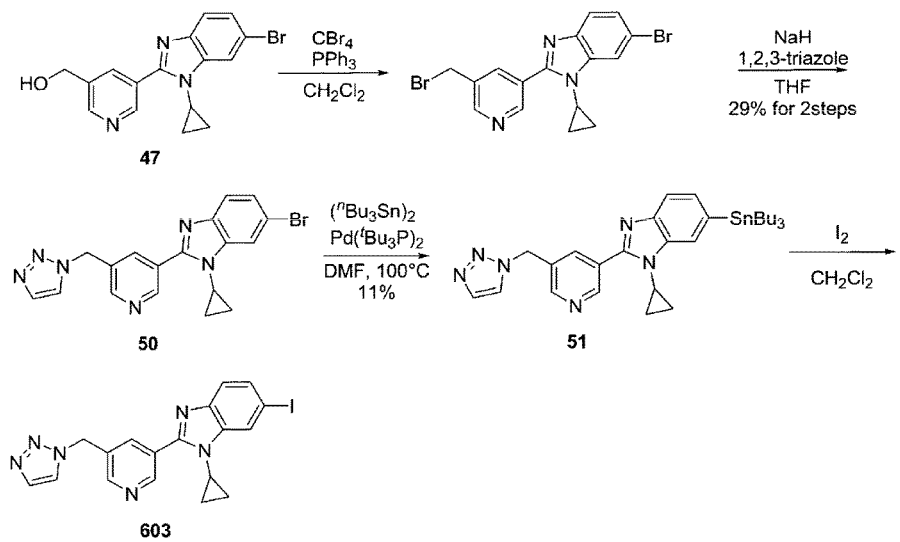
FIG. 9 is a drawing showing a synthesis example of 1-cyclopropyl-2-[3-(1H-1,2,3-triazol-1-ylmethyl)pyridin-5-yl]-6-iodo-1H-benzimidazole.

Compound 603 was synthesized in accordance with the scheme shown in FIG. 9.

Synthesis of 6-bromo-1-cyclopropyl-2-[3-(1H-1,2,3-triazol-1-ylmethyl)pyridin-5-yl]-1H-benzimidazole (Compound 50)

Compound 47 (245 mg, 0.712 mmol) synthesized by the method described in Example 12 was dissolved in dichloromethane (3.0 mL), and thereafter, triphenylphosphine (280 mg, 1.07 mmol) and carbon tetrabromide (354 mg, 1.07 mmol) were added to the solution. The obtained mixture was stirred at a room temperature for 1 hour. Thereafter, the solvent was distilled away under a reduced pressure, and the residue was then purified by flash silica gel column chromatography (chloroform), so as to obtain a crude product of 6-bromo-1-cyclopropyl-2-[3-(bromomethyl)pyridin-5-yl]-1H-benzimidazole (290 mg, 0.712 mmol).

Sodium hydride (approximately 60%, dispersed in liquid paraffin) (37.0 mg, 0.926 mmol) was dissolved in 5.0 mL of dimethylformamide, and 1,2,3-triazole (72.7 mg, 1.07 mmol) was then added to the solution. The obtained mixture was stirred at a room temperature for 2 minutes, and the crude product of 6-bromo-1-cyclopropyl-2-[3-(bromomethyl)pyridin-5-yl]-1H-benzimidazole (290 mg, 0.712 mmol) was then added to the reaction solution. The thus obtained mixture was stirred at a room temperature for 1 hour, and a saturated ammonium chloride aqueous solution and water were then added to the reaction solution. The obtained mixture was extracted with ethyl acetate three times. The combined ethyl acetate layer was washed with water and a saturated saline, and it was dried over anhydrous magnesium sulfate, and was then concentrated under a reduced pressure. The obtained crude product was purified by silica gel column chromatography (eluent: chloroform/methanol=10/1) to obtain Compound 50 (81.9 mg, 0.208 mmol, yield from Compound 47: 29%).

$^1$H-NMR of Compound 50 (solvent: deuterated dimethylformamide, resonance frequency: 500 MHz) δ 9.23 (s, 1H), 8.73 (s, 1H), 8.24 (s, 1H), 7.76 (s, 1H), 7.73 (s, 1H), 7.68 (s, 1H), 7.65-7.61 (m, 1H), 7.42-7.40 (m, 1H), 5.73 (s, 2H), 3.52-3.51 (m, 1H), 1.14-1.13 (m, 2H), 0.75-0.72 (m, 2H).

Synthesis of 1-cyclopropyl-2-[3-(1H-1,2,3-triazol-1-ylmethyl)pyridin-5-yl]-6-tributylstannyl-1H-benzimidazole (Compound 51)

Compound 50 (81.9 mg, 0.208 mmol) was dissolved in dimethylformamide (1.0 mL), and thereafter, bis(tributyltin)

(208 µL, 0.416 mmol) and bis(tri-t-butylphosphine)palladium (10.6 mg, 0.0208 mmol) were added to the solution. The obtained mixture was heated in an argon atmosphere at 100° C. for 4 hours. After completion of the reaction, the reaction solution was cooled to a room temperature, water was then added thereto, and the obtained mixture was then extracted with ethyl acetate three times. The combined ethyl acetate layer was washed with water and a saturated saline, and it was dried over anhydrous magnesium sulfate, and was then concentrated under a reduced pressure. The obtained crude product was purified twice by silica gel column chromatography (eluent: chloroform/methanol=10/1) to obtain Compound 51 (12.0 mg, 0.023 mmol, yield: 11%).

$^1$H-NMR of Compound 51 (solvent: deuterated chloroform, resonance frequency: 500 MHz): δ 9.25 (d, J=2.0 Hz, 1H), 8.69 (d, J=2.0 Hz, 1H), 8.23 (t, J=2.0 Hz, 1H), 7.77 (s, 1H), 7.76 (d, J=7.9 Hz, 1H), 7.69 (s, 1H), 7.64 (s, 1H), 7.39 (d, J=7.9 Hz, 1H), 5.71 (s, 2H), 3.55-3.52 (m, 1H), 1.65-1.51 (m, 6H), 1.45-1.23 (m, 6H), 1.19-1.05 (m, 8H), 0.87 (t, J=7.9 Hz, 9H), 0.74-0.71 (m, 2H).

Synthesis of Compound 603

Compound 51 (11.0 mg, 0.0182 mmol) was dissolved in dichloromethane (1.0 mL), and iodine (2.54 mg, 0.0200 mmol) was then added to the solution. The obtained mixture was stirred in an argon atmosphere at a room temperature for 10 minutes. After completion of the reaction, a saturated sodium hydrogen carbonate aqueous solution and a saturated sodium thiosulfate aqueous solution were added to the reaction solution, and the obtained mixture was then extracted with dichloromethane three times. The combined dichloromethane layer was washed with water and a saturated saline, and it was dried over anhydrous magnesium sulfate, and was then concentrated under a reduced pressure. The obtained crude product was purified by silica gel column chromatography (eluent: chloroform/methanol=10/1) to obtain Compound 603 (4.5 mg, 0.010 mmol).

$^1$H-NMR of Compound 603 (solvent: deuterated chloroform, resonance frequency: 500 MHz): δ 9.24 (d, J=1.9 Hz, 1H), 8.71 (d, J=2.1 Hz, 1H), 8.22 (t, J=2.1 Hz, 1H), 7.96 (d, J=1.2 Hz, 1H), 7.77 (d, J=1.0 Hz, 1H), 7.64 (d, J=1.2 Hz, 1H), 7.64-7.59 (m, 1H), 7.54-7.53 (m, 1H), 5.71 (s, 2H), 3.51-3.46 (m, 1H), 1.15-1.11 (m, 2H), 0.73-0.70 (m, 2H).

(Example 15) Synthesis of Compound [$^{123}$I] 603

An aqueous solution of [$^{123}$I] sodium iodide (1496 MBq/30 µL) in 1 mol/L hydrochloric acid (170 µL) and a 30% (w/v) hydrogen peroxide aqueous solution (5 µL) were added to an acetonitrile solution (concentration: 1 mg/mL, 90 µL) of Compound 51 synthesized by the method described in Example 14. The mixed solution was left at rest at 40° C. for 10 minutes, and was then subjected to HPLC under the below-mentioned conditions, so that a fraction with the same retention time as Compound 603 obtained in Example 14 was obtained as a fraction of Compound [$^{123}$I] 603.

<HPLC conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding 10 mL of water to the aforementioned fraction was supplied to a Sep-Pak C18 column (trade name: Sep-Pak (registered trademark) Light C18 Cartridges, manufactured by Waters, the amount of and captured in the column. This column was washed with 1 mL of water, and ethanol (0.3 mL) was then supplied to the column, so that Compound [$^{123}$I] 603 was eluted, and it was then diluted with a physiological saline to obtain a physiological saline aqueous solution of Compound [$^{123}$I] 603. The obtained radioactivity was 1010 MBq immediately after completion of the synthesis (42 minutes after initiation of the synthesis). Moreover, a TLC analysis was carried out under the below-mentioned conditions. As a result, the radiochemical purity was 95.5%.

<TLC analysis conditions>
TLC plate: Silica Gel 60 $F_{254}$ (product name, manufactured by Merck)
Development phase: ethyl acetate/methanol/diethylamine=10/2/1 (volume ratio)
RI detector: RitaStar, manufactured by Raytest (Example 16) Synthesis of Compound 604

Figure 10:
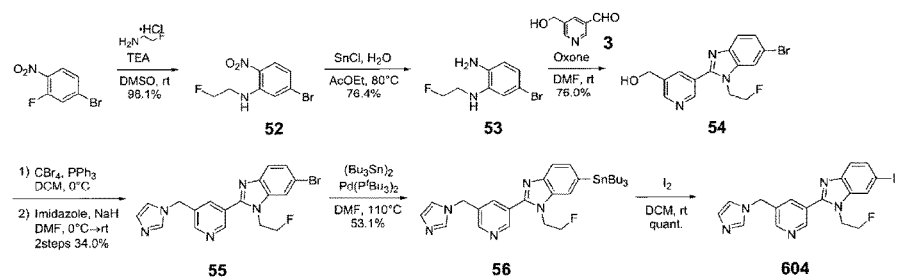
FIG. 10 is a drawing showing a synthesis example of 1-(2-fluoroethyl)-2-[5-{(imidazol-1-yl)methyl}pyridin-3-yl]-6-iodobenzimidazole.

Compound 604 was synthesized in accordance with the scheme shown in FIG. 10.

Synthesis of
5-bromo-N-(2-fluoroethyl)-2-nitrobenzenamine
(Compound 52)

4-Bromo-2-fluoronitrobenzene (1.00 g, 4.55 mmol) was dissolved in N,N'-dimethyl sulfoxide (5 mL), and thereafter, triethylamine (1.90 mL, 13.6 mmol) and 2-fluoroethylamine hydrochloride (679 mg, 6.82 mmol) were added to the solution at a room temperature. The obtained mixture was stirred overnight in an argon atmosphere at the same temperature as described above. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (hexane/ethyl acetate=5/1) to obtain Compound 52 (1.17 g, 4.46 mmol, and yield: 98%).

$^1$H-NMR of Compound 52 (solvent: deuterated chloroform, resonance frequency: 500 MHz): δ 8.23 (bs, 1H), 8.06 (d, J=9.1 Hz, 1H), 7.04 (d, J=2.0 Hz, 1H), 6.82 (dd, J=9.1, 2.0 Hz, 1H), 4.70 (dt, J=47.0, 5.0 Hz, 2H), 3.68-3.60 (m, 2H)

Synthesis of
5-bromo-N-(2-fluoroethyl)-1,2-phenylenediamine
(Compound 53)

Compound 52 (526 mg, 2.00 mmol) was dissolved in ethyl acetate (10.0 mL), and thereafter, tin(II) chloride (1.14 g, 6.00 mmol) and water (0.108 mL, 6.00 mmol) were added to the solution. The obtained mixture was heated overnight in an argon atmosphere at 80° C. After completion of the reaction, a 4 mol/L sodium hydroxide aqueous solution (10 mL) was added to the reaction solution, and the obtained mixture was then filtrated through Celite. The obtained filtrate was dried over anhydrous sodium sulfate, and was then concentrated under a reduced pressure. The obtained crude product was purified by silica gel chromatography (hexane/ethyl acetate=3/1) to obtain Compound 53 (356.0 mg, 1.53 mmol, yield: 76%).

¹H-NMR of Compound 53 (solvent: deuterated chloroform, resonance frequency: 500 MHz): δ 6.81 (dd, J=8.2, 2.1 Hz, 1H), 6.74 (d, J=2.1 Hz, 1H), 6.60 (d, J=8.2 Hz, 1H), 4.68 (dt, J=47.3, 4.9 Hz, 2H), 3.77 (t, J=5.7 Hz, 1H), 3.47-3.34 (m, 4H)

Synthesis of 5-[6-bromo-1-(2-fluoroethyl)benzimidazol-2-yl]pyridine-3-methanol (Compound 54)

Compound 3 (150 mg, 1.09 mmol) synthesized by the method described in Example 1 was dissolved in N,N'-dimethylformamide (5.0 mL), and thereafter, Compound 53 (356.0 mg, 1.53 mmol) and potassium peroxymonosulfate (Oxone (registered trademark) Monopersulfate Compound, manufactured by Wako Pure Chemical Industries, Ltd.) (807 mg, 1.31 mmol) were added to the above-obtained solution at a room temperature. The obtained mixture was stirred in an argon atmosphere at the same temperature as described above for 1 hour. After completion of the reaction, a saturated sodium thiosulfate aqueous solution and a saturated sodium hydrogen carbonate aqueous solution were added at 0° C. to the reaction solution, and the obtained mixture was then stirred for 10 minutes. Thereafter, the reaction mixture was extracted with ethyl acetate three times. The combined ethyl acetate layer was dried over anhydrous sodium sulfate, and was then concentrated under a reduced pressure. The obtained crude product was purified by silica gel chromatography (ethyl acetate/methanol/diethylamine=50/1/0→20/1/0→10/1/0.3) to obtain Compound 54 (291 mg, 0.831 mmol, and yield: 76%).

¹H-NMR of Compound 54 (solvent: deuterated chloroform, resonance frequency: 500 MHz): δ 8.87 (d, J=2.1 Hz, 1H), 8.77 (d, J=2.1 Hz, 1H), 8.13 (s, 1H), 7.65 (d, J=5.8 Hz, 1H), 7.59 (d, J=8.7 Hz, 1H), 4.87-4.83 (m, 3H), 4.75 (t, J=4.8 Hz, 1H), 4.53 (t, J=4.8 Hz, 1H), 4.48 (t, J=4.8 Hz, 1H), 1.99 (d, J=5.6 Hz, 1H)

Synthesis of 6-bromo-1-(2-fluoroethyl)-2-[5-(imidazol-1-ylmethyl)pyridin-3-yl]benzimidazole (Compound 55)

Compound 54 (291 mg, 0.831 mmol) was dissolved in dichloromethane (9.0 mL), and thereafter, carbon tetrabromide (412 mg, 1.24 mmol) and triphenylphosphine (434 mg, 1.66 mmol) were added at 0° C. to the solution. The obtained mixture was stirred in an argon atmosphere at the same temperature as described above for 1 hour. After completion of the reaction, the reaction solution was concentrated under a reduced pressure, and the obtained crude product was then purified by silica gel chromatography (ethyl acetate), so as to obtain a mixture containing 2-(5-bromomethylpyridin-3-yl)-6-bromo-5-fluoro-1-(2-fluoroethyl)benzimidazole.

Imidazole (56.4 mg, 0.831 mmol) was dissolved in N,N'-dimethylformamide (2.5 mL), and sodium hydride (23.8 mg, 0.997 mmol) was then added at 0° C. to the solution. The obtained mixture was stirred for 30 minutes. An N,N'-dimethylformamide solution (2.5 mL), in which the mixture containing 2-(5-bromomethylpyridin-3-yl)-6-bromo-5-fluoro-1-(2-fluoroethyl)benzimidazole had been dissolved, was added to the reaction solution, and the thus obtained mixture was then stirred in an argon atmosphere at a room temperature for 1.5 hours. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (chloroform/methanol=20/1→8/1) to obtain Compound 55 (113.0 mg, 0.282 mmol, two-step yield from Compound 54: 34%).

¹H-NMR of Compound 55 (solvent: deuterated chloroform, resonance frequency: 500 MHz): δ 8.95 (d, J=2.0 Hz, 1H), 8.65 (d, J=2.0 Hz, 1H), 7.88 (t, J=2.0 Hz, 1H), 7.70 (d, J=8.6 Hz, 1H), 7.62-7.58 (m, 2H), 7.47 (dd, J=8.6, 1.8 Hz, 1H), 7.15 (s, 1H), 6.96 (s, 1H), 5.26 (s, 2H), 4.77 (dt, J=46.8, 4.8 Hz, 2H), 4.42 (dt, J=25.0, 4.8 Hz, 2H)

Synthesis of 1-(2-fluoroethyl)-2-[5-{(imidazol-1-yl)methyl}pyridin-3-yl]-6-tributylstannylbenzimidazole (Compound 56)

Compound 55 (110.0 mg, 0.275 mmol) was dissolved in N,N'-dimethylformamide (1.0 mL), and thereafter, bis(tributyltin) (275 μL, 0.550 mmol) and bis(tri-tert-butylphosphine)palladium (28.1 mg, 0.0550 mmol) were added to the solution at a room temperature. The obtained mixture was stirred overnight in an argon atmosphere at 110° C. After completion of the reaction, ethyl acetate and water were added to the reaction solution, and an ethyl acetate layer was extracted three times. The combined ethyl acetate layer was dried over anhydrous sodium sulfate, and was then concentrated under a reduced pressure. The obtained crude product was purified by silica gel column chromatography (eluent: chloroform/methanol=50/1→20/1) to obtain Compound 56 (89.0 mg, 0.145 mmol, yield: 53%).

¹H-NMR of Compound 56 (solvent: deuterated chloroform, resonance frequency: 500 MHz): δ 8.96 (d, J=2.0 Hz, 1H), 8.62 (d, J=2.0 Hz, 1H), 7.91 (t, J=2.0 Hz, 1H), 7.82 (d, J=7.9 Hz, 1H), 7.62 (s, 1H), 7.47 (s, 1H), 7.44 (d, J=7.9 Hz, 1H), 7.14 (s, 1H), 6.96 (s, 1H), 5.26 (s, 2H), 4.79 (dt, J=46.8, 4.8 Hz, 2H), 4.47 (dt, J=24.7, 4.8 Hz, 2H), 1.69-1.49 (m, 6H), 1.39-1.30 (m, 6H), 1.24-1.04 (m, 6H), 0.90 (t, J=7.3 Hz, 9H)

Synthesis of Compound 604

Compound 56 (20.0 mg, 0.0327 mmol) was dissolved in dichloromethane (1.50 mL), and iodine (15.7 mg, 0.127 mmol) was then added to the solution at a room temperature. The obtained mixture was stirred in an argon atmosphere at the same temperature as described above for 2 hours. After completion of the reaction, a saturated sodium thiosulfate aqueous solution and a saturated sodium hydrogen carbonate aqueous solution were added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel column chromatography (eluent: chloroform/methanol=10/1), so as to quantitatively obtain Compound 604 (15.5 mg, 0.0347 mmol).

¹H-NMR of Compound 604 (solvent: deuterated chloroform, resonance frequency: 500 MHz): δ 8.95 (d, J=2.1 Hz, 1H), 8.64 (d, J=2.1 Hz, 1H), 7.88 (s, 1H), 7.77 (d, J=1.4 Hz, 1H), 7.65-7.58 (m, 3H), 7.14 (s, 1H), 6.96-6.95 (m, 1H), 5.26 (s, 2H), 4.76 (dt, J=46.8, 4.8 Hz, 2H), 4.41 (dt, J=24.9, 4.8 Hz, 2H)

(Example 17) Synthesis of Compound [$^{123}$I] 604

An aqueous solution of [$^{123}$I] sodium iodide (1178 MBq/15 μL) in 1 mol/L hydrochloric acid (42.5 μL) and a 30% (w/v) hydrogen peroxide aqueous solution (2.5 μL) were added to an acetonitrile solution (concentration: 1 mg/mL, 22.5 μL) of Compound 56 synthesized by the method described in Example 16. The mixed solution was left at rest at 40° C. for 10 minutes, and was then subjected to HPLC under the below-mentioned conditions, so that a fraction with the same retention time as Compound 604 obtained in Example 16 was obtained as a fraction of Compound [$^{123}$I] 604.
<HPLC Conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding 10 mL of water to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 604 was adsorbed and captured in the column. This column was washed with water (1 mL), and ethanol (0.4 mL) was then supplied to the column, so that Compound [$^{123}$I] 604 was eluted, and it was then diluted with a physiological saline to obtain a physiological saline aqueous solution of Compound [$^{123}$I] 604. The obtained radioactivity was 252 MBq immediately after completion of the synthesis (66 minutes after initiation of the synthesis). Moreover, a TLC analysis was carried out under the below-mentioned conditions. As a result, the radiochemical purity was 98.8%.
<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 18) Synthesis of Compound 605

Figure 11:
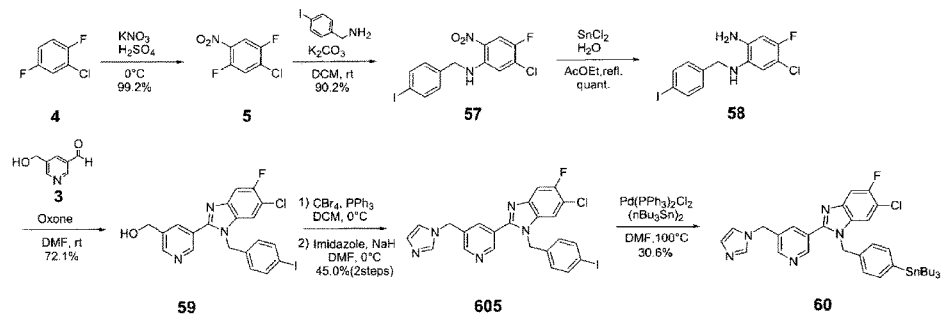
FIG. 11 is a drawing showing a synthesis example of 6-chloro-5-fluoro-1-(4-iodobenzyl)-2-[5-(1H-imidazol-1-ylmethyl)-3-pyridinyl]-1H-benzimidazole.

Compound 605 was synthesized in accordance with the scheme shown in FIG. 11.

Synthesis of 5-chloro-4-fluoro-N-(4-iodobenzyl)-2-nitrobenzenamine (Compound 57)

Compound 5 (500 mg, 2.58 mmol) synthesized by the method described in Example 1 was dissolved in dichloromethane (15.0 mL), and potassium carbonate (1.07 g, 7.74 mmol) was then added to the solution. Then, 4-iodobenzylamine (902 mg, 3.87 mmol) was added to the mixture, and the thus obtained mixture was then heated to reflux overnight in an argon atmosphere. After completion of the reaction, water was added to the reaction solution, and the obtained mixture was then extracted with dichloromethane three times. The combined dichloromethane layer was dried over anhydrous sodium sulfate, and was then concentrated under a reduced pressure. The obtained crude product was purified by silica gel column chromatography (eluent: hexane/chloroform=5/1→1/1) to obtain Compound 57 (946 mg, 2.33 mmol, yield: 90%).
$^1$H-NMR of Compound 57 (solvent: deuterated chloroform, resonance frequency: 500 MHz): δ 8.27 (s, 1H), 8.02 (d, J=9.2 Hz, 1H), 7.72 (d, J=8.4 Hz, 2H), 7.09 (d, J=8.4 Hz, 2H), 6.81 (d, J=6.2 Hz, 1H), 4.46 (d, J=5.7 Hz, 2H).

Synthesis of 5-chloro-4-fluoro-N1-(4-iodobenzyl)-1,2-benzenediamine (Compound 58)

Compound 57 (100 mg, 0.246 mmol) was dissolved in ethyl acetate (2.00 mL), and thereafter, water (0.0441 mL, 2.45 mmol) and tin(II) chloride (233 mg, 1.23 mmol) were added to the solution. The obtained mixture was heated to reflux in an argon atmosphere for 3.5 hours. After completion of the reaction, a saturated sodium hydrogen carbonate aqueous solution was added to the reaction solution, and the precipitated solid was then removed by filtration. The resultant was extracted with ethyl acetate three times, and the combined ethyl acetate layer was dried over anhydrous sodium sulfate and was then concentrated under a reduced pressure, so as to quantitatively obtain Compound 58 (93.3 mg, 0.248 mmol).
$^1$H-NMR of Compound 58 (solvent: deuterated chloroform, resonance frequency: 500 MHz): δ 7.69 (d, J=8.4 Hz, 2H), 7.12 (d, J=8.4 Hz, 2H), 6.57 (d, J=7.0 Hz, 1H), 6.54 (d, J=9.9 Hz, 1H), 4.19 (s, 2H), 3.47 (s, 3H).

Synthesis of 6-chloro-5-fluoro-1-(4-iodobenzyl)-2-[5-hydroxy-1-ylmethyl)-3-pyridinyl]-1H-benzimidazole (Compound 59)

Compound 3 (30.3 mg, 0.221 mmol) synthesized by the method described in Example 1 was dissolved in dimethylformamide (2.00 mL), and thereafter, Compound 58 (92.6 mg, 0.246 mmol) and potassium peroxymonosulfate (Oxone (registered trademark) Monopersulfate Compound, manufactured by Wako Pure Chemical Industries, Ltd.) (181 mg, 0.295 mmol) were added to the above-obtained solution. The obtained mixture was stirred in an argon atmosphere at a room temperature for 2 hours. After completion of the reaction, a saturated sodium hydrogen carbonate aqueous solution and a saturated sodium thiosulfate aqueous solution were added to the reaction solution under cooling on ice, and the obtained mixture was then extracted with ethyl acetate three times. The combined ethyl acetate layer was dried over anhydrous sodium sulfate, and was then concentrated under a reduced pressure. The obtained crude product was purified by silica gel column chromatography (eluent: ethyl acetate) to obtain Compound 59 (78.7 mg, 0.159 mmol, yield: 72%).
$^1$H-NMR of Compound 59 (solvent: deuterated chloroform, resonance frequency: 500 MHz): δ 8.75-8.73 (m, 2H), 8.07 (s, 1H), 7.70-7.68 (m, 2H), 7.63 (d, J=9.1 Hz, 1H), 7.24 (s, 1H), 6.80 (d, J=8.5 Hz, 2H), 5.37 (s, 2H), 4.81 (d, J=5.5 Hz, 2H)

Synthesis of Compound 605

Compound 59 (78.7 mg, 0.159 mmol) was dissolved in dichloromethane (1.60 mL), and thereafter, triphenylphosphine (83.4 mg, 0.318 mmol) and carbon tetrabromide (79.3 mg, 0.239 mmol) were added to the solution under cooling on ice. The obtained mixture was stirred in an argon atmosphere at 0° C. for 15 minutes. After completion of the reaction, the reaction solution was concentrated under a reduced pressure to obtain a crude product.

To a solution prepared by dissolving imidazole (21.6 mg, 0.318 mmol) in dimethylformamide (0.800 mL), sodium hydride (12.7 mg, 0.318 mmol) was added under cooling on ice. The previously obtained crude product was dissolved in dimethylformamide (0.800 mL), and the obtained solution was then added to the imidazole solution under cooling on ice. The obtained mixture was stirred under cooling on ice for 2 hours. After completion of the reaction, water was added to the reaction solution under cooling on ice, and the obtained mixture was then extracted with ethyl acetate three times. The combined ethyl acetate layer was dried over anhydrous sodium sulfate, and was then concentrated under a reduced pressure. The obtained crude product was purified by silica gel column chromatography (eluent: chloroform/ methanol=7/1) to obtain Compound 605 (38.9 mg, 0.0715 mmol, two-step yield from Compound 59: 45%).

$^1$H-NMR of Compound 605 (solvent: deuterated chloroform, resonance frequency: 500 MHz): δ 8.80 (s, 1H), 8.61 (s, 1H), 7.78 (s, 1H), 7.69 (d, J=6.9 Hz, 2H), 7.63-7.61 (m, 1H), 7.53 (s, 1H), 7.25 (d, J=8.0 Hz, 1H), 7.11 (s, 1H), 6.85 (s, 1H), 6.73 (d, J=7.9 Hz, 2H), 5.30 (s, 2H), 5.19 (s, 2H).

(Example 19) Synthesis of Compound [$^{123}$I] 605

As shown in FIG. 11, Compound 605 (23.1 mg, 0.0425 mmol) synthesized by the method described in Example 18 was dissolved in dimethylformamide (0.500 mL), and thereafter, bis(tributyltin) (0.0425 mL, 0.0850 mmol) and bis(tri-tert-butylphosphine)palladium (2.17 mg, 0.00425 mmol) were added to the solution. The obtained mixture was stirred overnight in an argon atmosphere at 100° C. After completion of the reaction, the reaction mixture was extracted with ethyl acetate three times, and the combined ethyl acetate layer was dried over anhydrous sodium sulfate and was then concentrated under a reduced pressure. The obtained crude product was purified by silica gel column chromatography (eluent: ethyl acetate→ethyl acetate/methanol=9/1), so as to quantitatively obtain 6-chloro-5-fluoro-1-(4-tributylstannyl-benzyl)-2-[5-(1H-imidazol-1-ylmethyl)-3-pyridinyl]-1H-benzimidazole (Compound 60) (9.2 mg, 0.0130 mmol).

$^1$H-NMR of Compound 60 (solvent: deuterated chloroform, resonance frequency: 500 MHz): δ 8.84 (d, J=2.0 Hz, 1H), 8.59 (d, J=2.2 Hz, 1H), 7.88 (s, 1H), 7.61 (d, J=9.1 Hz, 1H), 7.55 (s, 1H), 7.46 (d, J=8.0 Hz, 2H), 7.30 (d, J=6.3 Hz, 1H), 7.10 (s, 1H), 6.96 (d, J=8.0 Hz, 2H), 6.85 (s, 1H), 5.36 (s, 2H), 5.17 (s, 2H), 1.56-1.50 (m, 6H), 1.36-1.29 (m, 6H), 1.08-1.04 (m, 6H), 0.88 (t, J=7.3, 9H).

To an acetonitrile solution of Compound 60 (concentration: 1 mg/mL, 45 μL), an aqueous solution of [$^{123}$I] sodium iodide (1178 MBq/30 μL) in 1 mol/L hydrochloric acid (85 μL) and a 30% (w/v) hydrogen peroxide aqueous solution (5 μL) were added. The mixed solution was left at rest at 40° C. for 10 minutes, and was then subjected to HPLC under the below-mentioned conditions, so that a fraction with the same retention time as Compound 605 obtained in Example 18 was obtained as a fraction of Compound [$^{123}$I] 605.
<HPLC Conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding 10 mL of water to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 605 was adsorbed and captured in the column. This column was washed with 1 mL of water, and ethanol (0.2 mL) was then supplied to the column, so that Compound [$^{123}$I] 605 was eluted, and it was then diluted with a physiological saline to obtain a physiological saline aqueous solution of Compound [$^{123}$I] 605. The obtained radioactivity was 334 MBq immediately after completion of the synthesis (116 minutes after initiation of the synthesis). Moreover, a TLC analysis was carried out under the below-mentioned conditions. As a result, the radiochemical purity was 98.2%.

<TLC Analysis Conditions>
TLC plate: Silica Gel 60 $F_{254}$ (product name, manufactured by Merck)
Development phase: ethyl acetate/methanol/diethylamine=10/2/1 (volume ratio)
RI detector: RitaStar, manufactured by Raytest (Example 20) Synthesis of Compound 606

Figure 12:
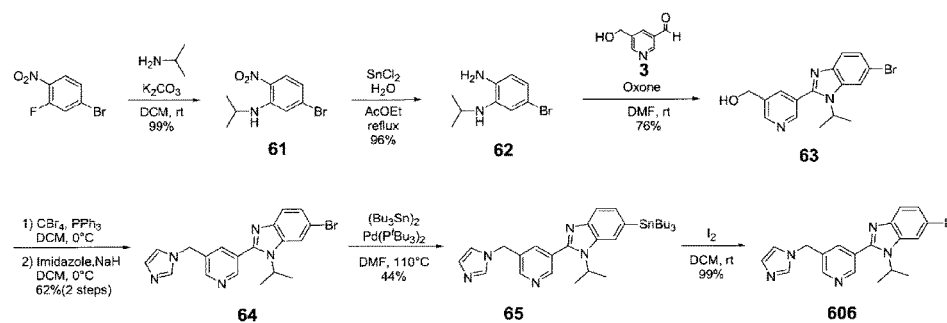
FIG. 12 is a drawing showing a synthesis example of 2-[5-{(1H-imidazol-1-yl)methyl}pyridin-3-yl]-6-iodo-1-isopropyl-1H-benzo[d]imidazole.

Compound 606 was synthesized in accordance with the scheme shown in FIG. 12.

Synthesis of 5-bromo-N-isopropyl-2-nitroaniline (Compound 61)

4-Bromo-2-fluoronitrobenzene (880 mg, 4.00 mmol) was dissolved in dichloromethane (6.00 mL), and potassium carbonate (2.76 g, 20.0 mmol) was then added to the solution. Thereafter, isopropylamine (1.03 mL, 12.0 mmol) was added to the mixed solution, and the thus obtained mixture was then stirred overnight in an argon atmosphere at a room temperature. After completion of the reaction, water was added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (eluent: hexane/ethyl acetate=10/1) to obtain Compound (1.04 g, 4.01 mmol, yield: 99%).

$^1$H-NMR of Compound 61 (solvent: deuterated chloroform, resonance frequency: 500 MHz): δ 8.03 (d, J=9.1 Hz, 2H), 7.02 (d, J=2.0 Hz, 1H), 6.72 (dd, J=2.0 Hz, 1H), 3.79 (sext, J=6.5, 19.5 Hz, 1H), 1.34 (d, J=6.4 Hz, 6H)

Synthesis of 5-bromo-N1-isopropylbenzene-1,2-diamine (Compound 62)

Compound 61 (1.04 g, 4.01 mmol) was dissolved in ethyl acetate (15.0 mL), and thereafter, water (0.289 mL, 16.0 mmol) and tin(II) chloride (3.04 g, 16.0 mmol) were added to the solution. The obtained mixture was heated to reflux in an argon atmosphere for 5 hours. After completion of the reaction, a 4 mol/L sodium hydroxide aqueous solution was added to the reaction solution, and the precipitated solid was then removed by filtration. The resultant was extracted with ethyl acetate twice, and the combined ethyl acetate layer was dried over anhydrous sodium sulfate, and was then concentrated under a reduced pressure. The obtained crude product was purified by silica gel chromatography (eluent: chloroform/methanol=40/1) to obtain Compound 62 (883 mg, 3.84 mmol, yield: 96%).

$^1$H-NMR of Compound 62 (solvent: deuterated chloroform, resonance frequency: 500 MHz): δ 6.74-6.71 (m, 2H), 6.57 (d, J=8.6 Hz, 1H), 3.55 (quin, J=6.3, 12.6 Hz, 1H), 3.23 (br, 3H), 1.23 (d, J=6.3 Hz, 6H)

Synthesis of {5-(6-bromo-1-isopropyl-1H-benzo[d] imidazol-2-yl)pyridin-3-yl}methanol (Compound 63)

Compound 3 (473 mg, 3.45 mmol) synthesized by the method described in Example 1 was dissolved in dimethylformamide (5.00 mL), and thereafter, a dimethylformamide solution (10.0 mL), in which Compound 62 (881 mg, 3.84 mmol) had been dissolved, and potassium peroxymonosulfate (Oxone (registered trademark) Monopersulfate Compound, manufactured by Wako Pure Chemical Industries, Ltd.) (2.83 g, 4.60 mmol), were added to the above-obtained solution. The obtained mixture was stirred in an argon atmosphere at a room temperature for 1 hour. After completion of the reaction, a saturated sodium hydrogen carbonate aqueous solution and a saturated sodium thiosulfate aqueous solution were added to the reaction solution under cooling on ice, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (eluent: chloroform/methanol=10/1) to obtain Compound 63 (1.01 g, 2.92 mmol, yield: 76%).

$^1$H-NMR of Compound 63 (solvent: deuterated chloroform, resonance frequency: 500 MHz): δ 8.73 (d, J=2.1 Hz, 1H), 8.67 (d, J=2.1 Hz, 1H), 7.98 (t, J=2.1 Hz, 1H), 7.79 (d, J=1.7 Hz, 1H), 7.69 (d, J=8.7 Hz, 1H), 7.42 (dd, J=1.8 Hz, 1H), 4.82 (d, J=3.3 Hz, 2H), 4.72 (quin, J=7.0, 13.9 Hz, 1H), 3.52 (s, 1H), 1.65 (d, J=7.0 Hz, 6H).

Synthesis of 2-[5-{(1H-imidazol-1-yl)methyl}pyridin-3-yl]-6-bromo-1-isopropyl-1H-benzo[d]imidazole (Compound 64)

Compound 63 (500 mg, 1.44 mmol) was dissolved in dichloromethane (14.4 mL), and thereafter, triphenylphosphine (755 mg, 2.88 mmol) and carbon tetrabromide (716 mg, 2.16 mmol) were added to the solution under cooling on ice. The obtained mixture was stirred in an argon atmosphere at 0° C. for 15 minutes. After completion of the reaction, the reaction mixture was concentrated under a reduced pressure to obtain a crude product.

To a solution prepared by dissolving imidazole (196 mg, 2.88 mmol) in dimethylformamide (0.50 mL), sodium hydride (115 mg, 2.88 mmol) was added under cooling on ice, and the obtained mixture was then stirred in an argon atmosphere at 0° C. for 10 minutes. The previously obtained crude product was dissolved in dimethylformamide (1.50 mL), and the obtained solution was then added to the imidazole solution under cooling on ice. The obtained mixture was stirred for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (eluent: chloroform/methanol=20/1) to obtain Compound 64 (353 mg, 0.890 mmol, two-step yield from Compound 63: 52%).

$^1$H-NMR of Compound 64 (solvent: deuterated chloroform, resonance frequency: 500 MHz): δ 8.84 (d, J=2.0 Hz, 1H), 8.63 (d, J=2.2 Hz, 1H), 7.78-7.76 (m, 2H), 7.67 (d, J=8.6 Hz, 1H), 7.62 (s, 1H), 7.42 (dd, J=1.8 Hz, 1H), 7.15 (s, 1H), 6.97 (t, J=1.3 Hz, 1H), 5.27 (s, 2H), 4.66 (quin, J=7.0, 13.9 Hz, 1H), 1.64 (d, J=7.0 Hz, 6H).

Synthesis of 2-[5-{(1H-imidazol-1-yl)methyl}pyridin-3-yl]-1-isopropyl-6-(tributylstannyl)-1H-benzo[d]imidazole (Compound 65)

Compound 64 (353 mg, 0.890 mmol) was dissolved in dimethylformamide (2.00 mL), and thereafter, bis(tributyltin) (1.34 mL, 2.67 mmol) and bis(tri-tert-butylphosphine) palladium (92.0 mg, 0.180 mmol) were added to the solution. The obtained mixture was stirred overnight in an argon atmosphere at 110° C. After completion of the reaction, the reaction mixture was extracted with ethyl acetate twice, and the combined ethyl acetate layer was dried over anhydrous sodium sulfate, and was then concentrated under a reduced pressure. The obtained crude product was purified by silica gel chromatography (eluent: chloroform/methanol=10/1) to obtain Compound 65 (238 mg, 0.392 mmol, yield: 44%).

$^1$H-NMR of Compound 65 (solvent: deuterated chloroform, resonance frequency: 500 MHz): δ 8.84 (d, J=2.0 Hz, 1H), 8.60 (d, J=2.3 Hz, 1H), 7.81-7.79 (m, 2H), 7.72 (s, 1H), 7.62 (s, 1H), 7.38 (dd, J=0.6 Hz, 1H), 7.14 (t, J=1.0, 1H), 6.97 (t, J=1.3 Hz, 1H), 5.26 (s, 2H), 4.69 (quin, J=6.9 Hz, 13.9 Hz, 1H), 1.67 (d, J=6.9 Hz, 6H), 1.62-1.56 (m, 6H), 1.40-1.33 (m, 6H), 1.14-1.11 (m, 6H), 0.90 (t, J=7.3 Hz, 9H)

Synthesis of Compound 606

Compound 65 (30.0 mg, 0.0495 mmol) was dissolved in dichloromethane (2.00 mL), and iodine (25.4 mg, 0.200 mmol) was then added to the solution. The obtained mixture was stirred in an argon atmosphere at a room temperature for 15 minutes. After completion of the reaction, a saturated sodium hydrogen carbonate aqueous solution and a saturated sodium thiosulfate aqueous solution were added to the reaction solution, and the obtained mixture was then extracted with dichloromethane twice. Thereafter, the combined dichloromethane layer was dried over anhydrous sodium sulfate, and was then concentrated under a reduced pressure. The obtained crude product was purified by silica gel chromatography (eluent: chloroform/methanol=20/1) to obtain Compound 606 (22.0 mg, 0.0496 mmol, yield: 99%).

$^1$H-NMR of Compound 606 (solvent: deuterated chloroform, resonance frequency: 500 MHz): δ 8.83 (d, J=2.0 Hz, 1H), 8.63 (d, J=2.2 Hz, 1H), 7.97 (d, J=1.0 Hz, 1H), 7.77 (t, J=2.1 Hz, 1H), 7.62 (s, 1H), 7.59-7.55 (m, 2H), 7.15 (s, 1H), 6.97 (s, 1H), 5.27 (s, 2H), 4.65 (quin, J=7.0, 13.9 Hz, 1H), 1.63 (d, J=7.0 Hz, 6H).

(Example 21) Synthesis of Compound [$^{123}$I] 606

To an acetonitrile solution of Compound 65 synthesized by the method described in Example 20 (concentration: 1 mg/mL, 45 μL), an aqueous solution of [$^{123}$I] sodium iodide (720 MBq/30 μL) in 1 mol/L hydrochloric acid (85 μL) and a 30% (w/v) hydrogen peroxide aqueous solution (5 μL) were added. The mixed solution was left at rest at 40° C. for 10 minutes, and was then subjected to HPLC under the below-mentioned conditions, so that a fraction with the same retention time as Compound 606 obtained in Example 20 was obtained as a fraction of Compound [$^{123}$I] 606.
<HPLC conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding 10 mL of water to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 606 was adsorbed and captured in the column. This column was washed with water (1 mL), and ethanol (0.2 mL) was then supplied to the column, so that Compound [$^{123}$I] 606 was eluted, and it was then diluted with a physiological saline to obtain a physiological saline aqueous solution of Compound [$^{123}$I] 606.

The obtained radioactivity was 229 MBq immediately after completion of the synthesis (53 minutes after initiation of the synthesis). Moreover, a TLC analysis was carried out under the below-mentioned conditions. As a result, the radiochemical purity was 98.1%.

<TLC Analysis Conditions>
TLC plate: Silica Gel 60 $F_{254}$ (product name, manufactured by Merck)
Development phase: ethyl acetate/methanol/diethylamine=10/2/1 (volume ratio)
RI detector: RitaStar, manufactured by Raytest (Example 22) Synthesis of Compound 607

Figure 13:
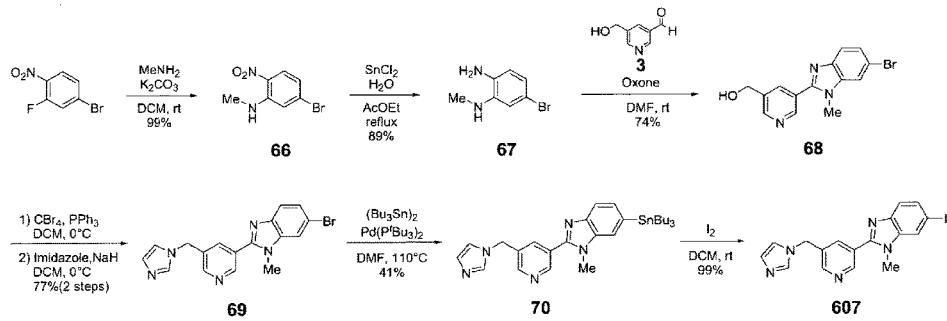
FIG. 13 is a drawing showing a synthesis example of 2-[5-{(1H-imidazol-1-yl)methyl}pyridin-3-yl]-6-iodo-1-methyl-1H-benzo[d]imidazole.

Compound 607 was synthesized in accordance with the scheme shown in FIG. 13.

Synthesis of 5-bromo-N-methyl-2-nitroaniline (Compound 66)

4-Bromo-2-fluoronitrobenzene (220 mg, 1.00 mmol) was dissolved in dichloromethane (5.00 mL), and potassium carbonate (691 mg, 5.00 mmol) was then added to the solution. Thereafter, methylamine (1.50 mL, 3.00 mmol) was added to the mixed solution, and the thus obtained mixture was stirred overnight in an argon atmosphere at a room temperature. After completion of the reaction, water was added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (eluent: hexane/ethyl acetate=10/1) to obtain Compound 66 (230 mg, 1.00 mmol, yield: 99%).

$^1$H-NMR of Compound 66 (solvent: deuterated chloroform, resonance frequency: 500 MHz): δ 8.03 (d, J=9.1 Hz, 2H), 7.01 (d, J=2.0 Hz, 1H), 6.77 (dd, J=2.0 Hz, 1H), 3.02 (d, J=5.1 Hz, 3H).

Synthesis of 5-bromo-N1-methylbenzene-1,2-diamine (Compound 67)

Compound 66 (231 mg, 1.00 mmol) was dissolved in ethyl acetate (5.00 mL), and thereafter, water (72.0 μL, 4.00 mmol) and tin(II) chloride (758 mg, 4.00 mmol) were added to the solution. The obtained mixture was heated to reflux in an argon atmosphere for 5 hours. After completion of the reaction, a 4 mol/L sodium hydroxide aqueous solution was added to the reaction solution, and the precipitated solid was then removed by filtration. The resultant was extracted with ethyl acetate twice, and the combined ethyl acetate layer was dried over anhydrous sodium sulfate, and was then concentrated under a reduced pressure. The obtained crude product was purified by silica gel chromatography (eluent: chloroform/methanol=40/1) to obtain Compound 67 (196 mg, 0.973 mmol, yield: 89%).

$^1$H-NMR of Compound 67 (solvent: deuterated chloroform, resonance frequency: 500 MHz): δ 6.77-6.75 (m, 1H), 6.72 (d, J=2.2 Hz, 1H), 6.57 (d, J=8.1 Hz, 1H), 3.48 (br, 1H) 3.24 (br, 2H), 2.84 (s, 3H).

Synthesis of {5-(6-bromo-1-methyl-1H-benzo[d]imidazol-2-yl)pyridin-3-yl}methanol (Compound 68)

Compound 3 (119 mg, 0.870 mmol) synthesized by the method described in Example 1 was dissolved in dimethylformamide (1.00 mL), and thereafter, a dimethylformamide solution (1.00 mL), in which Compound 67 (196 mg, 0.973 mmol) had been dissolved, and potassium peroxymonosulfate (Oxone (registered trademark) Monopersulfate Compound, manufactured by Wako Pure Chemical Industries, Ltd.) (713 mg, 1.16 mmol), were added to the above-obtained solution. The obtained mixture was stirred in an argon atmosphere at a room temperature for 25 minutes. After completion of the reaction, a saturated sodium hydrogen carbonate aqueous solution and a saturated sodium thiosulfate aqueous solution were added to the reaction solution under cooling on ice, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (eluent: chloroform/methanol=10/1) to obtain Compound 68 (230 mg, 0.722 mmol, yield: 74%).

$^1$H-NMR of Compound 68 (solvent: deuterated chloroform, resonance frequency: 500 MHz): δ 8.92 (d, J=2.1 Hz, 1H), 8.75 (d, J=2.1 Hz, 1H), 8.18 (t, J=2.1 Hz, 1H), 7.69 (d, J=8.6 Hz, 1H), 7.60 (d, J=1.8 Hz, 1H), 7.45-7.43 (m, 1H), 4.87 (s, 2H), 3.89 (s, 3H)

Synthesis of 2-[5-{(1H-imidazol-1-yl)methyl}pyridin-3-yl]-6-bromo-1-methyl-1H-benzo[d]imidazole (Compound 69)

Compound 68 (230 mg, 0.722 mmol) was dissolved in dichloromethane (7.20 mL), and thereafter, triphenylphosphine (378 mg, 1.44 mmol) and carbon tetrabromide (358 mg, 1.08 mmol) were added to the solution under cooling on ice. The obtained mixture was stirred in an argon atmosphere at 0° C. for 20 minutes. After completion of the reaction, the reaction mixture was concentrated under a reduced pressure to obtain a crude product.

To a solution prepared by dissolving imidazole (98.0 mg, 1.44 mmol) in dimethylformamide (0.50 mL), sodium hydride (57.6 mg, 1.44 mmol) was added under cooling on ice. The obtained mixture was stirred in an argon atmosphere at 0° C. for 10 minutes. The previously obtained crude product was dissolved in dimethylformamide (1.50 mL), and the obtained solution was then added to the imidazole solution under cooling on ice. The obtained mixture was stirred for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (eluent: chloroform/methanol=20/1) to obtain Compound 69 (205 mg, 0.558 mmol, two-step yield from Compound 68: 77%).

$^1$H-NMR of Compound 69 (solvent: deuterated chloroform, resonance frequency: 500 MHz): δ 8.97 (d, J=2.1 Hz, 1H), 8.64 (d, J=2.2 Hz, 1H), 7.92 (t, J=2.2 Hz, 1H), 7.67 (d, J=8.6 Hz, 1H), 7.62 (s, 1H), 7.58 (d, J=1.8 Hz, 1H), 7.44 (dd, J=1.8 Hz, 1H), 7.15 (s, 1H), 7.12 (s, 1H), 6.97 (t, J=1.3 Hz, 1H), 5.27 (s, 2H), 3.84 (s, 3H)

Synthesis of 2-[5-{(1H-imidazol-1-yl)methyl}pyridin-3-yl]-1-methyl-6-(tributylstannyl)-1H-benzo[d]imidazole (Compound 70)

Compound 69 (205 mg, 0.558 mmol) was dissolved in dimethylformamide (2.00 mL), and thereafter, bis(tributyltin) (0.840 mL, 1.68 mmol) and bis(tri-tert-butylphosphine)

palladium (56.2 mg, 0.110 mmol) were added to the solution. The obtained mixture was stirred at 110° C. overnight. After completion of the reaction, the reaction mixture was extracted with ethyl acetate twice, and the combined ethyl acetate layer was dried over anhydrous sodium sulfate and was then concentrated under a reduced pressure. The obtained crude product was purified by silica gel chromatography (eluent: chloroform/methanol=20/1) to obtain Compound 70 (133 mg, 0.230 mmol, yield: 41%).

$^1$H-NMR of Compound 70 (solvent: deuterated chloroform, resonance frequency: 500 MHz): δ 8.97 (d, J=2.1 Hz, 1H), 8.60 (d, J=2.2 Hz, 1H), 7.95 (t, J=2.2 Hz, 1H), 7.80 (dd, J=0.7 Hz, 1H), 7.62 (s, 1H), 7.48 (s, 1H), 7.41 (dd, J=0.6 Hz, 1H), 7.14 (s, 1H), 6.97 (s, 1H), 5.26 (s, 2H), 3.88 (s, 3H), 1.61-1.55 (m, 6H), 1.39-1.32 (m, 6H), 1.14-1.11 (m, 6H), 0.90 (t, J=7.3 Hz, 9H)

Synthesis of Compound 607

Compound 70 (30.0 mg, 0.0500 mmol) was dissolved in dichloromethane (2 mL), and iodine (25.4 mg, 0.200 mmol) was then added to the solution at a room temperature. The obtained mixture was stirred in an argon atmosphere for 25 minutes. After completion of the reaction, a saturated sodium hydrogen carbonate aqueous solution and a saturated sodium thiosulfate aqueous solution were added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (eluent: chloroform/methanol=20/1) to obtain Compound 607 (20.7 mg, 0.0499 mmol, yield: 99%).

$^1$H-NMR of Compound 607 (solvent: deuterated chloroform, resonance frequency: 500 MHz): δ 8.96 (d, J=2.1 Hz, 1H), 8.63 (d, J=2.2 Hz, 1H), 7.92 (t, J=2.1 Hz, 1H), 7.78 (d, J=1.4 Hz, 1H), 7.63-7.61 (m, 2H), 7.57 (d, J=8.5 Hz, 1H), 7.15 (s, 1H), 6.97 (s, 1H), 5.27 (s, 2H), 3.83 (s, 3H)

(Example 23) Synthesis of Compound [$^{123}$I] 607

To an acetonitrile solution of Compound 70 synthesized by the method described in Example 22 (concentration: 1 mg/mL, 45 μL), an aqueous solution of [$^{123}$I] sodium iodide (846 MBq/30 μL) in 1 mol/L hydrochloric acid (85 μL) and 5 μL of a 30% (w/v) hydrogen peroxide aqueous solution were added. The mixed solution was left at rest at 40° C. for 10 minutes, and was then subjected to HPLC under the below-mentioned conditions, so that a fraction with the same retention time as Compound 607 obtained in Example 22 was obtained as a fraction of Compound [$^{123}$I] 607.

<HPLC Conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding 10 mL of water to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 607 was adsorbed and captured in the column. This column was washed with water (10 mL), and ethanol (0.2 mL) was then supplied to the column, so that Compound [$^{123}$I] 607 was eluted, and it was then diluted with a physiological saline to obtain a physiological saline aqueous solution of Compound [$^{123}$I] 607. The obtained radioactivity was 295 MBq immediately after completion of the synthesis (110 minutes after initiation of the synthesis). Moreover, a TLC analysis was carried out under the below-mentioned conditions. As a result, the radiochemical purity was 98.8%.

<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 24) Synthesis of Compound 608

Figure 14:
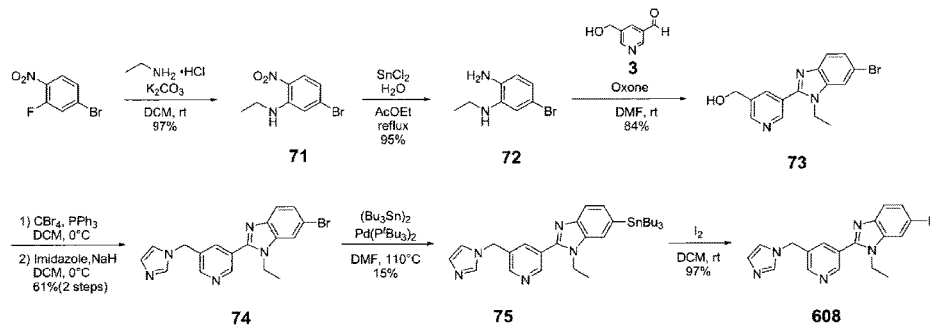
FIG. 14 is a drawing showing a synthesis example of 2-[5-{(1H-imidazol-1-yl)methyl}pyridin-3-yl]-1-ethyl-6-iodo-1H-benzo[d]imidazole.

Compound 608 was synthesized in accordance with the scheme shown in FIG. 14.

Synthesis of 5-bromo-N-ethyl-2-nitroaniline (Compound 71)

4-Bromo-2-fluoronitrobenzene (220 mg, 1.00 mmol) was dissolved in dichloromethane (6.00 mL), and potassium carbonate (691 mg, 5.00 mmol) was then added to the solution. Thereafter, ethylamine hydrochloride (245 mg, 3.00 mmol) was added to the mixed solution, and the thus obtained mixture was then stirred overnight in an argon atmosphere at a room temperature. After completion of the reaction, water was added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (eluent: hexane/ethyl acetate=10/1) to obtain Compound (239 mg, 0.975 mmol, yield: 97%).

$^1$H-NMR of Compound 71 (solvent: deuterated chloroform, resonance frequency: 500 MHz): δ 8.03 (d, J=9.1 Hz, 1H), 7.01 (d, J=2.0 Hz, 1H), 6.75 (dd, J=2.0 Hz. 1H), 3.36-3.30 (m, 2H), 1.38 (t, J=7.2 Hz, 3H)

Synthesis of 5-bromo-N1-ethylbenzene-1,2-diamine (Compound 72)

Compound 71 (245 mg, 1.00 mmol) was dissolved in ethyl acetate (5.00 mL), and thereafter, water (72.0 μL, 4.00 mmol) and tin(II) chloride (758 mg, 4.00 mmol) were added to the solution. The obtained mixture was heated to reflux in an argon atmosphere for 4 hours. After completion of the reaction, a 4 mol/L sodium hydroxide aqueous solution was added to the reaction solution, and the precipitated solid was then removed by filtration. The resultant was extracted with ethyl acetate twice, and the combined ethyl acetate layer was dried over anhydrous sodium sulfate and was then concentrated under a reduced pressure. The obtained crude product was purified by silica gel chromatography (hexane/ethyl acetate=5/1) to obtain Compound 72 (204 mg, 0.950 mmol, and yield: 95%).

$^1$H-NMR of Compound 72 (solvent: deuterated chloroform, resonance frequency: 500 MHz): δ 6.76-6.72 (m, 2H), 6.56 (d, J=8.1 Hz, 1H), 3.27 (br, 3H), 3.12 (q, J=14.3 Hz. 2H), 1.30 (t, J=7.1 Hz, 3H).

Synthesis of {5-(6-bromo-1-ethyl-1H-benzo[d]imidazol-2-yl)pyridin-3-yl}methanol (Compound 73)

Compound 3 (118 mg, 0.860 mmol) synthesized by the method described in Example 1 was dissolved in dimethylformamide (1.00 mL), and thereafter, a dimethylformamide solution (1.00 mL), in which Compound (204 mg, 0.950 mmol) had been dissolved, and potassium peroxymonosulfate (Oxone (registered trademark) Monopersulfate Compound, manufactured by Wako Pure Chemical Industries, Ltd.) (701 mg, 1.14 mmol), were added to the above-obtained solution. The obtained mixture was stirred in an argon atmosphere at a room temperature for 1 hour. After completion of the reaction, a saturated sodium hydrogen carbonate aqueous solution and a saturated sodium thiosulfate aqueous solution were added to the reaction solution under cooling on ice, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (eluent: chloroform/methanol=10/1) to obtain Compound 73 (205 mg, 0.617 mmol, yield: 84%).

$^1$H-NMR of Compound 73 (solvent: deuterated chloroform, resonance frequency: 500 MHz): δ 8.87 (d, J=2.1 Hz, 1H), 8.74 (d, J=2.1 Hz, 1H), 8.13 (t, J=2.1 Hz, 1H), 7.69 (d, J=8.6 Hz, 1H), 7.61 (d, J=1.7 Hz, 1H), 7.44 (dd, J=1.8 Hz. 1H), 4.86 (d, J=4.8 Hz, 2H), 4.28 (q, J=7.3 Hz, 2H), 2.33 (br, 1H), 1.50 (t, J=7.3 Hz, 3H)

Synthesis of 2-[5-{(1H-imidazol-1-yl)methyl}pyridin-3-yl]-6-bromo-1-ethyl-1H-benzo[d]imidazole (Compound 74)

Compound 73 (265 mg, 0.798 mmol) was dissolved in dichloromethane (8.00 mL), and thereafter, triphenylphosphine (420 mg, 1.60 mmol) and carbon tetrabromide (398 mg, 1.20 mmol) were added to the solution under cooling on ice. The obtained mixture was stirred in an argon atmosphere at 0° C. for 20 minutes. After completion of the reaction, the reaction mixture was concentrated under a reduced pressure to obtain a crude product.

To a solution prepared by dissolving imidazole (109 mg, 1.60 mmol) in dimethylformamide (0.50 mL), sodium hydride (64.0 mg, 1.60 mmol) was added under cooling on ice. The obtained mixture was stirred in an argon atmosphere at 0° C. for 10 minutes. The previously obtained crude product was dissolved in dimethylformamide (1.50 mL), and the obtained solution was then added to the imidazole solution under cooling on ice. The obtained mixture was stirred for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (eluent: chloroform/methanol=10/1) to obtain Compound 74 (186 mg, 0.487 mmol, two-step yield from Compound 74: 61%).

$^1$H-NMR of Compound 74 (solvent: deuterated chloroform, resonance frequency: 500 MHz): δ 8.94 (d, J=2.0 Hz, 1H), 8.64 (d, J=2.2 Hz, 1H), 7.85 (t, J=2.2 Hz, 1H), 7.68 (dd, J=0.3 Hz, 1H), 7.62 (s, 1H), 7.60-7.59 (m, 1H), 7.44 (dd, J=1.8 Hz. 1H), 7.15 (t, J=1.0 Hz, 1H), 6.96 (t, J=1.3 Hz, 1H), 5.28 (s, 2H), 4.21 (q, J=7.3 Hz, 2H), 1.47 (t, J=7.3 Hz, 3H)

Synthesis of 2-[5-{(1H-imidazol-1-yl)methyl}pyridin-3-yl]-1-ethyl-6-(tributylstannyl)-1H-benzo[d]imidazole (Compound 75)

Compound 74 (131 mg, 0.343 mmol) was dissolved in dimethylformamide (2.00 mL), and thereafter, bis(tributyltin) (0.51 mL, 1.02 mmol) and bis(tri-tert-butylphosphine)palladium (35.8 mg, 0.0700 mmol) were added to the solution. The obtained mixture was stirred overnight in an argon atmosphere at 110° C. After completion of the reaction, the reaction mixture was extracted with ethyl acetate twice, and the combined ethyl acetate layer was dried over anhydrous sodium sulfate and was then concentrated under a reduced pressure. The obtained crude product was purified by silica gel chromatography (eluent: chloroform/methanol=20/1) to obtain Compound 75 (30.0 mg, 0.0506 mmol, yield: 15%).

$^1$H-NMR of Compound 75 (solvent: deuterated chloroform, resonance frequency: 500 MHz): δ 8.94 (d, J=2.1 Hz, 1H), 8.61 (d, J=2.2 Hz, 1H), 7.89 (t, J=2.1 Hz, 1H), 7.80 (dd, J=0.6 Hz, 1H), 7.63 (s, 1H), 7.51 (s, 1H), 7.41 (dd, J=0.6 Hz. 1H), 7.15 (s, 1H), 7.00 (s, 1H), 5.27 (s, 2H), 4.26 (q, J=14.5 Hz, 2H), 1.61-1.55 (m, 6H), 1.48 (t, J=7.3 Hz, 3H), 1.40-1.32 (m, 6H), 1.14-1.11 (m, 6H), 0.90 (t, J=7.3 Hz, 9H).

Synthesis of Compound 608

Compound 75 (12.0 mg, 0.0203 mmol) was dissolved in dichloromethane (1.00 mL), and iodine (9.60 mg, 0.0757 mmol) was then added to the solution. The obtained mixture was stirred for 30 minutes. After completion of the reaction, a saturated sodium hydrogen carbonate aqueous solution and a saturated sodium thiosulfate aqueous solution were added to the reaction solution, and the obtained mixture was then extracted with dichloromethane twice. The combined dichloromethane layer was dried over anhydrous sodium sulfate, and was then concentrated under a reduced pressure. The obtained crude product was purified by silica gel chromatography (eluent: chloroform/methanol=20/1) to obtain Compound 608 (8.30 mg, 0.0193 mmol, yield: 97%).

$^1$H-NMR of Compound 608 (solvent: deuterated chloroform, resonance frequency: 500 MHz): δ 8.94 (d, J=2.0 Hz, 1H), 8.64 (d, J=2.2 Hz, 1H), 7.85 (t, J=2.1 Hz, 1H), 7.79 (d, J=1.2 Hz, 1H), 7.62 (s, 1H), 7.60 (d, J=1.5 Hz, 1H), 7.56 (d, J=8.5 Hz. 1H), 7.15 (s, 1H), 7.00 (s, 1H), 5.27 (s, 2H), 4.20 (q, J=7.3 Hz, 2H), 1.46 (t, J=7.3 Hz, 3H).

(Example 25) Synthesis of Compound [$^{123}$I] 608

To an acetonitrile solution of Compound 75 (concentration: 1 mg/mL, 45 µL), an aqueous solution of [$^{123}$I] sodium iodide (845 MBq/30 µL) in 1 mol/L hydrochloric acid (85 µL) and a 30% (w/v) hydrogen peroxide aqueous solution (5 µL) were added. The mixed solution was left at rest at 40° C. for 10 minutes, and was then subjected to HPLC under the below-mentioned conditions, so that a fraction with the same retention time as Compound 608 obtained in Example 24 was obtained as a fraction of Compound [$^{123}$I] 608.

<HPLC Conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding water (10 mL) to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 608 was adsorbed and captured in the column. This column was washed with 10 mL of water, and 0.2 mL of ethanol was then supplied to the column, so that Compound [$^{123}$I] 608 was eluted, and it was then diluted with a physiological saline to obtain a physiological saline aqueous solution of 2-[5-Compound [$^{123}$I] 608. The obtained radioactivity was 253 MBq immediately after completion of the synthesis (40 minutes after initiation of the synthesis). Moreover, a TLC analysis was carried out under the below-mentioned conditions. As a result, the radiochemical purity was 98.4%.

<TLC Analysis Conditions>
TLC plate: Silica Gel 60 F$_{254}$ (product name, manufactured by Merck)
Development phase: ethyl acetate/methanol/diethylamine=10/2/1 (volume ratio)
RI detector: RitaStar, manufactured by Raytest (Example 26) Synthesis of Compound 609

Figure 15:
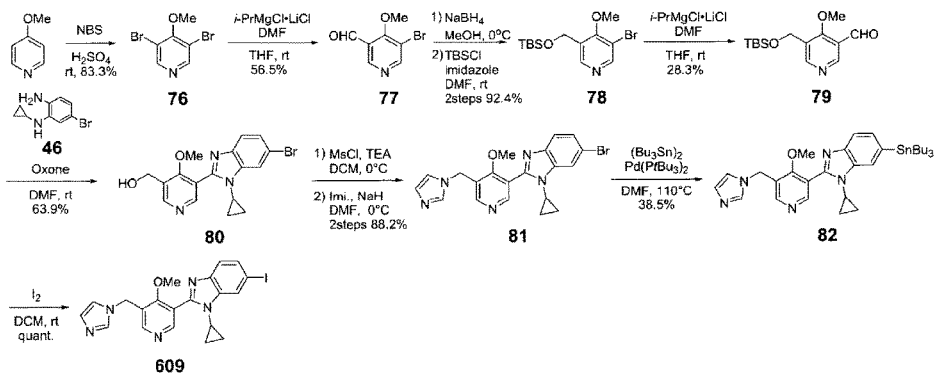
FIG. 15 is a drawing showing a synthesis example of 1-cyclopropyl-2-[5-(imidazol-1-ylmethyl)pyridin-3-yl]-6-iodo-4-methoxybenzimidazole.

Compound 609 was synthesized in accordance with the scheme shown in FIG. 15.

Synthesis of 3,5-dibromo-4-methoxypyridine (Compound 76)

4-Methoxypyridine (550 mg, 5.04 mmol) was dissolved in concentrated sulfuric acid (8 mL), and N-bromosuccinimide (3.59 g, 20.2 mmol) was then added to the solution at a room temperature. The obtained mixture was stirred overnight in an argon atmosphere at 60° C. After completion of the reaction, the reaction solution was added dropwise at 0° C. to a mixed solution of a saturated sodium thiosulfate aqueous solution and a 4 mol/L sodium hydroxide aqueous solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (hexane/ethyl acetate=10/1) to obtain Compound 76 (1.12 g, 4.19 mmol, and yield: 83%).

$^1$H-NMR of Compound 76 (solvent: deuterated chloroform, resonance frequency: 500 MHz): δ 8.59 (s, 2H), 4.00 (s, 3H)

Synthesis of 5-bromo-4-methoxy-3-pyridinecarboxaldehyde (Compound 77)

Compound 76 (267 mg, 1.00 mmol) was dissolved in tetrahydrofuran (1 mL), and thereafter, an isopropylmagnesium chloride-lithium chloride complex tetrahydrofuran solution (approximately 14%) (1.56 mL, 1.50 mmol) was added dropwise to the above-obtained solution at a room temperature. The obtained mixture was stirred in an argon atmosphere at the same temperature as described above for 1 hour. Thereafter, N,N'-dimethylformamide (0.775 mL, 10.0 mmol) was added dropwise to the reaction solution, and the obtained mixture was then stirred in an argon atmosphere at the same temperature as described above for 3 hours. After completion of the reaction, a saturated ammonium chloride aqueous solution was added at 0° C. to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (hexane/ethyl acetate=3/2) to obtain Compound 77 (122 mg, 0.565 mmol, and yield: 57%).

$^1$H-NMR of Compound 77 (solvent: deuterated chloroform, resonance frequency: 500 MHz): δ 10.38 (s, 1H), 8.88-8.86 (m, 2H), 4.13 (s, 3H).

Synthesis of 5-bromo-4-methoxy-3-(tert-butyldimethylsilyloxy)methylpyridine (Compound 78)

Compound 77 (122 mg, 0.565 mmol) was dissolved in methanol (5 mL), and sodium borohydride (21.1 mg, 0.565 mmol) was then added at 0° C. to the solution. The obtained mixture was stirred in an argon atmosphere at the same temperature as described above for 1 hour. After completion of the reaction, 2 mol/L hydrochloric acid and a 3 mol/L sodium hydroxide aqueous solution were added to the reaction solution, and the obtained mixture was then stirred. Thereafter, the reaction mixture was extracted with chloroform twice. The combined chloroform layer was dried over anhydrous sodium sulfate, and was then concentrated under a reduced pressure, so as to obtain a crude product.

This crude product was dissolved in N,N'-dimethylformamide (1 mL), and thereafter, tert-butyldimethylchlorosilane (166 mg, 1.10 mmol) and imidazole (93.7 mg, 1.38 mmol) were added to the solution at a room temperature. The obtained mixture was stirred in an argon atmosphere at the same temperature as described above for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (hexane/ethyl acetate=15/1) to obtain Compound 78 (169 mg, 0.509 mmol, two-step yield from Compound 77: 92%).

$^1$H-NMR of Compound 78 (solvent: deuterated chloroform, resonance frequency: 500 MHz): δ 8.86 (s, 1H), 8.53 (s, 1H), 4.79 (s, 2H), 3.95 (s, 3H), 0.94 (s, 9H), 0.13 (s, 6H)

Synthesis of 4-methoxy-5-(tert-butyldimethylsilyloxy)methyl-3-pyridinecarboxyaldehyde (Compound 79)

Compound 78 (167 mg, 0.503 mmol) was dissolved in tetrahydrofuran (1 mL), and thereafter, an isopropylmagnesium chloride-lithium chloride complex tetrahydrofuran solution (approximately 14%) (0.783 mL, 0.755 mmol) was added dropwise to the above-obtained solution at a room temperature. The obtained mixture was stirred in an argon atmosphere at the same temperature as described above for 1 hour. Thereafter, N,N'-dimethylformamide (0.389 mL, 5.03 mmol) was added dropwise to the reaction solution. The obtained mixture was stirred in an argon atmosphere at the same temperature as described above for 2 hours. After completion of the reaction, a saturated ammonium chloride aqueous solution was added at 0° C. to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (hexane/ethyl acetate=3/1) to obtain Compound 79 (40.0 mg, 0.142 mmol, and yield: 28%).

$^1$H-NMR of Compound 79 (solvent: deuterated chloroform, resonance frequency: 500 MHz): δ 10.35 (s, 1H), 8.90 (s, 1H), 8.80 (s, 1H), 4.82 (s, 2H), 4.05 (s, 3H), 0.95 (s, 9H), 0.14 (s, 6H)

Synthesis of {5-(6-bromo-1-cyclopropylbenzimidazol-2-yl)-4-methoxypyridin-3-yl}methanol (Compound 80)

Compound 79 (40.0 mg, 0.142 mmol) was dissolved in N,N'-dimethylformamide (1.0 mL), and thereafter, Compound 46 (42.0 mg, 0.185 mmol) synthesized by the method described in Example 12 and potassium peroxymonosulfate (Oxone (registered trademark) Monopersulfate Compound, manufactured by Wako Pure Chemical Industries, Ltd.) (114 mg, 0.185 mmol) were added to the above-obtained solution at a room temperature. The obtained mixture was stirred in an argon atmosphere at the same temperature as described above for 1 hour. After completion of the reaction, a saturated sodium thiosulfate aqueous solution and a saturated sodium hydrogen carbonate aqueous solution were added to the reaction solution, and the obtained mixture was then stirred for 10 minutes. Thereafter, the reaction mixture was extracted with ethyl acetate three times. The combined ethyl acetate layer was dried over anhydrous sodium sulfate, and was then concentrated under a reduced pressure. The obtained crude product was purified by silica gel chromatography (dichloromethane/methanol=10/1) to obtain Compound 80 (34.0 mg, 0.0909 mmol, and yield: 64%).

$^1$H-NMR of Compound 80 (solvent: deuterated chloroform, resonance frequency: 500 MHz): δ 8.70 (s, 1H), 8.69 (s, 1H), 7.79 (d, J=1.7 Hz, 1H), 7.68 (d, J=8.6 Hz, 1H), 7.44 (dd, J=8.6, 1.7 Hz, 1H), 4.84 (d, J=6.3 Hz, 2H), 3.57 (s, 3H), 3.38-3.34 (m, 1H), 2.12 (t, J=6.3 Hz, 1H), 0.98-0.94 (m, 2H), 0.69-0.66 (m, 2H)

Synthesis of 6-bromo-1-cyclopropyl-2-[5-(imidazol-1-ylmethyl)pyridin-3-yl]-4-methoxybenzimidazole (Compound 81)

Compound 80 (50.0 mg, 0.134 mmol) was dissolved in dichloromethane (3.0 mL), and thereafter, methanesulfonyl chloride (20.7 μL, 0.268 mmol) and triethylamine (55.9 μL, 0.402 mmol) were added at 0° C. to the solution. The obtained mixture was stirred in an argon atmosphere at the same temperature as described above for 20 minutes. After completion of the reaction, the reaction solution was concentrated under a reduced pressure to obtain a crude product.

Imidazole (90.9 mg, 1.34 mmol) was dissolved in N,N'-dimethylformamide (0.5 mL), and sodium hydride (21.4 mg, 0.532 mmol) was then added at 0° C. to the solution. The obtained mixture was stirred for 10 minutes. An N,N'-dimethylformamide solution (0.8 mL), in which the above described crude product had been dissolved, was added to the reaction solution, and the obtained mixture was then stirred in an argon atmosphere at the same temperature as described above for 1 hour. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel chromatography (chloroform/methanol=10/1) to obtain Compound 81 (50.0 mg, 0.118 mmol, two-step yield from Compound 80: 88%).

$^1$H-NMR of Compound 81 (solvent: deuterated chloroform, resonance frequency: 500 MHz): δ 8.74 (s, 1H), 8.57 (s, 1H), 7.78 (d, J=1.8 Hz, 1H), 7.67 (d, J=8.6 Hz, 1H), 7.61 (s, 1H), 7.44 (dd, J=8.6, 1.8 Hz, 1H), 7.07 (m, 1H), 6.94 (s, 1H), 2.21 (s, 2H), 3.41 (s, 3H), 3.28-3.24 (m, 1H), 0.88-0.84 (m, 2H), 0.61-0.58 (m, 2H)

Synthesis of 1-cyclopropyl-2-[5-(imidazol-1-ylmethyl)pyridin-3-yl]-4-methoxy-6-tributylstannylbenzimidazole (Compound 82)

Compound 81 (40.0 mg, 0.943 mmol) was dissolved in N,N'-dimethylformamide (1.0 mL), and thereafter, bis(tributyltin) (94.3 μL, 0.186 mmol) and bis(tri-tert-butylphosphine)palladium (9.6 mg, 0.0186 mmol) were added to the above-obtained solution at a room temperature. The obtained mixture was stirred overnight in an argon atmosphere at 110° C. After completion of the reaction, ethyl acetate and water were added to the reaction solution, and the obtained mixture was then filtered. Thereafter, the filtrate ethyl acetate layer was extracted twice. The combined ethyl acetate layer was dried over anhydrous sodium sulfate, and was then concentrated under a reduced pressure. The obtained crude product was purified by silica gel column chromatography (eluent: chloroform/methanol=20/1) to obtain Compound 82 (23.0 mg, 0.0363 mmol, yield: 39%).

$^1$H-NMR of Compound 82 (solvent: deuterated chloroform, resonance frequency: 500 MHz): δ 8.74 (s, 1H), 8.55 (s, 1H), 7.80 (d, J=7.9 Hz, 1H), 7.71 (s, 1H), 7.61 (s, 1H), 7.41 (d, J=7.9 Hz, 1H), 7.07-7.06 (m, 1H), 6.95-6.94 (m, 1H), 5.21 (s, 2H), 3.44 (s, 3H), 3.32-3.28 (m, 1H), 1.68-1.56 (m, 6H), 1.41-1.33 (m, 6H), 1.20-1.05 (m, 6H), 0.91 (t, J=7.3 Hz, 9H), 0.87-0.82 (m, 2H), 0.62-0.58 (m, 2H)

Synthesis of Compound 609

Compound 82 (21.4 mg, 0.0337 mmol) was dissolved in dichloromethane (1.00 mL), and iodine (21.4 mg, 0.169 mmol) was then added to the solution at a room temperature. The obtained mixture was stirred in an argon atmosphere at the same temperature as described above for 2.5 hours. After completion of the reaction, a saturated sodium thiosulfate aqueous solution and a saturated sodium hydrogen carbonate aqueous solution were added to the reaction solution, and the obtained mixture was then extracted with dichloromethane three times. The combined dichloromethane layer was dried over anhydrous sodium sulfate, and was then concentrated under a reduced pressure. The obtained crude product was purified by silica gel column chromatography (eluent: chloroform/methanol=10/1), so as to quantitatively obtain Compound 609 (16.0 mg, 0.0339 mmol).

$^1$H-NMR of Compound 609 (solvent: deuterated chloroform, resonance frequency: 500 MHz): δ 8.73 (s, 1H), 8.57 (s, 1 Hz), 7.98 (t, J=1.5 Hz, 1H), 7.63-7.56 (m, 3H), 7.08 (s, 1H), 6.95 (s, 1H), 5.21 (s, 2H), 3.40 (s, 3H), 3.27-3.23 (m, 1H), 0.85 (d, J=6.3 Hz, 2H), 0.58 (d, J=2.5 Hz, 2H).

(Example 27) Synthesis of Compound [$^{123}$I] 609

To an acetonitrile solution of Compound 82 (concentration: 1 mg/mL, 45 μL), an aqueous solution of [$^{123}$I] sodium iodide (934 MBq/30 μL) in 1 mol/L hydrochloric acid (85 μL) and a 30% (w/v) hydrogen peroxide aqueous solution (5 μL) were added. The mixed solution was left at rest at 40° C. for 10 minutes, and was then subjected to HPLC under the below-mentioned conditions, so that a fraction with the same retention time as Compound 609 obtained in Example 26 was obtained as a fraction of Compound [$^{123}$I] 609.

<HPLC Conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min Detectors: ultraviolet visible spectrophotometer (detection wavelength: 260 nm) and radiation detector (Raytest, STEFFI-type)

A liquid prepared by adding 10 mL of water to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 609 was adsorbed and captured in the column. This column was washed with 10 mL of water, and 0.2 mL of ethanol was then supplied to the column, so that Compound [$^{123}$I] 609 was eluted, and it was then diluted with a physiological saline to obtain a physiological saline aqueous solution of 1-Compound [$^{123}$I] 609. The obtained radioactivity was 213 MBq immediately after completion of the synthesis (46 minutes after initiation of the synthesis). Moreover, a TLC analysis was carried out under the below-mentioned conditions. As a result, the radiochemical purity was 95.0%.

<TLC Analysis Conditions>
TLC plate: Silica Gel 60 $F_{254}$ (product name, manufactured by Merck)
Development phase: ethyl acetate/methanol/diethylamine=10/2/1 (volume ratio)
RI detector: RitaStar, manufactured by Raytest (Example 28) Synthesis of Compound 610

Figure 16:
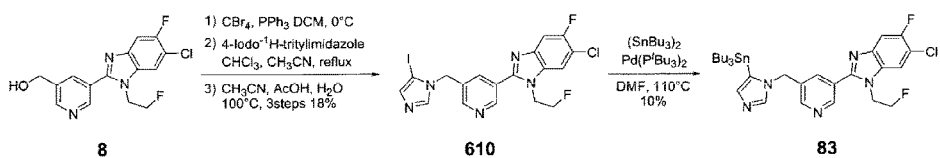
FIG. 16 is a drawing showing a synthesis example of 6-chloro-5-fluoro-1-(2-fluoroethyl)-2-{5-(5-iodo-1H-imidazol-1-ylmethyl)pyridin-3-yl}benzimidazole.

Compound 610 was synthesized in accordance with the scheme shown in FIG. 16.

Compound 8 (100 mg, 0.309 mmol) synthesized by the method described in Example 1 was dissolved in dichloromethane (3.0 mL), and thereafter, triphenylphosphine (113 mg, 0.340 mmol) and carbon tetrabromide (97.2 mg, 0.371 mmol) were added at 0° C. to the above-obtained solution. The obtained mixture was stirred in an argon atmosphere at the same temperature as described above for 2 hours. Thereafter, triphenylphosphine (56.4 mg, 0.170 mmol) and carbon tetrabromide (48.6 mg, 0.186 mmol) were added at 0° C. to the reaction solution, and the obtained mixture was then stirred in an argon atmosphere at the same temperature as described above for 1 hour. After completion of the reaction, the reaction solution was concentrated under a reduced pressure to obtain a crude product.

This crude product was dissolved in chloroform (1.0 mL), and 4-iodo-1-tritylimidazole (270 mg, 0.618 mmol) was then added to the solution at a room temperature. The obtained mixture was heated to reflux overnight in an argon atmosphere. After completion of the reaction, the reaction solution was concentrated under a reduced pressure.

Acetonitrile (1.5 mL) and water (1.5 mL) were added to the obtained crude product, so that the crude product was dissolved therein. Thereafter, acetic acid (1.5 mL) was added to the solution, and the obtained mixture was then heated at 100° C. for 30 minutes. After completion of the reaction, the reaction solution was neutralized with a saturated sodium hydrogen carbonate aqueous solution, and was then extracted with dichloromethane twice. The combined dichloromethane layer was dried over anhydrous sodium sulfate, and was then concentrated under a reduced pressure. The obtained crude product was purified by silica gel chromatography (dichloromethane/methanol=20/1) twice, so as to obtain Compound 610 (26.0 mg, 0.0520 mmol, three-step yield from Compound 8: 18%).

$^1$H-NMR of Compound 610 (solvent: deuterated chloroform, resonance frequency: 500 MHz): δ 8.94 (d, J=2.1 Hz, 1H), 8.66 (d, J=2.1 Hz, 1H), 7.79 (s, 1H), 7.75 (s, 1H), 7.60 (d, J=9.1 Hz, 1H), 7.47 (d, J=6.2 Hz, 1H), 7.23 (s, 1H), 5.29 (s, 2H), 4.75 (dt, J=46.8, 4.7 Hz, 2H), 4.41 (dt, J=25.0, 4.7 Hz, 2H)

(Example 29) Synthesis of Compound [$^{123}$I] 610

As shown in FIG. 16, Compound 610 (22.0 mg, 0.0440 mmol) was dissolved in N,N'-dimethylformamide (0.5 mL), and thereafter, bis(tributyltin) (44.0 μL, 0.0881 mmol) and bis(tri-tert-butylphosphine)palladium (4.5 mg, 0.00881 mmol) were added to the solution at a room temperature. The obtained mixture was stirred overnight in an argon atmosphere at 110° C. After completion of the reaction, water was added to the reaction solution, and the obtained mixture was then extracted with ethyl acetate twice. The combined ethyl acetate layer was dried over anhydrous sodium sulfate, and was then concentrated under a reduced pressure. The obtained crude product was purified by silica gel column chromatography (eluent: dichloromethane/methanol=12/1), so as to obtain 6-chloro-5-fluoro-1-(2-fluoroethyl)-2-{5-(5-tributylstannyl-1H-imidazol-1-ylmethyl)pyridin-3-yl}benzimidazole (Compound 83) (4.8 mg, 0.00724 mmol, yield: 10%).

$^1$H-NMR of Compound 83 (solvent: deuterated chloroform, resonance frequency: 500 MHz): δ 8.94 (d, J=2.1 Hz, 1H), 8.50 (d, J=2.1 Hz, 1H), 7.76 (s, 1H), 7.62 (s, 1H), 7.58 (d, J=9.1 Hz, 1H), 7.47 (d, J=6.2 Hz, 1H), 7.14 (s, 1H), 5.28 (s, 2H), 4.72 (dt, J=46.7, 4.7 Hz, 2H), 4.38 (dt, J=25.0, 4.7 Hz, 2H), 1.66-1.37 (m, 6H), 1.34-1.20 (m, 6H), 1.02-0.88 (m, 6H), 0.83 (t, J=7.3 Hz, 9H)

To an acetonitrile solution of Compound 83 (concentration: 1 mg/mL, 45 μL), an aqueous solution of [$^{123}$I] sodium iodide (495 MBq/30 μL) in 1 mol/L hydrochloric acid (85 μL) and a 30% (w/v) hydrogen peroxide aqueous solution (5 μL) were added. The mixed solution was left at rest at 40° C. for 10 minutes, and was then subjected to HPLC under the below-mentioned conditions, so that a fraction with the same retention time as Compound 610 obtained in Example 28 was obtained as a fraction of Compound [$^{123}$I] 610.

<HPLC Conditions>
Column: YMC PackPro C8 (trade name, manufactured by YMC, size: 4.5×150 mm)
Mobile phase: 0.1% trifluoroacetic acid-containing water/0.1% trifluoroacetic acid-containing acetonitrile (volume ratio)=gradient from 80/20 to 10/90 over 40 minutes
Flow rate: 1.0 mL/min
Detectors: ultraviolet visible spectrophotometer (detection wavelength: 260 nm) and radiation detector (Raytest, STEFFI-type)

A liquid prepared by adding water (10 mL) to the aforementioned fraction was supplied to a Sep-Pak C18 column (trade name: Sep-Pak (registered trademark) Light C18 Cartridges, manufactured by Waters, the amount of filler: 130 mg), so that Compound [$^{123}$I] 610 was adsorbed and captured in the column. This column was washed with 1 mL of water, and ethanol (0.2 mL) was then supplied to the column, so that Compound [$^{123}$I] 610 was eluted, and it was then diluted with a physiological saline to obtain a physiological saline aqueous solution of Compound [$^{123}$I] 610. The obtained radioactivity was 298 MBq immediately after completion of the synthesis (55 minutes after initiation of the synthesis). Moreover, a TLC analysis was carried out under the below-mentioned conditions. As a result, the radiochemical purity was 98.2%.

<TLC Analysis Conditions>
TLC plate: Silica Gel 60 $F_{254}$ (product name, manufactured by Merck)
Development phase: ethyl acetate/methanol/diethylamine=10/2/1 (volume ratio)
RI detector: RitaStar, manufactured by Raytest
Evaluation 1: Evaluation of Affinity and Selectivity Chinese hamster lung-derived fibroblasts, V79 cells (acquired from ECACC (European Collection of Cell Cultures) through DS Pharma Biomedical), were allowed to express human CYP11B2, so as to produce V79-B2, and were also allowed to express human CYP11B1, so as to produce V79-B1. V79 cells were cultured in a DMEM medium (containing 4,500 mg/L D-glucose, L-glutamine, and 110 mg/L sodium pyruvate; manufactured by Life Technologies). V79-B2 or V79-B1 was inoculated on a microplate, and then cultured overnight. Thereafter, a mixed solution of corticosterone and a compound as a test target was added into a culture supernatant of V79-B2, and a mixed solution of 11-deoxycortisol and a compound as a test target was added into a culture supernatant of V79-B1. As a solvent for these mixed solutions, the aforementioned DMEM medium further containing 0.1 v/v % dimethyl sulfoxide was used. The concentration of corticosterone or 11-deoxycortisol was adjusted to be 100 nmol/L by addition of the solvent. As test target compounds, (R)-4-iodometomidate (IMTO), and Compounds 100, 200, 300, 400, 500, and 601 to 610 synthesized by methods shown in Examples 1, 3, 5, 6, 8, 10, 12, 14, 16, 18, 20, 22, 24, 26, and 28, respectively, were used. The aforementioned mixed solution was prepared such that the concentration of each compound was $10^{-4}$ to $10^4$ nmol/L in the mixed solution. One hour later, the culture supernatant of V79-B1 was recovered, and the concentration of cortisol as a metabolite of CYP11B1 was measured by ELISA (Enzyme-Linked ImmunoSorbent Assay). Moreover, four hours later, the culture supernatant of V79-B2 was recovered, and the concentration of aldosterone as a metabolite of CYP11B2 was measured by ELISA. Provided that the concentration of aldosterone or the concentration of cortisol obtained when none of IMTO and Compounds 100, 200, 300, 400 and 500 was added was defined as 100%, an inhibition curve was produced, and the inhibitory activity ($IC_{50}$) of each compound was then calculated.

Tables 5 and 6 show $IC_{50}$ values for aldosterone production inhibition and $IC_{50}$ values for cortisol production inhibition with IMTO and Compounds 100, 200, 300, 400, 500, and 601 to 610, expressed as mean value or mean value±standard deviation. In Tables 5 and 6, the term "Selectivity factor" indicates a quotient of the mean value of $IC_{50}$ for cortisol production inhibition divided by the mean value of $IC_{50}$ for aldosterone production inhibition. In addition, the symbol "n" indicates the number of tests.

TABLE 5

| Compound | Aldosterone production inhibition $IC_{50}$ (nM) | Cortisol production inhibition $IC_{50}$ (nM) | Selectivity factor |
|---|---|---|---|
| IMTO | 0.21 ± 0.21 (n = 22) | 0.22 ± 0.17 (n = 22) | 1.01 |
| Compound 100 | 6.90 ± 2.87 (n = 3) | 109 ± 15.8 (n = 3) | 15.8 |
| Compound 200 | 7.47 (n = 1) | 142 (n = 1) | 19.0 |
| Compound 300 | 10.6 (n = 1) | 19.0 (n = 1) | 1.79 |
| Compound 400 | 44.5 (n = 1) | 345 (n = 1) | 7.77 |
| Compound 500 | 3.94 (n = 1) | 33.5 (n = 1) | 8.51 |

TABLE 6

| Compound | Aldosterone production inhibition $IC_{50}$ (nM) | Cortisol production inhibition $IC_{50}$ (nM) | Selectivity factor |
|---|---|---|---|
| IMTO | 0.24 | 0.25 | 1.03 |
| Compound 601 | 3.09 | 37.8 | 12.2 |
| Compound 602 | 2.17 | 44.5 | 20.5 |
| Compound 603 | 18.1 | 296 | 16.4 |
| Compound 604 | 4.54 | 54.0 | 11.9 |
| Compound 605 | 204 | 359 | 1.76 |
| Compound 606 | 116 | 368 | 3.17 |
| Compound 607 | 0.93 | 7.07 | 7.62 |
| Compound 608 | 6.58 | 52.2 | 7.93 |
| Compound 609 | 1.49 | 15.5 | 10.4 |
| Compound 610 | 9.81 | 91.0 | 9.27 |

From the above results, it was demonstrated that all of Compounds 100, 200, 300, 400, 500, and 601 to 610 have higher specificity to CYP11B2, in comparison to IMTO.

Evaluation 2: In Vitro Autoradiography Using Human Adrenal Adenoma

Figure 17A:
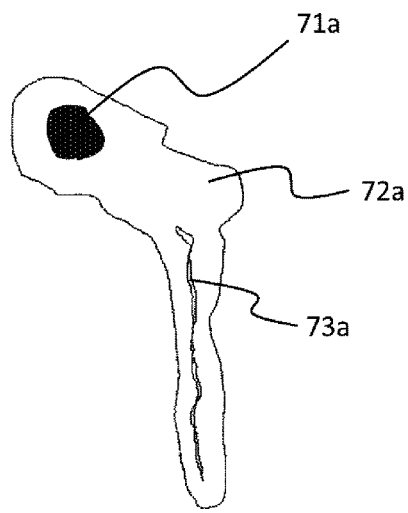
FIG. 17A is a schematic view showing a human adrenal gland section used in the in vitro autoradiography shown in FIG. 18 to FIG. 23
Figure 17B:
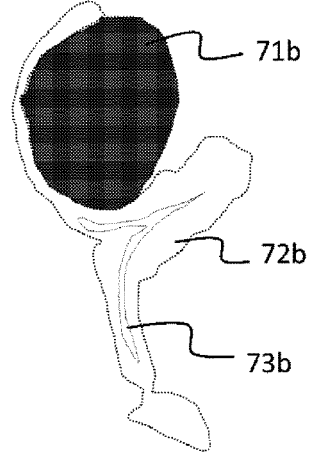
FIG. 17B is a schematic view showing a human adrenal gland section used in the in vitro autoradiography shown in FIG. 24 to FIG. 31.

From adrenal gland excised from a human patient for treatment of primary aldosteronism, a portion containing aldosterone-producing adenoma was removed and was then frozen. The frozen adrenal gland was embedded in an embedding agent for production of a frozen tissue section (Tissue-Tek O.C.T. Compound, Sakura Finetek Japan). Using a freezing microtome (CM3050S, Leica Microsystems), a 7-μm thin slice section, which is schematically shown in FIGS. 17(a) and 17(b), was produced, and was preserved at −20° C. before use. In FIGS. 17, 71a and 71b indicate aldosterone-producing adenomas, 72a and 72b indicate normal adrenal cortexes, and 73a and 73b indicate normal adrenal medullas. A 5-33 kBq/mL solution was prepared by adding a suitable amount of each of Compounds [$^{18}$F] 100, [$^{18}$F] 200, [$^{123}$I] 400, [$^{18}$F] 500, and [$^{123}$I] 601 to [$^{123}$I] 610, which were obtained by the methods described in Examples 2, 4, 7, 9, 11, 13, 15, 17, 19, 21, 23, 25, 27, and 29, or [$^{123}$I] IMTO to a phosphate-buffered physiological saline containing 1 w/v % bovine serum albumin (not containing fatty acid). The radioactivity concentration was measured using an autowell gamma system (ARC-7001, manufactured by Hitachi Aloka Medical, Ltd.). The section was immersed in the obtained sample solution for 10 minutes. For Compounds [$^{18}$F] 100, [$^{18}$F] 200, [$^{123}$I] 400, [$^{18}$F] 500, [$^{123}$I] 601 and [$^{123}$I] 602, the section shown in FIG. 17(a) was used, and for Compounds [$^{123}$I] 603 to 610, the section shown in FIG. 17(b) was used. For [$^{123}$I] IMTO, both sections shown in FIGS. 17(a) and (b) were used. Each sample solution was washed off, and the section was then exposed to an imaging plate (BAS-SR2040, manufactured by FUJIFILM Holdings Corporation) (IP) for 16-20 hours, and thereafter, an autoradiogram was obtained using a fluoro-image analyzer (FLA-7000, manufactured by FUJIFILM Holdings Corporation).

In order to quantitatively compare differences between images caused by $^{123}$I and $^{18}$F nuclides, a correction was made by calculating accumulation of radioactivity within the range of a region of interest (ROI) by means of integral calculation based on half-life, added radioactivity and IP contact time.

Figure 18A:
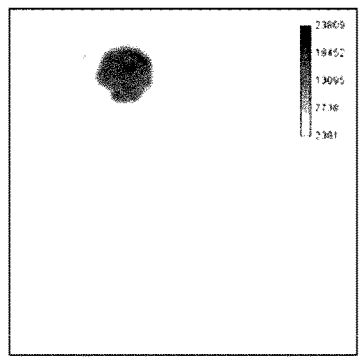
FIGS. 18A and 18B are views showing the results of in vitro autoradiography, in which a human adrenal gland section expressing aldosterone-producing adenoma is used.
Figure 18B:
Figure 19A:
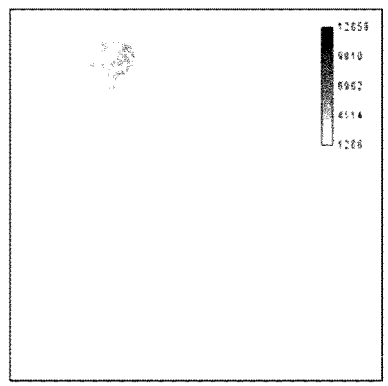
FIGS. 19A and 19B are views showing the results of in vitro autoradiography, in which a human adrenal gland section expressing aldosterone-producing adenoma is used.
Figure 19B:
Figure 20A:
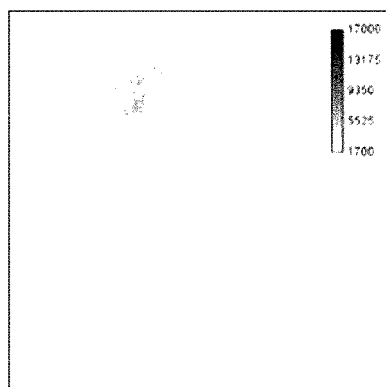
FIGS. 20A and 20B are views showing the results of in vitro autoradiography, in which a human adrenal gland section expressing aldosterone-producing adenoma is used.
Figure 20B:
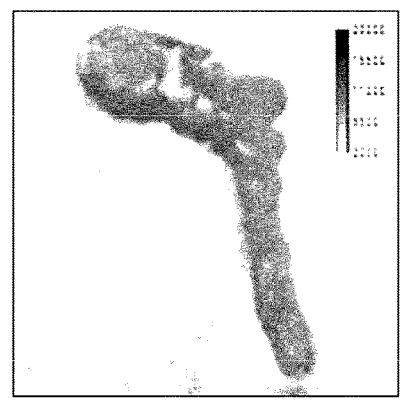
Figure 21A:
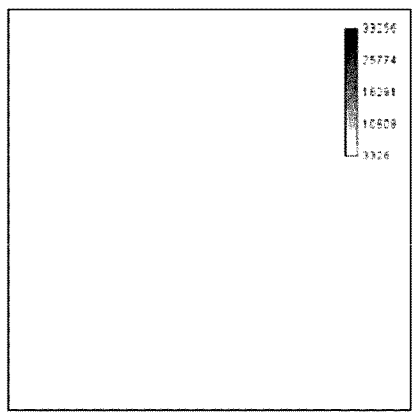
FIGS. 21A and 21B are views showing the results of in vitro autoradiography, in which a human adrenal gland section expressing aldosterone-producing adenoma is used.
Figure 21B:
Figure 22A:
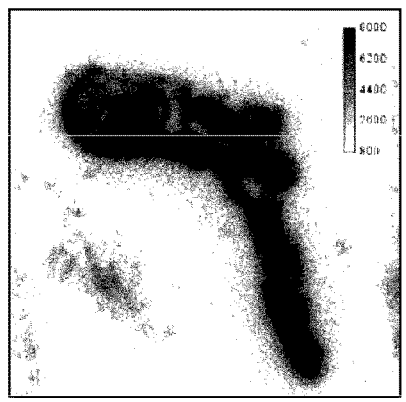
FIGS. 22A and 22B are views showing the results of in vitro autoradiography, in which a human adrenal gland section expressing aldosterone-producing adenoma is used.
Figure 22B:
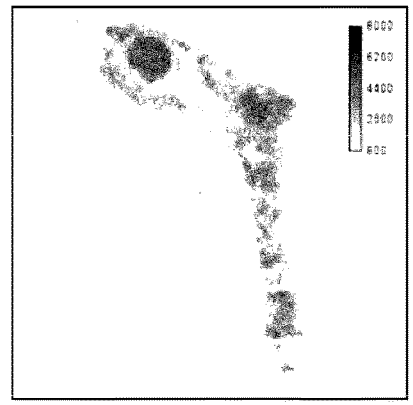
Figure 23A:
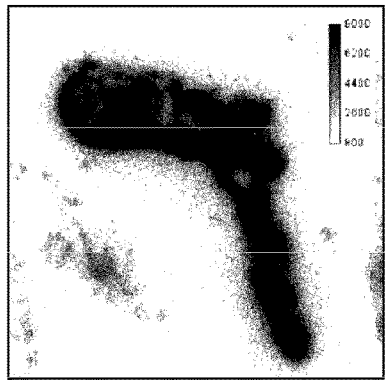
FIGS. 23A and 23B are views showing the results of in vitro autoradiography, in which a human adrenal gland section expressing aldosterone-producing adenoma is used.
Figure 23B:
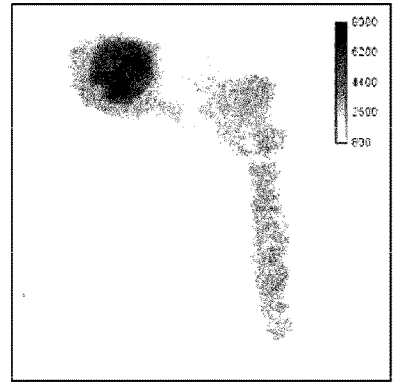
Figure 24A:
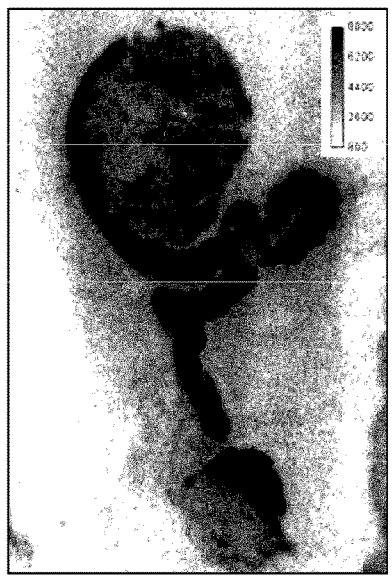
FIGS. 24A and 24B are views showing the results of in vitro autoradiography, in which a human adrenal gland section expressing aldosterone-producing adenoma is used.
Figure 24B:
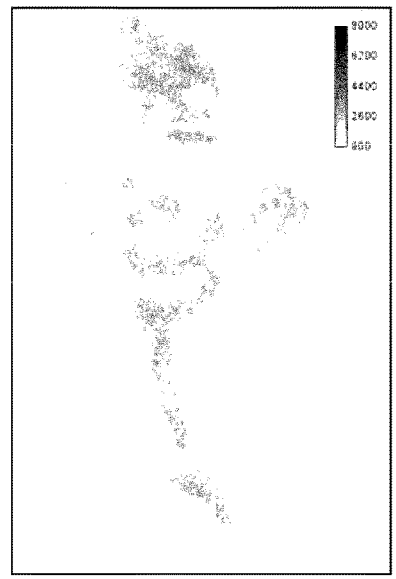
Figure 27A:
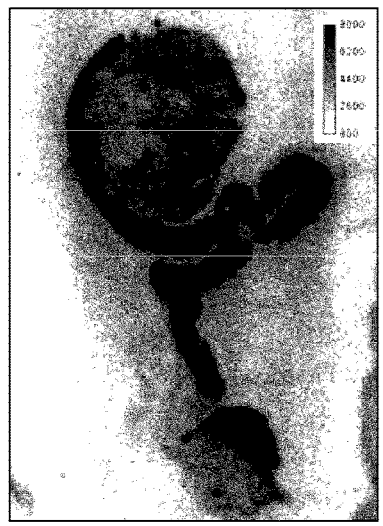
FIGS. 27A and 27B are views showing the results of in vitro autoradiography, in which a human adrenal gland section expressing aldosterone-producing adenoma is used.
Figure 27B:
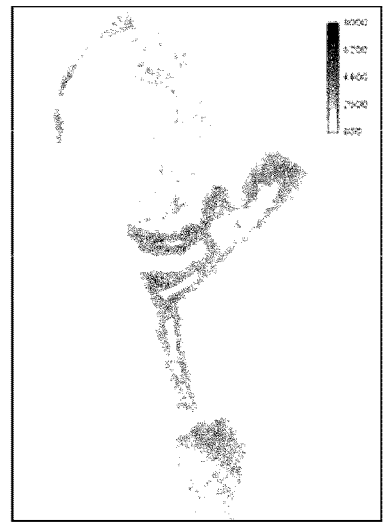
Figure 28A:
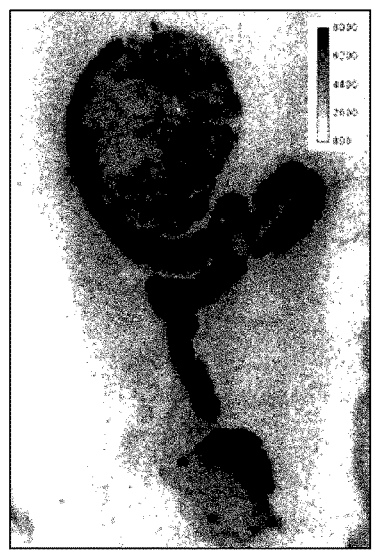
FIGS. 28A and 28B are views showing the results of in vitro autoradiography, in which a human adrenal gland section expressing aldosterone-producing adenoma is used.
Figure 28B:
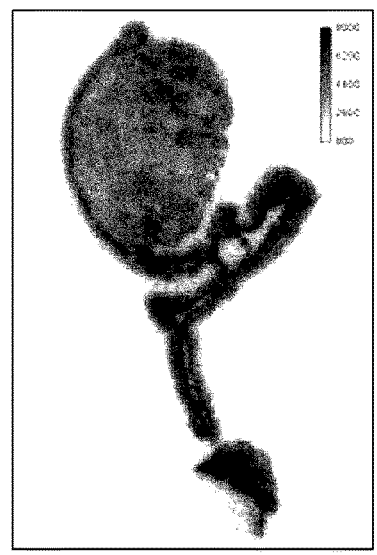
Figure 29A:
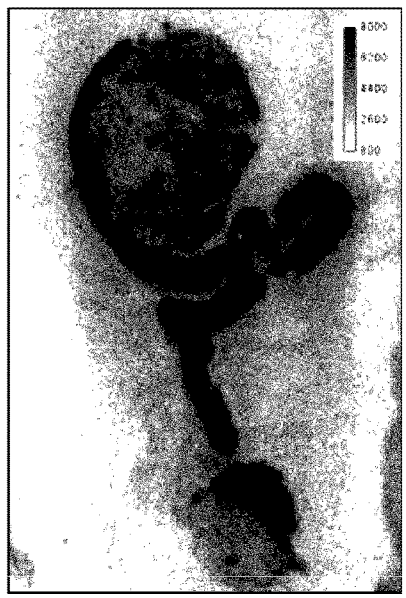
FIGS. 29A and 29B are views showing the results of in vitro autoradiography, in which a human adrenal gland section expressing aldosterone-producing adenoma is used.
Figure 29B:
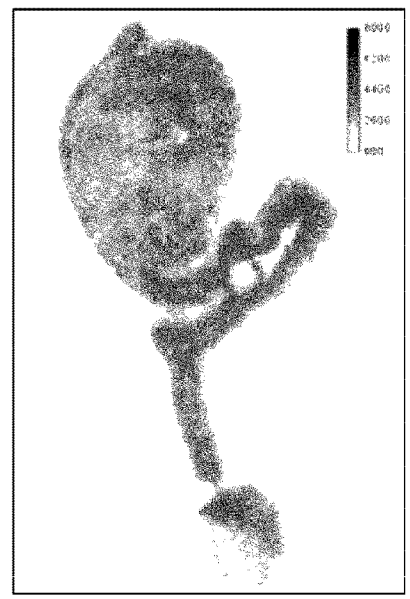
Figure 30A:
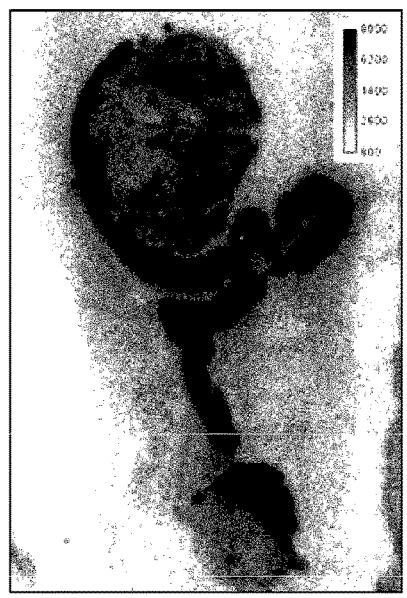
FIGS. 30A and 30B are views showing the results of in vitro autoradiography, in which a human adrenal gland section expressing aldosterone-producing adenoma is used.
Figure 30B:
Figure 31A:
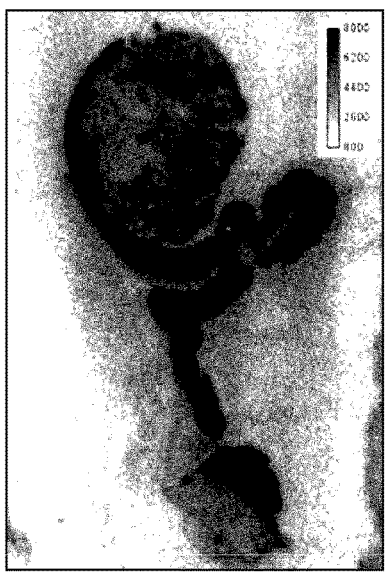
FIGS. 31A and 31B are views showing the results of in vitro autoradiography, in which a human adrenal gland section expressing aldosterone-producing adenoma is used.
Figure 31B:
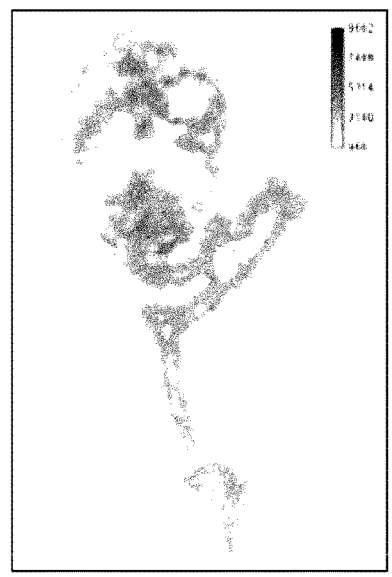

The obtained results are shown in FIGS. 18 to 31. FIG. 18(a) shows an autoradiogram of [$^{18}$F] 100, FIG. 19(a) shows an autoradiogram of [$^{18}$F] 200, FIG. 20(a) shows an autoradiogram of [$^{123}$I] 400, FIG. 21(a) shows an autoradiogram of [$^{18}$F] 500, FIG. 22(b) shows an autoradiogram of [$^{123}$I] 601, FIG. 23(b) shows an autoradiogram of [$^{123}$I] 602, FIG. 24(b) shows an autoradiogram of [$^{123}$I] 603, FIG. 25(b) shows an autoradiogram of [$^{123}$I] 604, FIG. 26(b) shows an autoradiogram of [$^{123}$I] 605, FIG. 27(b) shows an autoradiogram of [$^{123}$I] 606, FIG. 28(b) shows an autoradiogram of [$^{123}$I] 607, FIG. 29(b) shows an autoradiogram of [$^{123}$I] 608, FIG. 30(b) shows an autoradiogram of [$^{123}$I] 609, and FIG. 31(b) shows an autoradiogram of [$^{123}$I] 610. FIG. 18(b), FIG. 19(b), FIG. 20(b), FIG. 21(b), FIG. 22(a), FIG. 23(a), FIG. 24(a), FIG. 25(a), FIG. 26(a), FIG. 27(a), FIG. 28(a), FIG. 29(a), FIG. 30(a), and FIG. 31(a) each show an autoradiogram of [$^{123}$I] IMTO. As shown in the figures, in the case of [$^{123}$I] IMTO, accumulation of radioactivity was observed in the entire adrenal gland section, whereas in all of the cases of [$^{18}$F] 100, [$^{18}$F] 200, [$^{123}$I] 400, [$^{18}$F] 500, and [$^{123}$I] 601 to [$^{123}$I] 610, accumulation of radioactivity was selectively observed in a region in which aldosterone-producing adenoma had been pathologically observed. The ROI having the same area as each other was established in a normal site and in a site in which aldosterone-producing adenoma had developed. Then, the PSL value (B1) indicating accumulation of radioactivity in the sites of normal adrenal cortexes 72a and 72b was compared with the PSL value (B2) indicating accumulation of radioactivity in the sites of aldosterone-producing adenomas 71a and 71b. The results are shown in Tables 7 and 8. In Table 7, the B1, B2 and B2/B1 values of [$^{18}$F] 100 indicate the mean values for the number of tests (n), respectively.

TABLE 7

| | n | B2 | B1 | B2/B1 accumulation ratio |
|---|---|---|---|---|
| [$^{123}$I] IMTO | 1 | 7863 | 9415 | 0.84 |
| [$^{18}$F] 100 | 2 | 16480 | 3241 | 5.08 |
| [$^{18}$F] 200 | 1 | 4409 | 1321 | 3.34 |
| [$^{123}$I] 400 | 1 | 4611 | 1596 | 2.89 |
| [$^{18}$F] 500 | 1 | 3619 | 643 | 5.63 |
| [$^{123}$I] 601 | 1 | 3201 | 3040 | 1.05 |
| [$^{123}$I] 602 | 1 | 6142 | 2981 | 2.06 |

TABLE 8

| | n | B2 | B1 | B2/B1 accumulation ratio |
|---|---|---|---|---|
| [$^{123}$I] IMTO | 2 | 6649 | 8453 | 0.79 |
| [$^{123}$I] 603 | 1 | 2043 | 2027 | 1.01 |
| [$^{123}$I] 604 | 2 | 3493 | 1813 | 1.93 |
| [$^{123}$I] 605 | 1 | 4065 | 4318 | 0.94 |
| [$^{123}$I] 606 | 1 | 1655 | 1913 | 0.87 |
| [$^{123}$I] 607 | 1 | 5332 | 5945 | 0.90 |
| [$^{123}$I] 608 | 1 | 3580 | 3303 | 1.08 |
| [$^{123}$I] 609 | 1 | 3805 | 4479 | 0.85 |
| [$^{123}$I] 610 | 1 | 2786 | 2931 | 0.95 |

Evaluation 3: In Vivo Kinetics Experiment

Each of Compounds [$^{18}$F] 100, [$^{18}$F] 200, [$^{123}$I] 400, [$^{18}$F] 500, and [$^{123}$I] 601 to 610 obtained by the methods described in Examples 2, 4, 7, 9, 11, 13, 15, 17, 19, 21, 23, 25, 27, and 29, or [$^{123}$I] IMTO, was diluted with a physiological saline containing 1 w/v % ascorbic acid to prepare a solution to be administered. The above described compound (approximately 1 to 3.7 MBq) was injected into the caudal vein of a Wistar male rat (9 weeks old) under anesthesia with a mixed gas of isoflurane/air, and ten minutes after the injection, the rat was sacrificed by exsanguination. From the thus sacrificed rat, blood and organs (heart, lung, stomach, liver, spleen, small intestine, large intestine, kidney, bladder (including urine), muscle (lower limbs), brain, adrenal gland, testis, fat, femur, or thyroid gland) were excised, and the weights thereof were then measured. Thereafter, radioactivity was measured in the blood, the individual excised organs, and the remaining whole body. Further, 30 and 60 minutes after the administration, the same operations as those described above were carried out. The radioactivity distribution (% injected dose (ID)/g) in the blood, the individual excised organs, and the remaining whole body is shown as mean value±standard deviation in Tables 9 to 23 (Table 11 shows the mean values only concerning the radioactivity distributions 10 and 30 minutes after the administration). The symbol "n" in Tables 9 to 23 indicates the number of rats used. In addition, Tables 9 to 23 also show the ratio of radioactivity accumulation in adrenal grand (% ID/g) to radioactivity accumulation in each of blood, liver, kidney, small intestine, muscle and fat (% ID/g).

TABLE 9

[$^{18}$F] 100

| | Radioactivity distribution (% ID/g) | | |
|---|---|---|---|
| | 10 min after administration (n = 8) | 30 min after administration (n = 9) | 60 min after administration (n = 9) |
| Blood | 0.08 ± 0.01 | 0.08 ± 0.01 | 0.09 ± 0.01 |
| Heart | 0.32 ± 0.08 | 0.27 ± 0.06 | 0.26 ± 0.03 |
| Lung | 0.63 ± 0.08 | 0.43 ± 0.07 | 0.45 ± 0.05 |
| Stomach | 0.56 ± 0.17 | 0.73 ± 0.11 | 1.02 ± 0.19 |
| Liver | 5.39 ± 0.99 | 5.55 ± 0.80 | 4.11 ± 0.66 |
| Spleen | 3.85 ± 0.65 | 4.57 ± 1.32 | 4.40 ± 1.15 |
| Small intestine | 1.03 ± 0.14 | 1.78 ± 0.21 | 2.85 ± 0.37 |
| Large intestine | 0.15 ± 0.02 | 0.20 ± 0.02 | 0.38 ± 0.22 |
| Kidney | 1.70 ± 0.40 | 1.10 ± 0.16 | 1.13 ± 0.17 |
| Bladder (including urine) | 0.22 ± 0.08 | 1.17 ± 0.77 | 2.41 ± 0.97 |
| Muscle (lower limbs) | 0.23 ± 0.24 | 0.12 ± 0.03 | 0.09 ± 0.01 |
| Whole brain | 0.01 ± 0.00 | 0.01 ± 0.00 | 0.02 ± 0.00 |
| Adrenal gland | 10.19 ± 3.35 | 19.61 ± 4.29 | 21.34 ± 5.24 |
| Femur | 0.63 ± 0.08 | 0.71 ± 0.18 | 0.77 ± 0.13 |
| Testis | 0.05 ± 0.01 | 0.06 ± 0.01 | 0.08 ± 0.01 |
| Fat | 0.08 ± 0.02 | 0.07 ± 0.02 | 0.06 ± 0.03 |
| Remaining whole body | 0.22 ± 0.03 | 0.18 ± 0.03 | 0.18 ± 0.02 |
| Adrenal gland/blood | 137.96 ± 52.72 | 249.08 ± 51.81 | 247.32 ± 64.42 |
| Adrenal gland/liver | 1.93 ± 0.69 | 3.58 ± 0.82 | 5.20 ± 1.19 |
| Adrenal gland/kidney | 6.14 ± 2.01 | 18.18 ± 4.58 | 18.96 ± 4.83 |
| Adrenal gland/small intestine | 9.89 ± 2.73 | 11.12 ± 2.64 | 7.66 ± 2.34 |
| Adrenal gland/muscle | 63.25 ± 34.56 | 179.35 ± 63.77 | 236.89 ± 62.76 |
| Adrenal gland/fat | 141.33 ± 57.27 | 352.33 ± 208.06 | 397.01 ± 160.35 |

TABLE 10

[$^{18}$F] 200

| | Radioactivity distribution (% ID/g) | | |
|---|---|---|---|
| | 10 min after administration (n = 3) | 30 min after administration (n = 3) | 60 min after administration (n = 3) |
| Blood | 0.15 ± 0.01 | 0.16 ± 0.00 | 0.13 ± 0.01 |
| Heart | 0.32 ± 0.03 | 0.33 ± 0.02 | 0.27 ± 0.02 |
| Lung | 0.54 ± 0.07 | 0.48 ± 0.04 | 0.39 ± 0.09 |
| Stomach | 0.36 ± 0.04 | 0.56 ± 0.06 | 0.65 ± 0.16 |
| Liver | 5.54 ± 0.78 | 4.48 ± 0.13 | 3.18 ± 0.23 |
| Spleen | 1.49 ± 0.32 | 1.09 ± 0.25 | 0.68 ± 0.05 |

TABLE 10-continued

[18F] 200

| | Radioactivity distribution (% ID/g) | | |
|---|---|---|---|
| | 10 min after administration (n = 3) | 30 min after administration (n = 3) | 60 min after administration (n = 3) |
| Small intestine | 1.07 ± 0.07 | 2.70 ± 0.21 | 4.13 ± 0.83 |
| Large intestine | 0.16 ± 0.01 | 0.27 ± 0.04 | 0.41 ± 0.06 |
| Kidney | 1.39 ± 0.39 | 1.33 ± 0.03 | 1.21 ± 0.04 |
| Bladder (including urine) | 1.28 ± 0.11 | 2.82 ± 1.27 | 5.83 ± 2.21 |
| Muscle (lower limbs) | 0.16 ± 0.00 | 0.14 ± 0.01 | 0.12 ± 0.00 |
| Whole brain | 0.02 ± 0.00 | 0.01 ± 0.00 | 0.01 ± 0.00 |
| Adrenal gland | 14.35 ± 4.09 | 22.61 ± 2.12 | 21.73 ± 3.25 |
| Femur | 0.38 ± 0.03 | 0.40 ± 0.10 | 0.28 ± 0.00 |
| Testis | 0.04 ± 0.00 | 0.05 ± 0.04 | 0.09 ± 0.00 |
| Fat | 0.08 ± 0.02 | 0.06 ± 0.02 | 0.05 ± 0.00 |
| Remaining whole body | 0.15 ± 0.00 | 0.13 ± 0.02 | 0.12 ± 0.00 |
| Adrenal gland/blood | 100.87 ± 36.73 | 145.45 ± 14.69 | 168.33 ± 36.80 |
| Adrenal gland/liver | 2.68 ± 1.01 | 5.06 ± 0.59 | 6.87 ± 1.26 |
| Adrenal gland/kidney | 11.40 ± 5.81 | 17.00 ± 1.67 | 18.05 ± 3.00 |
| Adrenal gland/small intestine | 13.32 ± 3.08 | 8.44 ± 1.36 | 5.43 ± 1.42 |
| Adrenal gland/muscle | 88.35 ± 26.16 | 158.65 ± 18.59 | 180.41 ± 24.02 |
| Adrenal gland/fat | 174.42 ± 63.32 | 425.84 ± 103.54 | 417.70 ± 25.29 |

TABLE 11

[123I] 400

| | Radioactivity distribution (% ID/g) | | |
|---|---|---|---|
| | 10 min after administration (n = 2) | 30 min after administration (n = 2) | 60 min after administration (n = 3) |
| Blood | 0.32 | 0.43 | 0.40 ± 0.01 |
| Heart | 0.63 | 0.49 | 0.35 ± 0.03 |
| Lung | 1.06 | 0.76 | 0.60 ± 0.03 |
| Stomach | 1.03 | 2.24 | 4.35 ± 0.25 |
| Liver | 2.98 | 1.24 | 0.70 ± 0.05 |
| Spleen | 5.26 | 5.44 | 5.27 ± 0.89 |
| Small intestine | 1.30 | 1.83 | 1.85 ± 0.44 |
| Large intestine | 0.19 | 0.19 | 0.43 ± 0.19 |
| Kidney | 1.54 | 0.95 | 0.62 ± 0.08 |
| Bladder (including urine) | 0.32 | 1.35 | 1.27 ± 0.07 |
| Muscle (lower limbs) | 0.17 | 0.15 | 0.12 ± 0.02 |
| Whole brain | 0.02 | 0.02 | 0.02 ± 0.00 |
| Adrenal gland | 9.09 | 16.93 | 11.65 ± 1.54 |
| Thyroid gland | 3.54 | 9.97 | 19.76 ± 1.03 |
| Testis | 0.07 | 0.12 | 0.15 ± 0.01 |
| Fat | 0.10 | 0.12 | 0.11 ± 0.02 |
| Remaining whole body | 0.27 | 0.31 | 0.33 ± 0.02 |
| Adrenal gland/blood | 28.34 | 40.26 | 29.41 ± 3.13 |
| Adrenal gland/liver | 3.02 | 13.82 | 16.66 ± 3.13 |
| Adrenal gland/kidney | 5.85 | 17.90 | 18.87 ± 3.12 |
| Adrenal gland/small intestine | 6.95 | 9.24 | 6.64 ± 2.31 |
| Adrenal gland/muscle | 54.21 | 110.91 | 95.38 ± 22.07 |
| Adrenal gland/fat | 89.23 | 147.73 | 105.17 ± 28.98 |

TABLE 12

[18F] 500

| | Radioactivity distribution (% ID/g) | | |
|---|---|---|---|
| | 10 min after administration (n = 3) | 30 min after administration (n = 3) | 60 min after administration (n = 3) |
| Blood | 0.12 ± 0.02 | 0.10 ± 0.01 | 0.10 ± 0.02 |
| Heart | 0.31 ± 0.03 | 0.25 ± 0.02 | 0.24 ± 0.04 |
| Lung | 0.68 ± 0.08 | 0.44 ± 0.02 | 0.48 ± 0.04 |
| Stomach | 0.86 ± 0.06 | 1.11 ± 0.14 | 1.66 ± 0.45 |
| Liver | 5.32 ± 0.21 | 4.76 ± 0.15 | 3.08 ± 0.99 |
| Spleen | 0.93 ± 0.10 | 0.41 ± 0.06 | 0.32 ± 0.09 |
| Small intestine | 1.32 ± 0.13 | 3.54 ± 0.51 | 5.36 ± 1.39 |
| Large intestine | 0.23 ± 0.03 | 0.28 ± 0.04 | 0.41 ± 0.09 |
| Kidney | 1.28 ± 0.08 | 1.10 ± 0.08 | 1.23 ± 0.22 |
| Bladder (including urine) | 0.86 ± 0.38 | 2.02 ± 1.20 | 3.87 ± 0.37 |
| Muscle (lower limbs) | 0.27 ± 0.08 | 0.13 ± 0.01 | 0.11 ± 0.03 |
| Whole brain | 0.02 ± 0.00 | 0.01 ± 0.00 | 0.02 ± 0.00 |
| Adrenal gland | 18.45 ± 3.39 | 20.88 ± 2.82 | 21.41 ± 4.42 |
| Femur | 0.25 ± 0.01 | 0.14 ± 0.01 | 0.12 ± 0.03 |
| Testis | 0.06 ± 0.01 | 0.08 ± 0.01 | 0.11 ± 0.03 |
| Fat | 0.09 ± 0.02 | 0.07 ± 0.02 | 0.06 ± 0.02 |
| Remaining whole body | 0.20 ± 0.02 | 0.11 ± 0.01 | 0.10 ± 0.02 |
| Adrenal gland/blood | 158.10 ± 31.05 | 206.39 ± 28.57 | 214.22 ± 75.71 |
| Adrenal gland/liver | 3.45 ± 0.50 | 4.39 ± 0.61 | 7.45 ± 2.80 |
| Adrenal gland/kidney | 14.57 ± 3.27 | 19.08 ± 3.40 | 17.62 ± 3.44 |
| Adrenal gland/small intestine | 13.90 ± 1.21 | 5.99 ± 1.25 | 4.17 ± 1.22 |
| Adrenal gland/muscle | 74.08 ± 27.27 | 160.44 ± 36.00 | 210.35 ± 70.86 |
| Adrenal gland/fat | 210.51 ± 56.26 | 295.05 ± 101.53 | 371.37 ± 112.38 |

TABLE 13

[123I] 601

| | Radioactivity distribution (% ID/g) | | |
|---|---|---|---|
| | 10 min after administration (n = 3) | 30 min after administration (n = 3) | 60 min after administration (n = 3) |
| Blood | 0.27 ± 0.01 | 0.20 ± 0.03 | 0.12 ± 0.02 |
| Heart | 0.61 ± 0.03 | 0.42 ± 0.08 | 0.26 ± 0.05 |
| Lung | 0.54 ± 0.01 | 0.43 ± 0.07 | 0.26 ± 0.03 |
| Stomach | 0.83 ± 0.25 | 0.86 ± 0.23 | 0.50 ± 0.29 |
| Liver | 4.15 ± 0.27 | 2.71 ± 0.39 | 1.80 ± 0.26 |
| Spleen | 0.51 ± 0.02 | 0.35 ± 0.07 | 0.20 ± 0.03 |
| Small intestine | 1.99 ± 0.27 | 5.54 ± 1.72 | 9.33 ± 1.02 |
| Large intestine | 0.14 ± 0.01 | 0.15 ± 0.01 | 0.14 ± 0.02 |
| Kidney | 1.16 ± 0.02 | 0.80 ± 0.39 | 0.84 ± 0.09 |
| Bladder (urine) | 0.65 ± 0.26 | 0.41 ± 0.03 | 1.17 ± 0.51 |
| Muscle (lower limbs) | 0.26 ± 0.02 | 0.24 ± 0.04 | 0.14 ± 0.02 |
| Whole brain | 0.15 ± 0.01 | 0.11 ± 0.02 | 0.10 ± 0.04 |
| Adrenal gland | 13.40 ± 2.41 | 17.21 ± 1.46 | 8.87 ± 3.98 |
| Thyroid gland | 0.62 ± 0.09 | 0.69 ± 0.26 | 0.93 ± 0.47 |
| Testis | 0.32 ± 0.01 | 0.31 ± 0.05 | 0.22 ± 0.05 |
| Fat | 0.34 ± 0.16 | 0.50 ± 0.03 | 0.50 ± 0.09 |
| Remaining whole body | 0.30 ± 0.01 | 0.24 ± 0.03 | 0.15 ± 0.01 |
| Adrenal gland/blood | 49.76 ± 8.04 | 88.31 ± 19.36 | 73.52 ± 21.70 |
| Adrenal gland/liver | 3.21 ± 0.44 | 6.49 ± 1.59 | 4.79 ± 1.48 |
| Adrenal gland/kidney | 11.53 ± 2.04 | 28.94 ± 22.29 | 10.42 ± 4.49 |
| Adrenal gland/small intestine | 6.93 ± 2.04 | 3.30 ± 0.96 | 0.99 ± 0.55 |

TABLE 13-continued

[¹²³I] 601

| | Radioactivity distribution (% ID/g) | | |
|---|---|---|---|
| | 10 min after administration (n = 3) | 30 min after administration (n = 3) | 60 min after administration (n = 3) |
| Adrenal gland/muscle | 51.74 ± 11.28 | 72.90 ± 18.29 | 63.30 ± 21.65 |
| Adrenal gland/fat | 48.18 ± 26.02 | 34.33 ± 3.72 | 18.31 ± 9.45 |

TABLE 14

[¹²³I] 602

| | Radioactivity distribution (% ID/g) | | |
|---|---|---|---|
| | 10 min after administration (n = 3) | 30 min after administration (n = 3) | 60 min after administration (n = 3) |
| Blood | 0.32 ± 0.01 | 0.43 ± 0.05 | 0.40 ± 0.01 |
| Heart | 0.63 ± 0.07 | 0.49 ± 0.01 | 0.35 ± 0.03 |
| Lung | 1.06 ± 0.09 | 0.76 ± 0.04 | 0.60 ± 0.03 |
| Stomach | 1.03 ± 0.28 | 2.24 ± 0.39 | 4.35 ± 0.25 |
| Liver | 2.98 ± 0.35 | 1.24 ± 0.09 | 0.70 ± 0.05 |
| Spleen | 5.26 ± 1.78 | 5.44 ± 1.82 | 5.27 ± 0.89 |
| Small intestine | 1.30 ± 0.05 | 1.83 ± 0.07 | 1.85 ± 0.44 |
| Large intestine | 0.19 ± 0.00 | 0.19 ± 0.00 | 0.43 ± 0.19 |
| Kidney | 1.54 ± 0.11 | 0.95 ± 0.06 | 0.62 ± 0.08 |
| Bladder (including urine) | 0.32 ± 0.15 | 1.35 ± 0.14 | 1.27 ± 0.07 |
| Muscle (lower limbs) | 0.17 ± 0.00 | 0.15 ± 0.01 | 0.12 ± 0.02 |
| Whole brain | 0.02 ± 0.00 | 0.02 ± 0.00 | 0.02 ± 0.00 |
| Adrenal gland | 9.09 ± 2.28 | 16.93 ± 3.32 | 11.65 ± 1.54 |
| Thyroid gland | 3.54 ± 0.37 | 9.97 ± 0.74 | 19.76 ± 1.03 |
| Testis | 0.07 ± 0.02 | 0.12 ± 0.00 | 0.15 ± 0.01 |
| Fat | 0.10 ± 0.01 | 0.12 ± 0.04 | 0.11 ± 0.02 |
| Remaining whole body | 0.27 ± 0.01 | 0.31 ± 0.01 | 0.33 ± 0.02 |
| Adrenal gland/blood | 28.34 ± 5.95 | 40.26 ± 12.64 | 29.41 ± 3.13 |
| Adrenal gland/liver | 3.02 ± 0.41 | 13.82 ± 3.67 | 16.66 ± 3.13 |
| Adrenal gland/kidney | 5.85 ± 1.07 | 17.90 ± 4.66 | 18.87 ± 3.12 |
| Adrenal gland/small intestine | 6.95 ± 1.48 | 9.24 ± 1.46 | 6.64 ± 2.31 |
| Adrenal gland/muscle | 54.21 ± 12.64 | 110.91 ± 25.83 | 95.38 ± 22.07 |
| Adrenal gland/fat | 89.23 ± 14.22 | 147.73 ± 74.06 | 105.17 ± 28.98 |

TABLE 15

[¹²³I] 603

| | Radioactivity distribution (% ID/g) | | |
|---|---|---|---|
| | 10 min after administration (n = 3) | 30 min after administration (n = 3) | 60 min after administration (n = 3) |
| Blood | 0.13 ± 0.01 | 0.10 ± 0.02 | 0.06 ± 0.01 |
| Heart | 0.65 ± 0.09 | 0.64 ± 0.04 | 0.56 ± 0.01 |
| Lung | 0.98 ± 0.16 | 0.97 ± 0.10 | 0.78 ± 0.03 |
| Stomach | 0.66 ± 0.34 | 0.61 ± 0.14 | 0.89 ± 0.21 |
| Liver | 4.09 ± 0.45 | 1.89 ± 0.21 | 0.96 ± 0.10 |
| Spleen | 5.59 ± 1.78 | 6.71 ± 0.48 | 5.62 ± 1.11 |
| Small intestine | 1.29 ± 0.12 | 3.40 ± 0.80 | 3.98 ± 1.32 |
| Large intestine | 0.11 ± 0.01 | 0.14 ± 0.02 | 0.55 ± 0.52 |
| Kidney | 2.09 ± 0.09 | 1.65 ± 0.27 | 1.23 ± 0.01 |
| Bladder (including urine) | 0.43 ± 0.13 | 1.13 ± 0.19 | 3.04 ± 1.32 |
| Muscle (lower limbs) | 0.18 ± 0.05 | 0.16 ± 0.02 | 0.14 ± 0.01 |
| Whole brain | 0.01 ± 0.00 | 0.01 ± 0.00 | 0.01 ± 0.00 |
| Adrenal gland | 10.24 ± 4.48 | 15.46 ± 8.64 | 18.65 ± 1.67 |
| Femur | 0.85 ± 0.40 | 0.83 ± 0.03 | 0.90 ± 0.10 |
| Testis | 0.04 ± 0.01 | 0.05 ± 0.01 | 0.05 ± 0.01 |
| Fat | 0.11 ± 0.01 | 0.12 ± 0.03 | 0.12 ± 0.04 |
| Remaining whole body | 0.24 ± 0.01 | 0.27 ± 0.01 | 0.28 ± 0.04 |
| Adrenal gland/blood | 52.24 ± 16.82 | 199.21 ± 91.92 | 235.46 ± 58.57 |
| Adrenal gland/liver | 4.37 ± 1.12 | 17.77 ± 9.08 | 20.07 ± 5.16 |
| Adrenal gland/kidney | 3.95 ± 1.50 | 12.16 ± 7.12 | 13.73 ± 3.51 |
| Adrenal gland/small intestine | 3.44 ± 1.04 | 3.25 ± 1.07 | 2.42 ± 0.71 |
| Adrenal gland/muscle | 34.85 ± 6.45 | 98.15 ± 67.95 | 124.82 ± 30.33 |
| Adrenal gland/fat | 49.21 ± 30.24 | 106.15 ± 23.20 | 108.45 ± 23.85 |

TABLE 16

[¹²³I] 604

| | Radioactivity distribution (% ID/g) | | |
|---|---|---|---|
| | 10 min after administration (n = 3) | 30 min after administration (n = 3) | 60 min after administration (n = 3) |
| Blood | 0.13 ± 0.01 | 0.10 ± 0.02 | 0.06 ± 0.01 |
| Heart | 0.65 ± 0.09 | 0.64 ± 0.04 | 0.56 ± 0.01 |
| Lung | 0.98 ± 0.16 | 0.97 ± 0.10 | 0.78 ± 0.03 |
| Stomach | 0.66 ± 0.34 | 0.61 ± 0.14 | 0.89 ± 0.21 |
| Liver | 4.09 ± 0.45 | 1.89 ± 0.21 | 0.96 ± 0.10 |
| Spleen | 5.59 ± 1.78 | 6.71 ± 0.48 | 5.62 ± 1.11 |
| Small intestine | 1.29 ± 0.12 | 3.40 ± 0.80 | 3.98 ± 1.32 |
| Large intestine | 0.11 ± 0.01 | 0.14 ± 0.02 | 0.55 ± 0.52 |
| Kidney | 2.09 ± 0.09 | 1.65 ± 0.27 | 1.23 ± 0.01 |
| Bladder (including urine) | 0.43 ± 0.13 | 1.13 ± 0.19 | 3.04 ± 1.32 |
| Muscle (lower limbs) | 0.18 ± 0.05 | 0.16 ± 0.02 | 0.14 ± 0.01 |
| Whole brain | 0.01 ± 0.00 | 0.01 ± 0.00 | 0.01 ± 0.00 |
| Adrenal gland | 10.24 ± 4.48 | 15.46 ± 8.64 | 18.65 ± 1.67 |
| Femur | 0.85 ± 0.40 | 0.83 ± 0.03 | 0.90 ± 0.10 |
| Testis | 0.04 ± 0.01 | 0.05 ± 0.01 | 0.05 ± 0.01 |
| Fat | 0.11 ± 0.01 | 0.12 ± 0.03 | 0.12 ± 0.04 |
| Remaining whole body | 0.24 ± 0.01 | 0.27 ± 0.01 | 0.28 ± 0.04 |
| Adrenal gland/blood | 75.41 ± 30.78 | 170.18 ± 126.19 | 329.57 ± 56.14 |
| Adrenal gland/liver | 2.48 ± 1.00 | 8.55 ± 5.73 | 19.61 ± 2.12 |
| Adrenal gland/kidney | 4.89 ± 2.15 | 9.69 ± 6.36 | 15.22 ± 1.37 |
| Adrenal gland/small intestine | 7.85 ± 3.21 | 4.37 ± 1.61 | 5.02 ± 1.64 |
| Adrenal gland/muscle | 67.00 ± 51.23 | 100.20 ± 67.99 | 130.19 ± 7.34 |
| Adrenal gland/fat | 92.23 ± 49.88 | 156.19 ± 135.29 | 161.46 ± 40.00 |

TABLE 17

[¹²³I] 605

| | Radioactivity distribution (% ID/g) | | |
|---|---|---|---|
| | 10 min after administration (n = 3) | 30 min after administration (n = 3) | 60 min after administration (n = 3) |
| Blood | 0.14 ± 0.00 | 0.12 ± 0.01 | 0.09 ± 0.02 |
| Heart | 0.73 ± 0.06 | 0.52 ± 0.04 | 0.35 ± 0.09 |
| Lung | 1.94 ± 0.16 | 0.99 ± 0.10 | 0.56 ± 0.15 |
| Stomach | 0.80 ± 0.23 | 1.38 ± 0.42 | 2.22 ± 0.73 |
| Liver | 4.12 ± 0.23 | 2.72 ± 0.12 | 1.93 ± 0.37 |
| Spleen | 1.08 ± 0.10 | 0.58 ± 0.09 | 0.34 ± 0.07 |
| Small intestine | 2.46 ± 0.61 | 3.99 ± 0.33 | 6.65 ± 0.98 |
| Large intestine | 0.13 ± 0.01 | 0.16 ± 0.01 | 0.19 ± 0.03 |
| Kidney | 2.17 ± 0.09 | 1.18 ± 0.14 | 0.83 ± 0.10 |
| Bladder (including urine) | 0.09 ± 0.06 | 0.15 ± 0.01 | 0.13 ± 0.05 |
| Muscle (lower limbs) | 0.16 ± 0.01 | 0.22 ± 0.02 | 0.16 ± 0.01 |
| Whole brain | 0.03 ± 0.00 | 0.03 ± 0.00 | 0.02 ± 0.01 |
| Adrenal gland | 5.67 ± 0.25 | 3.10 ± 1.06 | 1.70 ± 0.21 |
| Femur | 0.51 ± 0.02 | 0.44 ± 0.04 | 0.36 ± 0.03 |
| Testis | 0.03 ± 0.00 | 0.03 ± 0.00 | 0.03 ± 0.01 |
| Fat | 0.14 ± 0.02 | 0.14 ± 0.03 | 0.16 ± 0.02 |
| Remaining whole body | 0.20 ± 0.01 | 0.21 ± 0.02 | 0.13 ± 0.02 |
| Adrenal gland/blood | 39.83 ± 1.25 | 26.42 ± 7.24 | 20.07 ± 1.94 |
| Adrenal gland/liver | 1.38 ± 0.01 | 1.14 ± 0.36 | 0.88 ± 0.05 |
| Adrenal gland/kidney | 2.61 ± 0.04 | 2.58 ± 0.55 | 2.05 ± 0.09 |
| Adrenal gland/small intestine | 2.44 ± 0.80 | 0.79 ± 0.34 | 0.26 ± 0.08 |
| Adrenal gland/muscle | 36.77 ± 3.87 | 14.44 ± 5.54 | 10.90 ± 0.67 |
| Adrenal gland/fat | 41.90 ± 6.19 | 22.69 ± 9.87 | 10.82 ± 1.23 |

TABLE 18

[¹²³I] 606

| | Radioactivity distribution (% ID/g) | | |
|---|---|---|---|
| | 10 min after administration (n = 3) | 30 min after administration (n = 3) | 60 min after administration (n = 3) |
| Blood | 0.15 ± 0.01 | 0.14 ± 0.00 | 0.12 ± 0.01 |
| Heart | 0.56 ± 0.04 | 0.44 ± 0.01 | 0.40 ± 0.02 |
| Lung | 0.86 ± 0.07 | 0.65 ± 0.03 | 0.60 ± 0.03 |
| Stomach | 0.75 ± 0.09 | 1.66 ± 0.06 | 1.90 ± 0.35 |
| Liver | 3.24 ± 0.05 | 2.59 ± 0.07 | 2.24 ± 0.16 |
| Spleen | 4.55 ± 0.41 | 3.80 ± 0.26 | 3.05 ± 0.35 |
| Small intestine | 1.35 ± 0.04 | 2.75 ± 0.21 | 3.77 ± 0.38 |
| Large intestine | 0.17 ± 0.04 | 0.23 ± 0.01 | 0.35 ± 0.06 |
| Kidney | 1.29 ± 0.11 | 1.01 ± 0.04 | 0.87 ± 0.07 |
| Bladder (including urine) | 0.27 ± 0.01 | 1.17 ± 0.36 | 2.06 ± 0.40 |
| Muscle (lower limbs) | 0.22 ± 0.04 | 0.16 ± 0.01 | 0.12 ± 0.01 |
| Whole brain | 0.03 ± 0.00 | 0.03 ± 0.00 | 0.03 ± 0.00 |
| Adrenal gland | 13.01 ± 3.75 | 21.23 ± 4.43 | 19.67 ± 3.42 |
| Femur | 0.59 ± 0.02 | 0.50 ± 0.01 | 0.62 ± 0.04 |
| Testis | 0.08 ± 0.00 | 0.11 ± 0.01 | 0.16 ± 0.03 |
| Fat | 0.13 ± 0.01 | 0.12 ± 0.01 | 0.09 ± 0.02 |
| Remaining whole body | 0.29 ± 0.02 | 0.24 ± 0.01 | 0.22 ± 0.01 |
| Adrenal gland/blood | 85.09 ± 27.52 | 151.28 ± 30.77 | 161.94 ± 14.16 |
| Adrenal gland/liver | 4.02 ± 1.20 | 8.21 ± 1.88 | 8.81 ± 1.68 |
| Adrenal gland/kidney | 10.11 ± 2.69 | 20.98 ± 3.60 | 22.62 ± 2.40 |
| Adrenal gland/small intestine | 9.70 ± 3.04 | 7.82 ± 2.11 | 5.20 ± 0.46 |
| Adrenal gland/muscle | 57.42 ± 9.23 | 130.86 ± 25.55 | 168.08 ± 24.28 |
| Adrenal gland/fat | 100.88 ± 26.65 | 172.63 ± 42.67 | 229.99 ± 79.47 |

TABLE 19

[¹²³I] 607

| | Radioactivity distribution (% ID/g) | | |
|---|---|---|---|
| | 10 min after administration (n = 3) | 30 min after administration (n = 3) | 60 min after administration (n = 3) |
| Blood | 0.17 ± 0.02 | 0.09 ± 0.00 | 0.08 ± 0.01 |
| Heart | 0.66 ± 0.03 | 0.54 ± 0.05 | 0.43 ± 0.08 |
| Lung | 0.90 ± 0.07 | 0.72 ± 0.05 | 0.65 ± 0.15 |
| Stomach | 0.88 ± 0.20 | 1.17 ± 0.29 | 1.52 ± 0.61 |
| Liver | 2.93 ± 0.40 | 0.94 ± 0.06 | 0.67 ± 0.04 |
| Spleen | 4.93 ± 0.56 | 6.69 ± 1.24 | 6.95 ± 0.95 |
| Small intestine | 2.82 ± 0.12 | 5.06 ± 0.42 | 5.48 ± 0.49 |
| Large intestine | 0.12 ± 0.02 | 0.12 ± 0.01 | 0.16 ± 0.03 |
| Kidney | 1.96 ± 0.19 | 1.24 ± 0.36 | 1.04 ± 0.19 |
| Bladder (including urine) | 1.20 ± 0.71 | 2.79 ± 0.51 | 2.99 ± 1.26 |
| Muscle (lower limbs) | 0.17 ± 0.02 | 0.13 ± 0.00 | 0.11 ± 0.02 |
| Whole brain | 0.03 ± 0.00 | 0.02 ± 0.00 | 0.02 ± 0.00 |
| Adrenal gland | 11.13 ± 0.88 | 14.61 ± 1.60 | 18.47 ± 2.05 |
| Femur | 0.86 ± 0.02 | 0.98 ± 0.16 | 1.17 ± 0.10 |
| Testis | 0.06 ± 0.01 | 0.09 ± 0.02 | 0.11 ± 0.02 |
| Fat | 0.12 ± 0.02 | 0.13 ± 0.01 | 0.10 ± 0.02 |
| Remaining whole body | 0.27 ± 0.03 | 0.27 ± 0.03 | 0.26 ± 0.01 |
| Adrenal gland/blood | 64.15 ± 4.03 | 163.89 ± 22.78 | 241.20 ± 39.48 |
| Adrenal gland/liver | 3.85 ± 0.67 | 15.55 ± 2.37 | 27.59 ± 4.15 |
| Adrenal gland/kidney | 5.73 ± 1.00 | 12.63 ± 4.53 | 18.18 ± 3.94 |
| Adrenal gland/small intestine | 3.95 ± 0.40 | 2.89 ± 0.23 | 3.39 ± 0.53 |
| Adrenal gland/muscle | 64.58 ± 8.21 | 114.11 ± 13.20 | 177.15 ± 43.41 |
| Adrenal gland/fat | 92.36 ± 15.53 | 109.60 ± 14.02 | 194.91 ± 44.02 |

TABLE 20

[¹²³I] 608

| | Radioactivity distribution (% ID/g) | | |
|---|---|---|---|
| | 10 min after administration (n = 3) | 30 min after administration (n = 3) | 60 min after administration (n = 3) |
| Blood | 0.12 ± 0.01 | 0.06 ± 0.01 | 0.04 ± 0.01 |
| Heart | 0.74 ± 0.09 | 0.76 ± 0.16 | 0.72 ± 0.09 |
| Lung | 1.11 ± 0.11 | 1.14 ± 0.08 | 0.94 ± 0.08 |
| Stomach | 0.53 ± 0.16 | 1.34 ± 0.66 | 1.15 ± 0.26 |
| Liver | 3.03 ± 0.36 | 1.08 ± 0.13 | 0.57 ± 0.06 |
| Spleen | 3.79 ± 1.44 | 4.81 ± 0.73 | 4.13 ± 1.21 |
| Small intestine | 1.74 ± 0.42 | 3.18 ± 0.18 | 4.35 ± 0.69 |
| Large intestine | 0.12 ± 0.01 | 0.11 ± 0.00 | 0.16 ± 0.07 |

TABLE 20-continued

[¹²³I] 608

| | Radioactivity distribution (% ID/g) | | |
|---|---|---|---|
| | 10 min after administration (n = 3) | 30 min after administration (n = 3) | 60 min after administration (n = 3) |
| Kidney | 1.79 ± 0.11 | 1.82 ± 0.08 | 1.55 ± 0.21 |
| Bladder (including urine) | 0.82 ± 0.43 | 2.70 ± 1.51 | 2.67 ± 0.43 |
| Muscle (lower limbs) | 0.15 ± 0.00 | 0.17 ± 0.03 | 0.15 ± 0.03 |
| Whole brain | 0.03 ± 0.01 | 0.02 ± 0.00 | 0.02 ± 0.00 |
| Adrenal gland | 8.76 ± 2.34 | 10.75 ± 1.11 | 15.22 ± 7.58 |
| Femur | 0.82 ± 0.05 | 1.17 ± 0.02 | 1.28 ± 0.07 |
| Testis | 0.07 ± 0.01 | 0.11 ± 0.00 | 0.09 ± 0.01 |
| Fat | 0.10 ± 0.01 | 0.10 ± 0.01 | 0.11 ± 0.04 |
| Remaining whole body | 0.29 ± 0.05 | 0.30 ± 0.00 | 0.28 ± 0.01 |
| Adrenal gland/blood | 75.29 ± 24.87 | 172.72 ± 25.00 | 345.58 ± 116.00 |
| Adrenal gland/liver | 2.86 ± 0.42 | 10.03 ± 1.46 | 25.91 ± 10.25 |
| Adrenal gland/kidney | 4.95 ± 1.61 | 5.90 ± 0.47 | 10.46 ± 6.81 |
| Adrenal gland/small intestine | 5.04 ± 0.35 | 3.39 ± 0.42 | 3.39 ± 1.14 |
| Adrenal gland/muscle | 57.35 ± 15.85 | 65.62 ± 16.66 | 113.23 ± 76.79 |
| Adrenal gland/fat | 90.02 ± 14.66 | 103.83 ± 16.66 | 158.96 ± 131.25 |

TABLE 21

[¹²³I] 609

| | Radioactivity distribution (% ID/g) | | |
|---|---|---|---|
| | 10 min after administration (n = 3) | 30 min after administration (n = 3) | 60 min after administration (n = 3) |
| Blood | 0.12 ± 0.00 | 0.14 ± 0.01 | 0.13 ± 0.00 |
| Heart | 0.36 ± 0.01 | 0.36 ± 0.02 | 0.33 ± 0.02 |
| Lung | 0.51 ± 0.04 | 0.42 ± 0.05 | 0.38 ± 0.02 |
| Stomach | 0.65 ± 0.25 | 1.27 ± 0.17 | 1.47 ± 0.33 |
| Liver | 5.50 ± 0.46 | 4.36 ± 0.46 | 2.77 ± 0.15 |
| Spleen | 0.82 ± 0.05 | 0.43 ± 0.03 | 0.30 ± 0.01 |
| Small intestine | 1.71 ± 0.18 | 4.44 ± 0.63 | 7.17 ± 0.45 |
| Large intestine | 0.16 ± 0.01 | 0.18 ± 0.03 | 0.63 ± 0.43 |
| Kidney | 1.17 ± 0.08 | 1.00 ± 0.07 | 0.85 ± 0.03 |
| Bladder (including urine) | 0.17 ± 0.08 | 0.80 ± 0.10 | 2.03 ± 0.70 |
| Muscle (lower limbs) | 0.20 ± 0.06 | 0.17 ± 0.03 | 0.11 ± 0.00 |
| Whole brain | 0.02 ± 0.00 | 0.02 ± 0.00 | 0.01 ± 0.00 |
| Adrenal gland | 8.54 ± 1.17 | 11.21 ± 3.24 | 11.04 ± 1.72 |
| Femur | 0.37 ± 0.06 | 0.29 ± 0.04 | 0.33 ± 0.03 |
| Testis | 0.05 ± 0.00 | 0.07 ± 0.01 | 0.07 ± 0.01 |
| Fat | 0.09 ± 0.01 | 0.10 ± 0.02 | 0.07 ± 0.01 |
| Remaining whole body | 0.20 ± 0.03 | 0.14 ± 0.01 | 0.10 ± 0.00 |
| Adrenal gland/blood | 70.18 ± 9.10 | 78.36 ± 23.36 | 87.48 ± 12.64 |
| Adrenal gland/liver | 1.55 ± 0.09 | 2.54 ± 0.51 | 3.99 ± 0.57 |
| Adrenal gland/kidney | 7.38 ± 1.46 | 11.13 ± 2.62 | 13.00 ± 2.52 |
| Adrenal gland/small intestine | 5.04 ± 0.97 | 2.54 ± 0.80 | 1.53 ± 0.14 |
| Adrenal gland/muscle | 46.03 ± 17.74 | 66.27 ± 15.78 | 103.59 ± 13.53 |
| Adrenal gland/fat | 92.34 ± 17.88 | 110.76 ± 35.85 | 147.76 ± 20.75 |

TABLE 22

[¹²³I] 610

| | Radioactivity distribution (% ID/g) | | |
|---|---|---|---|
| | 10 min after administration (n = 3) | 30 min after administration (n = 3) | 60 min after administration (n = 3) |
| Blood | 0.46 ± 0.03 | 0.66 ± 0.04 | 0.68 ± 0.05 |
| Heart | 0.33 ± 0.02 | 0.31 ± 0.02 | 0.28 ± 0.04 |
| Lung | 0.49 ± 0.03 | 0.53 ± 0.02 | 0.50 ± 0.03 |
| Stomach | 0.66 ± 0.21 | 1.27 ± 0.33 | 2.97 ± 0.54 |
| Liver | 3.43 ± 0.26 | 2.46 ± 0.18 | 0.95 ± 0.10 |
| Spleen | 1.43 ± 0.11 | 1.00 ± 0.04 | 0.78 ± 0.25 |
| Small intestine | 0.71 ± 0.10 | 0.98 ± 0.06 | 1.18 ± 0.18 |
| Large intestine | 0.13 ± 0.02 | 0.16 ± 0.03 | 0.19 ± 0.02 |
| Kidney | 0.86 ± 0.06 | 0.55 ± 0.02 | 0.47 ± 0.02 |
| Bladder (including urine) | 0.22 ± 0.08 | 0.28 ± 0.08 | 0.29 ± 0.08 |
| Muscle (lower limbs) | 0.21 ± 0.05 | 0.17 ± 0.02 | 0.13 ± 0.01 |
| Whole brain | 0.04 ± 0.00 | 0.04 ± 0.00 | 0.03 ± 0.00 |
| Adrenal gland | 12.62 ± 2.99 | 15.71 ± 1.59 | 19.09 ± 6.65 |
| Femur | 3.25 ± 0.85 | 19.34 ± 6.00 | 44.38 ± 12.58 |
| Testis | 0.13 ± 0.02 | 0.25 ± 0.02 | 0.32 ± 0.05 |
| Fat | 0.13 ± 0.02 | 0.18 ± 0.01 | 0.16 ± 0.03 |
| Remaining whole body | 0.30 ± 0.04 | 0.31 ± 0.02 | 0.31 ± 0.02 |
| Adrenal gland/blood | 27.61 ± 6.22 | 23.78 ± 2.07 | 27.80 ± 8.18 |
| Adrenal gland/liver | 3.68 ± 0.80 | 6.43 ± 0.94 | 20.57 ± 8.91 |
| Adrenal gland/kidney | 14.48 ± 2.49 | 28.65 ± 3.77 | 40.68 ± 13.23 |
| Adrenal gland/small intestine | 18.10 ± 4.67 | 16.12 ± 2.61 | 15.84 ± 3.51 |
| Adrenal gland/muscle | 62.69 ± 29.38 | 94.79 ± 8.71 | 147.93 ± 55.03 |
| Adrenal gland/fat | 100.35 ± 29.67 | 88.69 ± 3.10 | 120.42 ± 43.06 |

TABLE 23

[¹²³I] IMTO

| | Radioactivity distribution (% ID/g) | | |
|---|---|---|---|
| | 10 min after administration (n = 3) | 30 min after administration (n = 3) | 60 min after administration (n = 3) |
| Blood | 1.40 ± 0.13 | 2.55 ± 0.16 | 2.91 ± 0.09 |
| Heart | 0.48 ± 0.07 | 0.74 ± 0.03 | 0.77 ± 0.03 |
| Lung | 0.72 ± 0.05 | 0.90 ± 0.09 | 1.01 ± 0.03 |
| Stomach | 0.52 ± 0.18 | 0.46 ± 0.11 | 0.41 ± 0.05 |
| Liver | 3.29 ± 0.08 | 1.82 ± 0.04 | 1.37 ± 0.06 |
| Spleen | 0.30 ± 0.02 | 0.43 ± 0.04 | 0.39 ± 0.03 |
| Small intestine | 0.62 ± 0.03 | 0.68 ± 0.06 | 0.79 ± 0.11 |
| Large intestine | 0.10 ± 0.02 | 0.12 ± 0.01 | 0.14 ± 0.02 |
| Kidney | 0.70 ± 0.01 | 1.10 ± 0.12 | 1.10 ± 0.10 |
| Bladder (including urine) | 0.25 ± 0.27 | 0.39 ± 0.08 | 0.68 ± 0.30 |
| Muscle (lower limbs) | 0.18 ± 0.05 | 0.18 ± 0.02 | 0.16 ± 0.02 |
| Whole brain | 0.30 ± 0.02 | 0.18 ± 0.02 | 0.11 ± 0.00 |
| Adrenal gland | 22.14 ± 6.98 | 17.66 ± 7.43 | 19.70 ± 8.14 |
| Thyroid gland | 1.30 ± 1.05 | 0.81 ± 0.16 | 1.29 ± 0.25 |
| Testis | 0.52 ± 0.08 | 0.32 ± 0.04 | 0.33 ± 0.02 |
| Remaining whole body | 0.29 ± 0.00 | 0.31 ± 0.03 | 0.34 ± 0.01 |
| Adrenal gland/blood | 15.93 ± 4.94 | 6.84 ± 2.49 | 6.73 ± 2.57 |
| Adrenal gland/liver | 6.72 ± 2.00 | 9.74 ± 4.16 | 14.20 ± 5.28 |
| Adrenal gland/kidney | 31.76 ± 10.16 | 16.66 ± 8.95 | 18.20 ± 8.58 |
| Adrenal gland/small intestine | 35.65 ± 9.43 | 25.49 ± 8.31 | 24.59 ± 8.26 |

TABLE 23-continued

[$^{123}$I] IMTO

| | Radioactivity distribution (% ID/g) | | |
|---|---|---|---|
| | 10 min after administration (n = 3) | 30 min after administration (n = 3) | 60 min after administration (n = 3) |
| Adrenal gland/muscle | 126.18 ± 54.27 | 97.10 ± 32.37 | 120.14 ± 30.92 |

As shown in Tables 9 to 22, in all cases of [$^{18}$F] 100, [$^{18}$F] 200, [$^{123}$I] 400, [$^{18}$F] 500, and [$^{123}$I] 601 to 610, high accumulation of radioactivity in adrenal gland was observed, in comparison to in blood and peripheral tissues.

Evaluation 4: Plasma Stability Evaluation

Evaluation was made using a heparin-treated normal human plasma pool (Kohjin Bio Co., Ltd.). Compounds [$^{18}$F] 100, [$^{18}$F] 200, [$^{123}$I] 400, [$^{18}$F] 500, and [$^{123}$I] 601 to 610 obtained by the methods shown in Examples 2, 4, 7, 9, 11, 13, 15, 17, 19, 21, 23, 25, 27, and 29 were each added to the aforementioned human plasma (5 mL), and the obtained mixture was then incubated at 37° C. for 60 minutes. Thereafter, the mixture was centrifuged with addition of methanol, so that a deproteinization treatment was carried out. Thereafter, stability was evaluated by TLC analysis. As TLC analysis conditions, the TLC analysis conditions applied upon the above described synthesis of each compound were applied.

TABLE 24

| | Radiochemical purity after incubation in human plasma |
|---|---|
| [$^{18}$F] 100 | 97% |
| [$^{18}$F] 200 | 92% |
| [$^{123}$I] 400 | 88% |
| [$^{18}$F] 500 | 88% |

TABLE 25

| | Radiochemical purity after incubation in human plasma |
|---|---|
| [$^{123}$I] 601 | 98% |
| [$^{123}$I] 602 | 82% |
| [$^{123}$I] 603 | 94% |
| [$^{123}$I] 604 | 85% |
| [$^{123}$I] 605 | 90% |
| [$^{123}$I] 606 | 88% |
| [$^{123}$I] 607 | 84% |
| [$^{123}$I] 608 | 88% |
| [$^{123}$I] 609 | 86% |
| [$^{123}$I] 610 | 92% |

Figure 32A:
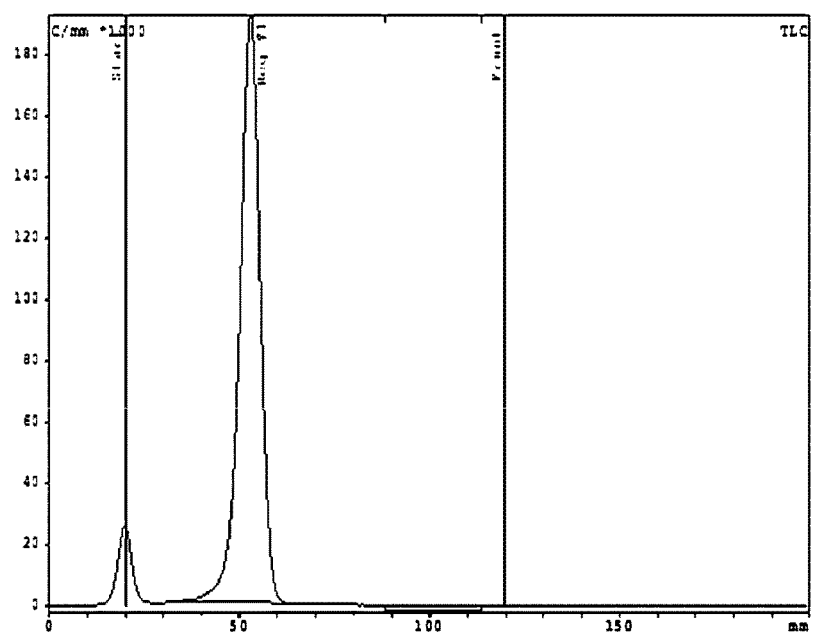
FIGS. 32A and 32B are views showing the plasma stability of 6-chloro-5-fluoro-1-(2-[$^{18}$F]fluoroethyl)-2-[5-(imidazol-1-ylmethyl)pyridin-3-yl]benzimidazole.
Figure 32B:
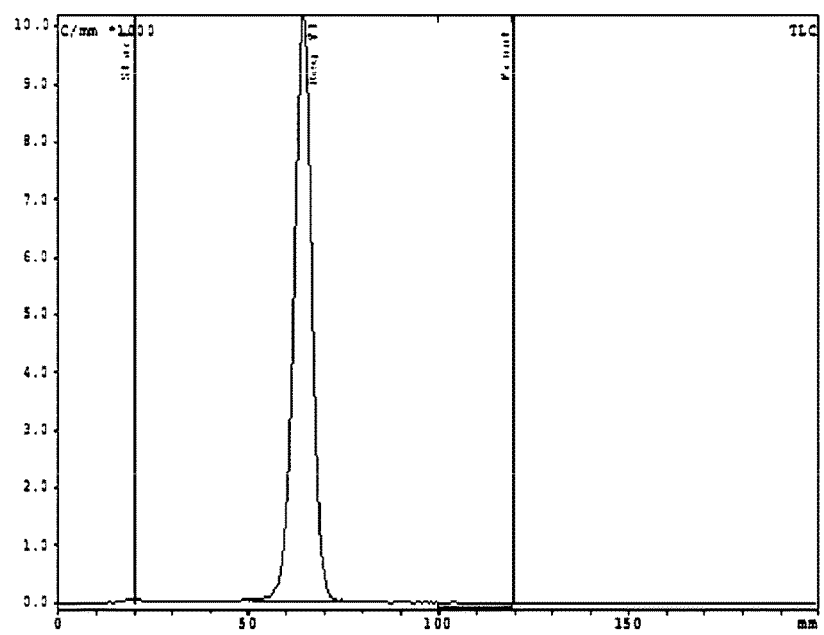
Figure 33A:
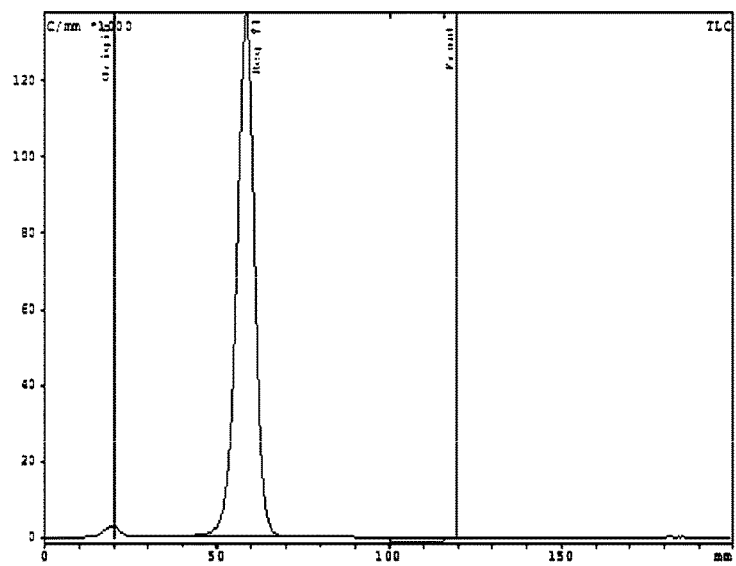
FIGS. 33A and 33B are views showing the plasma stability of 6-bromo-5-fluoro-1-(2-[$^{18}$F]fluoroethyl)-2-[5-(imidazol-1-ylmethyl)pyridin-3-yl]benzimidazole.
Figure 33B:
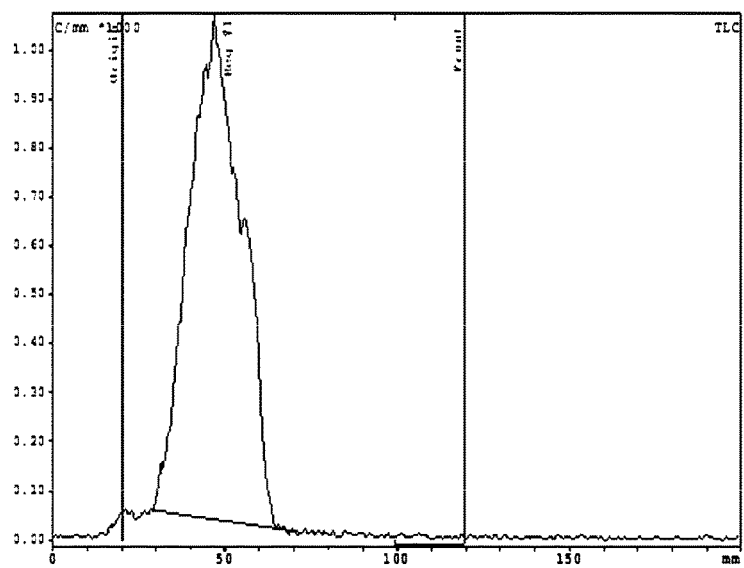
Figure 34A:
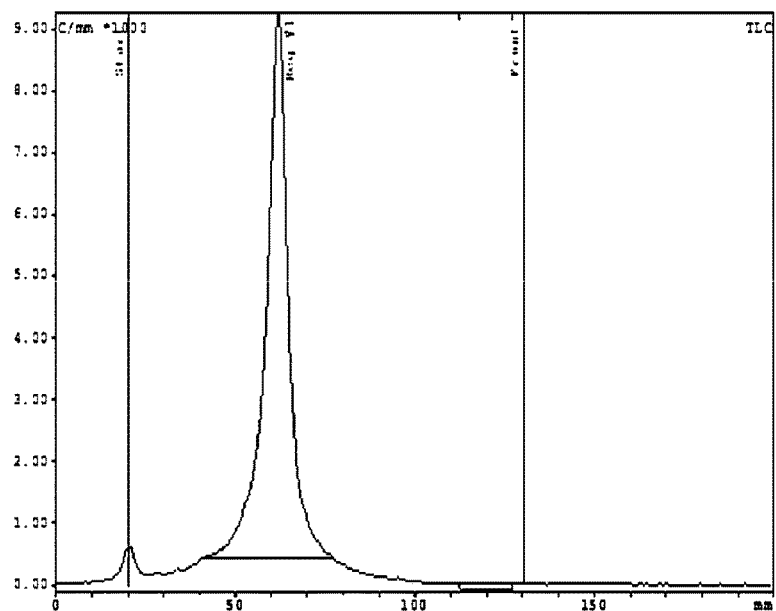
FIGS. 34A and 34B are views showing the plasma stability of 5-fluoro-1-(2-fluoroethyl)-2-[5-(imidazol-1-ylmethyl)pyridin-3-yl]-6-[$^{123}$I]iodobenzimidazole.
Figure 34B:
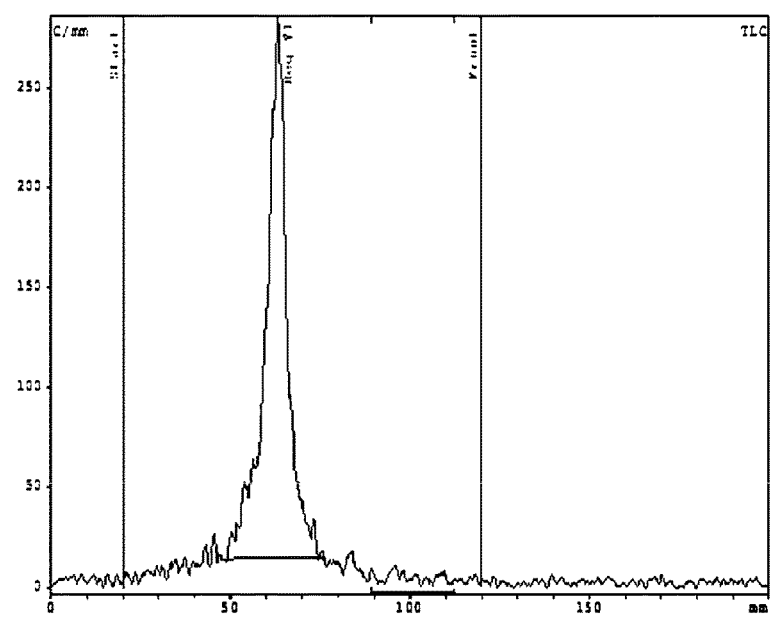
Figure 35A:
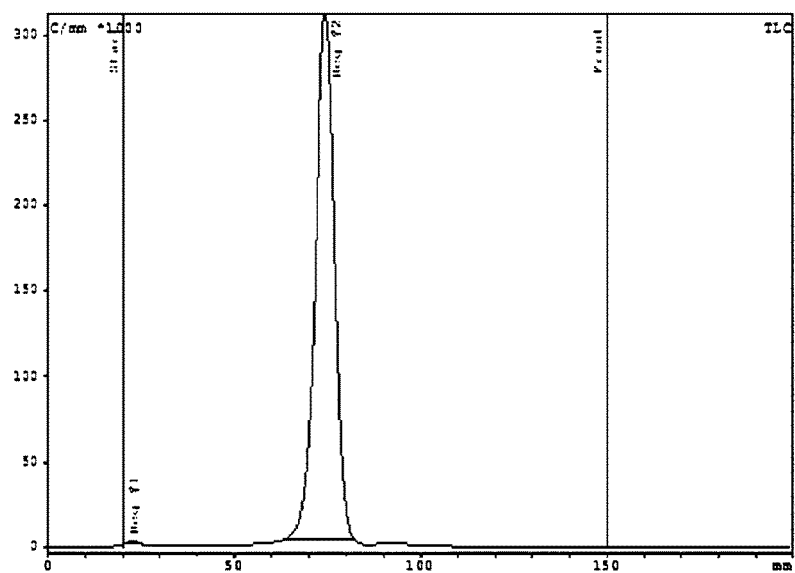
FIGS. 35A and 35B are views showing the plasma stability of 6-chloro-5-fluoro-1-(3-[$^{18}$F]fluoropropyl)-2-[5-(imidazol-1-ylmethyl)pyridin-3-yl]benzimidazole.
Figure 35B:
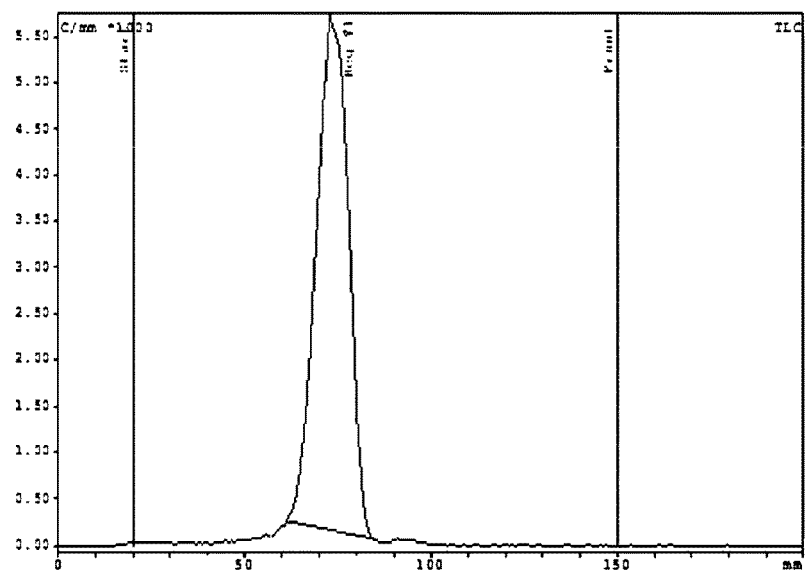
Figure 36A:
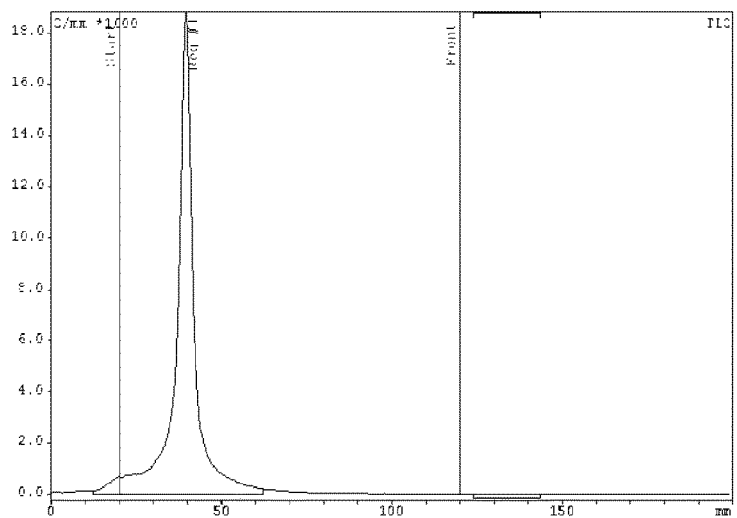
FIGS. 36A and 36B are views showing the plasma stability of methyl 1-[4-(1-cyclopropyl-6-[$^{123}$I]iodo-1H-imidazobenzo-2-yl)-3-pyridinylmethyl)]-1H-imidazolecarboxylate.
Figure 36B:
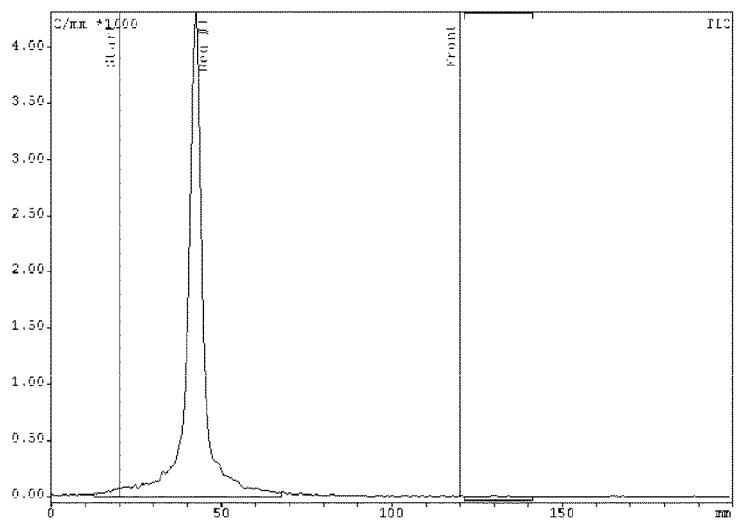
Figure 37A:
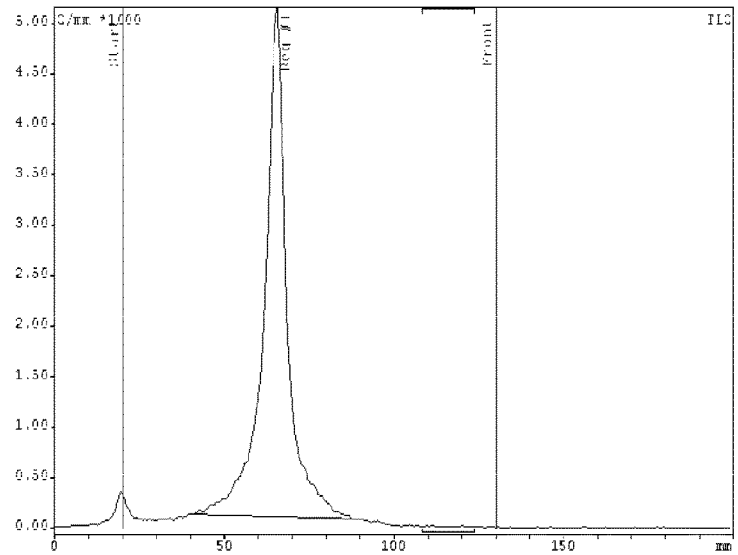
FIGS. 37A and 37B are views showing the plasma stability of 1-cyclopropyl-2-[3-(1H-imidazol-1-ylmethyl)pyridin-5-yl]-6-[$^{123}$I]iodo-1H-benzimidazole.
Figure 37B:
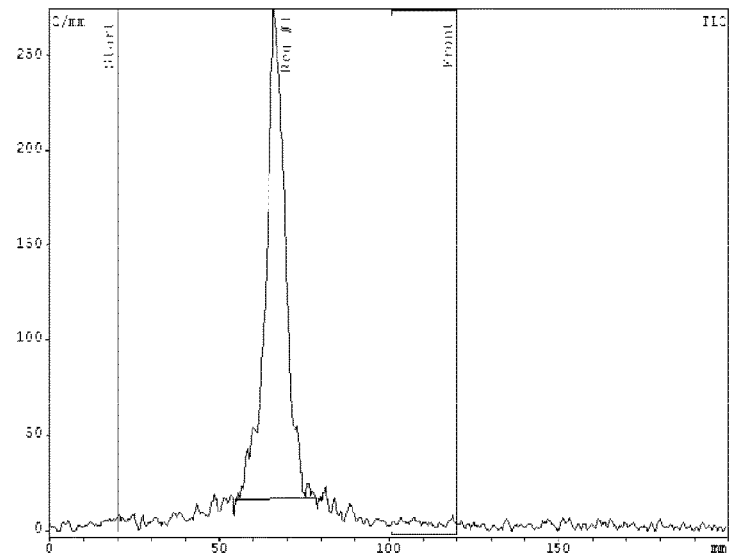
Figure 38A:
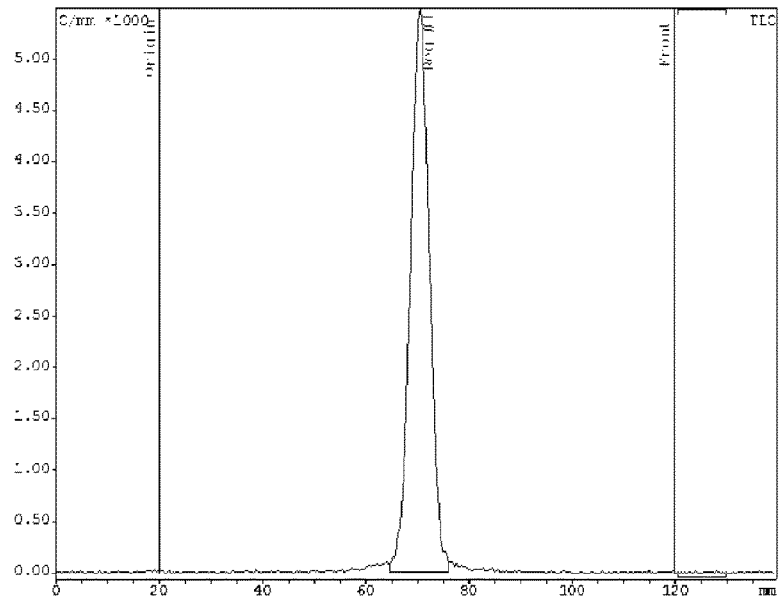
FIGS. 38A and 38B are views showing the plasma stability of 1-cyclopropyl-2-[3-(1H-1,2,3-triazol-1-ylmethyl)pyridin-5-yl]-6-[$^{123}$I]iodo-1H-benzimidazole.
Figure 38B:
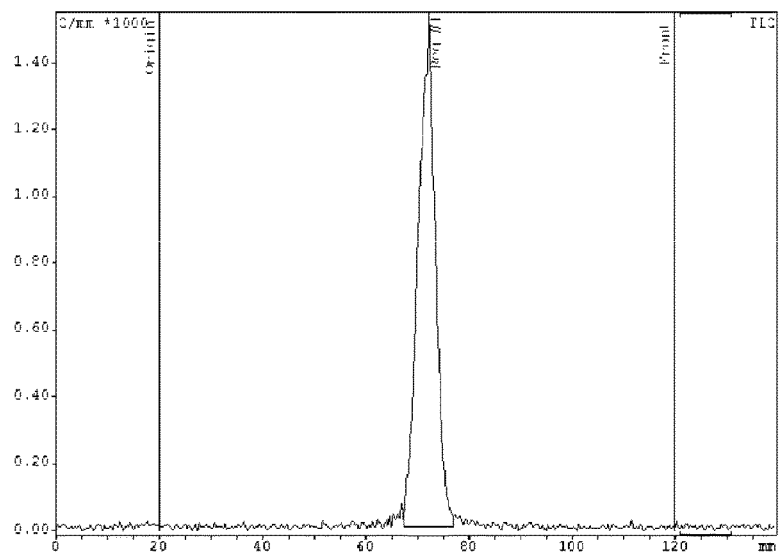
Figure 39A:
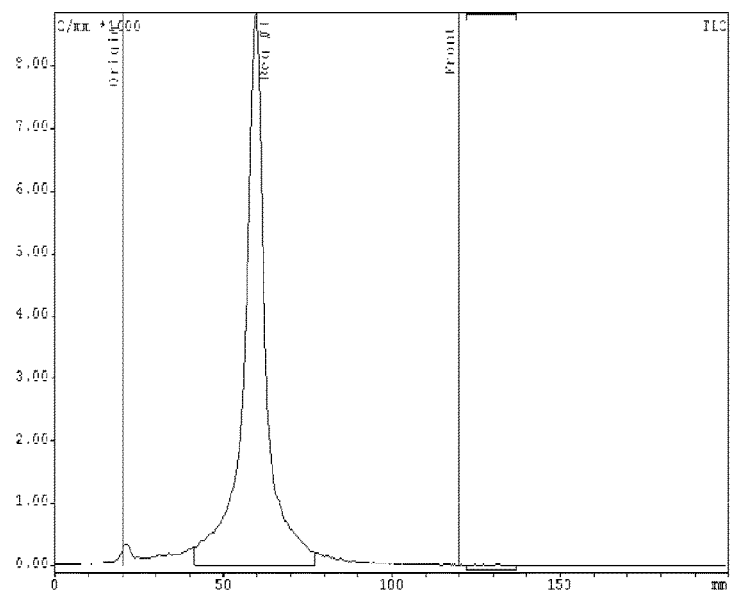
FIGS. 39A and 39B are views showing the plasma stability of 1-(2-fluoroethyl)-2-[5-{(imidazol-1-yl)methyl}pyridin-3-yl]-6-[$^{123}$I]iodobenzimidazole.
Figure 39B:
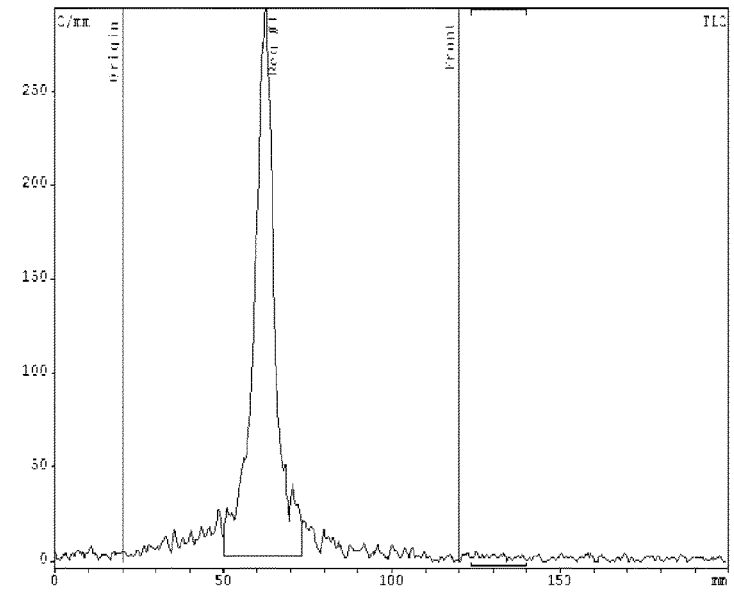
Figure 40A:
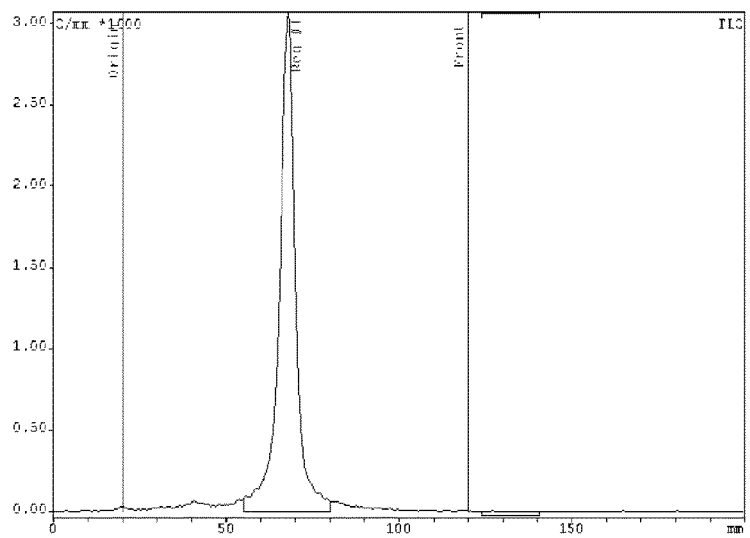
FIGS. 40A and 40B are views showing the plasma stability of 6-chloro-5-fluoro-1-(4-[$^{123}$I]iodobenzyl)-2-[5-(1H-imidazol-1-ylmethyl)-3-pyridinyl]-1H-benzimidazole.
Figure 40B:
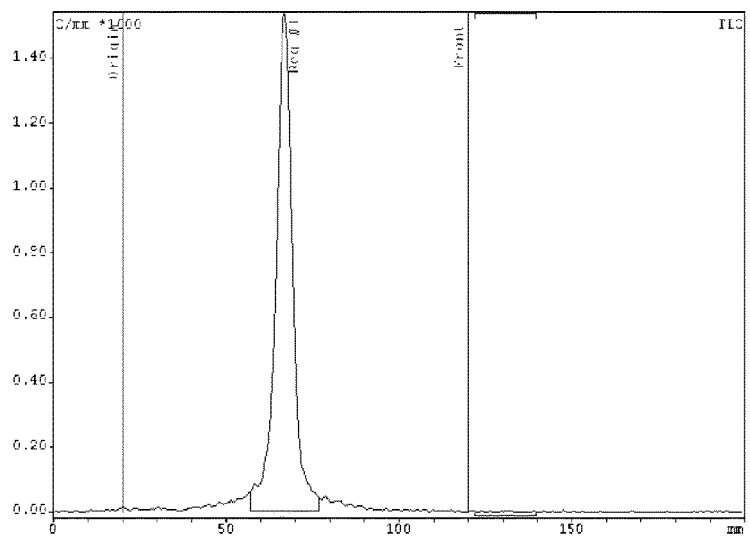
Figure 41A:
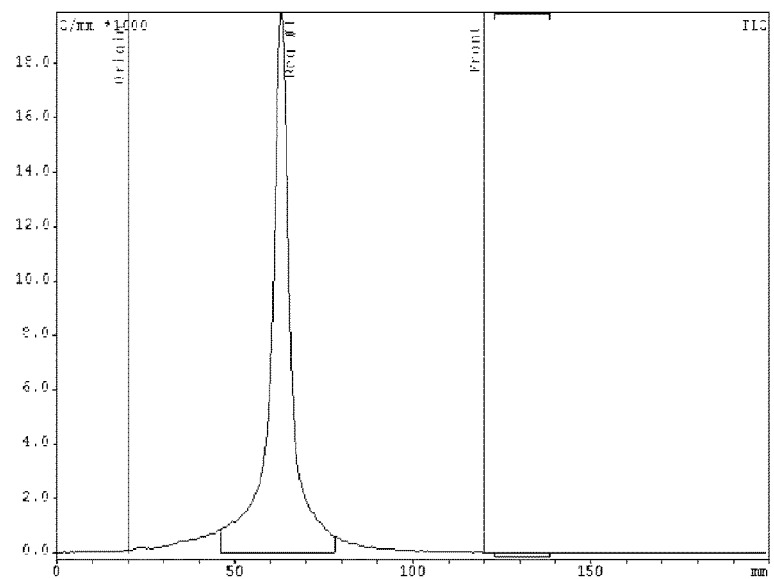
FIGS. 41A and 41B are views showing the plasma stability of 2-[5-{(1H-imidazol-1-yl)methyl}pyridin-3-yl]-6-[$^{123}$I]iodo-1-isopropyl-1H-benzo[d]imidazole.
Figure 41B:
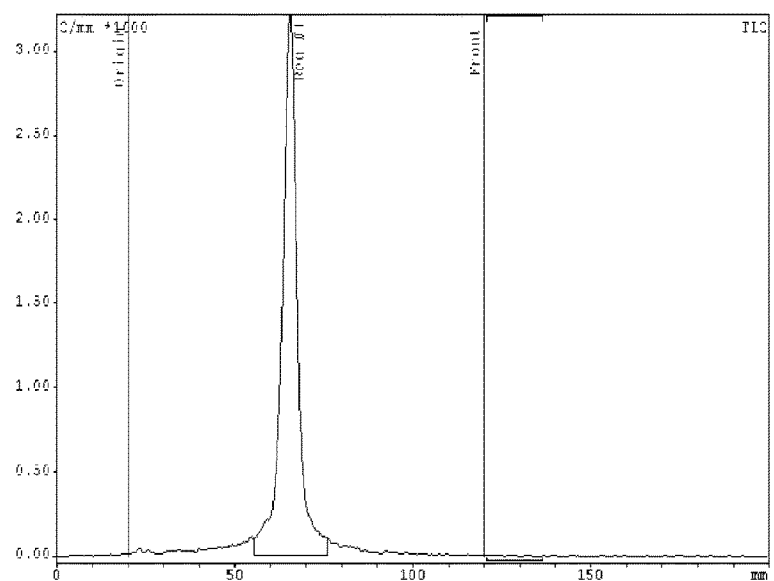
Figure 42A:
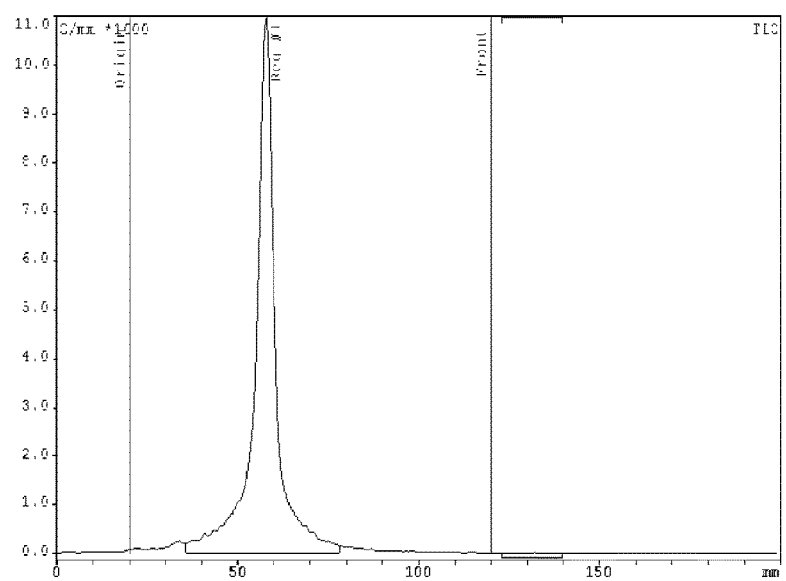
FIGS. 42A and 42B are views showing the plasma stability of 2-[5-{(1H-imidazol-1-yl)methyl}pyridin-3-yl]-6-[$^{123}$I]iodo-1-methyl-1H-benzo[d]imidazole.
Figure 42B:
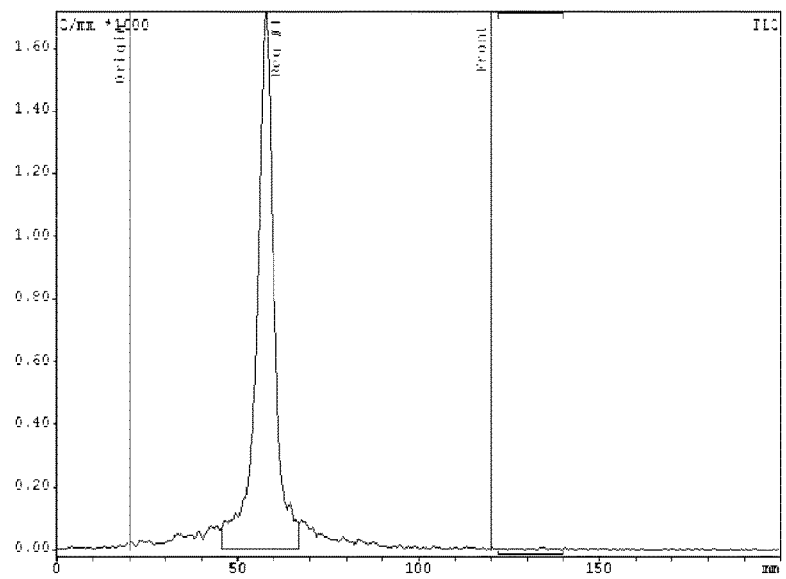
Figure 43A:
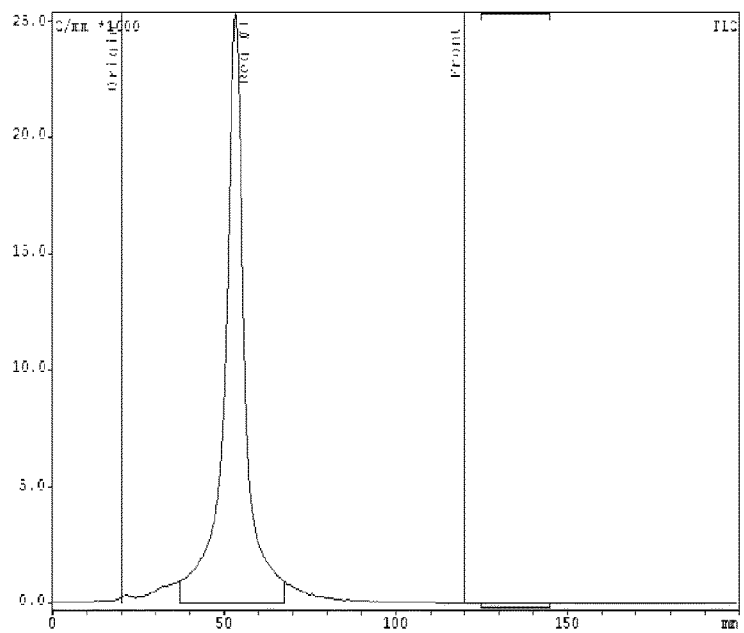
FIGS. 43A and 43B are views showing the plasma stability of 2-[5-{(1H-imidazol-1-yl)methyl}pyridin-3-yl]-1-ethyl-6-[$^{123}$I]iodo-1H-benzo[d]imidazole.
Figure 43B:
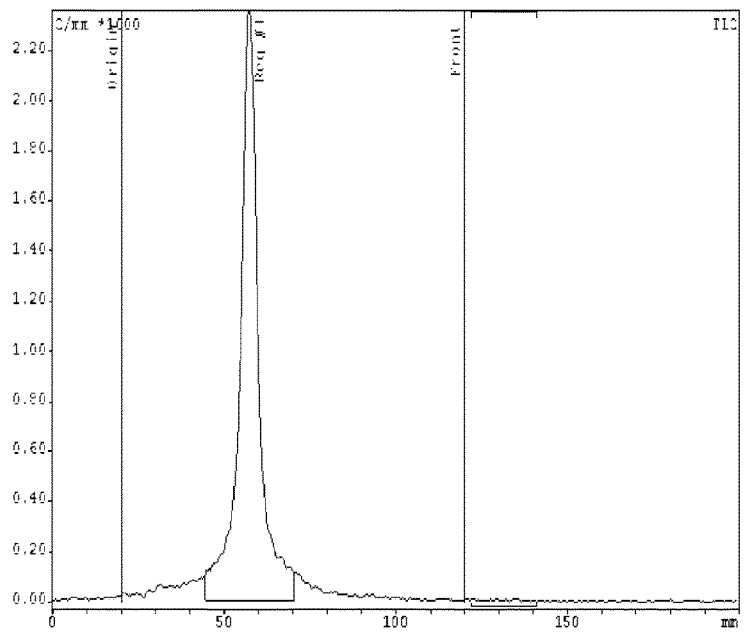
Figure 44A:
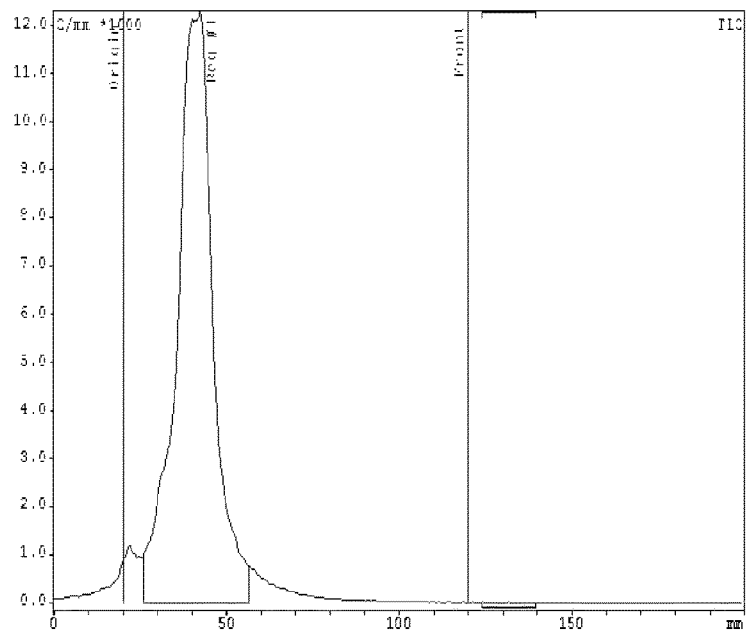
FIGS. 44A and 44B are views showing the plasma stability of 1-cyclopropyl-2-[5-(imidazol-1-ylmethyl)pyridin-3-yl]-6-[$^{123}$I]iodo-4-methoxybenzimidazole.
Figure 44B:
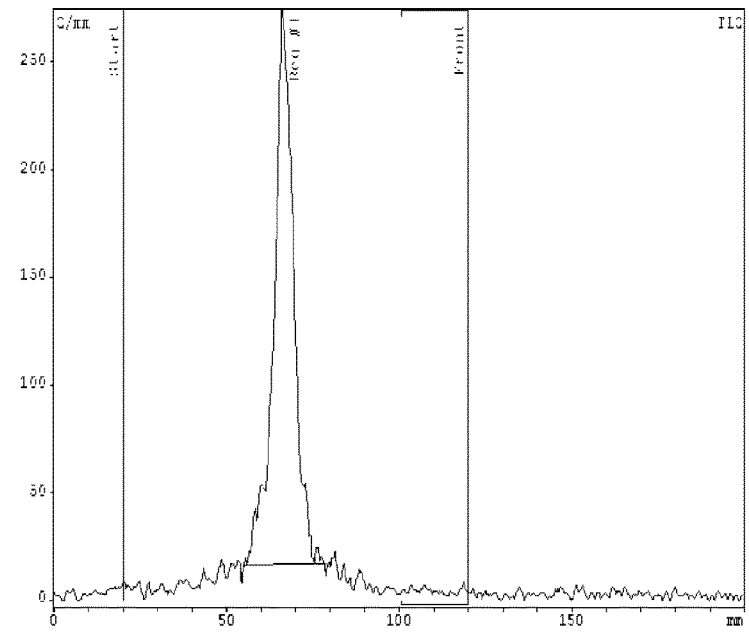
Figure 45A:
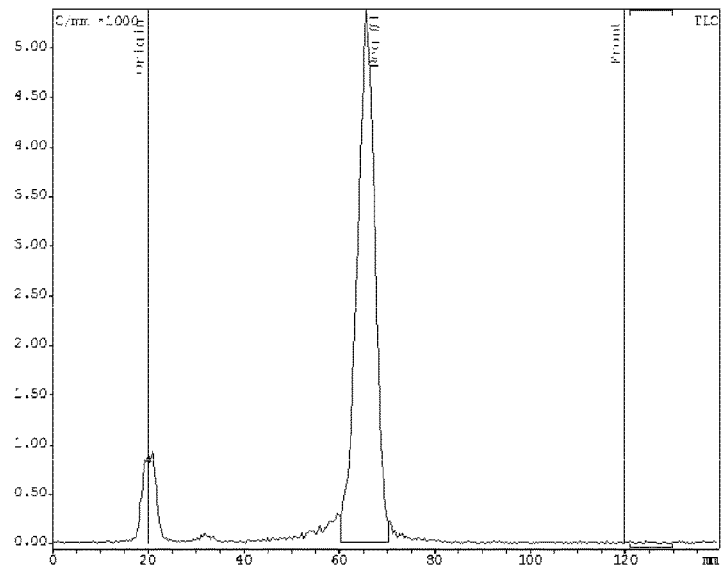
FIGS. 45A and 45B are views showing the plasma stability of 6-chloro-5-fluoro-1-(2-fluoroethyl)-2-{5-(5-[$^{123}$I]iodo-1H-imidazol-1-ylmethyl)pyridin-3-yl}benzimidazole.
Figure 45B:
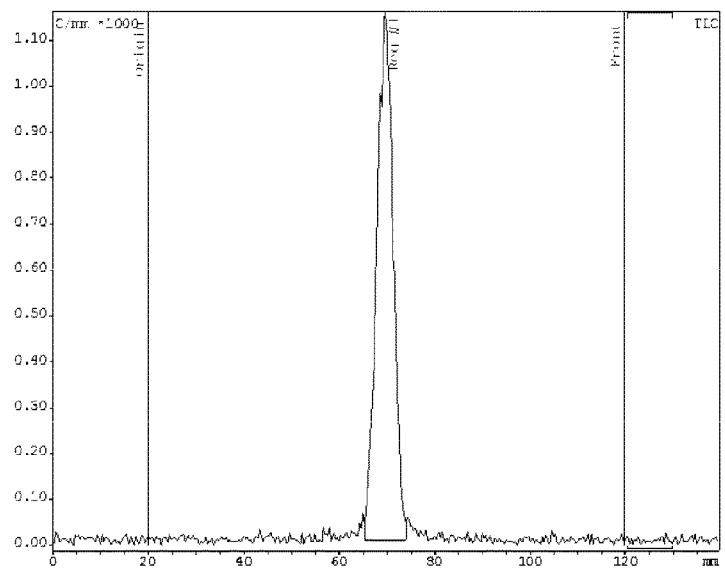

The results are shown in Tables 24 and 25 and FIGS. 32 to 45. FIGS. 32 to 45 show the comparison of the TLC analysis result of each compound with its reference sample (which is untreated with plasma). FIG. 32(a) shows the TLC analysis result of a reference sample for [$^{18}$F] 100, and FIG. 32(b) shows the TLC analysis result of [$^{18}$F] 100 after incubation in human plasma. FIG. 33(a) shows the TLC analysis result of a reference sample for [$^{18}$F] 200, and FIG. 33(b) shows the TLC analysis result of [$^{18}$F] 200 after incubation in human plasma. FIG. 34(a) shows the TLC analysis result of a reference sample for [$^{123}$I] 400, and FIG. 34(b) shows the TLC analysis result of [$^{123}$I] 400 after incubation in human plasma. FIG. 35(a) shows the TLC analysis result of a reference sample for [$^{18}$F] 500, and FIG. 35(b) shows the TLC analysis result of [$^{18}$F] 500 after incubation in human plasma. FIGS. 36(a), 37(a), 38(a), 39(a), 40(a), 41(a), 42(a), 43(a), 44(a) and 45(a) each show the TLC analysis results of each reference sample for [$^{123}$I] 601 to 610, and FIGS. 36(b), 37(b), 38(b), 39(b), 40(b), 41(b), 42(b), 43(b), 44(b) and 45(b) each show the TLC analysis results of [$^{123}$I] 601 to 610 after incubation in human plasma. From these results, it was demonstrated that [$^{18}$F] 100, [$^{18}$F] 200, [$^{123}$I] 400, [$^{18}$F] 500, and [$^{123}$I] 601 to 610 are hardly metabolized and decomposed in the plasma.

The invention claimed is:

1. A medicament comprising the compound represented by the following general formula (1) or a salt thereof:

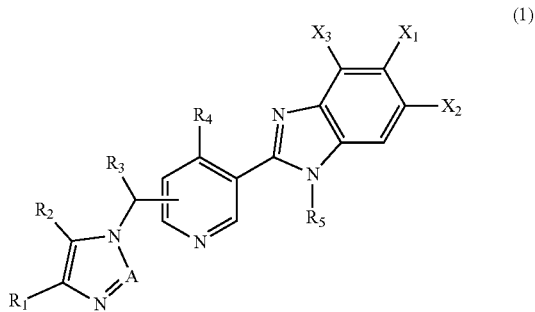

(1)

wherein $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_5$ represents a linear alkyl group containing 1 to 5 carbon atoms in which a hydrogen atom is optionally replaced by a halogen atom, a cyclic alkyl group containing 3 to 5 carbon atoms in which a hydrogen atom is optionally replaced by a halogen atom, a hydroxyalkyl group containing 1 to 5 carbon atoms, or an o-, p- or m-halobenzyl group, A represents CH or a nitrogen atom, $X_1$ and $X_3$ each independently represent a hydrogen atom or a halogen atom, $X_2$ represents a hydrogen atom, a halogen atom or a nitrile group, provided that at least one of $X_1$, $X_2$ and $X_3$ represents a halogen atom, and each $R_a$ independently represents an alkyl group containing 1 to 10 carbon atoms.

2. The medicament according to claim 1, wherein, in the general formula (1), $X_2$ is a halogen atom.

3. The medicament according to claim 1, wherein, in the general formula (1), $R_3$ is a hydrogen atom.

4. The medicament according to claim 1, wherein, in the general formula (1), $X_3$ is a hydrogen atom.

5. The medicament according to claim 1, wherein, in the general formula (1), $R_5$ is a methyl group, an ethyl group, a propyl group, an isopropyl group, a group represented by —$(CH_2)_nX_4$ (wherein n represents an integer of 1 to 5 and $X_4$ represents a halogen atom), a cyclopropyl group, or a p-halobenzyl group.

6. The medicament according to claim 1, which is an image diagnostic agent for an adrenal disease.

7. The medicament according to claim 6, which is an image diagnostic agent for use in positron emission tomography.

8. The medicament according to claim 6, which is an image diagnostic agent for use in single-photon emission computed tomography.

9. The medicament according to claim 1, which is a therapeutic agent for an aldosterone-producing tumor.

10. The medicament according to claim 9, which is an internal-use radiotherapeutic agent for an aldosterone-producing tumor.

11. A method for producing a radioactive compound represented by the following general formula (9) or a salt thereof from a compound represented by the following general formula (3) or a salt thereof by a radiohalogenation reaction:

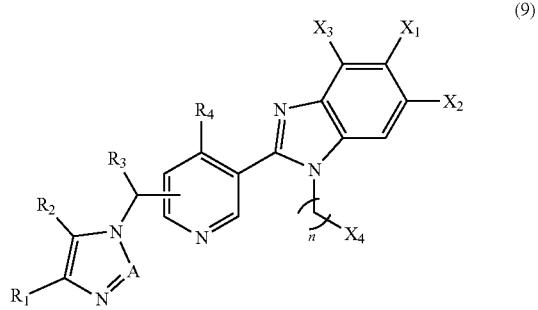
(9)

wherein $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, A represents CH or a nitrogen atom, $X_1$ and $X_3$ each independently represent a hydrogen atom or a halogen atom, $X_2$ represents a hydrogen atom, a halogen atom or a nitrile group, provided that at least one of $X_1$, $X_2$ and $X_3$ is a halogen atom, $X_4$ represents a radioactive halogen atom, n represents an integer of 1 to 5, and each $R_a$ independently represents an alkyl group containing 1 to 10 carbon atoms;

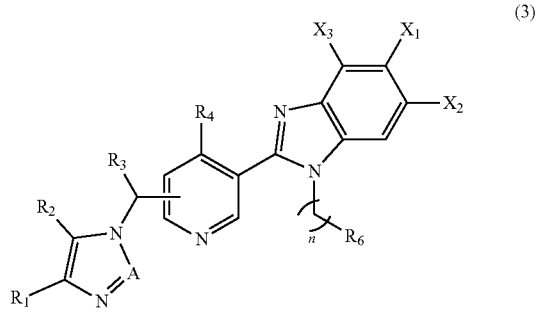
(3)

wherein $R_1$, $R_2$, $R_3$, $R_4$, A, $X_1$, $X_2$, $X_3$, $R_a$ and n are defined as above, and $R_6$ represents a halogen atom, a substituted or unsubstituted alkylsulfonyloxy group, or a substituted or unsubstituted arylsulfonyloxy group.

12. The method according claim 11, which is, for producing a radioactive compound represented by the following general formula (10) or a salt thereof from the following general formula (4) or a salt thereof by a radiohalogenation reaction:

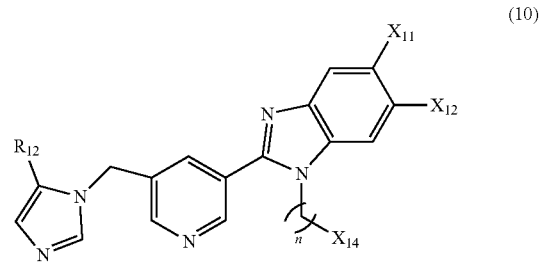
(10)

wherein $R_{12}$ represents a hydrogen atom or $CO_2R_a$, $X_{11}$ and $X_{12}$ each independently represent a different halogen atom, $X_{14}$ represents a radioactive halogen atom, n represents an integer of 1 to 5, and $R_a$ represents an alkyl group containing 1 to 10 carbon atoms,

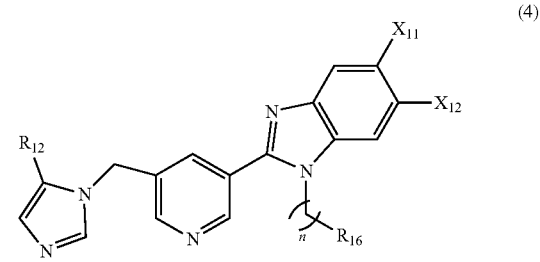
(4)

wherein $R_{12}$, $X_{ii}$, $X_{12}$, $R_a$ and n are defined above, and $R_{16}$ represents a halogen atom, a substituted or unsubstituted alkylsulfonyloxy group, or a substituted or unsubstituted arylsulfonyloxy group.

13. A method for producing a radioactive compound represented by the following general formula (11) or a salt thereof from a compound represented by the following general formula (5) or a salt thereof by a radiohalogenation reaction:

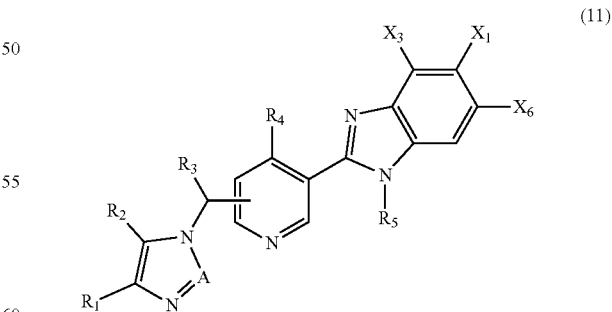
(11)

wherein $R_1$ represents a hydrogen atom or $CO_2R_a$, $R_2$ represents a hydrogen atom, a halogen atom or $CO_2R_a$, $R_3$ represents a hydrogen atom or a hydroxyalkyl group containing 1 to 10 carbon atoms, $R_4$ represents a hydrogen atom, a hydroxy group or an alkoxy group containing 1 to 10 carbon atoms, $R_5$ represents a linear alkyl group containing 1 to 5 carbon atoms in which a hydrogen atom is optionally replaced by a halogen atom, a cyclic alkyl group containing 3 to 5 carbon atoms in which a hydrogen atom is optionally replaced by a halogen atom, a hydroxyalkyl group containing 1 to 5 carbon atoms, or an o-, p- or m-halobenzyl group, A represents CH or a nitrogen atom, $X_1$ represents a hydrogen atom or a halogen atom, $X_3$ represents a hydrogen atom or a halogen atom, $X_6$ represents a radioactive halogen atom, and each $R_a$ independently represents an alkyl group containing 1 to 10 carbon atoms;

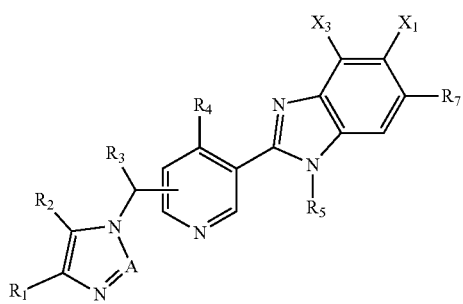
(5)

wherein $R_1$, $R_2$, $R_3$, $R_4$, $R_5$, A, $X_1$, $X_3$ and $R_a$ are defined as above, and $R_7$ represents a trialkyltin group or a trialkylsilyl group.

14. The method according claim 13, which is, for producing a radioactive compound represented by the following general formula (12) or a salt thereof from the compound represented by the following general formula (6) or a salt thereof by a radiohalogenation reaction:

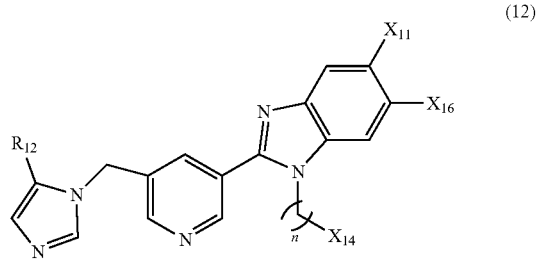
(12)

wherein $R_{12}$ represents a hydrogen atom or $CO_2R_a$, $X_{11}$ represents a hydrogen atom or a halogen atom, $X_{14}$ represents a halogen atom, $X_{16}$ represents a radioactive halogen atom, n represents an integer of 1 to 5, and $R_a$ represents an alkyl group containing 1 to 10 carbon atoms:

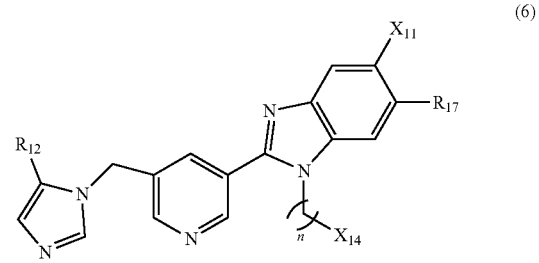
(6)

wherein $R_{12}$, $X_{11}$, $X_{14}$, n and $R_a$ is defined as above, and $R_{17}$ represents a trialkyltin group or a trialkylsilyl group.

* * * * *